US009505786B2

(12) United States Patent
Follmann et al.

(10) Patent No.: US 9,505,786 B2
(45) Date of Patent: Nov. 29, 2016

(54) SUBSTITUTED ANNULATED TRIAZINES AND USE THEREOF

(71) Applicants: BAYER INTELLECTUAL PROPERTY GMBH, Monheim (DE); BAYER PHARMA AKTIENGESELLSCHAFT, Berlin (DE)

(72) Inventors: Markus Follmann, Cologne (DE); Johannes-Peter Stasch, Solingen (DE); Gorden Redlich, Bochum (DE); Nils Griebenow, Dormagen (DE); Dieter Lang, Velbert (DE); Frank Wunder, Wuppertal (DE); Walter Hübsch, Wuppertal (DE); Alexandros Vakalopoulos, Hilden (DE); Adrian Tersteegen, Wuppertal (DE)

(73) Assignees: BAYER PHARMA AKTIENGESELLSCHAFT, Berlin (DE); BAYER INTELLECTUAL PROPERTY GMBH, Monheim (DE)

( * ) Notice: Subject to any disclaimer, the term of this patent is extended or adjusted under 35 U.S.C. 154(b) by 0 days.

(21) Appl. No.: 14/738,148

(22) Filed: Jun. 12, 2015

(65) Prior Publication Data
US 2015/0274754 A1    Oct. 1, 2015

Related U.S. Application Data

(62) Division of application No. 14/371,046, filed as application No. PCT/EP2013/050381 on Jan. 10, 2013.

(30) Foreign Application Priority Data

Jan. 11, 2012   (DE) ........................ 10 2012 200 349

(51) Int. Cl.
*C07D 471/04*   (2006.01)
*A61K 31/53*    (2006.01)
*A61P 9/10*     (2006.01)
*A61P 9/12*     (2006.01)
*A61P 7/02*     (2006.01)
*C07D 519/00*   (2006.01)
*A61K 31/519*   (2006.01)
*A61K 45/06*    (2006.01)

(52) U.S. Cl.
CPC ........... *C07D 519/00* (2013.01); *A61K 31/519* (2013.01); *A61K 31/53* (2013.01); *A61K 45/06* (2013.01); *C07D 471/04* (2013.01)

(58) Field of Classification Search
CPC .............. C07D 471/04; A61K 31/53
USPC .......................... 544/184; 514/243
See application file for complete search history.

(56) References Cited

U.S. PATENT DOCUMENTS

| 4,833,246 | A  | 5/1989  | Adachi et al. |
| 5,976,523 | A  | 11/1999 | Awaya et al. |
| 6,166,027 | A  | 12/2000 | Straub et al. |
| 6,180,656 | B1 | 1/2001  | Furstner et al. |
| 6,451,805 | B1 | 9/2002  | Straub et al. |
| 6,743,798 | B1 | 6/2004  | Straub et al. |
| 6,833,364 | B1 | 12/2004 | Straub et al. |
| 6,903,089 | B1 | 6/2005  | Stasch et al. |
| 7,173,037 | B2 | 2/2007  | Alonso-Alija et al. |
| 7,323,472 | B2 | 1/2008  | Adams et al. |
| 7,410,973 | B2 | 8/2008  | Feurer et al. |
| 7,414,136 | B2 | 8/2008  | Matsumura et al. |
| 7,528,132 | B2 | 5/2009  | Chan et al. |
| 7,541,367 | B2 | 6/2009  | Chiu et al. |
| 7,750,014 | B2 | 7/2010  | Ly et al. |
| 8,058,282 | B2 | 11/2011 | Adams et al. |
| 8,242,272 | B2 | 8/2012  | Jimenez et al. |
| 8,293,900 | B2 | 10/2012 | Jian et al. |
| 8,309,551 | B2 | 11/2012 | Schirok et al. |
| 8,420,656 | B2 | 4/2013  | Follmann et al. |
| 8,741,910 | B2 | 6/2014  | Brockunier et al. |
| 8,765,769 | B2 | 7/2014  | Follmann et al. |
| 8,859,569 | B2 | 10/2014 | Follmann et al. |
| 9,023,849 | B2 | 5/2015  | Follmann et al. |
| 9,040,538 | B2 | 5/2015  | Attardo et al. |
| 9,090,609 | B2 | 7/2015  | Follmann et al. |
| 9,090,610 | B2 | 7/2015  | Follmann et al. |

(Continued)

FOREIGN PATENT DOCUMENTS

| CA | 2804470 A1 | 1/2012 |
| CA | 2809911 A1 | 3/2012 |

(Continued)

OTHER PUBLICATIONS

Badesch et al., "Prostanoid Therapy for Pulmonary Arterial Hypertension," Journal of the American College of Cardiology, (Jun. 16, 2004), vol. 43, No. 12 Suppl S, pp. 56s-61s.

Banholzer et al., "277.Zum Mechanismus der Thermischen Decarbonylierung von Oxalessigestern," Helvetica Chimica Acta, (1959), vol. 42, No. 277, pp. 2584-2597.

Becker et al., "NO-independent regulatory site of direct sGC stimulators like YC-1 and BAY 41/2272," BMC Pharmacology, (Dec. 28, 2001), vol. 1, No. 13, pp. 1-12.

Cheng et al., "Potential Purine Antagonists VII. Synthesis of 6-Alkylpyrazolo-[3,4-d]pyrimidines," The Journal of Organic Chemistry, (Feb. 1958), vol. 23, No. 2, pp. 191-200.

(Continued)

Primary Examiner — Venkataraman Balasubramanian
(74) Attorney, Agent, or Firm — Buchanan Ingersoll & Rooney PC

(57) ABSTRACT

The present application relates to novel substituted fused pyrimidines and triazines, to processes for their preparation, to their use alone or in combinations for the treatment and/or prophylaxis of diseases, and to their use for producing medicaments for the treatment and/or prophylaxis of diseases, in particular for the treatment and/or prophylaxis of cardiovascular disorders.

6 Claims, No Drawings

(56) References Cited

U.S. PATENT DOCUMENTS

| | | | |
|---|---|---|---|
| 9,096,592 | B2 | 8/2015 | Follmann et al. |
| 9,133,191 | B2 | 9/2015 | Follmann et al. |
| 9,216,978 | B2 | 12/2015 | Follmann et al. |
| 9,266,871 | B2 | 2/2016 | Follmann et al. |
| 2004/0235863 | A1 | 11/2004 | Feurer et al. |
| 2008/0004257 | A1 | 1/2008 | Chan et al. |
| 2010/0298336 | A1 | 11/2010 | Attardo et al. |
| 2011/0218202 | A1 | 9/2011 | Brockunier et al. |
| 2012/0022084 | A1 | 1/2012 | Follmann et al. |
| 2012/0029002 | A1 | 2/2012 | Straub et al. |
| 2013/0072492 | A1 | 3/2013 | Raghavan et al. |
| 2013/0172372 | A1 | 7/2013 | Follmann et al. |
| 2013/0178475 | A1 | 7/2013 | Moore et al. |
| 2013/0210824 | A1 | 8/2013 | Follmann et al. |
| 2013/0211090 | A1 | 8/2013 | Follmann et al. |
| 2013/0338137 | A1 | 12/2013 | Follmann et al. |
| 2014/0088080 | A1 | 3/2014 | Koga et al. |
| 2014/0100229 | A1 | 4/2014 | Follmann et al. |
| 2014/0148433 | A1 | 5/2014 | Follmann et al. |
| 2014/0171434 | A1 | 6/2014 | Follmann et al. |
| 2014/0228366 | A1 | 8/2014 | Follmann et al. |
| 2014/0249168 | A1 | 9/2014 | Follmann et al. |
| 2014/0350020 | A1 | 11/2014 | Follmann et al. |
| 2014/0357637 | A1 | 12/2014 | Follmann et al. |
| 2015/0025090 | A1 | 1/2015 | Follmann et al. |
| 2015/0065533 | A1 | 3/2015 | Follmann et al. |
| 2015/0094308 | A1 | 4/2015 | Follmann et al. |
| 2016/0002267 | A1 | 1/2016 | Follmann et al. |
| 2016/0145271 | A1 | 5/2016 | Vakalopoulos et al. |

FOREIGN PATENT DOCUMENTS

| | | | |
|---|---|---|---|
| CA | 2834901 | A1 | 11/2012 |
| CA | 2840886 | A1 | 1/2013 |
| CN | 1613849 | A | 5/2005 |
| EP | 0 634 413 | A1 | 1/1995 |
| ES | 8601208 | A1 | 2/1986 |
| WO | 89/03833 | A1 | 5/1989 |
| WO | 96/34866 | A1 | 11/1996 |
| WO | 00/06568 | A1 | 2/2000 |
| WO | 00/06569 | A1 | 2/2000 |
| WO | 01/83490 | A1 | 11/2001 |
| WO | 02/059083 | A2 | 8/2002 |
| WO | 03/095451 | A1 | 11/2003 |
| WO | 2004/009590 | A1 | 1/2004 |
| WO | 2005/073234 | A2 | 8/2005 |
| WO | 2006/130673 | A1 | 12/2006 |
| WO | 2007/041052 | A2 | 4/2007 |
| WO | 2009/145814 | A2 | 12/2009 |
| WO | 2010/065275 | A1 | 6/2010 |
| WO | 2011/147809 | A1 | 12/2011 |
| WO | 2011/149921 | A1 | 12/2011 |
| WO | 2011/161099 | A1 | 12/2011 |
| WO | 2012/004258 | A1 | 1/2012 |
| WO | 2012/004259 | A1 | 1/2012 |
| WO | 2012/028647 | A1 | 3/2012 |
| WO | 2012/143510 | A1 | 10/2012 |
| WO | 2012/152629 | A1 | 11/2012 |
| WO | 2012/165399 | A1 | 12/2012 |
| WO | 2013/030138 | A1 | 3/2013 |
| WO | 2013/104597 | A1 | 7/2013 |

OTHER PUBLICATIONS

Daley et al., "The First Complete Identification of a Diastereomeric Catalyst-Substrate (Alkoxide) Species in an Enantioselective Ketone Hydrogenation. Mechanistic Investigations," Journal of the American Chemical Society, (Mar. 16, 2002), vol. 124, No. 14, pp. 3680-3691.

Evgenov et al., "NO-independent stimulators and activators of soluble guanylate cyclase: discovery and therapeutic potential," Nature Reviews Drug Discovery, (Sep. 2006), vol. 5, No. 9, pp. 755-768.

Glass et al., "Stimulation of Human Platelet Guanylate Cyclase by Fatty Acids," The Journal of Biological Chemistry, (Feb. 25, 1977), vol. 252, No. 4, pp. 1279-1285.

Greene et al., "The Role of Protective Groups in Organic Synthesis," Greene's Protective Groups in Organic Synthesis, Fourth Edition, (2007), pp. 1-15.

Ghofrani et al., "Soluble Guanylate Cyclase Stimulation: an Emerging Option in Pulmonary Hypertension Therapy," European Respiratory Review, (2009), vol. 18, No. 11, pp. 35-41.

Hassan et al., "Aryl-Aryl Bond Formation One Century after the Discovery of the Ullmann Reaction," Chemical Reviews, (Mar. 8, 2002), vol. 102, No. 5, pp. 1359-1470.

Herdemann et al., "Identification of Potent ITK Inhibitors Through Focused Compound Library Design Including Structural Information," Bioorganic & Medicinal Chemistry Letters, (Dec. 1, 2010), vol. 20, No. 23, pp. 6998-7003.

Hughes, "Progress in the Mitsunobu Reaction. A Review," Organic Preparations and Procedures Int., (1996), vol. 28, No. 2, pp. 127-164.

Kelley et al., "Synthesis and Anticonvulsant Activity of N-Benzylpyrrolo[2,3-d]-, -pyrazolo[3,4-d]-, and -triazolo[4,5-d] pyrimidines: Imidazole Ring-Modified Analogues of 9-(2-Fluorobenzyl) -6- (methylamino)-9H-purin," Journal of Medicinal Chemistry, (Sep. 1995), vol. 38, No. 19, pp. 3884-3888.

Ko et al., "YC-1, a Novel Activator of Platelet Guanylate Cyclase," Blood, (Dec. 15, 1994), vol. 84, No. 12, pp. 4226-4233.

Kozo et al., "Spontaneous Hypertension in Rats," Int Rev. Exp. Pathol, (1969), vol. 7, pp. 227-270.

Mittendorf et al., "Discovery of Riociguat (BAY 63-2521): A Potent, Oral Stimulator of Soluble Guanylate Cyclase for the Treatment of Pulmonary Hypertension," ChemMedChem, (May 2009), vol. 4, No. 5, pp. 853-865.

Mulsch et al., "Effect of YC-1, an NO-independent, Superoxide-Sensitive Stimulator of Soluble Guanylyl Cyclase, on Smooth Muscle Responsiveness to Nitrovasodilators," British Journal of Pharmacology, (Feb. 1997), vol. 120, No. 4, pp. 681-689.

Olah et al., "Synthesis and Investigation of Organic Fluorine Compounds. XXIII. *Preparation of Aromatic Fluorinated Esters as Local Anesthetics," The Journal of Organic Chemistry, (Aug. 1957), vol. 22, No. 8, pp. 879-881.

Oudot et al., "Combination of BAY 60-4552 and Vardenafil Exerts Proerectile Facilitator Effects in Rats With Cavernous Nerve Injury: A Proof of Concept Study for the Treatment of Phosphodiesterase Type 5 Inhibitor Failure," European Urology, (Nov. 2011),vol. 60, Issue 5, pp. 1020-1026.

Pettibone et al., "A Structurally Novel Stimulator of Guanylate Cyclase with Long-Lasting Hypotensive Activity in the Dog," European Journal of Pharmacology, (Oct. 22, 1985), vol. 116, No. 3, pp. 307-312.

Reichardt et al., "Darstellung von Fluor- and Jodmalondialdehyd," Liebigs Ann. Chem. (1970), 737, pp. 99-107.

Robins, "Potential Purine Antagonists. I. Synthesis of Some 4,B-Substituted Pyrazolo [3,4-d] pyrimidines," Journal of the American Chemical Society, (Feb. 1956), vol. 78, No. 4, pp. 784-790.

Rocaboy et al., "Syntheses and Reactivities of Disubstituted and Trisubstituted Fluorous Pyridines with High Fluorous Phase Affinities: Solid State, Liquid Crystal, and Ionic Liquid-Phase Properties," The Journal of Organic Chemistry, (Oct. 4, 2002), vol. 67, No. 20, pp. 6863-6870.

Saenz De Tejada et al., "The Phosphodiesterase Inhibitory Selectivity and the in Vitro and in Vivo Potency of the new PDE5 Inhibitor Vardenafil," International Journal of Impotence Research, (Oct. 2001), vol. 13, No. 5, pp. 282-290.

Sard et al., "Preparation of 4,5-Disubstituted Pyrimidines: Ring Substitution of 5-Mesyloxymethylpyrimidines," The Journal of Organic Chemistry, (Nov. 22, 2000), vol. 65, No. 26, pp. 9261-9264.

Sharkovska et al., "Nitric oxide-independent stimulation of soluble guanylate cyclase reduces organ damage in experimental low-renin and high-renin models," Journal of Hypertension, (Aug. 2010), vol. 28, No. 8, pp. 1666-1675.

Stasch et al., "Soluble Guanylate Cyclase as an Emerging Therapeutic Target in Cardiopulmonary Disease," Circulation, (May 24, 2011), vol. 123, No. 20, pp. 2263-2273.

(56) References Cited

OTHER PUBLICATIONS

Straub et al., "NO-Independent Stimulators of Soluble Guanylate Cyclase," Bioorganic & Medicinal Chemistry Letters, (Mar. 26, 2011), vol. 11, Issue 6, pp. 781-784.
Toche et al., "Synthesis of Pyrazolopyridine 3-Carboxylates by Friedlander Condensation," Journal of Heterocyclic Chemistry, (Mar. 2010), vol. 47, No. 2, pp. 287-291.
Van Den Buuse, "Circadian Rhythms of Blood Pressure, Heart Rate, and Locomotor Activity in Spontaneously Hypertensive Rats as Measured With Radio-Telemetry," Physiology & Behavior, (Apr. 1994), vol. 55, No. 4, pp. 783-787.
Wilson et al., "Development of a Scaleable Synthesis of a Partial Nicotinic Acid Receptor Agonist," Organic Process Research & Development, (Mar. 16, 2009), vol. 13, No. 3, pp. 543-547.
Winn et al., "2-(Alkylamino) Nicotinic Acid and Analogs. Potent Angiotensin II Antagonists," Journal of Medicinal Chemistry, (Sep. 1993), vol. 36, No. 18, pp. 2676-2688.
Witte et al., "Experimental heart failure in rats: effects on cardiovascular circadian rhythms and on myocardial β-adrenergic signaling," Cardiovascular Research, (Aug. 2000), vol. 47, No. 2, pp. 350-358.
Wunder et al., "A cell-based cGMP assay useful for ultra-high-throughput screening and identification of modulators of the nitric oxide/cGMP pathway," Analytical Biochemistry, (Apr. 1, 2005), vol. 339, No. 1, pp. 104-112.
Wunder et al., "Characterization of the First Potent and Selective PDE9 Inhibitor Using a cGMP Reporter Cell Line," Molecular Pharmacology, (Dec. 2005), vol. 68, No. 6, pp. 1775-1781.
Wu et al., "YC-1 Inhibited Human Platelet Aggregation Through NO-Independent Activation of Soluble Guanylate Cyclase," British Journal of Pharmacology, (Oct. 1995), vol. 116, No. 3, pp. 1973-1978.
Yu et al., "Vasorelaxant Effect of Isoliquiritigenin, a Novel Soluble Guanylate Cyclase Activator, in Rat Aorta," British Journal of Pharmacology, (Apr. 1995), vol. 114, No. 38, pp. 1587-1594.
International Search Report issued on Jun. 27, 2013, by the European Patent Office as the International Searching Authority in corresponding International Application No. PCT/EP2013/050381. (9 pages).
International Preliminary Report on Patentability (Form PCT/IB/373) and the Written Opinion of the International Searching Authority (Form PCT/ISA/237) issued on Jul. 15, 2014, in corresponding International Application No. PCT/EP2013/050381. (19 pages).
Follmann et al., U.S. Appl. No. 14/371,054, entitled "Substituted Triazine Derivatives and Use Thereof As Stimulators of Soluble Guanylate Cyclase" filed Jul. 8, 2014.
Follmann et al., U.S. Appl. No. 14/382,746, entitled "Substituted Azabicycles and Use Thereof" filed Sep. 3, 2014.
Ghofrani et al. Eur Respir Rev 2009; 18:111,35-41.
Freshney et ai.,Culture of Animal Cells, A Manual of Basic Technique, Alan R. Liss, Inc., 1983, New York, p4.
Dermer et al., Bio/Technology, 1994, 12:320.

Dumitrascu et al., "Activation of Soluble Guanylate Cyclase Reverses Experimental Pulmonary Hypertension and Vascular Remodeling," 113(2) Circulation 286, 286-95 (Jan. 2006).
Hobbs, "Soluble guanylate cyclase: an old therapeutic target revisited," 136 British J. Pharmacology 637, 637-40 (2002).
T.A. Michel, "Treatment of Myocardial Ischemia," in Goodman & Gilman's: The Pharmacological Basis of Therapeutics, 823-844 (L.L. Brunton et al., eds. 11th ed., 2006).
Poulos, "Soluble Guanylate Cyclase," Current Opinion in Structural Biology, 736-743 (2006).
Hackam et al., "Translation of Research Evidence From Animals to Humans," JAMA, (Oct. 11, 2006), vol. 296, No. 14, pp. 1731-1732.
Healthgrades Editorial Staff, "Ischemia—Causes" Ischemia—Symptoms, Causes, Treatments—Causes, (2013), http://www.healthgrades.com/conditions/ischemia-Causes, 2 pages.
Hjørringgaard et al., "An Automatic Solid-Phase Synthesis of Peptaibols," The Journal of Organic Chemistry, (2009), vol. 74, No. 3, pp, 1329-1332.
Hoenicka et al., "Purified Soluble Guanylyl Cyclase Expressed in a Baculovirus/Sf9 System: Stimulation by YC-1, Nitric Oxide, and Carbon Monoxide," Journal of Molecular Medicine, (Jan. 1999), vol. 77, No. 1, pp. 14-23.
Mayo Clinic, "Diseases and Conditions Heart Failure," http://www.mayoclinic.org/diseases-conditions/heart-failure/basics/prevention/con-20029801, Heart Failure Prevention—Mayo Clinic, (2015), 3 pages.
Mayo Clinic, "Diseases and Conditions Pulmonary Fibrosis," http://www.mayoclinic.org/diseases-conditions/pulmonary-fibrosis/basics/treatement/con-20029091, Pulmonary Fibrosis Treatments and Drugs—Mayo Clinic, (2016), 3 pages.
NIH, Prevention of High Blood Pressure, (2015), http://www.nhlbi.nih.gov/health/health-topics/topics/hbp/prevention, 1 page.
Nossaman et al., "Nitrates and Nitrites in the Treatment of Ischemic Cardiac Disease," Cardiol Rev., (Jul.-Aug. 2010), vol. 18, No. 4, pp. 190-197.
Palacios et al., "A New and Efficient Synthesis of Imidazo[1,5-a] pyridine Derivatives by a Tandem Aza-Wittig/Electrocyclic Ring Closure of N-vinylic phosphazenes," Tetrahedron, (Mar. 20, 1995), vol. 51, No. 12, pp. 3683-3690.
PubMed Health, Angina (2014) http://www.ncbi.nlm.hih.gov/pubmedhealth/PMH0062934_nhlbisec-prevention, 11 pages.
Stasch et al., "Cardiovascular Actions of a Novel NO-Independent Guanylyl Cyclase Stimulator, BAY 41-8543: in vivo Studies," British Journal of Pharmacology, (2002), vol. 135, No. 2, pp. 344-355.
WebMD, "How to Prevent Deep Vein Thrombosis (DVT)," (2016), http://www.webmd.com/dvt/deep-vein-thrombosis-prevent-dvt, 2 pages.
WebMD, Heart Disease Health Center the Heart and Vascular Disease, (2016), http://www.webmd.com/heart-disease/vascular-disease, Types of Vascular Disease, 6 pages.
WebMD, "Understanding Kidney Disease-Prevention," (2015), http://www.webmd.com/a-to-z-guides/understanding-kidney-disease-prevention, 2 pages.
Wermuth, "Molecular Variations Based on Isosteric Replacements," The Practice of Medical Chemistry, (1996), pp. 203-237.
Vakalopoulos et al., U.S. Appl. No. 14/910,519, entitled "Substituted Imidazo[1,2-A] Pyrazinecarboxamides and Use Thereof" filed Feb. 5, 2016.

SUBSTITUTED ANNULATED TRIAZINES AND USE THEREOF

This application is a divisional application of U.S. application Ser. No. 14/371,046 filed Jul. 8, 2014, which is incorporated herein by reference in its entirety, which is a national stage application under 35 U.S.C. §371 of PCT App. No. PCT/EP2013/050381, filed Jan. 10, 2013, which claims priority to German Application 102012200349.5 filed Jan. 11, 2012.

The present application relates to novel substituted fused pyrimidines and triazines, to processes for their preparation, to their use alone or in combinations for the treatment and/or prophylaxis of diseases, and to their use for producing medicaments for the treatment and/or prophylaxis of diseases, in particular for the treatment and/or prophylaxis of cardiovascular disorders.

One of the most important cellular transmission systems in mammalian cells is cyclic guanosine monophosphate (cGMP). Together with nitrogen monoxide (NO), which is released from the endothelium and transmits hormonal and mechanical signals, it forms the NO/cGMP system. Guanylate cyclases catalyse the biosynthesis of cGMP from guanosine triphosphate (GTP). The representatives of this family known to date can be divided into two groups either according to structural features or according to the type of ligands: the particulate guanylate cyclases which can be stimulated by natriuretic peptides, and the soluble guanylate cyclases which can be stimulated by NO. The soluble guanylate cyclases consist of two subunits and very probably contain one haem per heterodimer, which is part of the regulatory site. This is of central importance for the activation mechanism NO can bind to the iron atom of haem and thus markedly increase the activity of the enzyme. Haem-free preparations cannot, by contrast, be stimulated by NO. Carbon monoxide (CO) is also able to bind to the central iron atom of haem, but the stimulation by CO is much less than that by NO.

By forming cGMP, and owing to the resulting regulation of phosphodiesterases, ion channels and protein kinases, guanylate cyclase plays an important role in various physiological processes, in particular in the relaxation and proliferation of smooth muscle cells, in platelet aggregation and platelet adhesion and in neuronal signal transmission, and also in disorders which are based on a disruption of the abovementioned processes. Under pathophysiological conditions, the NO/cGMP system can be suppressed, which can lead, for example, to hypertension, platelet activation, increased cell proliferation, endothelial dysfunction, arteriosclerosis, angina pectoris, heart failure, myocardial infarction, thromboses, stroke and sexual dysfunction.

Owing to the expected high efficiency and low level of side effects, a possible NO-independent treatment for such disorders by targeting the influence of the cGMP signal pathway in organisms is a promising approach.

Hitherto, for the therapeutic stimulation of the soluble guanylate cyclase, use has exclusively been made of compounds such as organic nitrates whose effect is based on NO. The latter is formed by bioconversion and activates soluble guanylate cyclase by attack at the central iron atom of haem. In addition to the side effects, the development of tolerance is one of the crucial disadvantages of this mode of treatment.

Some years ago, a number of substances have been described which stimulate soluble guanylate cyclase directly, i.e. without prior release of NO, such as, for example, 3-(5'-hydroxymethyl-2'-furyl)-1-benzylindazole [YC-1; Wu et al., *Blood* 84 (1994), 4226; Miilsch et al., *Brit. J. Pharmacol.* 120 (1997), 681]. The more recent stimulators of soluble guanylate cyclase include among others BAY 41-2272, BAY 41-8543 and riociguat (BAY 63-2521) (see, for example, Stasch J.-P. et al., *Nat. Rev. Drug Disc.* 2006; 5: 755-768; Stasch J.-P. et al., *ChemMedChem* 2009; 4: 853-865. Stasch J.-P. et al., *Circulation* 2011; 123: 2263-2273). Interestingly, some of these sGC stimulators, for example YC-1 or BAY 41-2272, also exhibit PDE5-inhibitory action in addition to direct guanylate cyclase stimulation. In order to maximize the cGMP pathway, it is pharmacologically desirable to stimulate the synthesis of cGMP and simultaneously to inhibit degradation via PDE-5. This dual principle is particularly advantageous in pharmacological terms (see, for example, Oudout et al., *Eur. Urol.* 2011, 60, 1020-1026).

The dual principle is fulfilled in the context of the present invention when the inventive compounds exhibit an effect on recombinant guanylate cyclase reporter cell lines according to the study in B-2 as the minimal effective concentration (MEC) of ≤3 µM and exhibit inhibition of human phosphodiesterase 5 (PDE5) according to the study in B-6 as IC50<100 nM.

Phosphodiesterase-5 (PDE5) is the name of one of the enzymes which cleave the phosphoric ester bond in cGMP, forming 5'-guanosine monophosphate (5'-GMP). In humans, phosphodiesterase-5 occurs predominantly in the smooth musculature of the corpus cavernosum penis and the pulmonary arteries. Blockage of cGMP degradation by inhibition of PDE5 (with, for example, sildenafil, vardenafil or tadalafil) leads to increased signals of the relaxation signalling pathway and specifically to increased blood supply in the corpus cavernosum penis and lower pressure in the pulmonary blood vessels. They are used for treatment of erectile dysfunction and of pulmonary arterial hypertension. As well as PDE5, there are further, exclusively cGMP-cleaving phosphodiesterases (Stasch J.-P. et al. *Circulation* 2011).

As stimulators of soluble guanylate cyclase, WO 00/06568 and WO 00/06569 disclose fused pyrazole derivatives, and WO 03/095451 discloses carbamate-substituted 3-pyrimidinylpyrazolopyridines. 3-Pyrimidinylpyrazolopyridines with phenylamide substituents are described in E. M. Becker et al., *BMC Pharmacology* 1 (13), 2001. WO 2004/009590 describes pyrazolopyridines with substituted 4-aminopyrimidines for treatment of CNS disorders. WO 2010/065275 and WO 2011/149921 disclose substituted pyrrolo- and dihydropyridopyrimidines as sGC activators. As sGC stimulators, WO 2012/004259 describes fused aminopyrimidines, and WO 2012/004258, WO 2012/143510 and WO 2012/152629 fused pyrimidines and triazines. WO 2012/28647 discloses pyrazolopyridines with various azaheterocycles for treatment of cardiovascular disorders.

It was an object of the present invention to provide novel substances which act as stimulators of soluble guanylate cyclase and as stimulators of soluble guanylate cyclase and phosphodiesterase-5 inhibitors (dual principle) and have an identical or improved therapeutic profile compared to the compounds known from the prior art, for example with respect to their in vivo properties, for example their pharmacokinetic and pharmacodynamic characteristics and/or their metabolic profile and/or their dose-activity relationship.

The present invention provides compounds of the general formula (I)

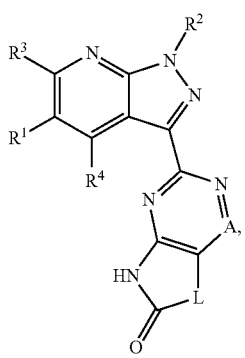

in which

A represents nitrogen or $CR^5$, where $R^5$ represents hydrogen, deuterium, halogen, difluoromethyl, trifluoromethyl, $(C_1-C_4)$-alkyl, $(C_2-C_4)$-alkenyl, $(C_2-C_4)$-alkynyl, cyclopropyl, cyclobutyl, hydroxy, phenyl or 5- or 6-membered heteroaryl which is attached via carbon, in which $(C_1-C_4)$-alkyl, $(C_2-C_4)$-alkenyl, $(C_2-C_4)$-alkynyl, phenyl and 5- or 6-membered heteroaryl which is attached via carbon may each be substituted by 1 to 3 substituents selected independently from the group comprising fluorine, difluoromethyl, trifluoromethyl, $(C_1-C_4)$-alkyl, difluoromethoxy, trifluoromethoxy, $(C_1-C_4)$-alkoxy, $(C_1-C_4)$-alkoxycarbonyl, cyclopropyl and cyclobutyl, L represents a $\#^1$—$CR^{6A}R^{6B}$—$(CR^{7A}R^{7B})_m$—$\#^2$ group where $\#^1$ is the point of attachment to the carbonyl group,

2 is the point of attachment to the pyrimidine or triazine ring, m represents a number 0, 1 or 2, $R^{6A}$ represents hydrogen, fluorine, $(C_1-C_4)$-alkyl, hydroxy or amino, in which $(C_1-C_4)$-alkyl may be substituted by 1 to 3 substituents independently of one another selected from the group consisting of fluorine, trifluoromethyl, hydroxy, $(C_1-C_4)$-alkoxy, hydroxycarbonyl, $(C_1-C_4)$-alkoxycarbonyl and amino, $R^{6B}$ represents hydrogen, fluorine, difluoromethyl, trifluoromethyl, $(C_1-C_6)$-alkyl, cyano, $(C_3-C_7)$-cycloalkyl, difluoromethoxy, trifluoromethoxy or a group of the formula -M-$R^{12}$, in which $(C_1-C_6)$-alkyl may be substituted by 1 to 3 substituents selected independently of one another from the group consisting of fluorine, cyano, trifluoromethyl, $(C_3-C_7)$-cycloalkyl, difluoromethoxy and trifluoromethoxy, and in which M represents a bond or $(C_1-C_4)$-alkanediyl, $R^{12}$ represents —(C=O)$_r$—$OR^8$, —(C=O)$_r$—$NR^8R^9$, —C(=S)—$NR^8R^9$, —$NR^8$—(C=O)—$R^{11}$, —$NR^8$—(C=O)—$OR^{11}$, —$NR^8$—(C=O)—$NR^9R^{10}$, —$NR^8$—$SO_2$—$NR^9R^{10}$, —$NR^8$—$SO_2$—$R^{11}$, —S(O)$_s$—$R^{11}$, —$SO_2$—$NR^8R^9$, 4- to 7-membered heterocyclyl, phenyl, benzyl or 5- or 6-membered heteroaryl, in which r represents the number 0 or 1, s represents the number 0, 1 or 2, $R^8$, $R^9$ and $R^{10}$ independently of one another each represent hydrogen, $(C_1-C_6)$-alkyl, $(C_3-C_8)$-cycloalkyl, 4- to 7-membered heterocyclyl, phenyl or 5- or 6-membered heteroaryl, or $R^8$ and $R^9$ together with the atom(s) to which they are respectively attached form a 4- to 7-membered heterocycle, in which the 4- to 7-membered heterocycle for its part may be substituted by 1 or 2 substituents independently of one another selected from the group consisting of cyano, trifluoromethyl, $(C_1-C_6)$-alkyl, hydroxy, oxo, $(C_1-C_6)$-alkoxy, trifluoromethoxy, $(C_1-C_6)$-alkoxycarbonyl, amino, mono-$(C_1-C_6)$-alkylamino and di-$(C_1-C_6)$-alkylamino, or $R^9$ and $R^{10}$ together with the atom(s) to which they are respectively attached form a 4- to 7-membered heterocycle, in which the 4- to 7-membered heterocycle for its part may be substituted by 1 or 2 substituents independently of one another selected from the group consisting of cyano, trifluoromethyl, $(C_1-C_6)$-alkyl, hydroxy, oxo, $(C_1-C_6)$-alkoxy, trifluoromethoxy, $(C_1-C_6)$-alkoxycarbonyl, amino, mono-$(C_1-C_6)$-alkylamino and di-$(C_1-C_6)$-alkylamino, $R^{11}$ represents $(C_1-C_6)$-alkyl or $(C_3-C_7)$-cycloalkyl, or $R^8$ and $R^{11}$ together with the atom(s) to which they are respectively attached form a 4- to 7-membered heterocycle, in which the 4- to 7-membered heterocycle for its part may be substituted by 1 or 2 substituents independently of one another selected from the group consisting of cyano, trifluoromethyl, $(C_1-C_6)$-alkyl, hydroxy, oxo, $(C_1-C_6)$-alkoxy, trifluoromethoxy, $(C_1-C_6)$-alkoxycarbonyl, amino, mono-$(C_1-C_6)$-alkylamino and di-$(C_1-C_6)$-alkylamino, and in which 4- to 7-membered heterocyclyl, phenyl and 5- or 6-membered heteroaryl for their part may be substituted by 1 to 3 substituents independently of one another selected from the group consisting of halogen, cyano, difluoromethyl, trifluoromethyl, $(C_1-C_6)$-alkyl, $(C_3-C_7)$-cycloalkyl, hydroxy, oxo, thioxo and $(C_1-C_4)$-alkoxy, and in which the aforementioned $(C_1-C_4)$-alkyl, $(C_1-C_6)$-alkyl, $(C_3-C_8)$-cycloalkyl and 4- to 7-membered heterocyclyl groups, unless stated otherwise, may each independently of one another additionally be substituted by 1 to 3 substituents independently of one another selected from the group consisting of fluorine, difluoromethyl, trifluoromethyl, $(C_1-C_6)$-alkyl, $(C_3-C_7)$-cycloalkyl, hydroxy, difluoromethoxy, trifluoromethoxy, $(C_1-C_4)$-alkoxy, hydroxycarbonyl, (C₁-C₄)-alkoxycarbonyl, amino, phenyl, 4- to 7-membered heterocyclyl and 5- or 6-membered heteroaryl, or $R^{6A}$ and $R^{6B}$ together with the carbon atom to which they are attached form a (C₂-C₄)-alkenyl group, an oxo group, a 3- to 6-membered carbocycle or a 4- to 7-membered heterocycle, in which the 3- to 6-membered carbocycle and the 4- to 7-membered heterocycle may be substituted by 1 or 2 substituents independently of one another selected from the group consisting of fluorine and (C₁-C₄)-alkyl, $R^{7A}$ represents hydrogen, fluorine, (C₁-C₄)-alkyl, (C₁-C₄)-alkoxycarbonyl or hydroxy, $R^{7B}$ represents hydrogen, fluorine, (C₁-C₄)-alkyl or trifluoromethyl, $R^1$ represents hydrogen, cyano, (C₁-C₄)-alkyl, (C₁-C₄)-alkoxy, trifluoromethyl, difluoromethyl, (C₃-C₆)-cycloalkyl or halogen, $R^2$ represents benzyl,
where benzyl is substituted by 1 to 3 substituents independently of one another selected from the group consisting of fluorine, chlorine, (C₁-C₄)-alkyl, cyclopropyl and (C₁-C₄)-alkoxy, $R^3$ represents hydrogen, cyano, (C₁-C₄)-alkyl, (C₁-C₄)-alkoxy, trifluoromethyl, difluoromethyl or (C₃-C₆)-cycloalkyl, $R^4$ represents hydrogen, cyano, (C₁-C₄)-alkyl, (C₁-C₄)-alkoxy, trifluoromethyl, difluoromethyl or (C₃-C₆)-cycloalkyl, and the N-oxides, salts, solvates, salts of the N-oxides and solvates of the N-oxides or salts thereof.

The present invention provides compounds of the general formula (I)

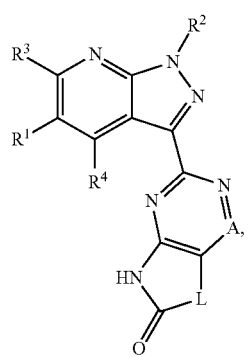

(I)

in which

A represents nitrogen or $CR^5$,
where
$R^5$ represents hydrogen, deuterium, chlorine, iodine, difluoromethyl, trifluoromethyl, (C₁-C₆)-alkyl, (C₂-C₄)-alkenyl, (C₂-C₄)-alkynyl, cyclopropyl, cyclobutyl, phenyl or 5- or 6-membered heteroaryl which is attached via carbon,
in which (C₁-C₆)-alkyl, (C₂-C₄)-alkenyl, (C₂-C₄)-alkynyl, phenyl and 5- or 6-membered heteroaryl which is attached via carbon may each be substituted by 1 to 3 substituents selected independently of one another from the group comprising cyano, fluorine, difluoromethyl, trifluoromethyl, (C₁-C₄)-alkyl, difluoromethoxy, trifluoromethoxy, (C₁-C₄)-alkoxy, (C₁-C₄)-alkoxycarbonyl, hydroxy, hydroxycarbonyl, cyclopropyl, cyclobutyl and —(C=O)—NR²¹R²²,
in which
(C₁-C₆)-alkyl may be substituted by an —NR¹³R¹⁴ group,
in which
$R^{13}$ represents hydrogen, methyl or ethyl,
in which
ethyl may be substituted by 1 to 3 fluorine substituents,
$R^{14}$ represents hydrogen, (C₁-C₄)-alkyl, —(C=O)—R¹⁵ or —S(O)₂—R¹⁶,
in which
(C₁-C₄)-alkyl may be substituted by 1 to 3 fluorine substituents,
and in which
$R^{15}$ represents (C₁-C₄)-alkyl or (C₃-C₅)-cycloalkyl,
$R^{16}$ represents (C₁-C₄)-alkyl or (C₃-C₅)-cycloalkyl,
or
$R^{13}$ and $R^{14}$ together with the nitrogen atom to which they are attached form a 4- to 7-membered heterocycle,
in which the 4- to 7-membered heterocycle for its part may be substituted by 1 or 2 substituents independently of one another selected from the group consisting of trifluoromethyl, (C₁-C₄)-alkyl, hydroxy and oxo,
in which
$R^{21}$ represents hydrogen or (C₁-C₄)-alkyl,
$R^{22}$ represents hydrogen or (C₁-C₄)-alkyl,
in which (C₁-C₄)-alkyl for its part may in each case be substituted by hydroxy or fluorine,
or
$R^{21}$ and $R^{22}$ together with the atom to which they are attached form a 4- to 7-membered heterocycle, L represents a $\#^1$—$CR^{6A}R^{6B}$—$(CR^{7A}R^{7B})_m$—$\#^2$ group
where
$\#^1$ is the point of attachment to the carbonyl group,
$\#^2$ is the point of attachment to the pyrimidine or triazine ring,
m is a number 0, 1 or 2,
$R^{6A}$ represents hydrogen, fluorine, (C₁-C₄)-alkyl, hydroxy or amino,
in which (C₁-C₄)-alkyl may be substituted by 1 to 3 substituents independently of one another selected from the group consisting of fluorine, trifluoromethyl, hydroxy, (C₁-C₄)-alkoxy, hydroxycarbonyl, (C₁-C₄)-alkoxycarbonyl and amino,
$R^{6B}$ represents hydrogen, fluorine, difluoromethyl, trifluoromethyl, (C₁-C₆)-alkyl, (C₂-C₆)-alkenyl, cyano, (C₃-C₇)-cycloalkyl, difluoromethoxy, trifluoromethoxy or a group of the formula -M-R¹²,
in which (C₁-C₆)-alkyl may be substituted by 1 to 3 substituents selected independently of one another from the group consisting of (C₁-C₄)-alkoxy, fluorine, cyano, trifluoromethyl, (C₃-C₇)-cycloalkyl, difluoromethoxy and trifluoromethoxy,
in which (C₁-C₄)-alkoxy may be substituted by phenyl, and in which
M represents a bond or (C₁-C₄)-alkanediyl,
$R^{12}$ represents —(C=O)ᵣ—OR⁸, —(C=O)ᵣ—NR⁸R⁹, —C(=S)—NR⁸R⁹, —NR⁸—(C=O)—R¹¹, —NR⁸—(C=O)—OR¹¹, —NR⁸—(C=O)—NR⁹R¹⁰, —NR⁸—SO₂—NR⁹R¹², —NR⁸—SO₂—R¹¹, —S(O)ₛ—R¹¹, —SO₂—NR⁸R⁹, 4- to 7-membered heterocyclyl, phenyl, benzyl or 5- or 6-membered heteroaryl, in which
r represents the number 0 or 1,
s represents the number 0, 1 or 2,
$R^8$, $R^9$ and $R^{10}$ independently of one another each represent hydrogen, $(C_1\text{-}C_6)$-alkyl, $(C_3\text{-}C_8)$-cycloalkyl, 4- to 7-membered heterocyclyl, phenyl or 5- or 6-membered heteroaryl,
or
$R^8$ and $R^9$ together with the atom(s) to which they are respectively attached form a 4- to 7-membered heterocycle,
in which the 4- to 7-membered heterocycle for its part may be substituted by 1 or 2 substituents independently of one another selected from the group consisting of cyano, alkoxy, trifluoromethoxy, $(C_1\text{-}C_6)$-alkoxycarbonyl, amino, mono-$(C_1\text{-}C_6)$-alkylamino and di-$(C_1\text{-}C_6)$-alkylamino,
or
$R^9$ and $R^{10}$ together with the atom(s) to which they are respectively attached form a 4- to 7-membered heterocycle,
in which the 4- to 7-membered heterocycle for its part may be substituted by 1 or 2 substituents independently of one another selected from the group consisting of cyano, trifluoromethyl, $(C_1\text{-}C_6)$-alkyl, hydroxy, oxo, $(C_1\text{-}C_6)$-alkoxy, trifluoromethoxy, $(C_1\text{-}C_6)$-alkoxycarbonyl, amino, mono-$(C_1\text{-}C_6)$-alkylamino and di-$(C_1\text{-}C_6)$-alkylamino,
$R^{11}$ represents $(C_1\text{-}C_6)$-alkyl or $(C_3\text{-}C_7)$-cycloalkyl,
or
$R^8$ and $R^{11}$ together with the atom(s) to which they are respectively attached form a 4- to 7-membered heterocycle,
in which the 4- to 7-membered heterocycle for its part may be substituted by 1 or 2 substituents independently of one another selected from the group consisting of cyano, trifluoromethyl, $(C_1\text{-}C_6)$-alkyl, hydroxy, oxo, $(C_1\text{-}C_6)$-alkoxy, trifluoromethoxy, $(C_1\text{-}C_6)$-alkoxycarbonyl, amino, mono-$(C_1\text{-}C_6)$-alkylamino and di-$(C_1\text{-}C_6)$-alkylamino,
and
in which 4- to 7-membered heterocyclyl, phenyl and 5- or 6-membered heteroaryl for their part may be substituted by 1 to 3 substituents independently of one another selected from the group consisting of halogen, cyano, difluoromethyl, trifluoromethyl, $(C_1\text{-}C_6)$-alkyl, $(C_3\text{-}C_7)$-cycloalkyl, hydroxy, oxo, thioxo and $(C_1\text{-}C_4)$-alkoxy,
and
in which the aforementioned $(C_1\text{-}C_4)$-alkyl, $(C_1\text{-}C_6)$-alkyl, $(C_3\text{-}C_8)$-cycloalkyl and 4- to 7-membered heterocyclyl groups, unless stated otherwise, may each independently of one another additionally be substituted by 1 to 3 substituents independently of one another selected from the group consisting of fluorine, difluoromethyl, trifluoromethyl, $(C_1\text{-}C_6)$-alkyl, $(C_3\text{-}C_7)$-cycloalkyl, hydroxy, difluoromethoxy, trifluoromethoxy, $(C_1\text{-}C_4)$-alkoxy, hydroxycarbonyl, $(C_1\text{-}C_4)$-alkoxycarbonyl, amino, phenyl, 4- to 7-membered heterocyclyl and 5- or 6-membered heteroaryl,
or
$R^{6A}$ and $R^{6B}$ together with the carbon atom to which they are attached form a $(C_2\text{-}C_4)$-alkenyl group, an oxo group, a 3- to 6-membered carbocycle or a 4- to 7-membered heterocycle, in which the 3- to 6-membered carbocycle and the 4- to 7-membered heterocycle may be substituted by 1 or 2 substituents independently of one another selected from the group consisting of fluorine and $(C_1\text{-}C_4)$-alkyl,
$R^{7A}$ represents hydrogen, fluorine, $(C_1\text{-}C_4)$-alkyl, $(C_1\text{-}C_4)$-alkoxycarbonyl or hydroxy,
$R^{7B}$ represents hydrogen, fluorine, $(C_1\text{-}C_4)$-alkyl or trifluoromethyl,
$R^1$ represents hydrogen, fluorine, cyano, $(C_1\text{-}C_4)$-alkyl, $(C_1\text{-}C_4)$-alkoxy, trifluoromethyl, difluoromethyl, $(C_3\text{-}C_6)$-cycloalkyl or halogen,
$R^2$ represents benzyl, 3,3,3-trifluoroprop-1-yl, 4,4,4-trifluorobut-1-yl or 3,3,4,4,4-pentafluorobut-1-yl,
where benzyl is substituted by 1 to 3 substituents independently of one another selected from the group consisting of fluorine, chlorine, $(C_1\text{-}C_4)$-alkyl, cyclopropyl and $(C_1\text{-}C_4)$-alkoxy,
$R^3$ represents hydrogen, cyano, $(C_1\text{-}C_4)$-alkyl, $(C_1\text{-}C_4)$-alkoxy, trifluoromethyl, difluoromethyl or $(C_3\text{-}C_6)$-cycloalkyl,
$R^4$ represents hydrogen, cyano, $(C_1\text{-}C_4)$-alkyl, $(C_1\text{-}C_4)$-alkoxy, trifluoromethyl, difluoromethyl or $(C_3\text{-}C_6)$-cycloalkyl,
and the N-oxides, salts, solvates, salts of the N-oxides and solvates of the N-oxides or salts thereof.

Compounds according to the invention are the compounds of the formula (I) and their salts, solvates and solvates of the salts, the compounds, comprised by formula (I), of the formulae mentioned below and their salts, solvates and solvates of the salts and the compounds comprised by formula (I), mentioned below as working examples, and their salts, solvates and solvates of the salts, if the compounds, comprised by formula (I), mentioned below are not already salts, solvates and solvates of the salts.

Preferred salts in the context of the present invention are physiologically acceptable salts of the compounds according to the invention. Also encompassed are salts which are not themselves suitable for pharmaceutical applications but can be used, for example, for isolation or purification of the compounds according to the invention.

Physiologically acceptable salts of the compounds according to the invention include acid addition salts of mineral acids, carboxylic acids and sulphonic acids, for example salts of hydrochloric acid, hydrobromic acid, sulphuric acid, phosphoric acid, methanesulphonic acid, ethanesulphonic acid, toluenesulphonic acid, benzenesulphonic acid, naphthalenedisulphonic acid, formic acid, acetic acid, trifluoroacetic acid, propionic acid, lactic acid, tartaric acid, malic acid, citric acid, fumaric acid, maleic acid and benzoic acid.

Physiologically acceptable salts of the compounds according to the invention also include salts of conventional bases, by way of example and with preference alkali metal salts (e.g. sodium and potassium salts), alkaline earth metal salts (e.g. calcium and magnesium salts) and ammonium salts derived from ammonia or organic amines having 1 to 16 carbon atoms, by way of example and with preference ethylamine, diethylamine, triethylamine, ethyldiisopropylamine, monoethanolamine, diethanolamine, triethanolamine, dicyclohexylamine, dimethylaminoethanol, procaine, dibenzylamine, N-methylmorpholine, arginine, lysine, ethylenediamine and N-methylpiperidine.

In the context of the invention, solvates refer to those forms of the compounds according to the invention which, in the solid or liquid state, form a complex by coordination with solvent molecules. Hydrates are a specific form of solvates in which the coordination is with water. Preferred solvates in the context of the present invention are hydrates.

The compounds according to the invention may, depending on their structure, exist in different stereoisomeric forms, i.e. in the form of configurational isomers or else optionally as conformational isomers (enantiomers and/or diastereomers, including those in the case of atropisomers). The present invention therefore encompasses the enantiomers and diastereomers, and the respective mixtures thereof. The stereoisomerically uniform constituents can be isolated from such mixtures of enantiomers and/or diastereomers in a known manner; chromatography processes are preferably used for this, in particular HPLC chromatography on an achiral or chiral phase.

Where the compounds according to the invention can occur in tautomeric forms, the present invention encompasses all the tautomeric forms.

The present invention also encompasses all suitable isotopic variants of the compounds according to the invention. An isotopic variant of a compound according to the invention is understood here to mean a compound in which at least one atom within the compound according to the invention has been exchanged for another atom of the same atomic number, but with a different atomic mass than the atomic mass which usually or predominantly occurs in nature. Examples of isotopes which can be incorporated into a compound according to the invention are those of hydrogen, carbon, nitrogen, oxygen, phosphorus, sulphur, fluorine, chlorine, bromine and iodine, such as $^2$H (deuterium), $^3$H (tritium), $^{13}$C, $^{14}$C, $^{15}$N, $^{17}$O, $^{18}$O, $^{32}$P, $^{33}$P, $^{33}$S, $^{34}$S, $^{35}$S, $^{36}$S, $^{18}$F, $^{36}$Cl, $^{82}$Br, $^{123}$I, $^{124}$I, $^{129}$I and $^{131}$I. Particular isotopic variants of a compound according to the invention, especially those in which one or more radioactive isotopes have been incorporated, may be beneficial, for example, for the examination of the mechanism of action or of the active ingredient distribution in the body; due to comparatively easy preparability and detectability, especially compounds labelled with $^3$H or $^{14}$C isotopes are suitable for this purpose. Furthermore, the incorporation of isotopes, for example of deuterium, can lead to particular therapeutic advantages as a consequence of greater metabolic stability of the compound, for example an extension of the half-life in the body or a reduction in the active dose required; such modifications of the compounds according to the invention may therefore, in some cases, also constitute a preferred embodiment of the present invention. Isotopic variants of the compounds according to the invention can be prepared by the processes known to those skilled in the art, for example by the methods described below and the procedures described in the working examples, by using corresponding isotopic modifications of the respective reagents and/or starting compounds.

Moreover, the present invention also encompasses prodrugs of the compounds according to the invention. Here, the term "prodrugs" refers to compounds which for their part can be biologically active or inactive, but are converted (for example metabolically or hydrolytically) into compounds according to the invention during their dwell time in the body.

In the context of the present invention, the substituents, unless specified otherwise, are each defined as follows:

Alkyl in the context of the invention is a straight-chain or branched alkyl radical having the number of carbon atoms specified in each case. The following may be mentioned by way of example and by way of preference: methyl, ethyl, n-propyl, isopropyl, n-butyl, isobutyl, 1-methylpropyl, tert-butyl, n-pentyl, isopentyl, 1-ethylpropyl, 1-methylbutyl, 2-methylbutyl, 3-methylbutyl, n-hexyl, 1-methylpentyl, 2-methylpentyl, 3-methylpentyl, 4-methylpentyl, 3,3-dimethylbutyl, 1-ethylbutyl and 2-ethylbutyl.

Alkanediyl in the context of the invention is a straight-chain or branched divalent alkyl radical having 1 to 4 carbon atoms. The following may be mentioned by way of example and by way of preference: methylene, ethane-1,2-diyl, ethane-1,1-diyl, propane-1,3-diyl, propane-1,1-diyl, propane-1,2-diyl, propane-2,2-diyl, butane-1,4-diyl, butane-1,2-diyl, butane-1,3-diyl and butane-2,3-diyl.

Cycloalkyl or carbocycle in the context of the invention is a monocyclic saturated alkyl radical having the number of carbon atoms specified in each case. The following may be mentioned by way of example and by way of preference: cyclopropyl, cyclobutyl, cyclopentyl, cyclohexyl and cycloheptyl.

Alkenyl in the context of the invention is a straight-chain or branched alkenyl radical having 2 to 4 carbon atoms and a double bond. The following may be mentioned by way of example and by way of preference: vinyl, allyl, isopropenyl and n-but-2-en-1-yl.

Alkynyl in the context of the invention is an alkynyl radical having 2 to 4 carbon atoms and a triple bond. The following may be mentioned by way of example and by way of preference: ethynyl, propynyl and butynyl.

Alkoxy in the context of the invention is a straight-chain or branched alkoxy radical having 1 to 6 or 1 to 4 carbon atoms. The following may be mentioned by way of example: methoxy, ethoxy, n-propoxy, isopropoxy, 1-methylpropoxy, n-butoxy, isobutoxy, tert-butoxy, n-pentoxy, isopentoxy, 1-ethylpropoxy, 1-methylbutoxy, 2-methylbutoxy, 3-methylbutoxy and n-hexoxy. Preference is given to a straight-chain or branched alkoxy radical having 1 to 4 carbon atoms. The following may be mentioned by way of example and by way of preference: methoxy, ethoxy, n-propoxy, isopropoxy, 1-methylpropoxy, n-butoxy, isobutoxy, tert-butoxy.

Alkoxycarbonyl in the context of the invention is a straight-chain or branched alkoxy radical having 1 to 4 carbon atoms and a carbonyl group attached to the oxygen. The following may be mentioned by way of example and by way of preference: methoxycarbonyl, ethoxycarbonyl, n-propoxycarbonyl, isopropoxycarbonyl and tert-butoxycarbonyl.

Monoalkylamino in the context of the invention is an amino group having a straight-chain or branched alkyl substituent having 1 to 6 carbon atoms. The following may be mentioned by way of example and by way of preference: methylamino, ethylamino, n-propylamino, isopropylamino and tert-butylamino.

Dialkylamino in the context of the invention is an amino group having two identical or different, straight-chain or branched alkyl substituents each having 1 to 6 carbon atoms. Preferred examples include: N,N-dimethylamino, N,N-diethylamino, N-ethyl-N-methylamino, N-methyl-N-n-propylamino, N-isopropyl-N-n-propylamino, N-tert-butyl-N-methylamino, N-ethyl-N-n-pentylamino and N-n-hexyl-N-methylamino.

Heterocyclyl or heterocycle in the context of the invention is a saturated heterocycle which has a total of 4 to 7 ring atoms, contains one or two ring heteroatoms from the group consisting of N, O, S, SO and/or $SO_2$ and is attached via a ring carbon atom. The following may be mentioned by way of example: azetidinyl, oxetanyl, pyrrolidinyl, pyrazolidinyl, tetrahydrofuranyl, piperidinyl, piperazinyl, tetrahydropyranyl, morpholinyl, thiomorpholinyl and dioxidothiomorpholinyl. Preference is given to azetidinyl, oxetanyl, pyrrolidinyl, tetrahydrofuranyl, piperidinyl, tetrahydropyranyl and morpholinyl.

5- or 6-membered heteroaryl which is attached via carbon in the context of the invention is a monocyclic aromatic heterocycle (heteroaromatic) which has a total of 5 or 6 ring atoms, contains up to three identical or different ring heteroatoms from the group consisting of N, O and/or S and is attached via a ring carbon atom. The following may be mentioned by way of example and by way of preference: furyl, pyrrolyl, thienyl, pyrazolyl, imidazolyl, thiazolyl, oxazolyl, isoxazolyl, isothiazolyl, triazolyl, oxadiazolyl, thiadiazolyl, pyridyl, pyrimidinyl, pyridazinyl, pyrazinyl and triazinyl. Preference is given to: pyrazol-3-yl, pyrazol-5-yl, pyrazol-5-yl, thiazolyl, oxadiazolyl, thiadiazolyl, pyridyl and pyrimidinyl.

5- or 6-membered heteroaryl in the context of the invention is a monocyclic aromatic heterocycle (heteroaromatic) which has a total of 5 or 6 ring atoms, contains up to three identical or different ring heteroatoms from the group consisting of N, O and/or S and is attached via a ring carbon atom or optionally via a ring nitrogen atom. The following may be mentioned by way of example and by way of preference: furyl, pyrrolyl, thienyl, pyrazolyl, imidazolyl, thiazolyl, oxazolyl, isoxazolyl, isothiazolyl, triazolyl, oxadiazolyl, thiadiazolyl, pyridyl, pyrimidinyl, pyridazinyl, pyrazinyl and triazinyl. Preference is given to: pyridyl, pyrimidinyl, pyridazinyl, pyrazinyl and triazinyl.

Halogen in the context of the invention is fluorine, chlorine, bromine and iodine. Preference is given to bromine and iodine.

An oxo group in the context of the invention is an oxygen atom attached via a double bond to a carbon atom.

A thiooxo group in the context of the invention is a sulphur atom attached via a double bond to a carbon atom.

In the formula of the group that L or $R^2$ may represent, the end point of the line marked by the symbol #$^1$, #$^2$ or * does not represent a carbon atom or a $CH_2$ group but is part of the bond to the respective atom to which L or $R^2$ is attached.

In the context of the present invention, the term "treatment" or "treating" includes inhibition, retardation, checking, alleviating, attenuating, restricting, reducing, suppressing, repelling or healing of a disease, a condition, a disorder, an injury or a health problem, or the development, the course or the progression of such states and/or the symptoms of such states. The term "therapy" is understood here to be synonymous with the term "treatment".

The terms "prevention", "prophylaxis" or "preclusion" are used synonymously in the context of the present invention and refer to the avoidance or reduction of the risk of contracting, experiencing, suffering from or having a disease, a condition, a disorder, an injury or a health problem, or a development or progression of such states and/or the symptoms of such states.

The treatment or prevention of a disease, a condition, a disorder, an injury or a health problem may be partial or complete.

Preference is given in the context of the present invention to compounds of the formula (I) in which A represents nitrogen or $CR^5$,
where
$R^5$ represents hydrogen, deuterium, fluorine, iodine, difluoromethyl, trifluoromethyl, $(C_1$-$C_4)$-alkyl, vinyl, allyl, ethynyl, cyclopropyl, cyclobutyl, hydroxy, phenyl, pyrazol-3-yl, pyrazol-4-yl, pyrazol-5-yl orpyridyl, where $(C_1$-$C_4)$-alkyl, vinyl, allyl, ethynyl, phenyl, pyrazol-3-yl, pyrazol-4-yl, pyrazol-5-yl and pyridyl may be substituted by 1 or 2 substituents independently of one another selected from the group consisting of fluorine, difluoromethyl, trifluoromethyl, methyl, ethyl, methoxy, ethoxy, cyclopropyl and cyclobutyl, L represents a #$^1$—$CR^{6A}R^{6B}$—$(CR^{7A}R^{7B})_m$—#$^2$ group where

$^1$ is the point of attachment to the carbonyl group,

$^2$ is the point of attachment to the pyrimidine or triazine ring, m represents a number 0 or 1, $R^{6A}$ represents hydrogen, fluorine, methyl, ethyl, hydroxy or amino, $R^{6B}$ represents hydrogen, fluorine, difluoromethyl, trifluoromethyl, $(C_1$-$C_4)$-alkyl, cyano, cyclopropyl, cyclobutyl, cyclopentyl or a group of the formula -M-$R^{12}$, in which $(C_1$-$C_4)$-alkyl may be substituted by 1 to 3 substituents independently of one another selected from the group consisting of fluorine, cyano, trifluoromethyl, cyclopropyl, cyclobutyl, cyclopentyl, difluoromethoxy, trifluoromethoxy, methoxy and ethoxy, and in which M is a bond, methylene, ethane-1,2-diyl or propane-1,3-diyl, $R^{12}$ represents —(C=O)$_r$—$OR^8$, —(C=O)$_r$—$NR^8R^9$, —C(=S)—$NR^8R^9$, —$NR^8$—(C=O)—$OR^{11}$, —$NR^8$—(C=O)—$NR^9R^{10}$, oxadiazolonyl, oxadiazolothionyl, phenyl, oxazolyl, thiazolyl, pyrazolyl, triazolyl, oxadiazolyl, thiadiazolyl, pyridyl, pyrimidinyl or pyrazinyl, in which r represents the number 0 or 1, $R^8$ and $R^9$ independently of one another each represent hydrogen, methyl, ethyl, isopropyl, cyclopropyl, cyclobutyl, cyclopentyl, oxetanyl, azetidinyl, tetrahydrofuranyl, pyrrolidinyl, tetrahydropyranyl, piperidinyl, piperazinyl, morpholinyl, phenyl, pyrazolyl or pyridyl, in which methyl, ethyl and isopropyl may additionally be substituted by 1 or 2 substituents independently of one another selected from the group consisting of fluorine, difluoromethyl, trifluoromethyl, cyclopropyl, cyclobutyl, cyclopentyl, hydroxy, difluoromethoxy, trifluoromethoxy, methoxy, ethoxy, hydroxycarbonyl, methoxycarbonyl, ethoxycarbonyl and amino, $R^{11}$ represents methyl, ethyl, isopropyl, cyclopropyl, cyclobutyl, cyclopentyl, and in which oxadiazolonyl, oxadiazolethionyl, phenyl, oxazolyl, thiazolyl, pyrazolyl, triazolyl, oxadiazolyl, thiadiazolyl, pyridyl, pyrimidinyl and pyrazinyl for their part may be substituted by 1 or 2 substituents independently of one another selected from the group consisting of fluorine, chlorine, cyano, difluoromethyl, trifluoromethyl, methyl, ethyl, isopropyl, 2,2,2-trifluoroethyl, 1,1,2,2,2- pentafluoroethyl, cyclopropyl, cyclobutyl, cyclopropylmethyl, cyclobutylmethyl, hydroxy, methoxy and ethoxy,
or
$R^{6A}$ and $R^{6B}$ together with the carbon atom to which they are attached form a cyclopropyl, cyclobutyl, cyclopentyl, azetidinyl, tetrahydrofuranyl, pyrrolidinyl or tetrahydropyranyl ring,
in which the cyclopropyl, cyclobutyl, cyclopentyl, azetidinyl, tetrahydrofuranyl, pyrrolidinyl and tetrahydropyranyl ring may be substituted by 1 or 2 substituents independently of one another selected from the group consisting of fluorine and methyl,
$R^{7A}$ represents hydrogen, fluorine, methyl, ethyl or hydroxy,
$R^{7B}$ represents hydrogen, fluorine, methyl, ethyl or trifluoromethyl,
$R^1$ represents hydrogen or fluorine,
$R^2$ represents benzyl,
where benzyl is substituted by 1 to 3 substituents independently of one another selected from the group consisting of fluorine, methyl and methoxy,
$R^3$ represents hydrogen or methyl,
$R^4$ represents hydrogen,
and the salts, solvates and solvates of the salts thereof.

Preference is given in the context of the present invention to compounds of the formula (I) in which
A represents nitrogen or $CR^5$,
where
$R^5$ represents hydrogen, deuterium, chlorine, iodine, difluoromethyl, trifluoromethyl, $(C_1\text{-}C_6)$-alkyl, vinyl, allyl, ethynyl, cyclopropyl, cyclobutyl, phenyl, pyrazol-3-yl, pyrazol-4-yl, pyrazol-5-yl, pyrrol-5-yl, 1,3-thiazol-5-yl, 1,3,4-thiadiazol-5-yl or pyridyl,
in which $(C_1\text{-}C_6)$-alkyl, vinyl, allyl, ethynyl, phenyl, pyrazol-3-yl, pyrazol-4-yl, pyrazol-5-yl, pyrrol-5-yl, 1,3-thiazol-5-yl, 1,3,4-thiadiazol-5-yl and pyridyl may be substituted by 1 or 2 substituents independently of one another selected from the group consisting of fluorine, cyano, difluoromethyl, trifluoromethyl, methyl, ethyl, isopropyl, methoxy, ethoxy, hydroxy, $(C_1\text{-}C_4)$-alkoxycarbonyl, hydroxycarbonyl, cyclopropyl, cyclobutyl and $-(C=O)-NR^{21}R^{22}$,
in which
$(C_1\text{-}C_6)$-alkyl may be substituted by an $-NR^{13}R^{14}$ group,
in which
$R^{13}$ represents hydrogen, methyl or ethyl,
in which
ethyl may be substituted by 1 to 3 fluorine substituents,
$R^{14}$ represents hydrogen, $(C_1\text{-}C_4)$-alkyl, $-(C=O)-R^{15}$ or $-S(O)_2-R^{16}$,
in which
$(C_1\text{-}C_4)$-alkyl may be substituted by 1 to 3 fluorine substituents,
and in which
$R^{15}$ represents $(C_1\text{-}C_4)$-alkyl or $(C_3\text{-}C_5)$-cycloalkyl,
$R^{16}$ represents $(C_1\text{-}C_4)$-alkyl or $(C_3\text{-}C_5)$-cycloalkyl,
or
$R^{13}$ and $R^{14}$ together with the nitrogen atom to which they are attached form a 4- to 6-membered heterocycle,
in which the 4- to 6-membered heterocycle for its part may be substituted by 1 or 2 substituents independently of one another selected from the group consisting of trifluoromethyl, $(C_1\text{-}C_4)$-alkyl and oxo,
and in which
$R^{21}$ represents hydrogen or $(C_1\text{-}C_4)$-alkyl,
$R^{22}$ represents hydrogen or $(C_1\text{-}C_4)$-alkyl,
in which $(C_1\text{-}C_4)$-alkyl for its part may in each case be substituted by hydroxy or fluorine,
or
$R^{21}$ and $R^{22}$ together with the atom to which they are attached form a 4- to 7-membered heterocycle,
L represents a $\#^1-CR^{6A}R^{6B}-(CR^{7A}R^{7B})_m-\#^2$ group
where
$\#^1$ is the point of attachment to the carbonyl group,
$\#^2$ is the point of attachment to the pyrimidine or triazine ring,
m represents a number 0 or 1,
$R^{6A}$ represents hydrogen, fluorine, methyl, ethyl, hydroxy or amino,
$R^{6B}$ represents hydrogen, fluorine, difluoromethyl, trifluoromethyl, $(C_1\text{-}C_4)$-alkyl, $(C_2\text{-}C_6)$-alkenyl, cyano, cyclopropyl, cyclobutyl, cyclopentyl or a group of the formula $-M-R^{12}$,
in which $(C_1\text{-}C_4)$-alkyl may be substituted by 1 to 3 substituents independently of one another selected from the group consisting of $(C_1\text{-}C_4)$-alkoxy, fluorine, cyano, trifluoromethyl, cyclopropyl, cyclobutyl, cyclopentyl, difluoromethoxy and trifluoromethoxy,
in which $(C_1\text{-}C_4)$-alkoxy may be substituted by phenyl,
and in which
M represents a bond, methylene, ethane-1,2-diyl or propane-1,3-diyl,
$R^{12}$ represents $-(C=O)_r-OR^8$, $-(C=O)_r-NR^8R^9$, $-C(=S)-NR^8R^9$, $-NR^8-(C=O)-OR^{11}$, $-NR^8-(C=O)-NR^9R^{10}$, oxadiazolonyl, oxadiazolothionyl, phenyl, oxazolyl, thiazolyl, pyrazolyl, triazolyl, oxadiazolyl, thiadiazolyl, pyridyl, pyrimidinyl or pyrazinyl,
in which
r represents the number 0 or 1,
$R^8$ and $R^9$ independently of one another each represent hydrogen, methyl, ethyl, isopropyl, cyclopropyl, cyclobutyl, cyclopentyl, oxetanyl, azetidinyl, tetrahydrofuranyl, pyrrolidinyl, tetrahydropyranyl, piperidinyl, piperazinyl, morpholinyl, phenyl, pyrazolyl or pyridyl,
in which methyl, ethyl and isopropyl may additionally be substituted by 1 or 2 substituents independently of one another selected from the group consisting of fluorine, difluoromethyl, trifluoromethyl, cyclopropyl, cyclobutyl, cyclopentyl, hydroxy, difluoromethoxy, trifluoromethoxy, methoxy, ethoxy, hydroxycarbonyl, methoxycarbonyl, ethoxycarbonyl and amino,
$R^{11}$ represents methyl, ethyl, isopropyl, cyclopropyl, cyclobutyl, cyclopentyl,
and
in which oxadiazolonyl, oxadiazolethionyl, phenyl, oxazolyl, thiazolyl, pyrazolyl, triazolyl, oxadiazolyl, thiadiazolyl, pyridyl, pyrimidinyl and pyrazinyl for their part may be substituted by 1 or 2 substituents independently of one another selected from the group consisting of fluorine, chlorine, cyano, difluoromethyl, trifluoromethyl, methyl, ethyl, isopropyl, 2,2,2-trifluoroethyl, 1,1,2,2,2- pentafluoroethyl, cyclopropyl, cyclobutyl, cyclopropylmethyl, cyclobutylmethyl, hydroxy, methoxy and ethoxy,
or
$R^{6A}$ and $R^{6B}$ together with the carbon atom to which they are attached form a cyclopropyl, cyclobutyl, cyclopentyl, azetidinyl, tetrahydrofuranyl, pyrrolidinyl or tetrahydropyranyl ring,
in which the cyclopropyl, cyclobutyl, cyclopentyl, azetidinyl, tetrahydrofuranyl, pyrrolidinyl and tetrahydropyranyl ring may be substituted by 1 or 2 substituents independently of one another selected from the group consisting of fluorine and methyl,
$R^{7A}$ represents hydrogen, fluorine, methyl, ethyl or hydroxy,
$R^{7B}$ represents hydrogen, fluorine, methyl, ethyl, trifluoromethyl or $(C_1-C_4)$-alkoxycarbonyl,
$R^1$ represents hydrogen or fluorine,
$R^2$ represents benzyl, 3,3,3-trifluoroprop-1-yl, 4,4,4-trifluorobut-1-yl or 3,3,4,4,4-pentafluorobut-1-yl,
where benzyl is substituted by 1 to 3 substituents independently of one another selected from the group consisting of fluorine, methyl and methoxy,
$R^3$ represents hydrogen, methyl or trifluoromethyl,
$R^4$ represents hydrogen,
and the salts, solvates and solvates of the salts thereof.

Preference is given in the context of the present invention to compounds of the formula (I) in which
A represents nitrogen or $CR^5$,
where
$R^5$ represents hydrogen, methyl, ethyl, vinyl, ethynyl, hydroxy, pyrazol-5-yl or pyridyl,
in which methyl, ethyl, vinyl and ethynyl are substituted by 1 cyclopropyl substituent,
and
in which pyridyl may be substituted by 1 methoxy substituent,
L represents a $\#^1$—$CR^{6A}R^{6B}$—$(CR^{7A}R^{7B})_m$—$\#^2$ group
where
$\#^1$ is the point of attachment to the carbonyl group,
$\#^2$ is the point of attachment to the pyrimidine or triazine ring,
m is a number 0,
$R^{6A}$ represents hydrogen, fluorine, methyl, ethyl, hydroxy or amino,
$R^{6B}$ represents hydrogen, fluorine, difluoromethyl, trifluoromethyl, methyl, ethyl, cyclopropyl, cyclobutyl, cyclopentyl or a group of the formula -M-$R^{12}$,
in which methyl and ethyl may be substituted by 1 to 3 substituents independently of one another selected from the group consisting of fluorine, cyano, trifluoromethyl, cyclopropyl, cyclobutyl, difluoromethoxy, trifluoromethoxy, methoxy and ethoxy,
and in which
M represents a bond,
$R^{12}$ represents —(C=O)$_r$—$NR^8R^9$, phenyl, thiazolyl, triazolyl, oxadiazolyl, thiadiazolyl or pyrimidinyl,
in which
r represents the number 1,
$R^8$ and $R^9$ independently of one another each represent hydrogen or cyclopropyl,
and
in which phenyl, thiazolyl, triazolyl, oxadiazolyl, thiadiazolyl and pyrimidinyl may each in turn be substituted 1 or 2 substituents selected independently from the group of fluorine, difluoromethyl, trifluoromethyl, methyl, ethyl, isopropyl, 2,2,2-trifluoroethyl, 1,1,2,2,2-pentafluoroethyl, cyclopropyl, cyclobutyl, cyclopropylmethyl and cyclobutylmethyl,
or
$R^{6A}$ and $R^{6B}$ together with the carbon atom to which they are attached form a cyclopropyl, cyclobutyl, cyclopentyl, azetidinyl, tetrahydrofuranyl, pyrrolidinyl or tetrahydropyranyl ring,
in which the cyclopropyl, cyclobutyl, cyclopentyl, azetidinyl, tetrahydrofuranyl, pyrrolidinyl and tetrahydropyranyl ring may be substituted by 1 or 2 substituents independently of one another selected from the group consisting of fluorine and methyl,
$R^1$ represents hydrogen or fluorine,
$R^2$ represents a group of the formula

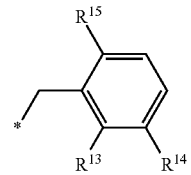

where
* is the point of attachment to the pyrazolopyridine,
$R^{13}$ represents fluorine,
$R^{14}$ represents hydrogen, fluorine, methyl or methoxy,
$R^{15}$ represents hydrogen or fluorine,
$R^3$ represents hydrogen or methyl,
$R^4$ represents hydrogen,
and the salts, solvates and solvates of the salts thereof.

Preference is given in the context of the present invention to compounds of the formula (I) in which
A represents nitrogen or $CR^5$,
where
$R^5$ represents hydrogen, $(C_1-C_6)$-alkyl, vinyl, ethynyl, pyrazol-5-yl, pyrrol-5-yl, 1,3-thiazol-5-yl, 1,3,4-thiadiazol-5-yl or pyridyl,
in which $(C_1-C_6)$-alkyl, vinyl and ethynyl may be substituted by 1 methyl, trifluoromethyl, methoxy, ethoxy, hydroxy, methoxycarbonyl, ethoxycarbonyl, cyclopropyl or —(C=O)—$NR^{21}R^{22}$ substituent,
in which pyridyl may be substituted by 1 methoxy substituent,
in which 1,3-thiazol-5-yl and 1,3,4-thiadiazol-5-yl independently of one another may be substituted by 1 or 2 substituents selected from the group consisting of methyl and ethyl,
in which pyrrol-5-yl may be substituted by methyl and cyano,
and in which
$R^{21}$ represents hydrogen or $(C_1-C_4)$-alkyl,
$R^{22}$ represents hydrogen or $(C_1-C_4)$-alkyl,
or
represents a —$CH_2$—$NR^{13}R^{14}$ or —$CH_2$—$CH_2$—$NR^{13}R^{14}$ group,
in which
$R^{13}$ represents hydrogen, methyl or ethyl,
$R^{14}$ represents hydrogen, methyl, ethyl, —(C=O)—$R^{15}$ or —$S(O)_2$—$R^{16}$, in which
ethyl may be substituted by 1 to 3 fluorine substituents,
and in which
$R^{15}$ represents methyl, ethyl or cyclopropyl,
$R^{16}$ represents methyl, ethyl or cyclopropyl,
or
$R^{13}$ and $R^{14}$ together with the nitrogen atom to which they are attached form a 5- or 6-membered heterocycle,
in which the 5- or 6-membered heterocycle for its part may be substituted by oxo,
L represents a $\#^1$—$CR^{6A}R^{6B}$—$(CR^{7A}R^{7B})_m$—$\#^2$ group,
where
$\#^1$ is the point of attachment to the carbonyl group,
$\#^2$ is the point of attachment to the pyrimidine or triazine ring,
m represents a number 0,
$R^{6A}$ represents hydrogen, methyl, ethyl, hydroxy or amino,
$R^{6B}$ represents hydrogen, fluorine, difluoromethyl, trifluoromethyl, 1,1,2,2,2-pentafluoroeth-1-yl, methyl, ethyl, allyl, but-3-en-1-yl or a group of the formula -M-$R^{12}$,
in which methyl and ethyl may be substituted by 1 to 3 substituents independently of one another selected from the group consisting of fluorine, cyano, trifluoromethyl, cyclopropyl, cyclobutyl, difluoromethoxy, trifluoromethoxy, methoxy and ethoxy,
in which methoxy and ethoxy may be substituted by phenyl,
and in which
M represents a bond,
$R^{12}$ represents —$(C=O)_r$—$NR^8R^9$ or 1,3,4-thiadiazol-5-yl,
in which
r represents the number 1,
$R^8$ and $R^9$ independently of one another each represent hydrogen or cyclopropyl,
and
in which 1,3,4-thiadiazol-5-yl may be substituted by 1 or 2 substituents independently of one another selected from the group consisting of fluorine, trifluoromethyl, methyl and ethyl,
or
$R^{6A}$ and $R^{6B}$ together with the carbon atom to which they are attached form a cyclopropyl, cyclobutyl, cyclopentyl, azetidinyl, tetrahydrofuranyl, pyrrolidinyl or tetrahydropyranyl ring,
in which the cyclopropyl, cyclobutyl, cyclopentyl, azetidinyl, tetrahydrofuranyl, pyrrolidinyl and tetrahydropyranyl ring may be substituted by 1 or 2 substituents independently of one another selected from the group consisting of fluorine and methyl,
$R^1$ represents hydrogen or fluorine,
$R^2$ represents a group of the formula

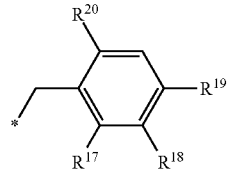

where
* is the point of attachment to the pyrazolopyridine, and
$R^{17}$, $R^{18}$, $R^{19}$ and $R^{20}$ independently of one another represent hydrogen, fluorine, methyl or methoxy, with the proviso that at least one of the radicals $R^{17}$, $R^{18}$, $R^{19}$ or $R^{20}$ is different from hydrogen,
and
with the proviso that at least one of the radicals $R^{17}$, $R^{18}$, $R^{19}$ or $R^{20}$ is hydrogen,
or
$R^2$ represents 3,3,3-trifluoroprop-1-yl or 3,3,4,4,4-pentafluorobut-1-yl,
$R^3$ represents hydrogen, methyl or trifluoromethyl,
$R^4$ represents hydrogen,
and the salts, solvates and solvates of the salts thereof.
Particular preference is given in the context of the present invention to compounds of the formula (I) in which
A represents nitrogen or $CR^5$,
where
$R^5$ represents hydrogen, methyl, ethyl, propyl, vinyl, ethynyl, pyrazol-5-yl, pyrrol-5-yl, 1,3-thiazol-5-yl, 1,3,4-thiadiazol-5-yl or pyridyl,
in which methyl, ethyl, propyl, vinyl and ethynyl may be substituted by 1 methyl, trifluoromethyl, methoxy, ethoxy, hydroxy, methoxycarbonyl, ethoxycarbonyl, cyclopropyl or —(C=O)—$NR^{21}R^{22}$ substituent,
in which pyridyl may be substituted by 1 methoxy substituent,
in which 1,3-thiazol-5-yl and 1,3,4-thiadiazol-5-yl independently of one another may be substituted by 1 or 2 substituents selected from the group consisting of methyl and ethyl,
in which pyrrol-5-yl may be substituted by methyl and cyano,
and in which
$R^{21}$ represents hydrogen or $(C_1-C_4)$-alkyl,
$R^{22}$ represents hydrogen or $(C_1-C_4)$-alkyl,
or
represents a —$CH_2$—$NR^{13}R^{14}$ or —$CH_2$—$CH_2$—$NR^{13}R^{14}$ group,
in which
$R^{13}$ represents hydrogen or methyl,
$R^{14}$ represents hydrogen, methyl, ethyl, —(C=O)—$R^{15}$ or —$S(O)_2$—$R^{16}$,
in which
ethyl may be substituted by 1 to 3 fluorine substituents,
in which
$R^{15}$ represents methyl, ethyl or cyclopropyl,
$R^{16}$ represents methyl, ethyl or cyclopropyl,
or
$R^{13}$ and $R^{14}$ together with the nitrogen atom to which they are attached form a 5-membered heterocycle,
in which the 5-membered heterocycle for its part may be substituted by oxo,
L represents a $\#^1$—$CR^{6A}R^{6B}$—$(CR^{7A}R^{7B})_m$—$\#^2$ group,
where
$\#^1$ is the point of attachment to the carbonyl group,
$\#^2$ is the point of attachment to the pyrimidine or triazine ring,
m represents a number 0,
$R^{6A}$ represents hydrogen, methyl, ethyl, hydroxy or amino,
$R^{6B}$ represents hydrogen, trifluoromethyl, 1,1,2,2,2-pentafluoroeth-1-yl, methyl, ethyl, allyl, but-3-en-1-yl or a group of the formula -M-$R^{12}$,
in which methyl and ethyl may be substituted by 1 to 2 substituents independently of one another selected from the group consisting of fluorine, trifluoromethyl, cyclopropyl, cyclobutyl, methoxy and ethoxy,
in which methoxy and ethoxy may be substituted by phenyl,
and in which
M represents a bond,
$R^{12}$ represents —(C=O)$_r$NR$^8$R$^9$ or thiadiazolyl,
in which
r represents the number 1,
$R^8$ and $R^9$ independently of one another each represent hydrogen or cyclopropyl,
or
$R^{6A}$ and $R^{6B}$ together with the carbon atom to which they are attached form a cyclobutyl or cyclopentyl ring,
$R^1$ represents hydrogen or fluorine,
$R^2$ represents a group of the formula

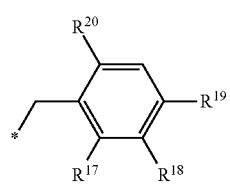

where
* is the point of attachment to the pyrazolopyridine,
and
$R^{17}$, $R^{18}$, $R^{19}$ and $R^{20}$ independently of one another represent hydrogen, fluorine, methyl or methoxy,
with the proviso that at least one of the radicals $R^{17}$, $R^{18}$, $R^{19}$ or $R^{20}$ is different from hydrogen,
with the proviso that at least one of the radicals $R^{17}$, $R^{18}$, $R^{19}$ or $R^{20}$ is hydrogen,
and
with the proviso that in each case only one of the radicals $R^{17}$, $R^{18}$, $R^{19}$ or $R^{20}$ represents methyl or methoxy,
or
$R^2$ represents 3,3,3-trifluoroprop-1-yl or 3,3,4,4,4-pentafluorobut-1-yl,
$R^3$ represents hydrogen, methyl or trifluoromethyl,
$R^4$ represents hydrogen,
and the salts, solvates and solvates of the salts thereof.

Particular preference is given in the context of the present invention to compounds of the formula (I) in which
A represents nitrogen or CR$^5$,
where
$R^5$ represents methyl or pyrazol-5-yl,
in which methyl is substituted by an —N$^{13}$R$^{14}$ group,
in which
$R^{13}$ represents hydrogen,
$R^{14}$ represents hydrogen, methyl, ethyl or —S(O)$_2$-R$^{16}$,
in which
ethyl may be substituted by 1 to 3 fluorine substituents,
and in which
$R^{16}$ represents methyl or cyclopropyl,
or
$R^{13}$ and $R^{14}$ together with the nitrogen atom to which they are attached form a 5-membered heterocycle,
in which the 5-membered heterocycle for its part may be substituted by oxo,
L represents a #$^1$—CR$^{6A}$R$^{6B}$—(CR$^{7A}$R$^{7B}$)$_m$—#$^2$ group,
where
$^1$ is the point of attachment to the carbonyl group,
$^2$ is the point of attachment to the pyrimidine or triazine ring,
m represents a number 0,
$R^{6A}$ represents methyl,
$R^{6B}$ represents methyl,
$R^1$ represents hydrogen or fluorine,
$R^2$ represents a group of the formula

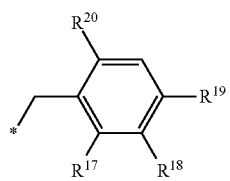

where
* is the point of attachment to the pyrazolopyridine,
and
$R^{17}$, $R^{18}$, $R^{19}$ and $R^{20}$ independently of one another represent hydrogen, fluorine, methyl or methoxy,
with the proviso that at least one of the radicals $R^{17}$, $R^{18}$, $R^{19}$ or $R^{20}$ is different from hydrogen,
and
with the proviso that at least one of the radicals $R^{17}$, $R^{18}$, $R^{19}$ or $R^{20}$ is hydrogen, and
with the proviso that in each case only one of the radicals $R^{17}$, $R^{18}$, $R^{19}$ or $R^{20}$ represents methyl or methoxy,
$R^3$ represents hydrogen, methyl or trifluoromethyl,
$R^4$ represents hydrogen,
and the salts, solvates and solvates of the salts thereof.

Particular preference is given in the context of the present invention to compounds of the formula (I) in which
A represents nitrogen or CR$^5$,
where
$R^5$ represents hydrogen,
L represents a #$^1$—CR$^{6A}$R$^{6B}$—(CR$^{7A}$R$^{7B}$)$_m$—#$^2$ group,
where
$^1$ is the point of attachment to the carbonyl group,
$^2$ is the point of attachment to the pyrimidine or triazine ring,
m is a number 0,
$R^{6A}$ represents amino,
$R^{6B}$ represents hydrogen, fluorine, difluoromethyl, trifluoromethyl, methyl, ethyl, cyclopropyl, cyclobutyl, cyclopentyl or a group of the formula -M-R$^{12}$,
in which methyl and ethyl may be substituted by 1 to 3 substituents independently of one another selected from the group consisting of fluorine, cyano, trifluoromethyl, cyclopropyl, cyclobutyl, difluoromethoxy, trifluoromethoxy, methoxy and ethoxy,
and in which
M represents a bond,
$R^{12}$ represents —(C=O)$_r$—NR$^8$R$^9$, phenyl, thiazolyl, triazolyl, oxadiazolyl, thiadiazolyl or pyrimidinyl, in which
r represents the number 1,
$R^8$ and $R^9$ independently of one another each represent hydrogen or cyclopropyl,
and
in which phenyl, thiazolyl, triazolyl, oxadiazolyl, thiadiazolyl and pyrimidinyl may each in turn be substituted by 1 or 2 substituents selected independently of one another from the group consisting of fluorine, difluoromethyl, trifluoromethyl, methyl, ethyl, isopropyl, 2,2,2-trifluoroethyl, 1,1,2,2,2-pentafluoroethyl, cyclopropyl, cyclobutyl, cyclopropylmethyl and cyclobutylmethyl,
$R^1$ represents hydrogen or fluorine,
$R^2$ is a group of the formula

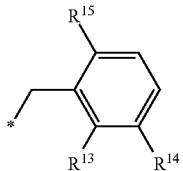

where
* is the point of attachment to the pyrazolopyridine,
$R^{13}$ represents fluorine,
$R^{14}$ represents hydrogen, fluorine, methyl or methoxy,
$R^{15}$ represents hydrogen or fluorine,
$R^3$ represents hydrogen or methyl,
$R^4$ represents hydrogen,
and the salts, solvates and solvates of the salts thereof.

Particular preference is given in the context of the present invention to compounds of the formula (I) in which
A represents nitrogen or $CR^5$,
where
$R^5$ represents hydrogen,
L represents a $\#^1$—$CR^{6A}R^{6B}$—$(CR^{7A}R^{7B})_m$—$\#^2$ group,
where
$\#^1$ is the point of attachment to the carbonyl group,
$\#^2$ is the point of attachment to the pyrimidine or triazine ring,
m is a number 0,
$R^{6A}$ represents methyl or hydroxy,
$R^{6B}$ represents pentafluoroethyl or cyclopropylmethyl,
$R^1$ represents hydrogen or fluorine,
$R^2$ is a group of the formula

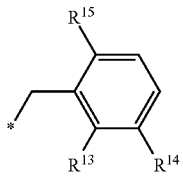

where
* is the point of attachment to the pyrazolopyridine,
$R^{13}$ represents fluorine,
$R^{14}$ represents hydrogen, fluorine, methyl or methoxy,
$R^{15}$ represents hydrogen or fluorine,
$R^3$ represents hydrogen or methyl,
$R^4$ represents hydrogen,
and the salts, solvates and solvates of the salts thereof.

In the context of the present invention, particular preference is also given to compounds of the formula (I) in which
A represents nitrogen or $CR^5$,
where
$R^5$ represents hydrogen, L represents a $\#^1$—$CR^{6A}R^{6B}$—$(CR^{7A}R^{7B})_m$—$\#^2$ group,
where
$\#^1$ is the point of attachment to the carbonyl group,
$\#^2$ is the point of attachment to the pyrimidine or triazine ring,
m is a number 0,
$R^{6A}$ represents amino,
$R^{6B}$ represents hydrogen, fluorine, difluoromethyl, trifluoromethyl, methyl, ethyl, cyclopropyl, cyclobutyl, cyclopentyl or a group of the formula -M-$R^{12}$,
in which methyl and ethyl may be substituted by 1 to 3 substituents independently of one another selected from the group consisting of fluorine, cyano, trifluoromethyl, cyclopropyl, cyclobutyl, difluoromethoxy, trifluoromethoxy, methoxy and ethoxy,
and in which
M represents a bond,
$R^{12}$ represents —(C=O)$_r$—$NR^8R^9$, phenyl, thiazolyl, triazolyl, oxadiazolyl, thiadiazolyl or pyrimidinyl,
in which
r represents the number 1,
$R^8$ and $R^9$ independently of one another each represent hydrogen or cyclopropyl,
and
in which phenyl, thiazolyl, triazolyl, oxadiazolyl, thiadiazolyl and pyrimidinyl may each in turn be substituted by 1 or 2 substituents selected independently of one another from the group consisting of fluorine, difluoromethyl, trifluoromethyl, methyl, ethyl, isopropyl, 2,2,2-trifluoroethyl, 1,1,2,2,2-pentafluoroethyl, cyclopropyl, cyclobutyl, cyclopropylmethyl and cyclobutylmethyl,
$R^1$ represents hydrogen or fluorine,
$R^2$ represents a group of the formula

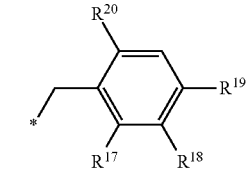

where
* is the point of attachment to the pyrazolopyridine,
and
$R^{17}$, $R^{18}$, $R^{19}$ and $R^{20}$ independently of one another represent hydrogen, fluorine, methyl or methoxy,
with the proviso that at least one of the radicals $R^{17}$, $R^{18}$, $R^{19}$ or $R^{20}$ is different from hydrogen,
with the proviso that at least one of the radicals $R^{17}$, $R^{18}$, $R^{19}$ or $R^{20}$ is hydrogen,
and
with the proviso that in each case only one of the radicals $R^{17}$, $R^{18}$, $R^{19}$ or $R^{20}$ represents methyl or methoxy,
$R^3$ represents hydrogen or methyl,
$R^4$ represents hydrogen,
and the salts, solvates and solvates of the salts thereof.

In the context of the present invention, particular preference is also given to compounds of the formula (I) in which
A represents nitrogen or $CR^5$,
where
$R^5$ represents hydrogen,
L represents a $\#^1$—$CR^{6A}R^{6B}$—$(CR^{7A}R^{7B})_m$—$\#^2$ group,
where
$\#^1$ is the point of attachment to the carbonyl group,
$\#^2$ is the point of attachment to the pyrimidine or triazine ring, m represents a number 0,
$R^{6A}$ represents hydroxy,
$R^{6B}$ represents 2,2,2-trifluoroethyl, pentafluoroethyl or $(C_1-C_4)$-alkyl,
 in which $(C_1-C_4)$-alkyl is substituted by 1 substituent selected from the group consisting of $(C_3-C_7)$-cycloalkyl, difluoromethoxy, trifluoromethoxy and $(C_1-C_4)$-alkoxy,
$R^1$ represents hydrogen or fluorine,
$R^2$ represents a group of the formula

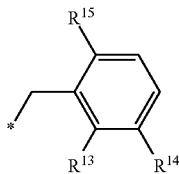

where
* is the point of attachment to the pyrazolopyridine,
$R^{13}$ represents fluorine,
$R^{14}$ represents hydrogen, fluorine, methyl or methoxy,
$R^{15}$ represents hydrogen or fluorine,
$R^3$ represents hydrogen or methyl,
$R^4$ represents hydrogen,
and the salts, solvates and solvates of the salts thereof.

In the context of the present invention, particular preference is also given to compounds of the formula (I) in which A represents nitrogen or $CR^5$,
 where
 $R^5$ represents hydrogen,
L represents a $\#^1—CR^{6A}R^{6B}—(CR^{7A}R^{7B})_m—\#^2$ group,
 where
 $\#^1$ is the point of attachment to the carbonyl group,
 $\#^2$ is the point of attachment to the pyrimidine or triazine ring,
 m is a number 0,
 $R^{6A}$ represents hydroxy,
 $R^{6B}$ represents 2,2,2-trifluoroethyl, pentafluoroethyl or $(C_1-C_4)$-alkyl,
  in which $(C_1-C_4)$-alkyl is substituted by 1 substituent selected from the group consisting of $(C_3-C_7)$-cycloalkyl, difluoromethoxy, trifluoromethoxy and $(C_1-C_4)$-alkoxy,
$R^1$ represents hydrogen or fluorine,
$R^2$ is a group of the formula

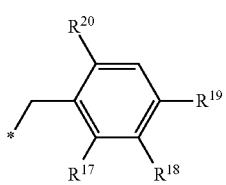

where
* is the point of attachment to the pyrazolopyridine,
and
$R^{17}$, $R^{18}$, $R^{19}$ and $R^{20}$ independently of one another represent hydrogen, fluorine, methyl or methoxy,
 with the proviso that at least one of the radicals $R^{17}$, $R^{18}$, $R^{19}$ or $R^{20}$ is different from hydrogen,
 with the proviso that at least one of the radicals $R^{17}$, $R^{18}$, $R^{19}$ or $R^{20}$ is hydrogen,
 and
 with the proviso that in each case only one of the radicals $R^{17}$, $R^{18}$, $R^{19}$ or $R^{20}$ represents methyl or methoxy,
$R^3$ represents hydrogen or methyl,
$R^4$ represents hydrogen,
and the salts, solvates and solvates of the salts thereof.

In the context of the present invention, preference is given to the compounds of the following structural formulae:

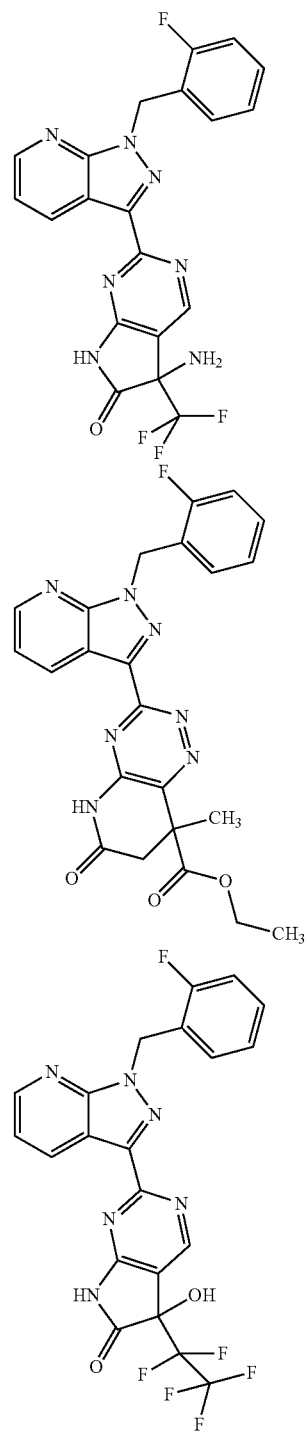

25
-continued
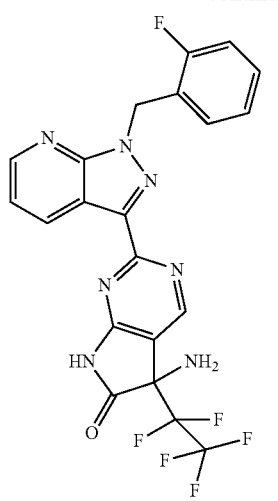
26
-continued
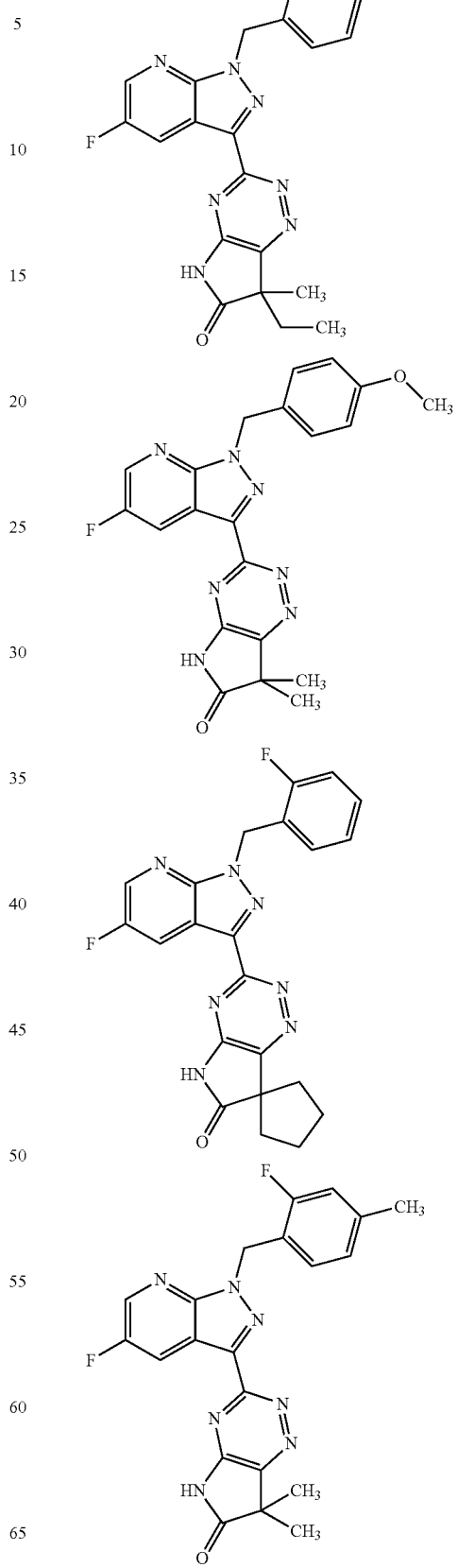

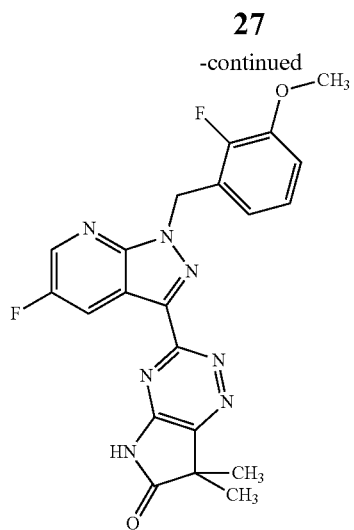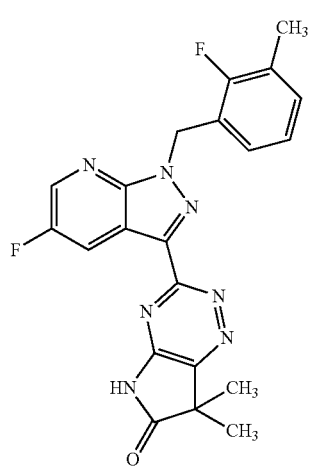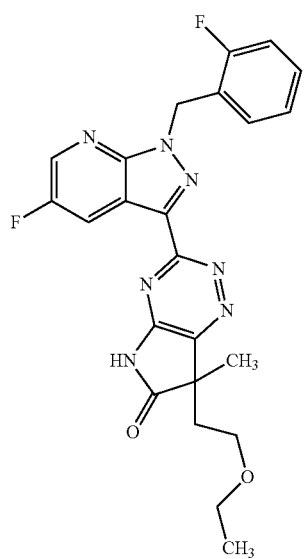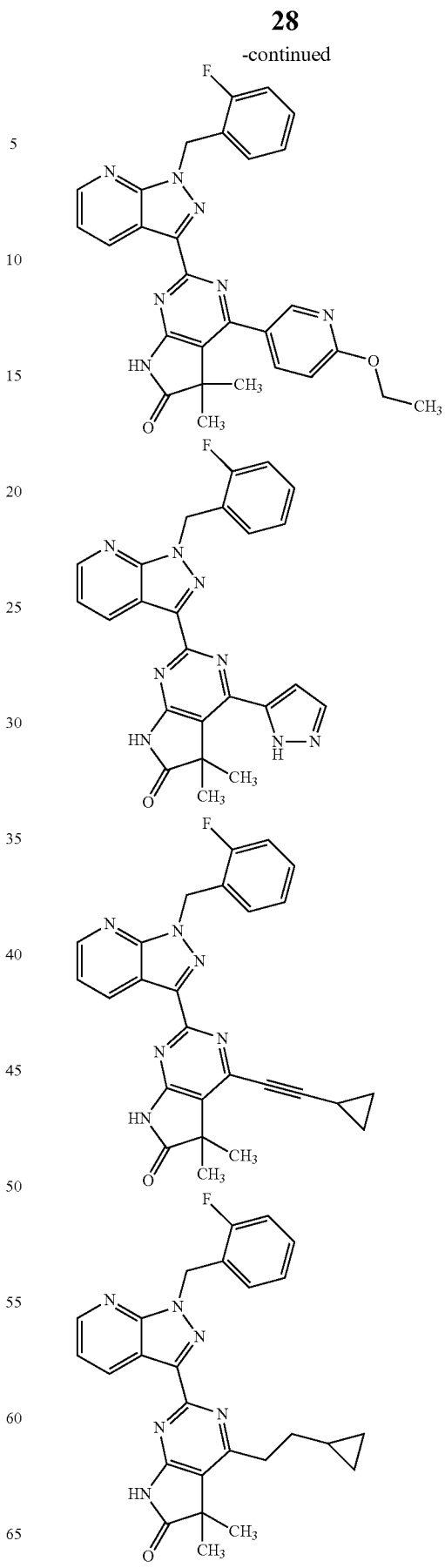

-continued
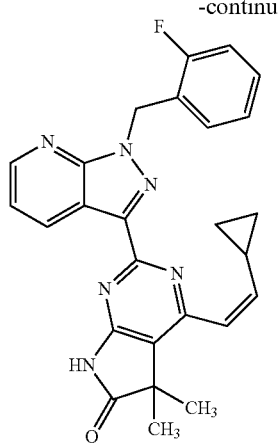
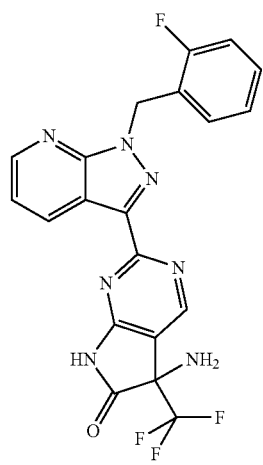
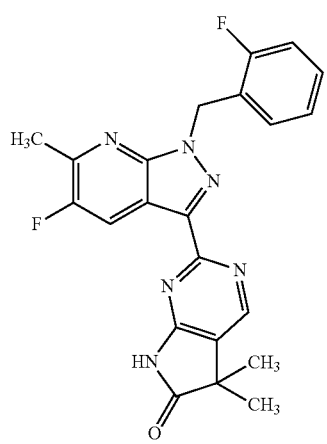
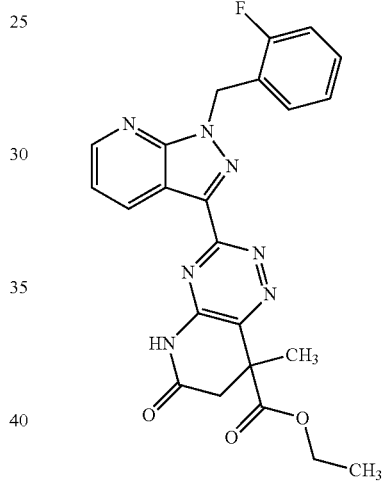
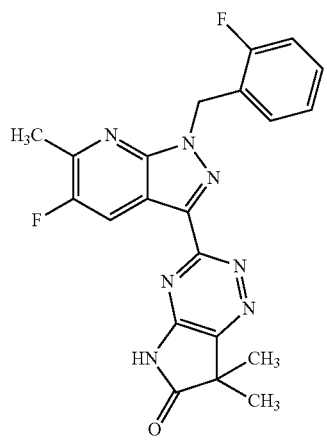
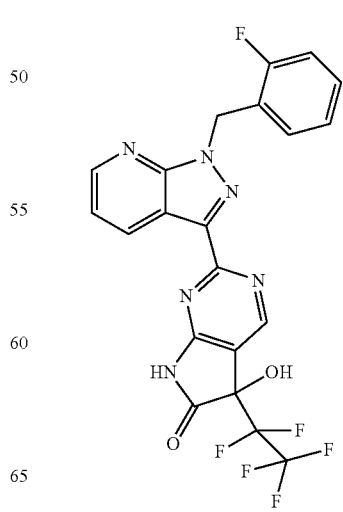
In the context of the present invention, particular preference is given to the compounds of the following structural formulae:

31
-continued
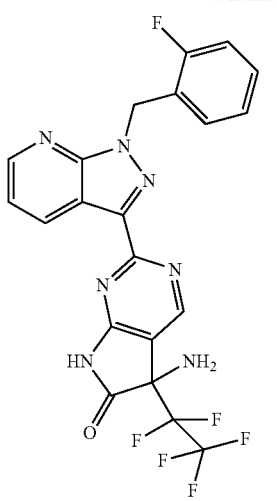
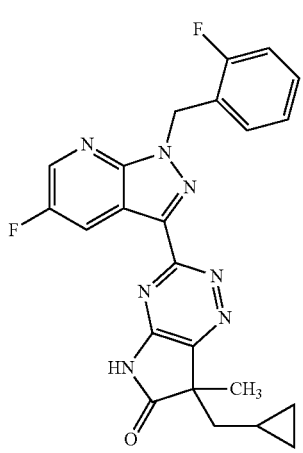
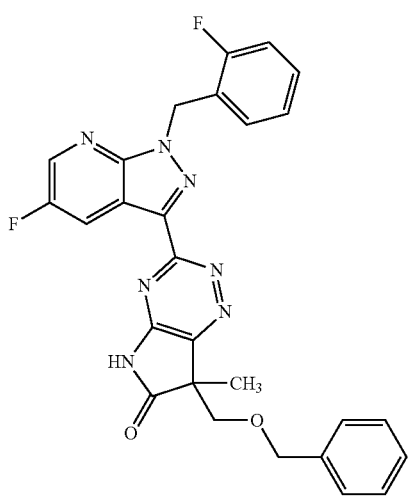
32
-continued
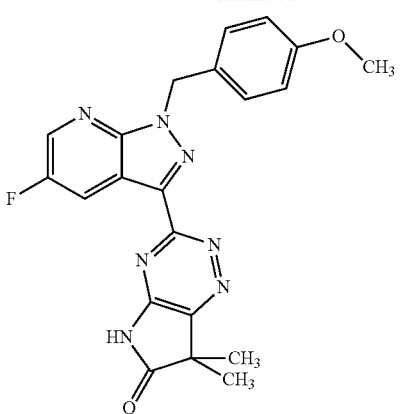
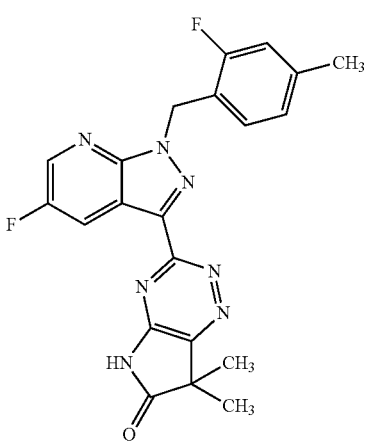
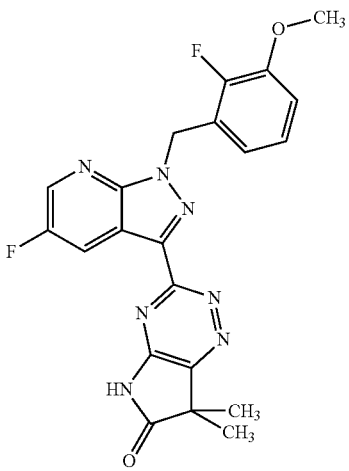

-continued
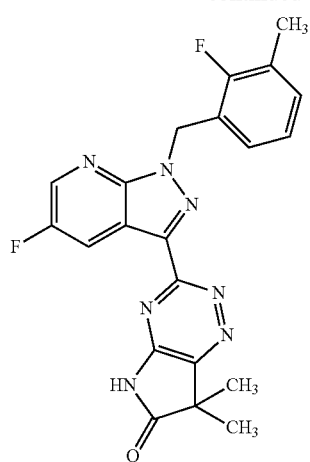
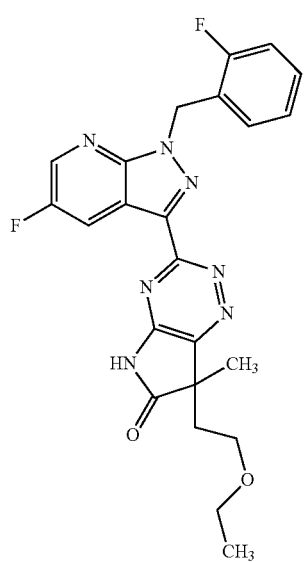
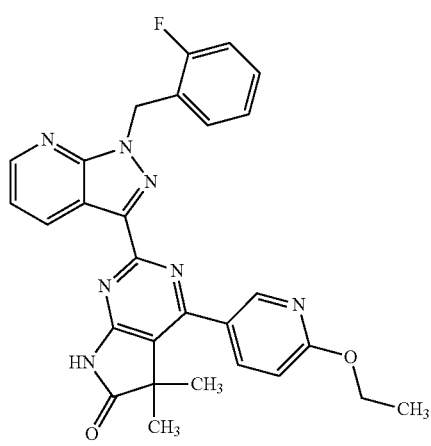
-continued
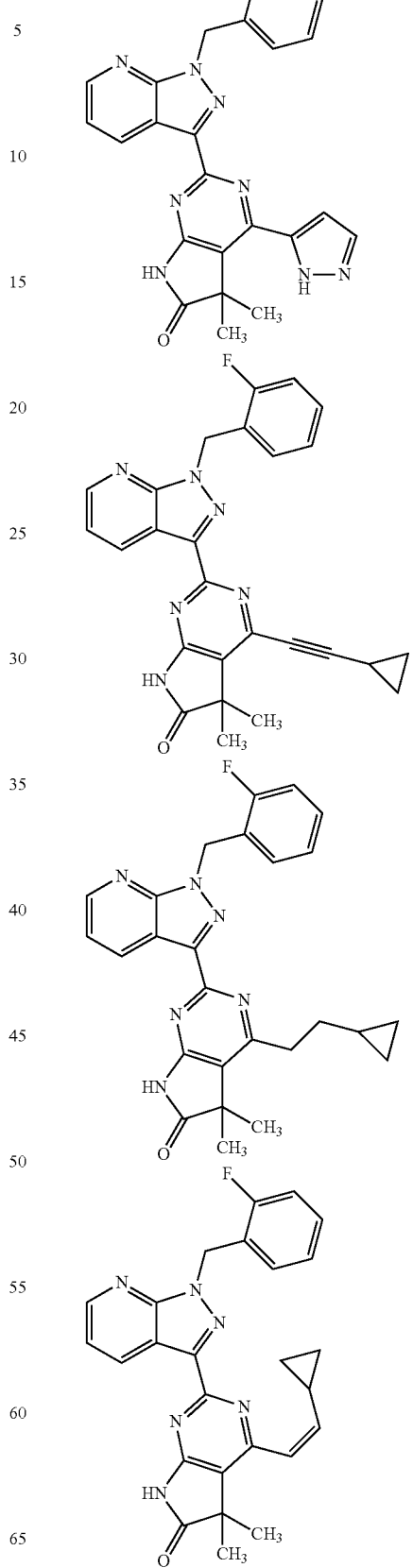

-continued
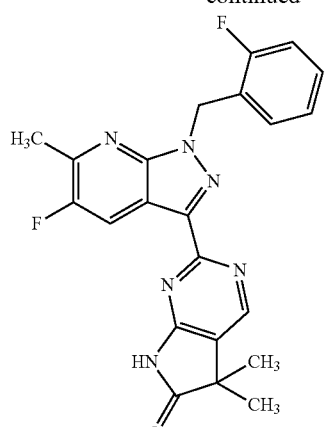
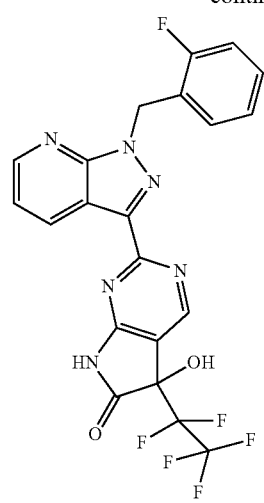
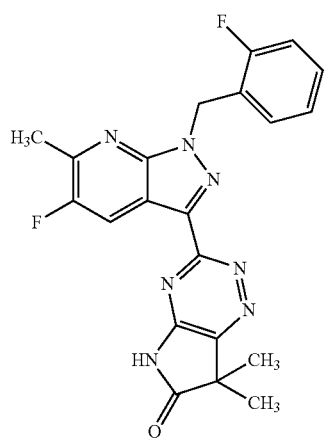 [SMILES: Cc1nc2c(cc1F)c(-c1nnc3c(n1)NC(=O)C3(C)C)nn2Cc1ccccc1F]
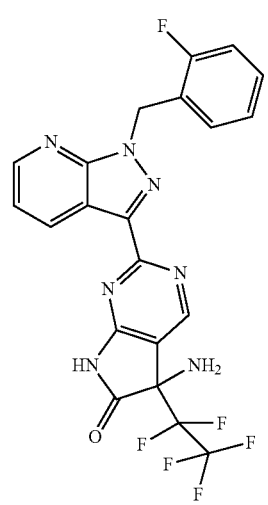
In the context of the present invention, very particular preference is given to the compounds of the following structural formulae:
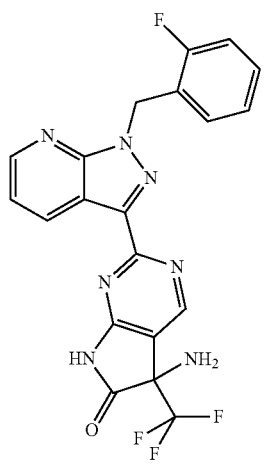
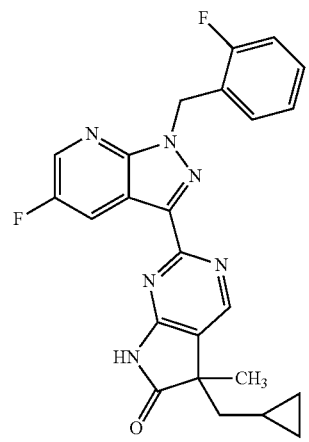

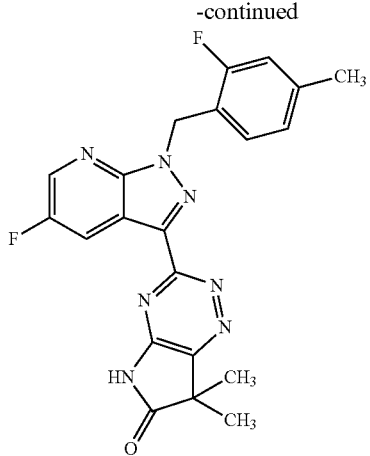
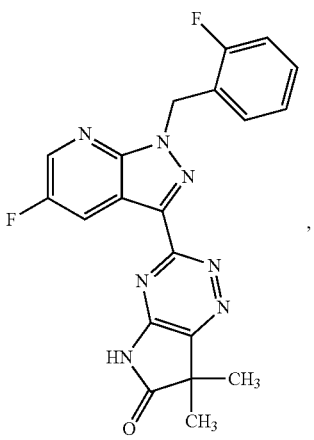
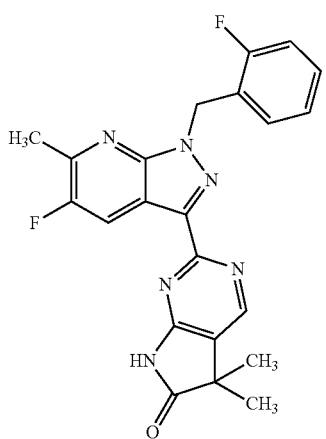
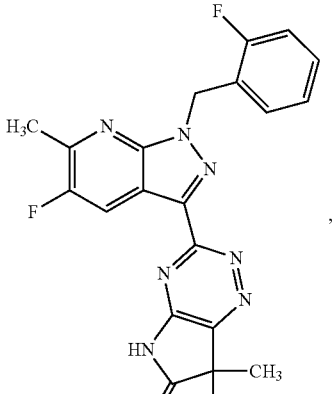
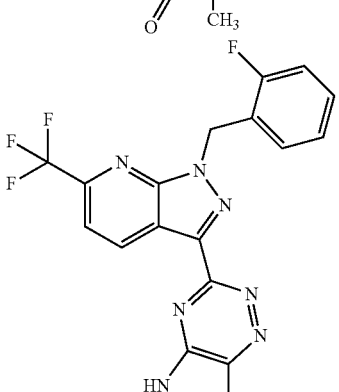
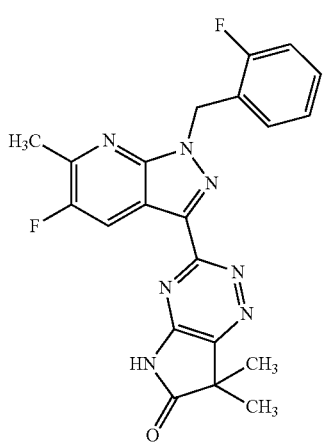
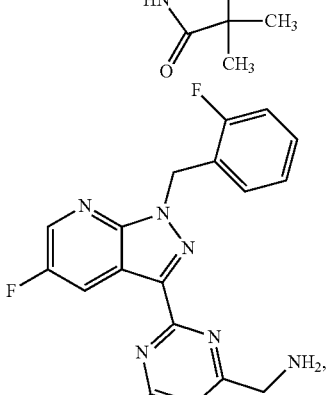
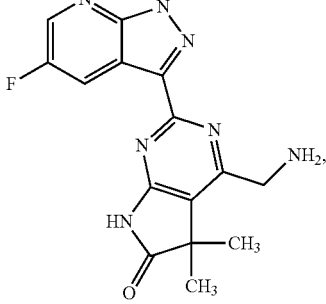
In the context of the present invention, very particular preference is given to the compounds of the following structural formulae:

-continued

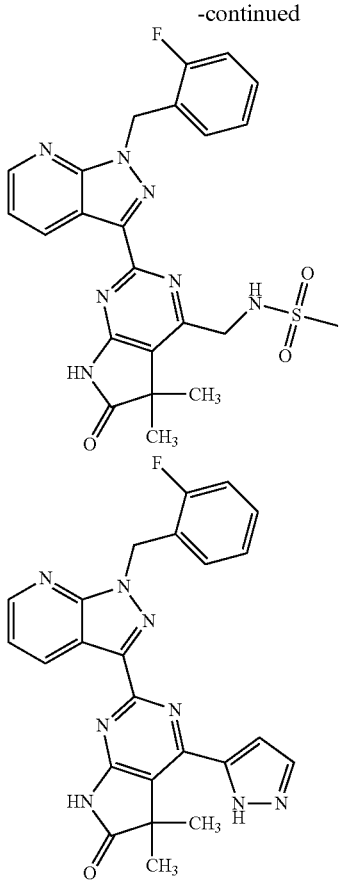

and the salts, solvates and solvates of the salts thereof.

In the context of the present invention, preference is also given to compounds of the formula (I) in which A represents $CR^5$,
where
$R^5$ represents $(C_1-C_4)$-alkyl, $(C_2-C_4)$-alkenyl, $(C_2-C_4)$-alkynyl, cyclopropyl, cyclobutyl, phenyl or 5- or 6-membered heteroaryl which is attached via carbon,
in which $(C_1-C_4)$-alkyl, $(C_2-C_4)$-alkenyl, $(C_2-C_4)$-alkynyl, phenyl and 5- or 6-membered heteroaryl are substituted by 1 to 3 substituents independently of one another selected from the group consisting of fluorine, difluoromethyl, trifluoromethyl, $(C_1-C_4)$-alkyl, difluoromethoxy, trifluoromethoxy, $(C_1-C_4)$-alkoxy, $(C_1-C_4)$-alkoxycarbonyl, cyclopropyl and cyclobutyl, and the salts, solvates and solvates of the salts thereof.

In the context of the present invention, preference is also given to compounds of the formula (I) in which A represents nitrogen,
L represents a $\#^1$—$CR^{6A}R^{6B}$—$(CR^{7A}R^{7B})_m$—$\#^2$ group,
where
$\#^1$ is the point of attachment to the carbonyl group,
$\#^2$ is the point of attachment to the triazine ring,
m is a number 0,
$R^{6A}$ represents amino,
$R^{6B}$ represents hydrogen, fluorine, difluoromethyl, trifluoromethyl, $(C_1-C_6)$-alkyl, cyano, $(C_3-C_7)$-cycloalkyl, difluoromethoxy, trifluoromethoxy or a group of the formula -M-$R^{12}$,
in which $(C_1-C_6)$-alkyl may be substituted by 1 to 3 substituents selected independently of one another from the group consisting of fluorine, cyano, trifluoromethyl, $(C_3-C_7)$-cycloalkyl, difluoromethoxy and trifluoromethoxy, and in which
M represents a bond or $(C_1-C_4)$-alkanediyl,
$R^{12}$ is —(C=O)$_r$—$OR^8$, —(C=O)$_r$—$NR^8R^9$, —C(=S)—$NR^8R^9$, —$NR^8$—(C=O)—$R^{11}$, —$NR^8$—(C=O)—$OR^{11}$, —$NR^8$—(C=O)—$NR^9R^{10}$, —$NR^8$—$SO_2$—$NR^9R^{10}$, —$NR^8$—$SO_2$—$R^{11}$, —$S(O)_s$—$R^{11}$, —$SO_2$—$NR^8R^9$, 4- to 7-membered heterocyclyl, phenyl or 5- or 6-membered heteroaryl,
in which
r represents the number 0 or 1,
s represents the number 0, 1 or 2,
$R^8$, $R^9$ and $R^{10}$ independently of one another each represent hydrogen, $(C_1-C_6)$-alkyl, $(C_3-C_8)$-cycloalkyl, 4- to 7-membered heterocyclyl, phenyl or 5- or 6-membered heteroaryl,
or
$R^8$ and $R^9$ together with the atom(s) to which they are respectively attached form a 4- to 7-membered heterocycle,
in which the 4- to 7-membered heterocycle for its part may be substituted by 1 or 2 substituents independently of one another selected from the group consisting of cyano, trifluoromethyl, $(C_1-C_6)$-alkyl, hydroxy, oxo, $(C_1-C_6)$-alkoxy, trifluoromethoxy, $(C_1-C_6)$-alkoxycarbonyl, amino, mono-$(C_1-C_6)$-alkylamino and di-$(C_1-C_6)$-alkylamino,
or
$R^9$ and $R^{10}$ together with the atom(s) to which they are respectively attached form a 4- to 7-membered heterocycle,
in which the 4- to 7-membered heterocycle for its part may be substituted by 1 or 2 substituents independently of one another selected from the group consisting of cyano, trifluoromethyl, $(C_1-C_6)$-alkyl, hydroxy, oxo, $(C_1-C_6)$-alkoxy, trifluoromethoxy, $(C_1-C_6)$-alkoxycarbonyl, amino, mono-$(C_1-C_6)$-alkylamino and di-$(C_1-C_6)$-alkylamino,
$R^{11}$ represents $(C_1-C_6)$-alkyl or $(C_3-C_7)$-cycloalkyl,
or
$R^8$ and $R^{11}$ together with the atom(s) to which they are respectively attached form a 4- to 7-membered heterocycle,
in which the 4- to 7-membered heterocycle for its part may be substituted by 1 or 2 substituents independently of one another selected from the group consisting of cyano, trifluoromethyl, hydroxy, oxo, alkoxy, trifluoromethoxy, $(C_1-C_6)$-alkoxycarbonyl, amino, mono-$(C_1-C_6)$-alkylamino and di-$(C_1-C_6)$-alkylamino,
and
in which 4- to 7-membered heterocyclyl, phenyl and 5- or 6-membered heteroaryl for their part may be substituted by 1 to 3 substituents independently of one another selected from the group consisting of halogen, cyano, difluoromethyl, trifluoromethyl, $(C_1-C_6)$-alkyl, $(C_3-C_7)$-cycloalkyl, hydroxy, oxo, thioxo and $(C_1-C_4)$-alkoxy,
and
in which the aforementioned $(C_1-C_4)$-alkyl, $(C_3-C_8)$-cycloalkyl and 4- to 7-membered heterocyclyl groups, unless stated otherwise, may each independently of one another additionally be substituted by 1 to 3 substituents independently of one another selected from the group consisting of fluorine, difluoromethyl, trifluoromethyl, $(C_1-C_6)$-alkyl, $(C_3-C_7)$-cycloalkyl, hydroxy, difluoromethoxy, trifluoromethoxy, $(C_1-C_4)$-alkoxy, hydroxycarbonyl, $(C_1-C_4)$-alkoxycarbonyl, amino, phenyl, 4- to 7-membered heterocyclyl and 5- or 6-membered heteroaryl, $R^1$, $R^2$, $R^3$ and $R^4$ each have the meanings given above, and the salts, solvates and solvates of the salts thereof.

In the context of the present invention, preference is also given to compounds of the formula (I) in which
A represents nitrogen,
L represents a $\#^1$—$CR^{6A}R^{6B}$—$(CR^{7A}R^{7B})_m$—$\#^2$ group,
where
$\#^1$ is the point of attachment to the carbonyl group,
$\#^2$ is the point of attachment to the triazine ring,
m is a number 0,
$R^{6A}$ represents amino,
$R^{6B}$ represents difluoromethyl, trifluoromethyl or $(C_1-C_6)$-alkyl,
in which $(C_1-C_6)$-alkyl may be substituted by 1 to 3 substituents independently of one another selected from the group consisting of fluorine, trifluoromethyl, $(C_3-C_7)$-cycloalkyl, difluoromethoxy, trifluoromethoxy and $(C_1-C_4)$-alkoxy,
$R^1$, $R^2$, $R^3$ and $R^4$ each have the meanings given above, and the salts, solvates and solvates of the salts thereof.

In the context of the present invention, preference is also given to compounds of the formula (I) in which $R^1$ represents H, and to the salts, solvates and solvates of the salts thereof.

In the context of the present invention, preference is also given to compounds of the formula (I) in which $R^1$ represents fluorine, and to the salts, solvates and solvates of the salts thereof.

In the context of the present invention, preference is also given to compounds of the formula (I) in which
$R^2$ represents 2-fluoro-3-methylbenzyl, 2-fluoro-4-methylbenzyl, 2-fluoro-3-methoxybenzyl or 4-methoxybenzyl,
and the salts, solvates and solvates of the salts thereof.

In the context of the present invention, preference is also given to compounds of the formula (I) in which $R^2$ represents 2-fluorobenzyl, and to the salts, solvates and solvates of the salts thereof.

In the context of the present invention, preference is also given to compounds of the formula (I) in which $R^3$ represents H, and to the salts, solvates and solvates of the salts thereof.

In the context of the present invention, preference is also given to compounds of the formula (I) in which $R^4$ represents H, and to the salts, solvates and solvates of the salts thereof.

In the context of the present invention, preference is also given to compounds of the formula (I) in which A represents N or CH, and to the salts, solvates and solvates of the salts thereof.

In the context of the present invention, preference is also given to compounds of the formula (I) in which A represents CH, and to the salts, solvates and solvates of the salts thereof.

In the context of the present invention, preference is also given to compounds of the formula (I) in which A represents N, and to the salts, solvates and solvates of the salts thereof.

In the context of the present invention, particular preference is also given to compounds of the formula (I) in which
L represents a *—$CR^{6A}R^{6B}$—$(CR^{7A}R^{7B})_p$—# group,
where
* represents the point of attachment to the carbonyl group,
# represents the point of attachment to the pyrimidine or triazine ring,
p represents a number 0,
$R^{6A}$ represents amino,
$R^{6B}$ represents pentafluoroethyl, ethoxyethyl, methoxycarbonyl, ethoxycarbonyl, (benzyloxy)methyl or cyclopropylmethyl,
and the salts, solvates and solvates of the salts thereof.

In the context of the present invention, particular preference is also given to compounds of the formula (I) in which
L represents a *—$CR^{6A}R^{6B}$—$(CR^{7A}R^{7B})_p$—# group,
where
* represents the point of attachment to the carbonyl group,
# represents the point of attachment to the pyrimidine or triazine ring,
P represents a number 0,
$R^{6A}$ represents methyl,
$R^{6B}$ represents pentafluoroethyl, ethoxyethyl, methoxycarbonyl, ethoxycarbonyl, (benzyloxy)methyl or cyclopropylmethyl,
and the salts, solvates and solvates of the salts thereof.

In the context of the present invention, particular preference is also given to compounds of the formula (I) in which
L represents a *—$CR^{6A}R^{6B}$—$(CR^{7A}R^{7B})_p$# group,
where
* represents the point of attachment to the carbonyl group,
# represents the point of attachment to the pyrimidine or triazine ring,
p represents a number 0,
$R^{6A}$ represents methyl,
$R^{6B}$ represents methyl,
and the salts, solvates and solvates of the salts thereof.

In the context of the present invention, particular preference is also given to compounds of the formula (I) in which
A represents nitrogen,
L represents a *—$CR^{6A}R^{6B}$—$(CR^{7A}R^{7B})_p$—# group,
where
* represents the point of attachment to the carbonyl group,
# represents the point of attachment to the pyrimidine or triazine ring,
p represents a number 0,
$R^{6A}$ represents methyl,
$R^{6B}$ represents methyl,
and the salts, solvates and solvates of the salts thereof.

In the context of the present invention, particular preference is also given to compounds of the formula (I) in which
A represents nitrogen or $CR^5$,
where
$R^5$ represents hydrogen, methyl, ethyl, propyl, vinyl, ethynyl, pyrazol-5-yl, pyrrol-5-yl, 1,3-thiazol-5-yl, 1,3,4-thiadiazol-5-yl or pyridyl,
in which methyl, ethyl, propyl, vinyl and ethynyl may be substituted by 1 methyl, trifluoromethyl, methoxy, ethoxy, hydroxy, methoxycarbonyl, ethoxycarbonyl, cyclopropyl or —(C=O)—$NR^{21}R^{22}$ substituent,
in which pyridyl may be substituted by 1 methoxy substituent,
in which 1,3-thiazol-5-yl and 1,3,4-thiadiazol-5-yl independently of one another may be substituted by 1 or 2 substituents selected from the group consisting of methyl and ethyl, in which pyrrol-5-yl is substituted by methyl and cyano,
in which
R²¹ represents hydrogen or $(C_1-C_4)$-alkyl,
R²² represents hydrogen or $(C_1-C_4)$-alkyl,
and
in which methyl and ethyl may be substituted by an —NR¹³R¹⁴ group,
in which
R¹³ represents hydrogen or methyl,
R¹⁴ represents hydrogen, methyl, ethyl, —(C=O)—R¹⁵ or —S(O)₂—R¹⁶,
in which
ethyl may be substituted by 1 to 5 fluorine substituents,
and in which
R¹⁵ represents methyl, ethyl or cyclopropyl,
R¹⁶ represents methyl, ethyl or cyclopropyl,
or
R¹³ and R¹⁴ together with the nitrogen atom to which they are attached form a 5-membered heterocycle,
in which the 5-membered heterocycle for its part may be substituted by oxo,
and the salts, solvates and solvates of the salts thereof.

In the context of the present invention, particular preference is also given to compounds of the formula (I) in which A represents CR⁵,
where
R⁵ represents methyl or pyrazol-5-yl,
in which methyl is substituted by an —NR¹³R¹⁴ group,
in which
R¹³ and R¹⁴ independently of one another represent hydrogen, methyl, ethyl or —S(O)₂—R¹⁶,
in which
ethyl may be substituted by 1 to 3 fluorine substituents,
and in which
R¹⁶ represents methyl or cyclopropyl,
or
R¹³ and R¹⁴ together with the nitrogen atom to which they are attached form a 5-membered heterocycle,
in which the 5-membered heterocycle for its part may be substituted by oxo,
and the salts, solvates and solvates of the salts thereof.

If radicals in the compounds according to the invention are substituted, the radicals may be mono- or polysubstituted, unless specified otherwise. In the context of the present invention, all radicals which occur more than once are defined independently of one another. Substitution by one, two or three identical or different substituents is preferred.

The individual radical definitions specified in the particular combinations or preferred combinations of radicals are, independently of the particular combinations of the radicals specified, also replaced as desired by radical definitions of other combinations.

Particular preference is given to combinations of two or more of the preferred ranges mentioned above.

The invention furthermore provides a process for preparing the compounds of the formula (I) according to the invention, characterized in that a compound of the formula (II)

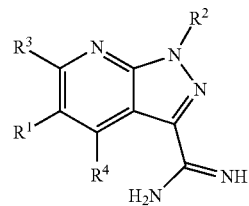

in which R¹, R², R³ and R⁴ each have the meanings given above

[A] is reacted in an inert solvent in the presence of a suitable base with a compound of the formula (III)

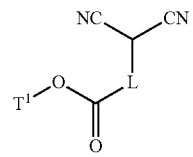

in which L has the meaning given above and
T¹ represents $(C_1-C_4)$-alkyl,
to give a compound of the formula (IV)

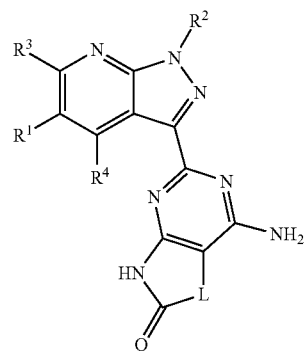

in which L, R¹, R², R³ and R⁴ each have the meanings given above,
this is then converted with isopentyl nitrite and a halogen equivalent into a compound of the formula (V)

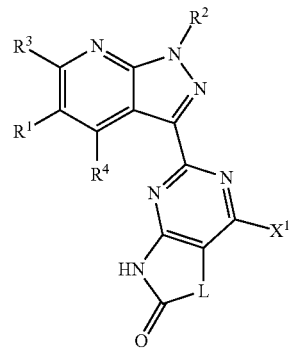

in which L, $R^1$, $R^2$, $R^3$ and $R^4$ each have the meanings given above and $X^1$ represents chlorine, bromine or iodine, and this is then reacted in an inert solvent, in the presence of a suitable transition metal catalyst, to give a compound of the formula (I-A)

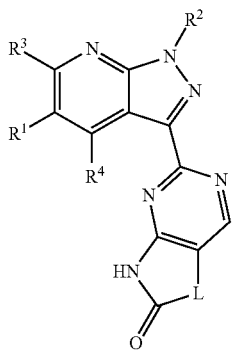
(I-A)

in which L, $R^1$, $R^2$, $R^3$ and $R^4$ each have the meanings given above, or

[B] is reacted in an inert solvent in the presence of a suitable base with a compound of the formula (VI)

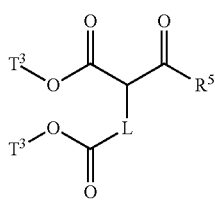
(VI)

in which L and $R^5$ each have the meanings given above and $T^3$ represents $(C_1-C_4)$-alkyl, to give a compound of the formula (VII)

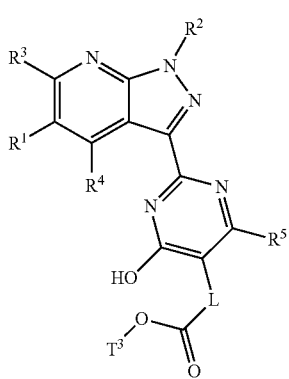
(VII)

in which L, $R^1$, $R^2$, $R^3$, $R^4$, $R^5$ and $T^3$ each have the meanings given above, this is then converted with phosphoryl chloride into a compound of the formula (VIII)

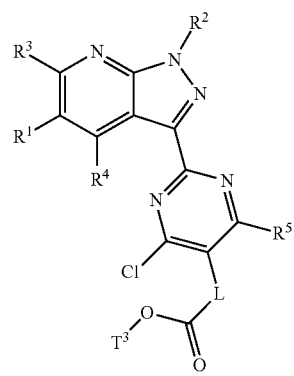
(VIII)

in which L, $R^1$, $R^2$, $R^3$, $R^4$, $R^5$ and $T^3$ each have the meanings given above, this is subsequently converted in an inert solvent into a corresponding azide compound and this is reduced directly to give a compound of the formula (IX)

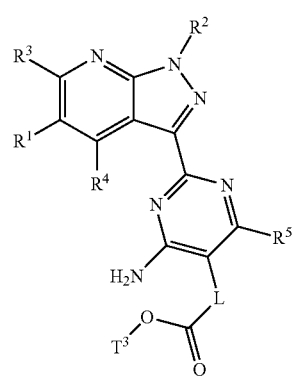
(IX)

in which L, $R^1$, $R^2$, $R^3$, $R^4$, $R^5$ and $T^3$ each have the meanings given above, and this is then reacted in an inert solvent, optionally in the presence of a suitable base, to give a compound of the formula (I-B)

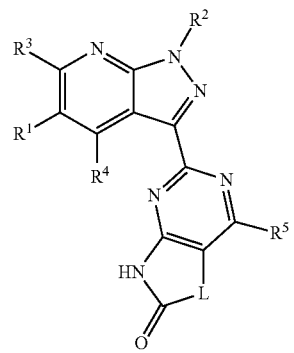
(I-B)

in which L, $R^1$, $R^2$, $R^3$, $R^4$, $R^5$ and $T^3$ each have the meanings given above, or

[C] is reacted in an inert solvent in the presence of a suitable base with hydrazine hydrate to give a compound of the formula (X)

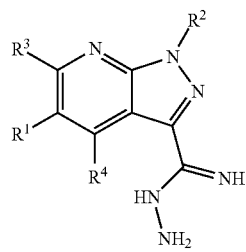
(X)

in which $R^1$, $R^2$, $R^3$ and $R^4$ each have the meanings given above, this is then reacted in an inert solvent with a compound of the formula (XI)

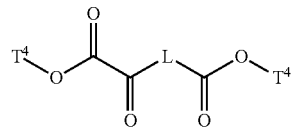
(XI)

in which L has the meaning given above and
$T^4$ represents $(C_1-C_4)$-alkyl, to give a compound of the formula (XII)

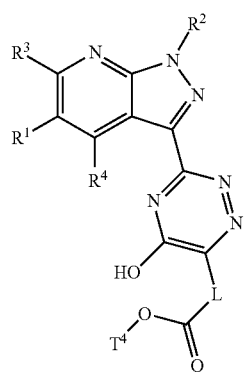
(XII)

in which L, $R^1$, $R^2$, $R^3$, $R^4$ and $T^4$ each have the meanings given above, this is then converted with phosphoryl chloride into a compound of the formula (XIII)

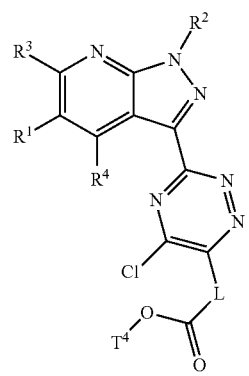
(XIII)

in which L, $R^1$, $R^2$, $R^3$, $R^4$ and $T^4$ each have the meanings given above, and this is reacted directly with ammonia to give a compound of the formula (XIV)

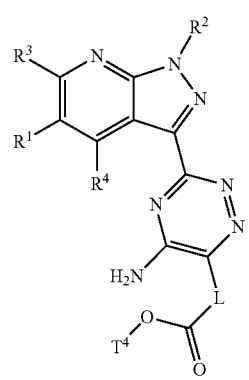
(XIV)

in which L, $R^1$, $R^2$, $R^3$, $R^4$ and $T^4$ each have the meanings given above, and finally cyclized in an inert solvent, optionally in the presence of a suitable base, to give a compound of the formula (I-C)

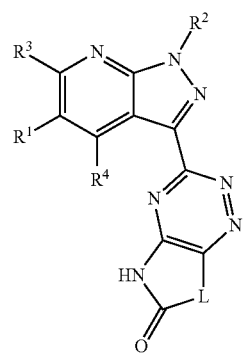
(I-C)

in which L, $R^1$, $R^2$, $R^3$ and $R^4$ each have the meanings given above, or

[D] a compound of the formula (V) is reacted in an inert solvent in the presence of a suitable transition metal catalyst with a compound of the formula (XV-A), (XV-B), (XV-C) or (XV-D)

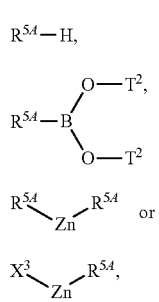

(XV-A)

(XV-B)

(XV-C)

(XV-D)

in which $R^{5A}$ in (XV-A) represents $(C_2-C_4)$-alkenyl or $(C_2-C_4)$-alkynyl, $R^{5A}$ in (XV-B), (XV-C) and (XV-D) represents halogen, difluoromethyl, trifluoromethyl, $(C_1-C_4)$-alkyl, $(C_2-C_4)$-alkenyl, $(C_2-C_4)$-alkynyl, cyclopropyl, cyclobutyl, phenyl or 5- or 6-membered heteroaryl, in which $(C_1-C_4)$-alkyl, $(C_2-C_4)$-alkenyl, $(C_2-C_4)$-alkynyl, phenyl and 5- or 6-membered heteroaryl may be substituted by 1 to 3 substituents independently of one another selected from the group consisting of fluorine, difluoromethyl, trifluoromethyl, $(C_1-C_4)$-alkyl, difluoromethoxy, trifluoromethoxy, $(C_1-C_4)$-alkoxy, $(C_1-C_4)$-alkoxycarbonyl, cyclopropyl and cyclobutyl, $T^2$ is hydrogen or $(C_1-C_4)$-alkyl, or both $R^{11}$ radicals together form a —C(CH$_3$)$_2$—C(CH$_3$)$_2$— bridge, and $X^3$ represents bromine or iodine, to give a compound of the formula (I-D)

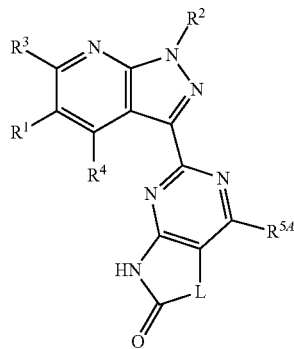

(I-D)

in which n, L, $R^1$, $R^2$, $R^3$, $R^4$ and $R^{5A}$ each have the meanings given above, or

[E] a compound of the formula (V) is converted by reaction with a compound of the formula (XVI)

$R^{25}$—Y (XVI)

in which $R^{25}$ represents 4-methoxybenzyl (PMB) or trimethylsilylethyloxymethyl (SEM)

and

Y represents chlorine, in an inert solvent in the presence of a suitable base into a compound of the formula (XVII)

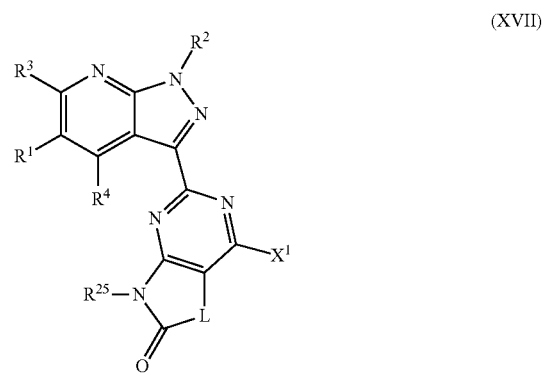

(XVII)

in which L, $R^1$, $R^2$, $R^3$, $R^4$, $X^1$ and $R^{25}$ have the meanings given above, and then in an inert solvent in the presence of a suitable transition metal catalyst with a compound of the formula (XV-A), (XV-B), (XV-C) or (XV-D)

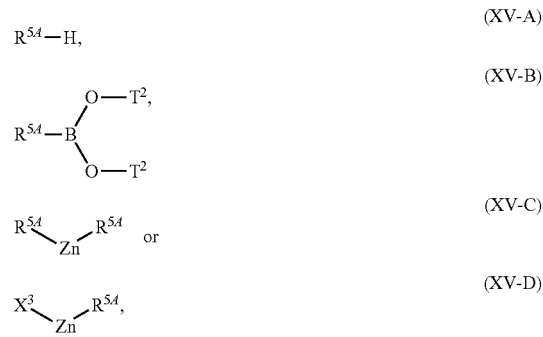

(XV-A)

(XV-B)

(XV-C)

(XV-D)

in which $R^{5A}$ in (XV-A) represents $(C_2-C_4)$-alkenyl or $(C_2-C_4)$-alkynyl, $R^{5A}$ in (XV-B), (XV-C) and (XV-D) represents halogen, difluoromethyl, trifluoromethyl, $(C_1-C_4)$-alkyl, $(C_2-C_4)$-alkenyl, $(C_2-C_4)$-alkynyl, cyclopropyl, cyclobutyl, phenyl or 5- or 6-membered heteroaryl, in which $(C_1-C_6)$-alkyl, $(C_2-C_4)$-alkenyl, $(C_2-C_4)$-alkynyl, phenyl and 5- or 6-membered heteroaryl may be substituted by 1 to 3 substituents independently of one another selected from the group consisting of cyano, fluorine, difluoromethyl, trifluoromethyl, $(C_1-C_4)$-alkyl, difluoromethoxy, trifluoromethoxy, $(C_1-C_4)$-alkoxy, $(C_1-C_4)$-alkoxycarbonyl, hydroxy, hydroxycarbonyl, cyclopropyl and cyclobutyl, $T^2$ is hydrogen or $(C_1-C_4)$-alkyl, or both $R^{11}$ radicals together form a —$C(CH_3)_2$—$C(CH_3)_2$— bridge, and $X^3$ represents bromine or iodine, to give a compound of the formula (XVIII)

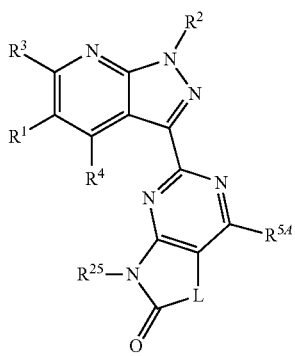

(XVIII)

in which n, L, $R^1$, $R^2$, $R^3$, $R^4$, $R^{54}$ and $R^{25}$ each have the meanings given above, and from this the PMB protective group is removed by reaction with a mixture of trifluoromethanesulphonic anhydride and trifluoroacetic acid or trifluoroacetic acid and trifluoromethanesulphonic acid or cerium(IV) ammonium nitrate and the SEM protective group by reaction initially with trifluoroacetic acid and then with aqueous mineral acid in suitable solvents, or

[F] a compound of the formula (XVII) is converted by reaction with a compound of the formula (XIX)

(XIX)

in an inert solvent in the presence of a suitable base into a compound of the formula (XX)

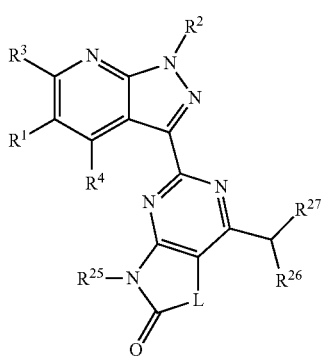

(XX)

in which L, $R^1$, $R^2$, $R^3$, $R^4$ and $R^{25}$ have the meanings given above and $R^{26}$ and $R^{27}$ independently of one another represent cyano or $(C_1-C_4)$-alkoxycarbonyl, and subsequently the protective group $R^{25}$ is removed as described in [E], where by hydrolysis and decarboxylation compound (1-E) is formed

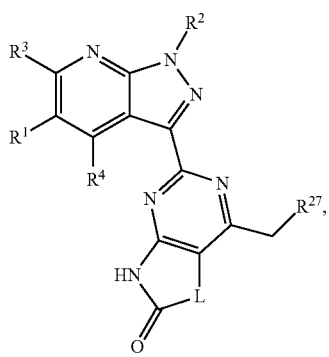

(1-E)

or

[G] a compound of the formula (V) is converted by reaction with CuCN in an inert solvent into a compound (XXI) in which L, $R^1$, $R^2$, $R^3$ and $R^4$ have the meanings mentioned above

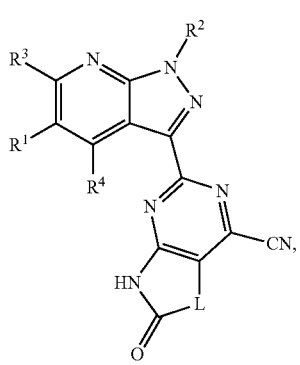

(XXI)

and this is converted by hydrogenation according to customary known methods into an amine of the formula (1-F)

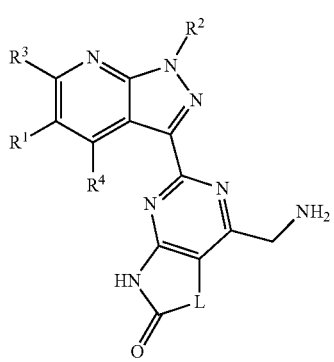

(1-F)

in which L, $R^1$, $R^2$, $R^3$ and $R^4$ have the meanings mentioned above, and this is finally reacted in an inert solvent in the presence of a suitable base with a compound of the formula (XXII)

$R^{14'}$—$X^1$    (XXII)

in which $R^{14'}$ has the meanings mentioned above for $R^{14}$, with the exception that $R^{14'}$ may not represent hydrogen, X¹ represents a suitable leaving group, in particular chlorine, bromine, iodine, mesylate, triflate or tosylate, to give a compound of the formula (1-G)

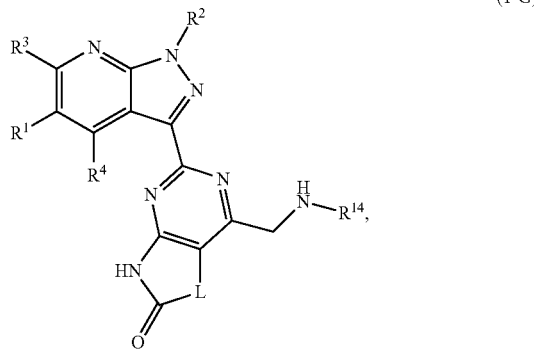

(1-G)

[delete this]
and, if appropriate, the resulting compounds of the formulae (I-A), (I-B), (I-C) I-D), (I-E), (I-D) and (I-G) are optionally converted with the appropriate (i) solvents and/or (ii) acids or bases to the solvates, salts and/or solvates of the salts thereof.

The compounds of the formulae (I-A), (I-B), (I-C), (I-D), (I-E), (I-F) and (I-G) together form the group of compounds according to the invention of the formula (I).

Inert solvents for the process step (II)+(III)→(IV) are, for example, alcohols such as methanol, ethanol, n-propanol, isopropanol, n-butanol or tert-butanol, ethers such as diethyl ether, dioxane, dimethoxyethane, tetrahydrofuran, glycol dimethyl ether or diethylene glycol dimethyl ether, hydrocarbons such as benzene, xylene, toluene, hexane, cyclohexane or mineral oil fractions, or other solvents such as dimethylformamide (DMF), dimethyl sulphoxide (DMSO), N,N'-dimethylpropyleneurea (DMPU), N-methylpyrrolidone (NMP), pyridine, acetonitrile, sulpholane or else water. It is also possible to use mixtures of the solvents mentioned. Preference is given to tert-butanol or methanol.

Suitable bases for the process step (II)+(III)→(IV) are alkali metal hydroxides such as, for example, lithium hydroxide, sodium hydroxide or potassium hydroxide, alkali metal carbonates such as lithium carbonate, sodium carbonate, potassium carbonate or caesium carbonate, alkali metal bicarbonates such as sodium bicarbonate or potassium bicarbonate, alkali metal alkoxides such as sodium methoxide or potassium methoxide, sodium ethoxide or potassium ethoxide or potassium tert-butoxide, or organic amines such as triethylamine, diisopropylethylamine, pyridine, 1,8-diazabicyclo[5.4.0]undec-7-ene (DBU) or 1,5-diazabicyclo[4.3.0]non-5-ene (DBN). Preference is given to potassium tert-butoxide or sodium methoxide.

The reaction (II)+(III)→(IV) is generally carried out in a temperature range from +20° C. to +150° C., preferably at from +75° C. to +100° C., optionally in a microwave. The conversion can be carried out at atmospheric, elevated or reduced pressure (for example from 0.5 to 5 bar). The reaction is generally carried out at atmospheric pressure.

Suitable halogen sources in the conversion (IV)→(V) are, for example, diiodomethane, a mixture of caesium iodide, iodine and copper(I) iodide or copper(II) bromide.

Process step (IV)→(V), in the case of diiodomethane as the halogen source, is carried out with a molar ratio of 10 to 30 mol of isopentyl nitrite and 10 to 30 mol of the iodine equivalent based on 1 mol of the compound of the formula (IV).

Process step (IV)→(V) is carried out with or without solvent. Suitable solvents are all organic solvents which are inert under the reaction conditions. The preferred solvent is dimethoxyethane.

The reaction (IV)→(V) is generally carried out in a temperature range from +20° C. to +100° C., preferably within the range from +50° C. to +100° C., optionally in a microwave. The conversion can be carried out at atmospheric, elevated or reduced pressure (for example in the range from 0.5 to 5 bar). The reaction is generally carried out at atmospheric pressure.

Inert solvents for the process step (V)→(I-A) are alcohols such as methanol, ethanol, n-propanol, isopropanol, n-butanol, tert-butanol or 1,2-ethanediol, ethers such as diethyl ether, dioxane, tetrahydrofuran, glycol dimethyl ether or diethylene glycol dimethyl ether, or other solvents such as dimethylformamide (DMF), dimethyl sulphoxide (DMSO), N,N'-dimethylpropyleneurea (DMPU), N-methylpyrrolidone (NMP), pyridine, acetonitrile or else water. It is also possible to use mixtures of the solvents mentioned. Preference is given to DMF.

The reduction (V)→(I-A) is carried out with hydrogen in conjunction with transition metal catalysts, for example palladium (10% on activated carbon), Raney nickel or palladium hydroxide.

The reaction (V)→(I-A) is generally carried out in a temperature range from +20° C. to +50° C. The conversion can be carried out at atmospheric or elevated pressure (for example in the range from 0.5 to 5 bar). The reaction is generally carried out at atmospheric pressure.

Inert solvents for the process step (II)+(VI)→(VII) are, for example, alcohols such as methanol, ethanol, n-propanol, isopropanol, n-butanol or tert-butanol, ethers such as diethyl ether, dioxane, dimethoxyethane, tetrahydrofuran, glycol dimethyl ether or diethylene glycol dimethyl ether, hydrocarbons such as benzene, xylene, toluene, hexane, cyclohexane or mineral oil fractions, or other solvents such as dimethylformamide (DMF), dimethyl sulphoxide (DMSO), N,N'-dimethylpropyleneurea (DMPU), N-methylpyrrolidone (NMP), pyridine or acetonitrile. It is also possible to use mixtures of the solvents mentioned. Preference is given to methanol or ethanol.

Suitable bases for the process step (II)+(VI)→(VII) are alkali metal hydroxides such as, for example, lithium hydroxide, sodium hydroxide or potassium hydroxide, alkali metal carbonates such as lithium carbonate, sodium carbonate, potassium carbonate or caesium carbonate, alkali metal bicarbonates such as sodium bicarbonate or potassium bicarbonate, alkali metal alkoxides such as sodium methoxide or potassium methoxide, sodium ethoxide or potassium ethoxide or potassium tert-butoxide, or organic amines such as triethylamine, diisopropylethylamine, pyridine, 1,8-diazabicyclo[5.4.0]undec-7-ene (DBU) or 1,5-diazabicyclo[4.3.0]non-5-ene (DBN). Preference is given to sodium methoxide or sodium ethoxide.

The reaction (II)+(VI)→(VII) is generally carried out in a temperature range from +50° C. to +120° C., preferably from +50° C. to +100° C., optionally in a microwave. The conversion can be performed at atmospheric or elevated pressure (for example in the range from 0.5 to 5 bar). The reaction is generally carried out at atmospheric pressure.

The conversions (VII)→(VIII) and (XII)→(XIII) can be carried out in a solvent which is inert under the reaction conditions or without solvent. The preferred solvent is sulpholane.

The reactions (VII)→(VIII) and (XII)→(XIII) are generally carried out in a temperature range from +70° C. to +150° C., preferably from +80° C. to +130° C., optionally in a microwave. The conversion can be performed at atmospheric or elevated pressure (for example in the range from 0.5 to 5 bar). The reaction is generally carried out at atmospheric pressure.

Especially preferably, the conversion (XII)→(XIII) is carried out without solvent in a temperature range from 0° C. to +50° C. at atmospheric pressure.

Process step (VIII)→(IX) is carried out by reaction with sodium azide with intermediate formation of the azide derivatives which are directly reduced further to give the corresponding amines. Inert solvents for the azide formation are, for example, ethers such as diethyl ether, dioxane, dimethoxyethane, tetrahydrofuran, glycol dimethyl ether or diethylene glycol dimethyl ether, hydrocarbons such as benzene, xylene, toluene, hexane, cyclohexane or mineral oil fractions, or other solvents such as dimethylformamide (DMF), dimethyl sulphoxide (DMSO), N,N'-dimethylpropyleneurea (DMPU), N-methylpyrrolidone (NMP), pyridine, acetonitrile or sulpholane. It is also possible to use mixtures of the solvents mentioned. Preference is given to DMF.

The azide formation is generally carried out in a temperature range from +50° C. to +100° C., preferably from +60° C. to +80° C., at atmospheric pressure.

The reduction is carried out in an inert solvent such as, for example, alcohols such as methanol, ethanol, n-propanol, isopropanol, n-butanol, tert-butanol or 1,2-ethanediol, ethers such as diethyl ether, dioxane, tetrahydrofuran, glycol dimethyl ether or diethylene glycol dimethyl ether, or other solvents such as dimethylformamide (DMF), dimethyl sulphoxide (DMSO), N,N'-dimethylpropyleneurea (DMPU), N-methylpyrrolidone (NMP), pyridine, acetonitrile or else water. It is also possible to use mixtures of the solvents mentioned. Preference is given to DMF.

The reduction is carried out at from +10° C. to +30° C. using hydrogen in combination with transition metal catalysts such as, for example, palladium (10% on activated carbon), platinum dioxide or palladium hydroxide, or without hydrogen using tin(II) chloride and hydrochloric acid.

Alternatively, the conversion (VIII)→(IX) can also be carried out in one step analogously to process step (XIII)→(XIV).

Process step (XIII)→(XIV) is carried out in a solvent which is inert under the reaction conditions. Suitable solvents are, for example, ethers such as diethyl ether, dioxane, tetrahydrofuran, glycol dimethyl ether or diethylene glycol dimethyl ether, or other solvents such as dimethylformamide (DMF), dimethyl sulphoxide (DMSO), N,N'-dimethylpropyleneurea (DMPU), N-methylpyrrolidone (NMP), pyridine, acetonitrile or else water. It is also possible to use mixtures of the solvents mentioned. Preference is given to acetonitrile.

The reaction (XIII)→(XIV) is generally carried out in a temperature range from +20° C. to +100° C., preferably from +40° C. to +70° C., optionally in a microwave. The conversion can be performed at atmospheric or elevated pressure (for example in the range from 0.5 to 5 bar). The reaction is generally carried out at atmospheric pressure.

The cyclizations (IX)→(I-B) and (XIV)→(I-C) are carried out in a solvent which is inert under the reaction conditions, for example alcohols such as methanol, ethanol, n-propanol, isopropanol, n-butanol or tert-butanol, ethers such as diethyl ether, dioxane, dimethoxyethane, tetrahydrofuran (THF), glycol dimethyl ether or diethylene glycol dimethyl ether, hydrocarbons such as benzene, xylene, toluene, hexane, cyclohexane or mineral oil fractions, or other solvents such as dimethylformamide (DMF), dimethyl sulphoxide (DMSO), N,N'-dimethylpropyleneurea (DMPU), N-methylpyrrolidone (NMP), pyridine, acetonitrile or sulpholane. It is also possible to use mixtures of the solvents mentioned. Preference is given to THF.

Suitable bases for the process steps (IX)→(I-B) and (XIV)→(I-C) are alkali metal hydroxides such as, for example, lithium hydroxide, sodium hydroxide or potassium hydroxide, alkali metal carbonates such as lithium carbonate, sodium carbonate, potassium carbonate or caesium carbonate, alkali metal bicarbonates such as sodium bicarbonate or potassium bicarbonate, alkali metal alkoxides such as sodium methoxide or potassium methoxide, sodium ethoxide or potassium ethoxide or potassium tert-butoxide, or organic amines such as triethylamine, diisopropylethylamine, pyridine, 1,8-diazabicyclo[5.4.0]undec-7-ene (DBU) or 1,5-diazabicyclo[4.3.0]non-5-ene (DBN). Preference is given to potassium tert-butoxide.

The reactions (IX)→(I-B) and (XIV)→(I-C) are generally carried out in a temperature range from 0° C. to +50° C., preferably from +10° C. to +30° C., optionally in a microwave. The reaction can be performed at atmospheric or elevated pressure (for example in the range from 0.5 to 5 bar). The reaction is generally carried out at atmospheric pressure.

Preferably, the cyclization to (I-B) or (I-C) occurs directly during the reduction of the azide to the corresponding amine (IX) or during the reaction (XIII)→(XIV) without addition of further reagents.

In the processes [B] and [C], the conversions (VIII)→(IX)→(I-B) and (XIII)→(XIV)→(I-C), respectively, are preferably carried out without isolation of the intermediates.

The conversions (XIII)→(XIV)→(XV)→(I-D) are preferably carried out without isolation of the intermediates.

Inert solvents for the process step (X)+(XI)→(XII) are, for example, alcohols such as methanol, ethanol, n-propanol, isopropanol, n-butanol or tert-butanol, ethers such as diethyl ether, dioxane, dimethoxyethane, tetrahydrofuran, glycol dimethyl ether or diethylene glycol dimethyl ether, hydrocarbons such as benzene, xylene, toluene, hexane, cyclohexane or mineral oil fractions, or other solvents such as dimethylformamide (DMF), dimethyl sulphoxide (DMSO), N,N'-dimethylpropyleneurea (DMPU), N-methylpyrrolidone (NMP), pyridine or acetonitrile. It is also possible to use mixtures of the solvents mentioned. Preference is given to methanol or ethanol.

The reaction (X)+(XI)→(XII) is generally carried out in a temperature range from +50° C. to +120° C., preferably from +50° C. to +100° C., optionally in a microwave. The reaction can be performed at atmospheric or elevated pressure (for example in the range from 0.5 to 5 bar). The reaction is generally carried out at atmospheric pressure.

Inert solvents for the process step (II)→(X) are, for example, alcohols such as methanol, ethanol, n-propanol, isopropanol, n-butanol or tert-butanol, ethers such as diethyl ether, dioxane, dimethoxyethane, tetrahydrofuran, glycol dimethyl ether or diethylene glycol dimethyl ether, hydrocarbons such as benzene, xylene, toluene, hexane, cyclohexane or mineral oil fractions, or other solvents such as dimethylformamide (DMF), dimethyl sulphoxide (DMSO), N,N'-dimethylpropyleneurea (DMPU), N-methylpyrrolidone (NMP), pyridine or acetonitrile. It is also possible to use mixtures of the solvents mentioned. Preference is given to ethanol.

Suitable bases for the process step (II)→(X) are alkali metal hydroxides such as, for example, lithium hydroxide, sodium hydroxide or potassium hydroxide, alkali metal carbonates such as lithium carbonate, sodium carbonate, potassium carbonate or caesium carbonate, alkali metal bicarbonates such as sodium bicarbonate or potassium bicarbonate, alkali metal alkoxides such as sodium methoxide or potassium methoxide, sodium ethoxide or potassium ethoxide or potassium tert-butoxide, or organic amines such as triethylamine, diisopropylethylamine, pyridine, 1,8-diazabicyclo[5.4.0]undec-7-ene (DBU) or 1,5-diazabicyclo[4.3.0]non-5-ene (DBN). Preference is given to triethylamine.

The reaction (II)→(X) is generally carried out in a temperature range of from 0° C. to +60° C., preferably from +10° C. to +30° C. The reaction can be performed at atmospheric or elevated pressure (for example in the range from 0.5 to 5 bar). The reaction is generally carried out at atmospheric pressure.

Process step (V)+(XV-A) or (XV-B) or (XV-C) or (XV-D)→(I-D) is carried out in a solvent which is inert under the reaction conditions. Suitable solvents are, for example, ethers such as diethyl ether, dioxane, tetrahydrofuran, glycol dimethyl ether or diethylene glycol dimethyl ether, or other solvents such as dimethylformamide (DMF), dimethyl sulphoxide (DMSO), N,N'-dimethylpropyleneurea (DMPU), N-methylpyrrolidone (NMP), pyridine, acetonitrile or else water. It is also possible to use mixtures of the solvents mentioned. Preference is given to acetonitrile, dioxane and tetrahydrofuran.

The reaction (V)+(XV-A) or (XV-B) or (XV-C) or (XV-D)→(I-D) can optionally be carried out in the presence of a suitable palladium and/or copper catalyst. A suitable palladium catalyst is, for example, palladium on activated carbon, palladium(II) acetate, tetrakis(triphenylphosphine)palladium(0), bis(triphenylphosphine)palladium(II) chloride, bis(acetonitrile)palladium(II) chloride and [1,1'-bis(diphenylphosphino)ferrocene]dichloropalladium(II) and the corresponding dichloromethane complex, optionally in conjunction with additional phosphane ligands, for example (2-biphenyl)di-tert-butylphosphine, dicyclohexyl[2',4',6'-tris(1-methylethyl)biphenyl-2-yl]phosphane (XPHOS), bis (2-phenylphosphinophenyl) ether (DPEphos) or 4,5-bis(diphenylphosphino)-9,9-dimethylxanthene (Xantphos) [cf., for example, Hassan J. et al., Chem. Rev. 102, 1359-1469 (2002)]. Suitable copper catalysts are, for example, copper bronze, copper(I) oxide, copper(I) iodide or copper(I) bromide.

The conversion (V)+(XV-A) or (XV-B) or (XV-C) or (XV-D)→(I-D) is optionally carried out in the presence of a suitable base. Suitable bases for this conversion are the customary inorganic or organic bases. These preferably include alkali metal hydroxides, for example lithium hydroxide, sodium hydroxide or potassium hydroxide, alkali metal or alkaline earth metal carbonates such as lithium carbonate, sodium carbonate, potassium carbonate, calcium carbonate or caesium carbonate, alkali metal alkoxides such as sodium methoxide or potassium methoxide, sodium ethoxide or potassium ethoxide or sodium or potassium tert-butoxide, alkali metal hydrides such as sodium hydride or potassium hydride, amides such as sodium amide, lithium bis(trimethylsilyl)amide, sodium bis(trimethylsilyl)amide or potassium bis(trimethylsilyl)amide or lithium diisopropylamide, or organic amines such as triethylamine, N-methylmorpholine, N-methylpiperidine, N,N-diisopropylethylamine, pyridine, 1,5-diazabicyclo[4.3.0]non-5-ene (DBN), 1,8-diazabicyclo[5.4.0]undec-7-ene (DBU) or 1,4-diazabicyclo[2.2.2]octane (DABCO®). Preference is given to using diisopropylamine.

The reaction (V)+(XV-A) or (XV-B) or (XV-C) or (XV-D)→(I-D) is generally carried out in a temperature range from 0° C. to +200° C., preferably from +10° C. to +150° C. The reaction can be carried out at atmospheric, elevated or reduced pressure (for example from 0.5 to 5 bar). The reaction is generally carried out at atmospheric pressure.

If the $R^{54}$ radical is unsaturated, it can subsequently be fully or partly saturated. The reduction is effected with hydrogen in conjunction with transition metal catalysts, for example palladium (10% on activated carbon), Raney nickel or palladium hydroxide. The reduction is generally carried out in a temperature range from +20° C. to +50° C. The reaction can be performed at atmospheric or elevated pressure (for example in the range from 1 to 150 bar). In general, 1 to 3 bar are employed.

Process step (V)+($R^{25}$—Y)→(XVII) is carried out in a solvent which is inert under the reaction conditions. Inert solvents for the process step (V)+($R^{25}$—Y)→(XVII) are, for example, halohydrocarbons such as dichloromethane, trichloromethane, tetrachloromethane, trichloroethylene or chlorobenzene, ethers such as diethyl ether, dioxane, tetrahydrofuran, glycol dimethyl ether or diethylene glycol dimethyl ether, hydrocarbons such as benzene, toluene, xylene, hexane, cyclohexane or mineral oil fractions, or other solvents such as acetone, methyl ethyl ketone, ethyl acetate, acetonitrile, N,N-dimethylformamide, N,N-dimethylacetamide, dimethyl sulphoxide, N,N'-dimethylpropyleneurea (DMPU), N-methylpyrrolidone (NMP) or pyridine. It is also possible to use mixtures of the solvents mentioned. Preference is given to using dimethylformamide or N-methylpyrrolidone (NMP).

The conversion (V)+($R^{25}$—Y)→(XVII) is carried out in the presence of a suitable base. Suitable bases for this conversion are the customary inorganic or organic bases. These preferably include alkali metal hydroxides, for example lithium hydroxide, sodium hydroxide or potassium hydroxide, alkali metal or alkaline earth metal carbonates such as lithium carbonate, sodium carbonate, potassium carbonate, calcium carbonate or caesium carbonate, alkali metal alkoxides such as sodium methoxide or potassium methoxide, sodium ethoxide or potassium ethoxide or sodium carbonate or caesium carbonates, alkali metal hydrides such as sodium hydride or potassium hydride, amides such as sodium amide, lithium bis(trimethylsilyl)amide, sodium bis(trimethylsilyl)amide or potassium bis(trimethylsilyl)amide or lithium diisopropylamide, or organic amines such as triethylamine, N-methylmorpholine, N-methylpiperidine, N,N-diisopropylethylamine, pyridine, 1,5-diazabicyclo[4.3.0]non-5-ene (DBN), 1,8-diazabicyclo[5.4.0]undec-7-ene (DBU) or 1,4-diazabicyclo[2.2.2]octane (DABCO®). Preference is given to using caesium carbonate.

The reaction (V)+($R^{25}$—Y)→(XVII) is generally carried out in a temperature range from −20° C. to +200° C., preferably at from +10° C. to +100° C. The conversion can be carried out at atmospheric, elevated or reduced pressure (for example from 0.5 to 5 bar). The reaction is generally carried out at atmospheric pressure.

Process step (XVII)+(XV-A) or (XV-B) or (XV-C) or (XV-D)→(XVIII) is carried out in a solvent which is inert under the reaction conditions. Suitable solvents are, for example, ethers such as diethyl ether, dioxane, tetrahydrofuran, glycol dimethyl ether or diethylene glycol dimethyl ether, or other solvents such as dimethylformamide (DMF), dimethyl sulphoxide (DMSO), N,N'-dimethylpropyleneurea (DMPU), N-methylpyrrolidone (NMP), toluene, acetonitrile or else water. It is also possible to use mixtures of the solvents mentioned. Preference is given to dioxane and tetrahydrofuran.

The conversion (XVII)+(XV-A) or (XV-B) or (XV-C) or (XV-D)→(XVIII) can optionally be carried out in the presence of a suitable palladium and/or copper catalyst. A suitable palladium catalyst is, for example, palladium on activated carbon, palladium(II) acetate, tetrakis(triphenylphosphine)palladium(0), bis(triphenylphosphine)palladium(II) chloride, bis(acetonitrile)palladium(II) chloride and [1,1'-bis(diphenylphosphino)ferrocene]dichloropalladium (II) and the corresponding dichloromethane complex, optionally in conjunction with additional phosphane ligands, for example (2-biphenyl)di-tert-butylphosphine, dicyclohexyl[2',4',6'-tris(1-methylethyl)biphenyl-2-yl]phosphane (XPHOS), bis(2-phenylphosphinophenyl) ether (DPEphos) or 4,5-bis(diphenylphosphino)-9,9-dimethylxanthene (Xantphos) [cf., for example, Hassan J. et al., *Chem. Rev.* 102, 1359-1469 (2002)]. Suitable copper catalysts are, for example, copper bronze, copper(I) oxide, copper(I) iodide or copper(I) bromide.

The conversion (XVII)+(XV-A) or (XV-B) or (XV-C) or (XV-D)→(XVIII) is optionally carried out in the presence of a suitable base. Suitable bases for this conversion are the customary inorganic or organic bases. These preferably include alkali metal or alkaline earth metal carbonates such as lithium carbonate, sodium carbonate, potassium carbonate, calcium carbonate or caesium carbonate or organic amines such as triethylamine, N-methylmorpholine, N-methylpiperidine, N,N-diisopropylethylamine, pyridine, 1,5-diazabicyclo[4.3.0]non-5-ene (DBN), 1,8-diazabicyclo[5.4.0]undec-7-ene (DBU) or 1,4-diazabicyclo[2.2.2]octane (DABCO®). Preference is given to using triethylamine or sodium bicarbonate.

The reaction (XVII)+(XV-A) or (XV-B) or (XV-C) or (XV-D)→(XVIII) is generally carried out in a temperature range from 0° C. to +200° C., preferably from +10° C. to +150° C. The conversion can be carried out at atmospheric, elevated or reduced pressure (for example from 0.5 to 5 bar). The reaction is generally carried out at atmospheric pressure.

Process step (XVIII)→(I-D) in the case of PMB is carried out by reaction with a mixture of trifluoromethanesulphonic anhydride and trifluoroacetic acid or trifluoroacetic acid and trifluoromethanesulphonic acid or cerium(IV) ammonium nitrate in suitable solvents such as acetonitrile, DMF or NMP and in the case of SEM as protective group by reaction initially with trifluoroacetic acid in suitable solvents such as dichloromethane and then with aqueous mineral acid in suitable solvents such as ethanol, THF or dioxane.

The reaction (XVIII)→(I-D) is generally carried out in a temperature range from 0° C. to +200° C., preferably at from +10° C. to +150° C., optionally in a microwave. The conversion can be carried out at atmospheric, elevated or reduced pressure (for example from 0.5 to 20 bar). The reaction is generally carried out at from 0.5 to 10 bar.

Process step (XVIII)+(XIX)→(XX) is carried out in a solvent which is inert under the reaction conditions. Suitable solvents are, for example, ethers such as diethyl ether, dioxane, dimethoxyethane, tetrahydrofuran, glycol dimethyl ether or diethylene glycol dimethyl ether, hydrocarbons such as benzene, xylene, toluene, hexane, cyclohexane or mineral oil fractions, or other solvents such as dimethylformamide (DMF), dimethyl sulphoxide (DMSO), N,N'-dimethylpropyleneurea (DMPU), N-methylpyrrolidone (NMP), pyridine, acetonitrile or sulpholane. It is also possible to use mixtures of the solvents mentioned. Preference is given to DMF.

The conversion (XVIII)+(XIX)→(XX) is optionally carried out in the presence of a suitable base. Suitable bases for this conversion are the customary inorganic or organic bases. These preferably include alkali metal or alkaline earth metal carbonates such as lithium carbonate, sodium carbonate, potassium carbonate, calcium carbonate or caesium carbonate, alkali metal alkoxides such as sodium methoxide or potassium methoxide, sodium ethoxide or potassium ethoxide or sodium or potassium tert-butoxide, alkali metal hydrides such as sodium hydride or potassium hydride, amides such as sodium amide, lithium bis(trimethylsilyl)amide, sodium bis(trimethylsilyl)amide or potassium bis(trimethylsilyl)amide or lithium diisopropylamide, or organic amines such as triethylamine, N-methylmorpholine, N-methylpiperidine, N,N-diisopropylethylamine, pyridine, 1,5-diazabicyclo[4.3.0]non-5-ene (DBN), 1,8-diazabicyclo[5.4.0]undec-7-ene (DBU) or 1,4-diazabicyclo[2.2.2]octane (DABCO®). Preference is given to using potassium tert-butoxide.

The reaction (XVIII)+(XIX)→(XX) is generally carried out in a temperature range from 0° C. to +200° C., preferably from +20° C. to +100° C. The conversion can be carried out at atmospheric, elevated or reduced pressure (for example from 0.5 to 5 bar). The reaction is generally carried out at atmospheric pressure.

Process step (V)+copper cyanide→(XXI) is carried out in a solvent which is inert under the reaction conditions. Suitable solvents are, for example, ethers such as diethyl ether, dioxane, dimethoxyethane, tetrahydrofuran, glycol dimethyl ether or diethylene glycol dimethyl ether, hydrocarbons such as benzene, xylene, toluene, hexane, cyclohexane or mineral oil fractions, or other solvents such as dimethylformamide (DMF), dimethyl sulphoxide (DMSO), N,N'-dimethylpropyleneurea (DMPU), N-methylpyrrolidone (NMP), pyridine, acetonitrile or sulpholane. It is also possible to use mixtures of the solvents mentioned. Preference is given to DMSO.

The reaction (V)+copper cyanide→(XXI) is generally carried out in a temperature range of from 0° C. to +200° C., preferably from +40° C. to +180° C. The conversion can be carried out at atmospheric, elevated or reduced pressure (for example from 0.5 to 5 bar). The reaction is generally carried out at atmospheric pressure.

The reduction (XXI)→(I-F) is carried out with hydrogen in conjunction with transition metal catalysts, for example palladium (10% on activated carbon), Raney nickel or palladium hydroxide.

The reaction (XXI)→(I-F) is generally carried out in a temperature range from +20° C. to +100° C. The conversion can be carried out at atmospheric or elevated pressure (for example in the range from 0.5 to 100 bar). In general, 1 to 3 bar are employed.

Process step (I-F)+(XXII)→(I-G) is carried out in a solvent which is inert under the reaction conditions. Suitable solvents are, for example, halogenated hydrocarbons such as dichloromethane, trichloromethane, carbon tetrachloride, trichloroethylene or chlorobenzene, ethers such as diethyl ether, dioxane, dimethoxyethane, tetrahydrofuran, glycol dimethyl ether or diethylene glycol dimethyl ether, hydrocarbons such as benzene, xylene, toluene, hexane, cyclohexane or mineral oil fractions, or other solvents such as dimethylformamide (DMF), dimethyl sulphoxide (DMSO), N,N'-dimethylpropyleneurea (DMPU), N-methylpyrrolidone (NMP), pyridine, acetonitrile or sulpholane. It is also possible to use mixtures of the solvents mentioned. Preference is given to DMF or a mixture of DMF and dichloromethane.

The conversion (I-F)+(XXII)→(I-G) is optionally carried out in the presence of a suitable base. Suitable bases for this conversion are the customary inorganic or organic bases. These preferably include alkali metal or alkaline earth metal carbonates such as lithium carbonate, sodium carbonate, potassium carbonate, calcium carbonate or caesium carbonate, alkali metal alkoxides such as sodium methoxide or potassium methoxide, sodium ethoxide or potassium ethoxide or sodium or potassium tert-butoxide, alkali metal hydrides such as sodium hydride or potassium hydride, amides such as sodium amide, lithium bis(trimethylsilyl)

amide, sodium bis(trimethylsilyl)amide or potassium bis(trimethylsilyl)amide or lithium diisopropylamide, or organic amines such as triethylamine, N-methylmorpholine, N-methylpiperidine, N,N-diisopropylethylamine, pyridine, 4-dimethylaminopyridine, 1,5-diazabicyclo[4.3.0]non-5-ene (DBN), 1,8-diazabicyclo[5.4.0]undec-7-ene (DBU) or 1,4-diazabicyclo[2.2.2]octane (DABCO®). Preference is given to using N,N-diisopropylethylamine.

The reaction (I-F)+(XXII)→(I-G) is generally carried out in a temperature range from 0° C. to +200° C., preferably from +10° C. to +50° C. The conversion can be carried out at atmospheric, elevated or reduced pressure (for example from 0.5 to 5 bar). The reaction is generally carried out at atmospheric pressure.

The preparation processes described can be illustrated by way of example by the following synthesis schemes (Schemes 1 to 8):

-continued

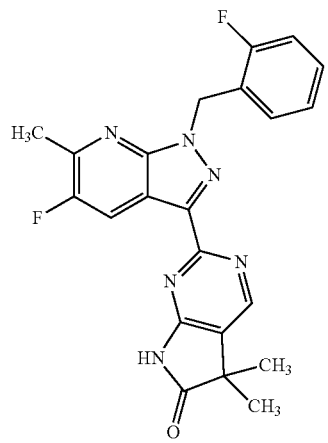

[a]: KOt-Bu, tert-butanol; b): diiodomethane, isopentyl nitrite; c): Pd/C, hydrogen, DMF].

Scheme 1

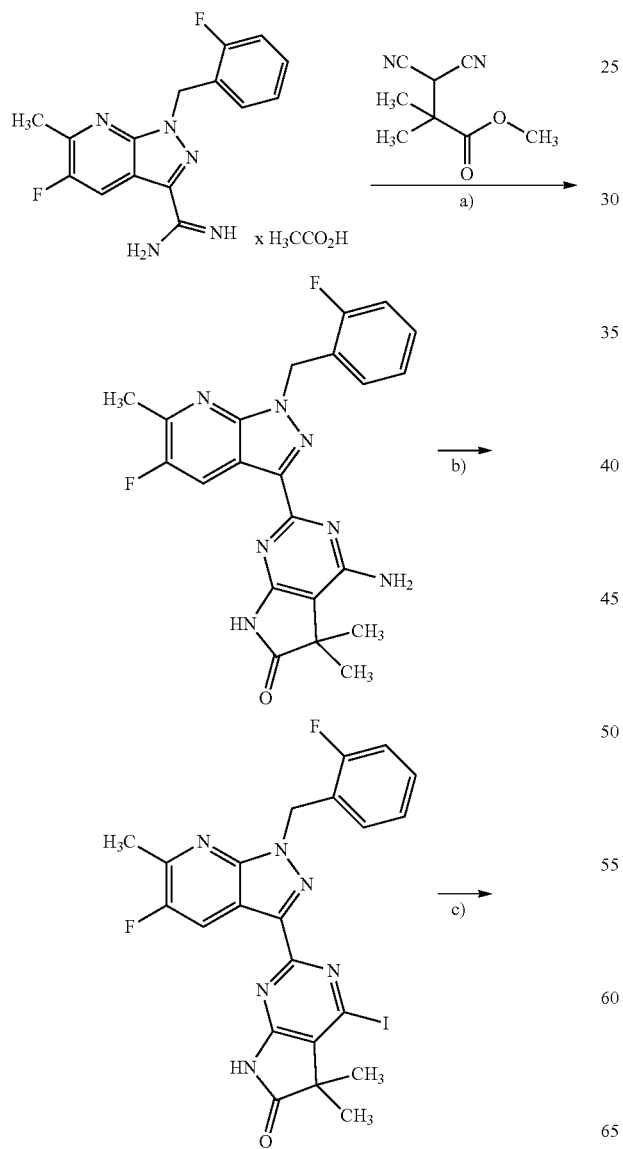

Scheme 2

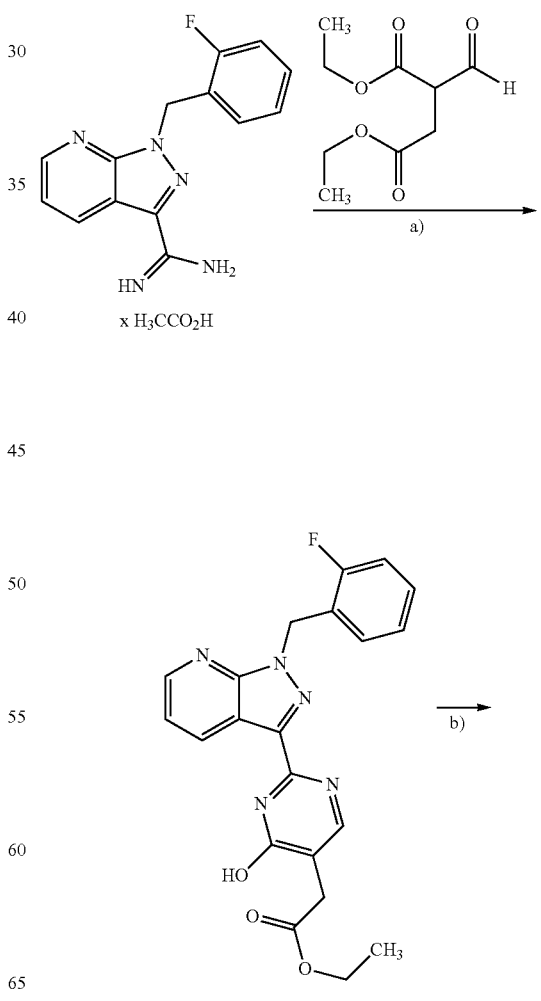

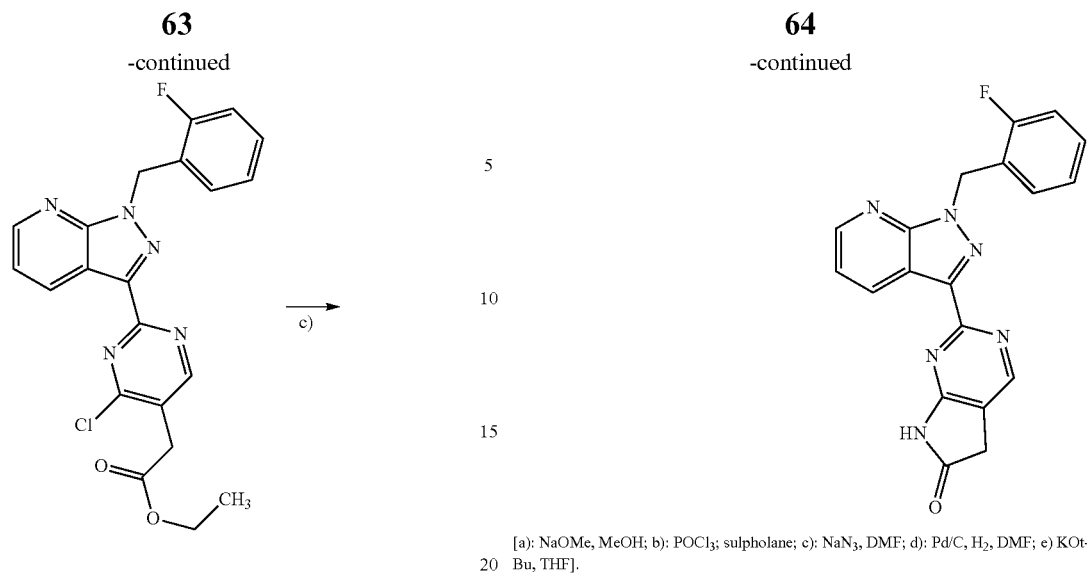
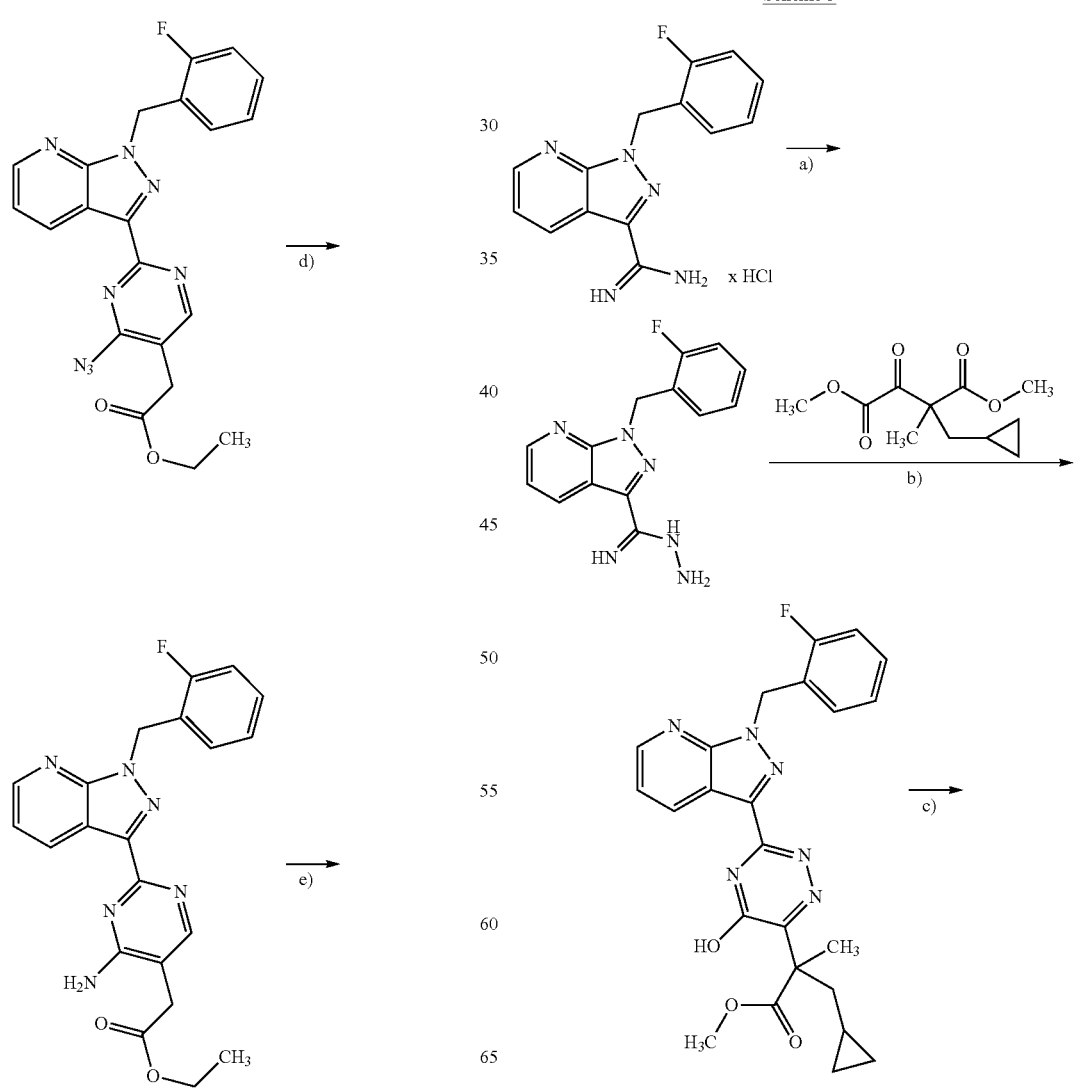
[a]: NaOMe, MeOH; b): POCl₃; sulpholane; c): NaN₃, DMF; d): Pd/C, H₂, DMF; e) KOt-Bu, THF].
Scheme 3

-continued
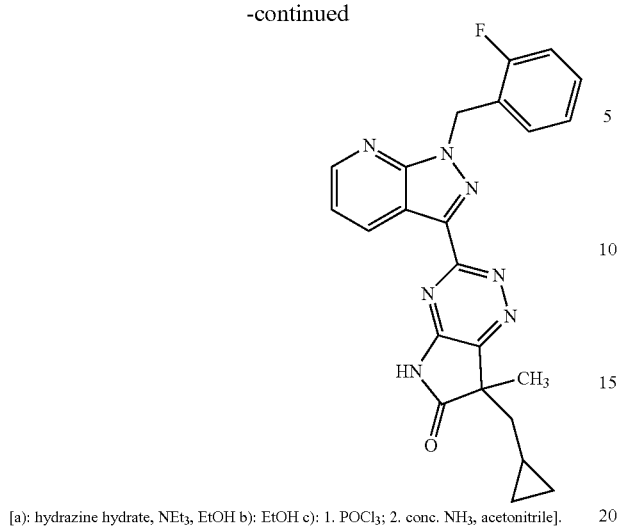
[a]: hydrazine hydrate, NEt3, EtOH b): EtOH c): 1. POCl3; 2. conc. NH3, acetonitrile].
Scheme 4
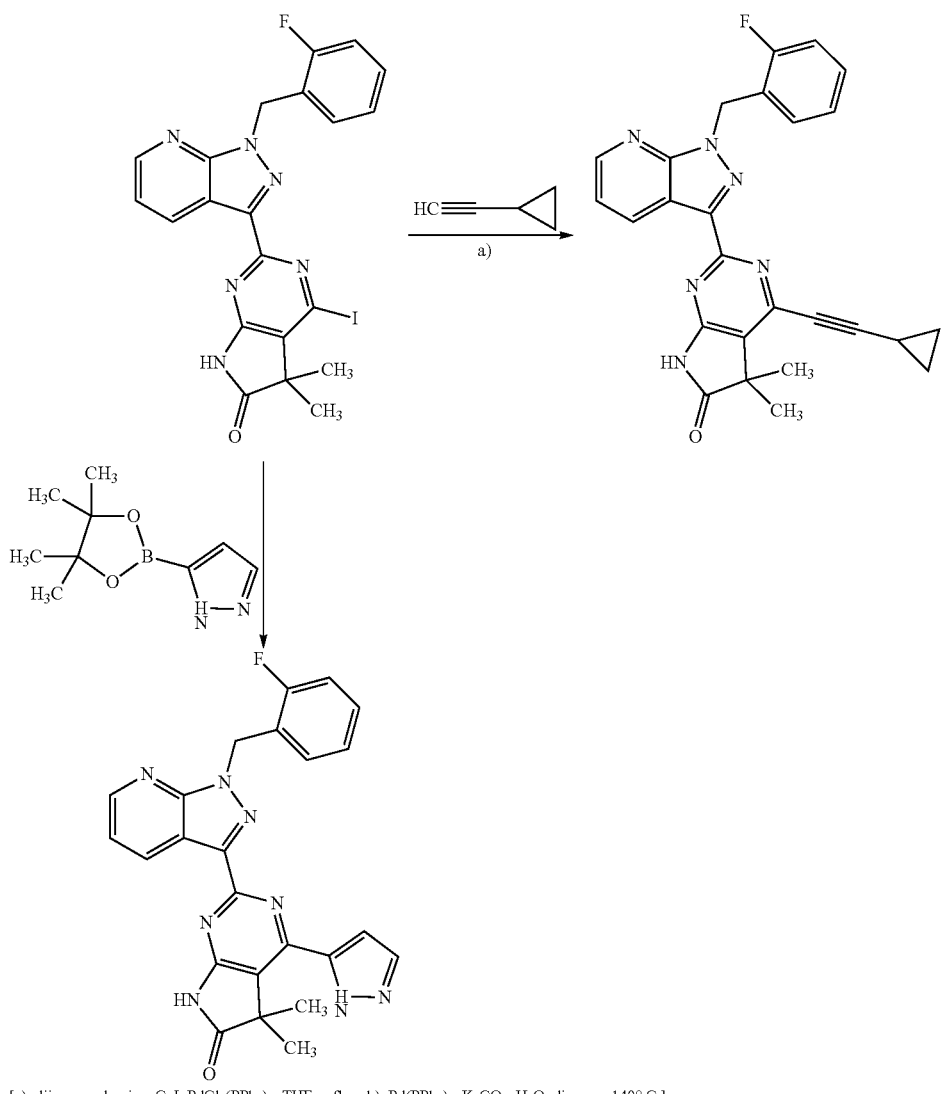
[a]: diisopropylamine, CuI, PdCl2(PPh3)2, THF, reflux; b): Pd(PPh3)4, K2CO3, H2O, dioxane, 140° C.].

Scheme 5
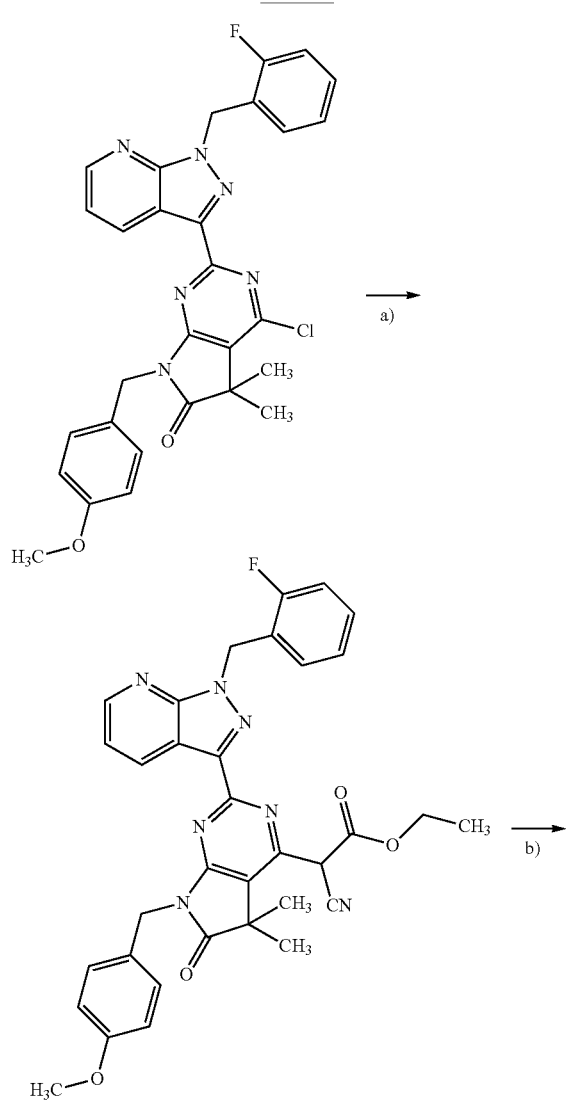
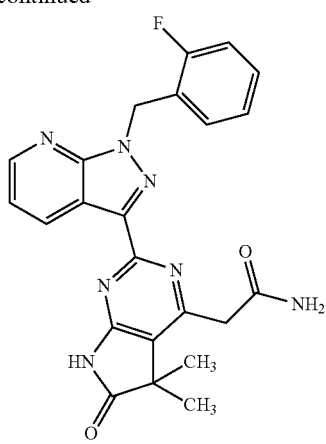
[a]: ethyl cyanoacetate, potassium tert-butoxide, DMF; b): trifluoroacetic acid, trifluoromethanesulphonic anhydride].
Scheme 6
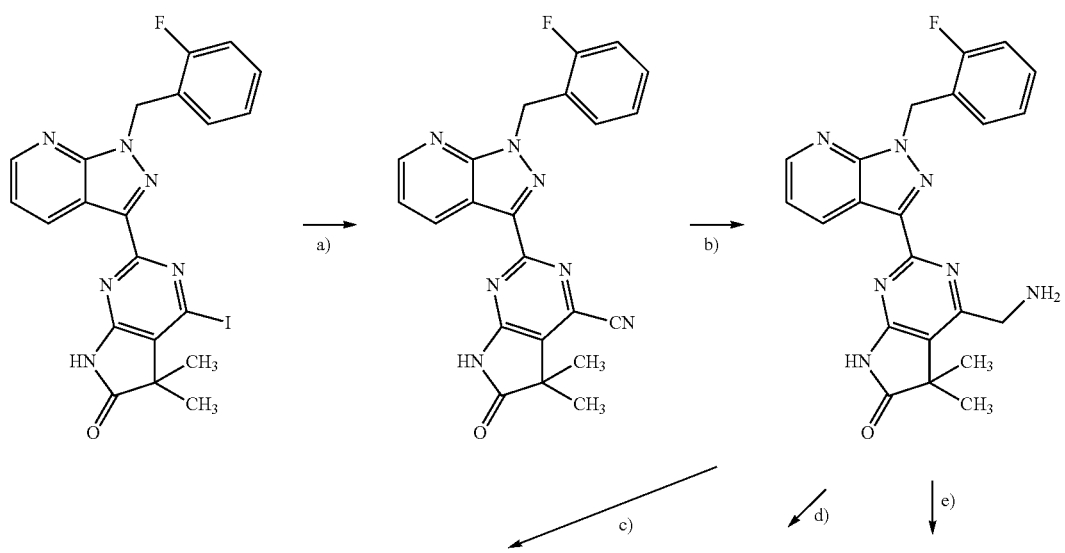

69 -continued 70

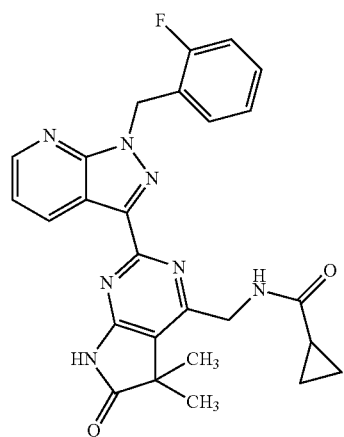
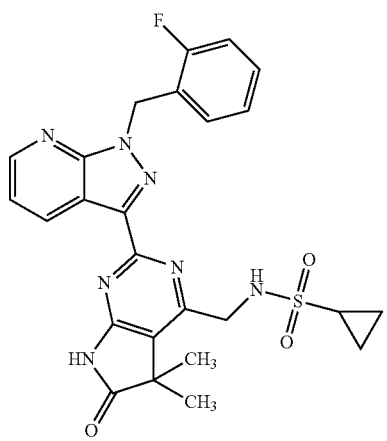
f)
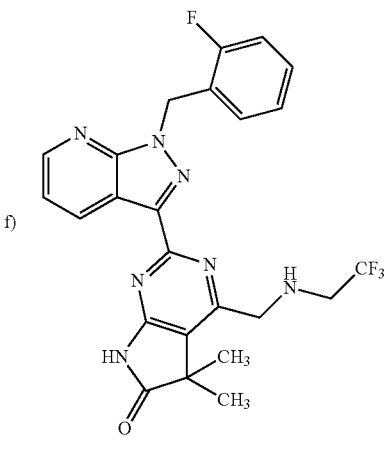

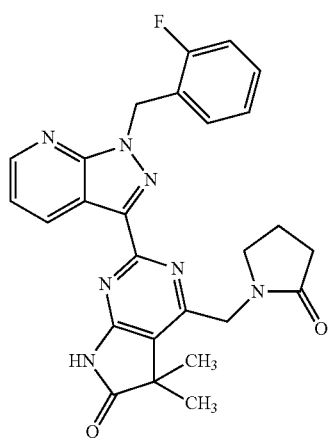

[a]: copper(I) cyanide, DMSO; b): hydrogen, palladium/carbon, acetic acid; c): cyclopropanecarbonyl chloride, N,N-diisopropylethylamine, dichloromethane, DMF; d): cyclopropanesulphonyl chloride, N,N-diisopropylethylamine, dichloromethane, DMF; e): 2,2,2-trifluoroethyl trichloromethanesulphonate, N,N-diisopropylethylamine, DMF; f): 1. 4-chlorobutanoyl chloride, N,N-diisopropylethylamine, dichloromethane, DMF, 2. sodium hydride].

Scheme 7

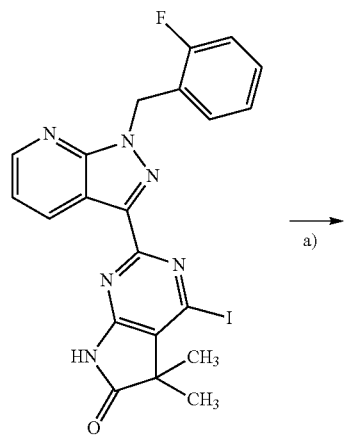
a)
-continued
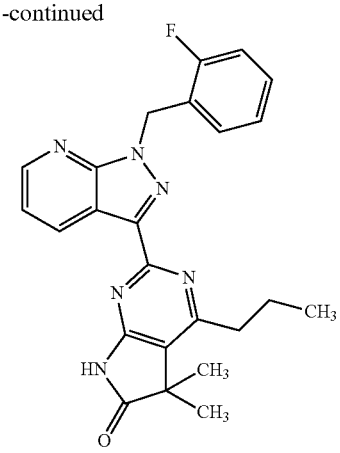

[a]: n-propylzine bromide, CuI, PdCl₂(dppf)CH₂Cl₂, dioxane, THF].

Scheme 8

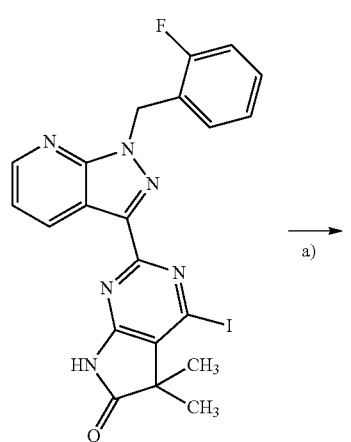

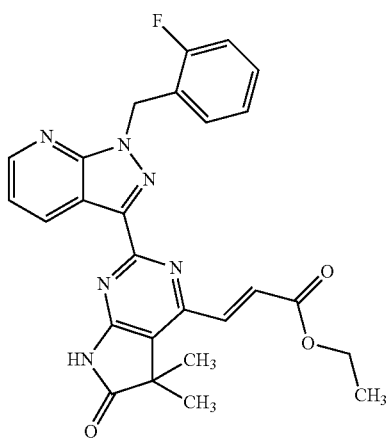

[a]: 2-(trimethylsilyl)ethoxymethyl chloride, Cs$_2$CO$_3$, DMF; b): ethyl acrylate, palladium(II) acetate, tetra-n-butylammonium iodide, triethylamine, DMF, water c): 1. trifluoroacetic acid, dichloromethane, 2. hydrochloric acid, dioxane].

In an alternative process, the preparation of the compounds of the formula (I) according to the invention can take place by reversing the order of the reaction steps using protective group chemistry, as shown by way of example in the synthesis scheme below (Scheme 9):

Scheme 9

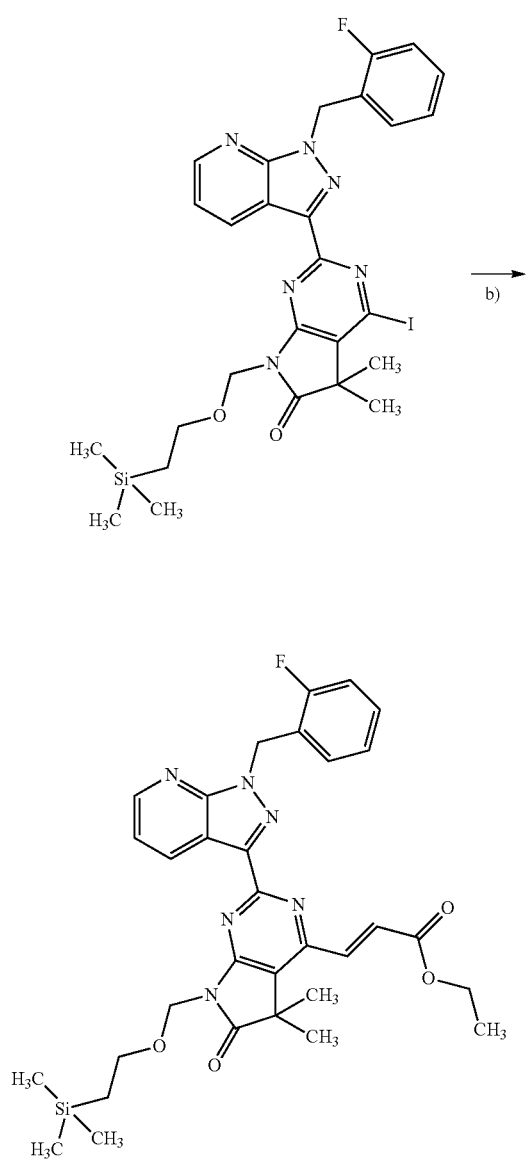

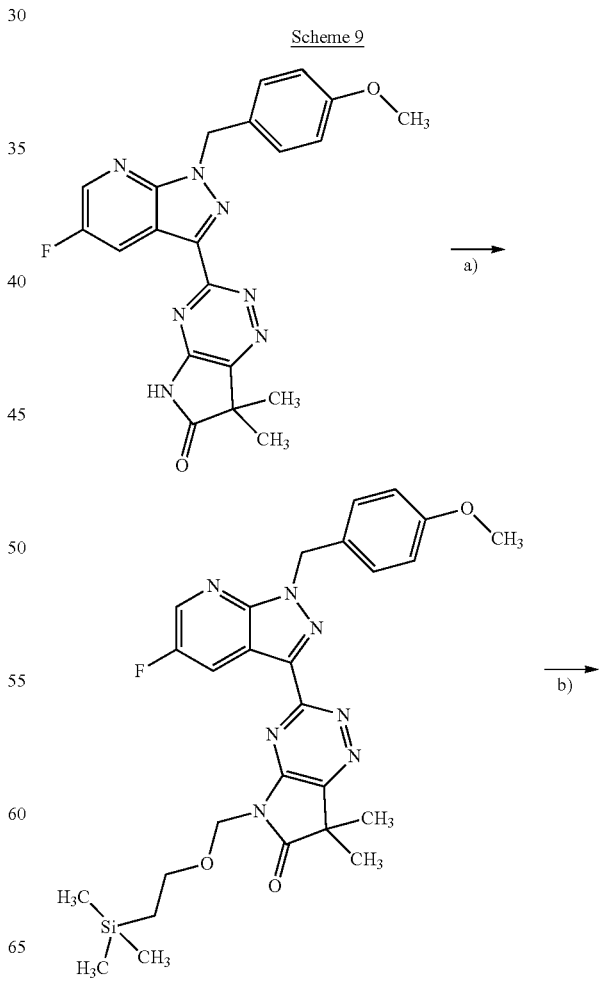

-continued

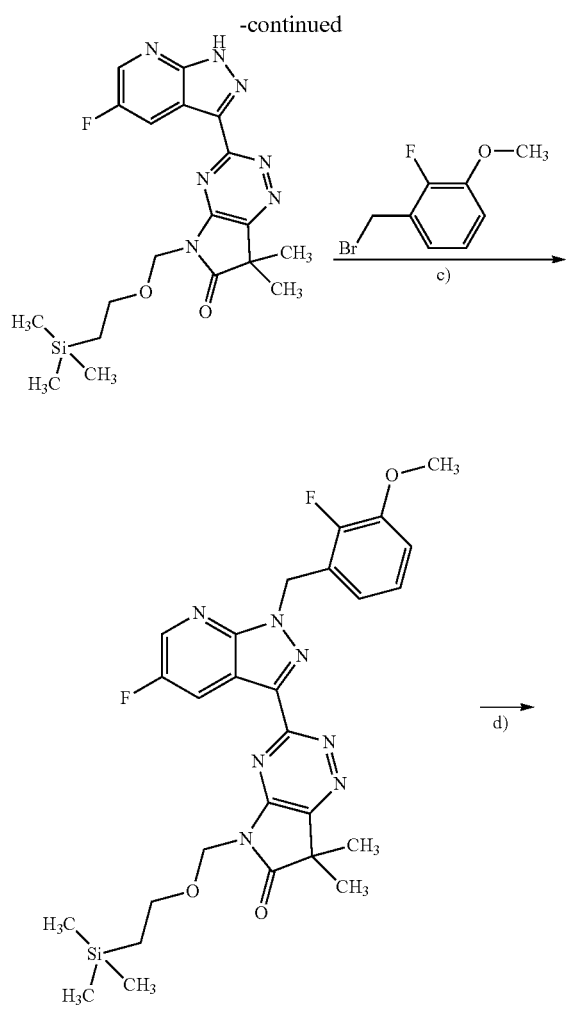

[a]: 2-(trimethylsilyl)ethoxymethyl chloride, Cs₂CO₃, DMF; b): ammonium cerium(IV) nitrate, acetonitrile, water; c): CS₂CO₃, DMF; d): 1) TFA, dichloromethane, 2) HCl, ethanol].

Further compounds according to the invention can optionally also be prepared by conversions of functional groups of individual substituents, especially those listed for L and $R^5$, proceeding from compounds of the formulae (I), (V), (VIII) and (XIII) obtained by the above processes. These conversions are performed by customary methods known to those skilled in the art and include, for example, reactions such as nucleophilic and electrophilic substitutions, oxidations, reductions, hydrogenations, transition metal-catalysed coupling reactions, Grignard reactions, eliminations, alkylation, acylation, amination, esterification, ester cleavage, etherification, ether cleavage, formation of carbonamides, and introduction and removal of temporary protective groups.

Preferred conversions are illustrated in an exemplary manner by the synthesis schemes below (Schemes 10-13).

Scheme 10

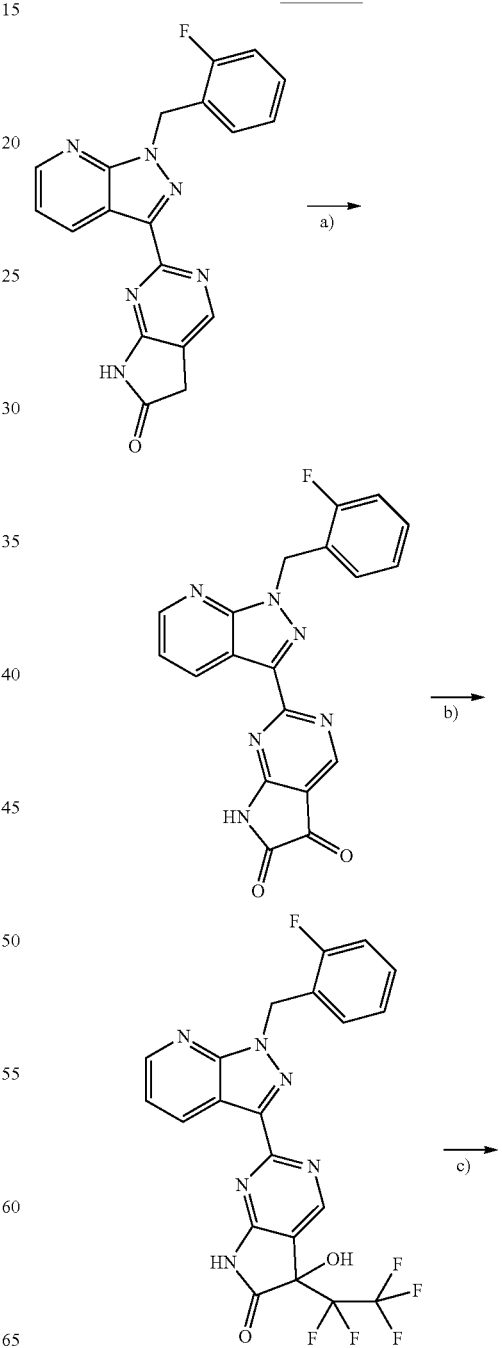

75
-continued
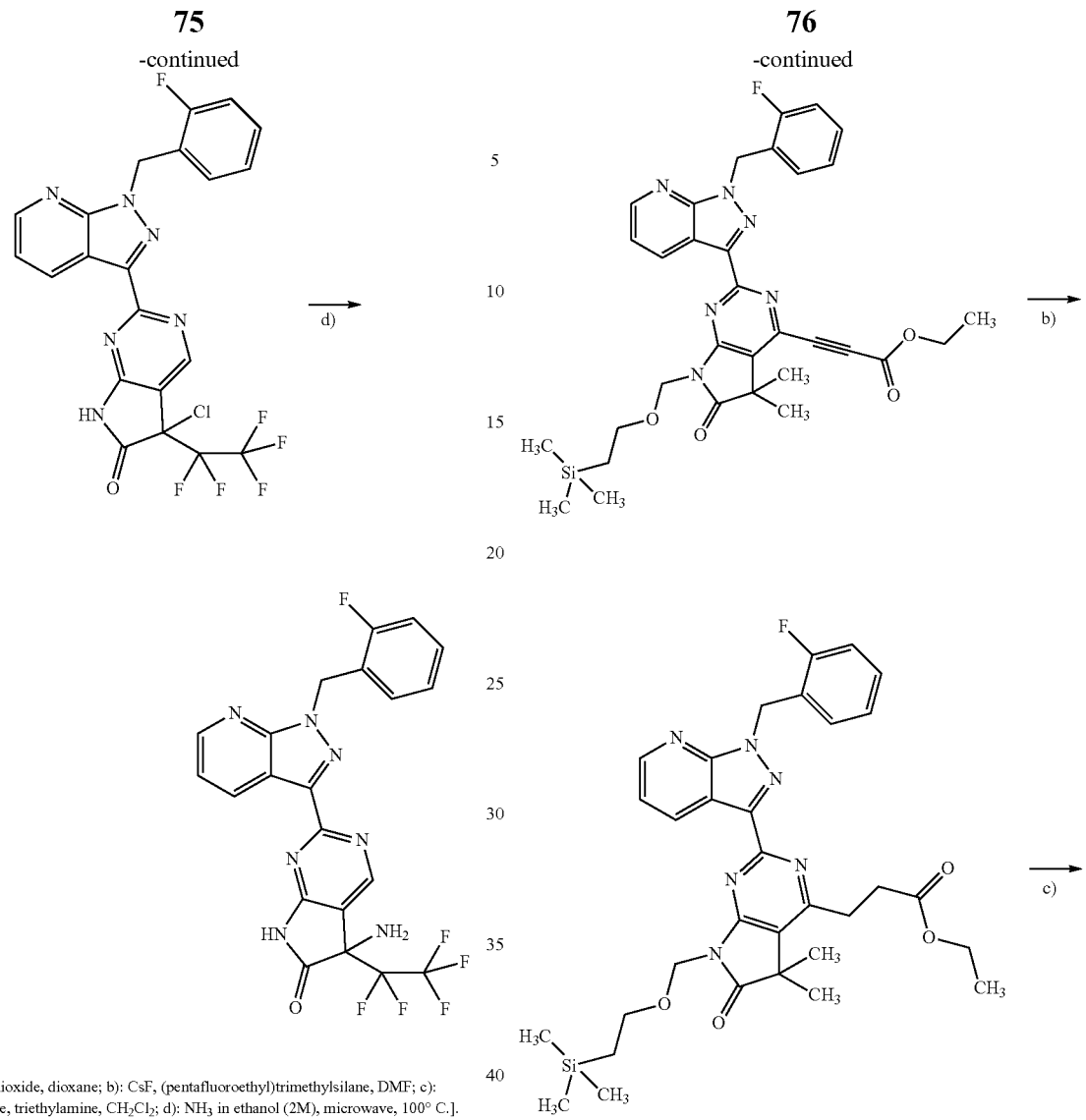
[a]: selenium dioxide, dioxane; b): CsF, (pentafluoroethyl)trimethylsilane, DMF; c): thionyl chloride, triethylamine, CH₂Cl₂; d): NH₃ in ethanol (2M), microwave, 100° C.].
Scheme 11
76
-continued
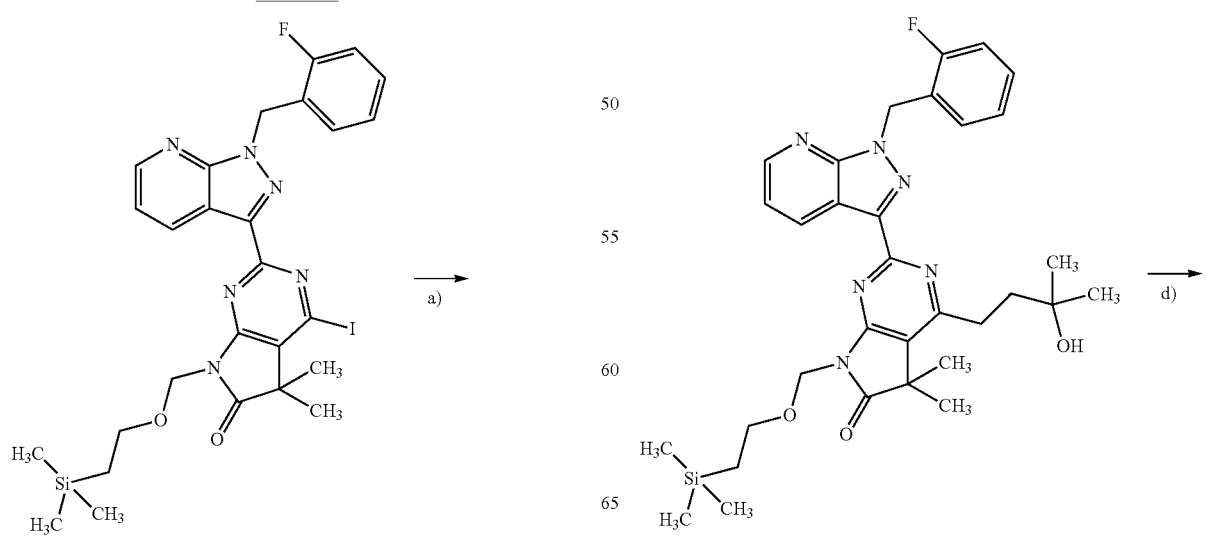

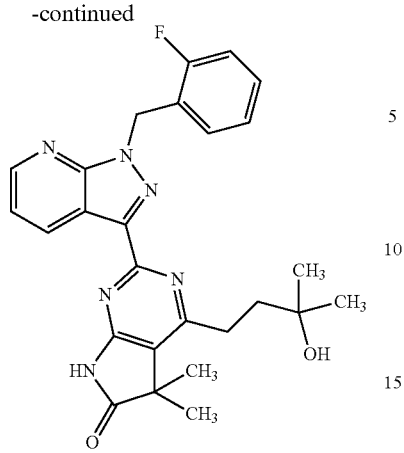

[a): ethyl propiolate, copper(I) iodide, sodium bicarbonate, dichlorobistriphenylphosphinepalladium(II), DMF; b): palladium/carbon, hydrogen, ethyl acetate c): methylmagnesium bromide, THF d): 1. trifluoroacetic acid, dichloromethane, 2. hydrochloric acid, dioxane.

Scheme 12

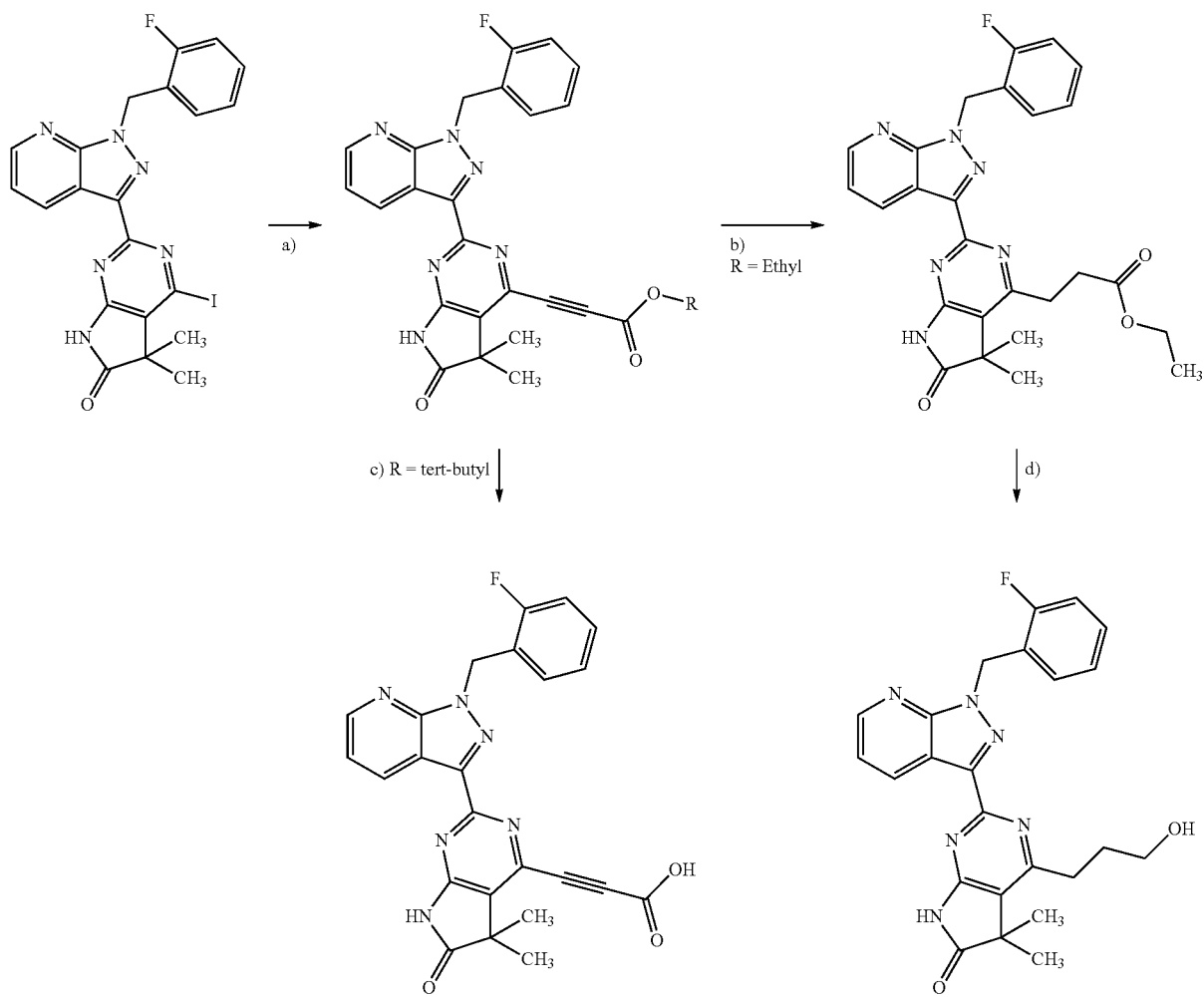

[a): ethyl propiolate, copper(I) iodide, sodium bicarbonate, dichlorobistriphenylphosphinepalladium(II), DMF; b): palladium/carbon, hydrogen, ethyl acetate c): trifluoroacetic acid, dichloromethane: d): lithium triethylborohydride, THF].

Scheme 13

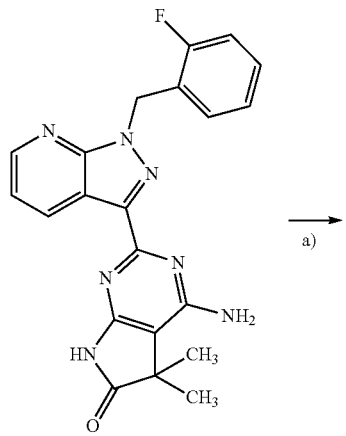

a)

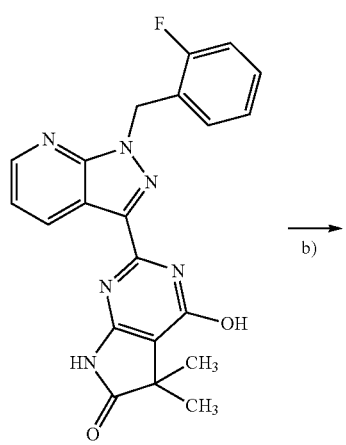

b)

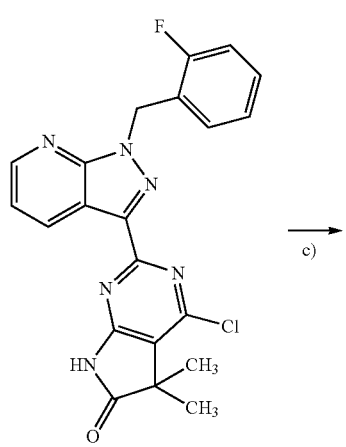

c)

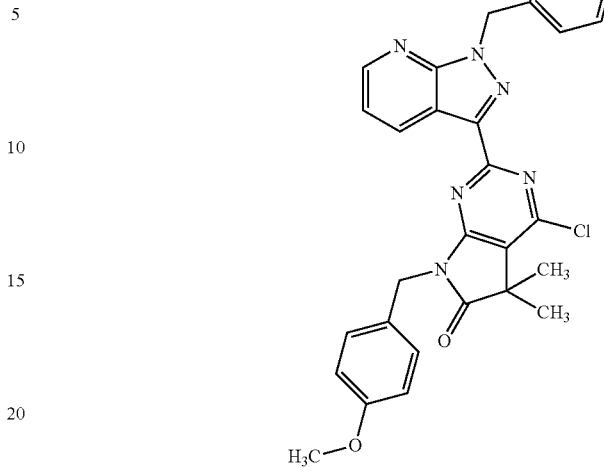

-continued

[a]: sodium nitrite, trifluoroacetic acid, water; b): phosphorus oxychloride; c): 4-methoxybenzyl chloride, Cs₂CO₃, DMF].

The compounds of the formula (II) are known from the literature (see, for example WO 2011/147809, WO 03/095451, Example 6A) or can be prepared analogously to processes known from the literature.

The compounds of the formulae (VI), (XI), (XV-A), (XV-B), (XV-C), (XV-D), (XVI), (XIX) and (XXII) are commercially available or known from the literature, or can be prepared in analogy to procedures known from the literature.

The compounds according to the invention act as potent stimulators of soluble guanylate cyclase and inhibitors of phosphodiesterase-5, have useful pharmacological properties and have an improved therapeutic profile, for example with respect to the in vivo properties thereof and/or the pharmacokinetic characteristics and/or metabolic profile thereof. They are therefore suitable for the treatment and/or prophylaxis of diseases in humans and animals The compounds according to the invention cause vasorelaxation and inhibition of platelet aggregation, and lead to a decrease in blood pressure and to a rise in coronary blood flow. These effects are mediated by a direct stimulation of soluble guanylate cyclase and an intracellular rise in cGMP. In addition, the compounds according to the invention enhance the action of substances which increase the cGMP level, for example EDRF (endothelium-derived relaxing factor), NO donors, protoporphyrin IX, arachidonic acid or phenylhydrazine derivatives.

The compounds according to the invention are suitable for the treatment and/or prophylaxis of cardiovascular, pulmonary, thromboembolic and fibrotic disorders.

Accordingly, the compounds according to the invention can be used in medicaments for the treatment and/or prophylaxis of cardiovascular disorders such as, for example, hypertension, resistant hypertension, acute and chronic heart failure, coronary heart disease, stable and unstable angina pectoris, peripheral and cardiac vascular disorders, arrhythmias, atrial and ventricular arrhythmias and impaired conduction such as, for example, atrioventricular blocks degrees I-III (AB block supraventricular tachyarrhythmia, atrial fibrillation, atrial flutter, ventricular fibrillation, ventricular flutter, ventricular tachyarrhythmia, Torsade de pointes tachycardia, atrial and ventricular extrasystoles, AV-junctional extrasystoles, sick sinus syndrome, syncopes, AV-nodal re-entry tachycardia, Wolff-Parkinson-White syndrome, of acute coronary syndrome (ACS), autoimmune cardiac disorders (pericarditis, endocarditis, valvolitis, aortitis, cardiomyopathies), shock such as cardiogenic shock, septic shock and anaphylactic shock, aneurysms, boxer cardiomyopathy (premature ventricular contraction (PVC)), for the treatment and/or prophylaxis of thromboembolic disorders and ischaemias such as myocardial ischaemia, myocardial infarction, stroke, cardiac hypertrophy, transient and ischaemic attacks, preeclampsia, inflammatory cardiovascular disorders, spasms of the coronary arteries and peripheral arteries, oedema formation such as, for example, pulmonary oedema, cerebral oedema, renal oedema or oedema caused by heart failure, peripheral circulatory disturbances, reperfusion damage, arterial and venous thromboses, microalbuminuria, myocardial insufficiency, endothelial dysfunction, to prevent restenoses, for example after thrombolysis therapies, percutaneous transluminal angioplasties (PTA), transluminal coronary angioplasties (PTCA), heart transplants and bypass operations, and also micro- and macrovascular damage (vasculitis), increased levels of fibrinogen and of low-density lipoprotein (LDL) and increased concentrations of plasminogen activator inhibitor 1 (PAI-1), and also for the treatment and/or prophylaxis of erectile dysfunction and female sexual dysfunction.

In the context of the present invention, the term "heart failure" encompasses both acute and chronic forms of heart failure, and also more specific or related types of disease, such as acute decompensated heart failure, right heart failure, left heart failure, global failure, ischaemic cardiomyopathy, dilated cardiomyopathy, hypertrophic cardiomyopathy, idiopathic cardiomyopathy, congenital heart defects, heart failure associated with heart valve defects, mitral valve stenosis, mitral valve insufficiency, aortic valve stenosis, aortic valve insufficiency, tricuspid valve stenosis, tricuspid valve insufficiency, pulmonary valve stenosis, pulmonary valve insufficiency, combined heart valve defects, myocardial inflammation (myocarditis), chronic myocarditis, acute myocarditis, viral myocarditis, diabetic heart failure, alcoholic cardiomyopathy, cardiac storage disorders, diastolic heart failure and systolic heart failure, and acute phases of worsening of existing chronic heart failure (worsening heart failure).

In addition, the compounds according to the invention can also be used for the treatment and/or prophylaxis of arteriosclerosis, impaired lipid metabolism, hypolipoproteinaemias, dyslipidaemias, hypertriglyceridaemias, hyperlipidaemias, hypercholesterolaemias, abetalipoproteinaemia, sitosterolaemia, xanthomatosis, Tangier disease, adiposity, obesity and of combined hyperlipidaemias and metabolic syndrome.

The compounds according to the invention can additionally be used for the treatment and/or prophylaxis of primary and secondary Raynaud's phenomenon, of microcirculation impairments, claudication, peripheral and autonomic neuropathies, diabetic microangiopathies, diabetic retinopathy, diabetic ulcers on the extremities, gangrene, CREST syndrome, erythematosis, onychomycosis, rheumatic disorders and for promoting wound healing. The compounds according to the invention are also suitable for treatment of muscular dystrophy, such as Becker-Kiener muscular dystrophy (BMD) and Duchenne muscular dystrophy (DMD).

The compounds according to the invention are furthermore suitable for treating urological disorders such as, for example, benign prostate syndrome (BPS), benign prostate hyperplasia (BPH), benign prostate enlargement (BPE), bladder outlet obstruction (BOO), lower urinary tract syndromes (LUTS, including Feline Urological Syndrome (FUS)), disorders of the urogenital system including neurogenic overactive bladder (OAB) and (IC), incontinence (UI) such as, for example, mixed urinary incontinence, urge urinary incontinence, stress urinary incontinence or overflow urinary incontinence (MUI, UUI, SUI, OUI), pelvic pain, benign and malignant disorders of the organs of the male and female urogenital system.

The compounds according to the invention are furthermore suitable for the treatment and/or prophylaxis of kidney disorders, in particular of acute and chronic renal insufficiency and acute and chronic renal failure. In the context of the present invention, the term renal insufficiency comprises both acute and chronic manifestations thereof, as well as underlying or related kidney diseases such as renal hypoperfusion, intradialytic hypotension, obstructive uropathy, glomerulopathies, glomerulonephritis, acute glomerulonephritis, glomerulosclerosis, tubulointerstitial diseases, nephropathic diseases such as primary and congenital kidney disease, nephritis, immunological kidney diseases such as kidney graft rejection and immunocomplex-induced kidney diseases, nephropathy induced by toxic substances, nephropathy induced by contrast agents, diabetic and non-diabetic nephropathy, pyelonephritis, renal cysts, nephrosclerosis, hypertensive nephrosclerosis and nephrotic syndrome, which can be characterized diagnostically for example by abnormally reduced creatinine and/or water excretion, abnormally raised blood concentrations of urea, nitrogen, potassium and/or creatinine, altered activity of renal enzymes such as, for example, glutamyl synthetase, altered urine osmolarity or urine volume, increased microalbuminuria, macroalbuminuria, lesions on glomerulae and arterioles, tubular dilatation, hyperphosphataemia and/or need for dialysis. The present invention also encompasses the use of the compounds according to the invention for the treatment and/or prophylaxis of sequelae of renal insufficiency, for example pulmonary oedema, heart failure, uraemia, anaemia, electrolyte disturbances (for example hyperkalaemia, hyponatraemia) and disturbances in bone and carbohydrate metabolism.

Furthermore, the compounds according to the invention are also suitable for the treatment and/or prophylaxis of asthmatic disorders, pulmonary arterial hypertension (PAH) and other forms of pulmonary hypertension (PH) including left-heart disease, HIV, sickle cell anaemia, thromboembolisms (CTEPH), sarcoidosis, COPD or pulmonary fibrosis-associated pulmonary hypertension, chronic-obstructive pulmonary disease (COPD), acute respiratory distress syndrome (ARDS), acute lung injury (ALI), alpha-1-antitrypsin deficiency (AATD), pulmonary fibrosis, pulmonary emphysema (for example pulmonary emphysema induced by cigarette smoke) and cystic fibrosis (CF). In addition, the compounds mentioned can be used as bronchodilators.

The compounds described in the present invention are also active compounds for control of central nervous system disorders characterized by disturbances of the NO/cGMP system. They are suitable in particular for improving perception, concentration, learning or memory after cognitive impairments like those occurring in particular in association with situations/diseases/syndromes such as mild cognitive impairment, age-associated learning and memory impairments, age-associated memory losses, vascular dementia, craniocerebral trauma, stroke, dementia occurring after strokes (post stroke dementia), post-traumatic craniocerebral trauma, general concentration impairments, concentration impairments in children with learning and memory problems, Alzheimer's disease, Lewy body dementia, dementia with degeneration of the frontal lobes including Pick's syndrome, Parkinson's disease, progressive nuclear palsy, dementia with corticobasal degeneration, amyolateral sclerosis (ALS), Huntington's disease, demyelinisation, multiple sclerosis, thalamic degeneration, Creutzfeld-Jacob dementia, HIV dementia, schizophrenia with dementia or Korsakoff's psychosis. They are also suitable for the treatment and/or prophylaxis of central nervous system disorders such as states of anxiety, tension and depression, CNS-related sexual dysfunctions and sleep disturbances, and for controlling pathological disturbances of the intake of food, stimulants and addictive substances.

Furthermore, the compounds according to the invention are also suitable for regulating cerebral blood flow and are thus effective agents for control of migraine. They are also suitable for prophylaxis and control of sequelae of cerebral infarction (cerebral apoplexy) such as stroke, cerebral ischaemia and craniocerebral trauma. The compounds according to the invention can likewise be employed for controlling states of pain and tinnitus.

In addition, the compounds according to the invention have antiinflammatory action and can therefore be used as antiinflammatory agents for the treatment and/or prophylaxis of sepsis (SIRS), multiple organ failure (MODS, MOF), inflammatory disorders of the kidney, chronic intestinal inflammations (IBD, Crohn's disease, UC), pancreatitis, peritonitis, rheumatoid disorders, inflammatory skin diseases and inflammatory eye diseases.

Furthermore, the compounds according to the invention can also be used for the treatment and/or prophylaxis of autoimmune diseases.

The compounds according to the invention are furthermore suitable for the treatment and/or prophylaxis of fibrotic disorders of the internal organs such as, for example, the lung, the heart, the kidney, the bone marrow and in particular the liver, and also dermatological fibroses and fibrotic eye disorders. In the context of the present invention, the term fibrotic disorders includes in particular the following terms: hepatic fibrosis, cirrhosis of the liver, pulmonary fibrosis, endomyocardial fibrosis, nephropathy, glomerulonephritis, interstitial renal fibrosis, fibrotic damage resulting from diabetes, bone marrow fibrosis and similar fibrotic disorders, scleroderma, morphea, keloids, hypertrophic scarring (also following surgical procedures), naevi, diabetic retinopathy, proliferative vitroretinopathy and disorders of the connective tissue (for example sarcoidosis).

The compounds according to the invention are furthermore suitable for controlling postoperative scarring, for example as a result of glaucoma operations.

The compounds according to the invention can also be used cosmetically for ageing and keratinized skin.

Moreover, the compounds according to the invention are suitable for the treatment and/or prophylaxis of hepatitis, neoplasms, osteoporosis, glaucoma and gastroparesis.

The present invention further provides for the use of the compounds according to the invention for the treatment and/or prophylaxis of disorders, in particular the disorders mentioned above.

The present invention further provides for the use of the compounds according to the invention for the treatment and/or prophylaxis of heart failure, angina pectoris, hypertension, pulmonary hypertension, ischaemias, vascular disorders, renal insufficiency, thromboembolic disorders, fibrotic disorders and arteriosclerosis.

The present invention further provides the compounds according to the invention for use in a method for treatment and/or prophylaxis of heart failure, angina pectoris, hypertension, pulmonary hypertension, ischaemias, vascular disorders, renal insufficiency, thromboembolic disorders, fibrotic disorders and arteriosclerosis.

The present invention further provides for the use of the compounds according to the invention for production of a medicament for the treatment and/or prophylaxis of disorders, especially of the aforementioned disorders.

The present invention further provides for the use of the compounds according to the invention for producing a medicament for the treatment and/or prophylaxis of heart failure, angina pectoris, hypertension, pulmonary hypertension, ischaemias, vascular disorders, renal insufficiency, thromboembolic disorders, fibrotic disorders and arteriosclerosis.

The present invention further provides a method for the treatment and/or prophylaxis of disorders, in particular the disorders mentioned above, using an effective amount of at least one of the compounds according to the invention.

The present invention further provides a method for the treatment and/or prophylaxis of heart failure, angina pectoris, hypertension, pulmonary hypertension, ischaemias, vascular disorders, renal insufficiency, thromboembolic disorders, fibrotic disorders and arteriosclerosis using an effective amount of at least one of the compounds according to the invention.

The compounds according to the invention can be employed alone or, if required, in combination with other active compounds. The present invention further provides medicaments comprising at least one of the compounds according to the invention and one or more further active compounds, especially for the treatment and/or prophylaxis of the aforementioned disorders. Preferred examples of suitable active compound combinations include:

organic nitrates and NO donors, for example sodium nitroprusside, nitroglycerin, isosorbide mononitrate, isosorbide dinitrate, molsidomine or SIN-1, and inhaled NO;

compounds which inhibit the breakdown of cyclic guanosine monophosphate (cGMP), for example inhibitors of phosphodiesterases (PDE) 1, 2 and/or 5, in particular PDE 5 inhibitors such as sildenafil, vardenafil and tadalafil;

agents having antithrombotic activity, for example and with preference from the group of platelet aggregation inhibitors, of anticoagulants or of profibrinolytic substances;

active compounds lowering blood pressure, for example and preferably from the group of calcium antagonists, angiotensin AII antagonists, ACE inhibitors, endothelin antagonists, renin inhibitors, alpha-receptor blockers, beta-receptor blockers, mineralocorticoid receptor antagonists, and of diuretics; and/or active compounds altering lipid metabolism, for example and with preference from the group of thyroid receptor agonists, cholesterol synthesis inhibitors such as, by way of example and preferably, HMG-CoA reductase inhibitors or squalene synthesis inhibitors, of ACAT inhibitors, CETP inhibitors, MTP inhibitors, PPAR-alpha, PPAR-gamma and/or PPAR-delta agonists, cholesterol absorption inhibitors, lipase inhibitors, polymeric bile acid adsorbents, bile acid reabsorption inhibitors and lipoprotein(a) antagonists.

Antithrombotic agents are preferably understood to mean compounds from the group of the platelet aggregation inhibitors, the anticoagulants or the profibrinolytic substances.

In a preferred embodiment of the invention, the compounds according to the invention are administered in combination with a platelet aggregation inhibitor, by way of example and with preference aspirin, clopidogrel, ticlopidin or dipyridamole.

In a preferred embodiment of the invention, the compounds according to the invention are administered in combination with a thrombin inhibitor, by way of example and with preference ximelagatran, dabigatran, melagatran, bivalirudin or clexane.

In a preferred embodiment of the invention, the compounds according to the invention are administered in combination with a GPIIb/IIIa antagonist such as, by way of example and with preference, tirofiban or abciximab.

In a preferred embodiment of the invention, the inventive compounds are administered in combination with a factor Xa inhibitor, preferred examples being rivaroxaban, DU-176b, apixaban, otamixaban, fidexaban, razaxaban, fondaparinux, idraparinux, PMD-3112, YM-150, KFA-1982, EMD-503982, MCM-17, MLN-1021, DX 9065a, DPC 906, JTV 803, SSR-126512 or SSR-128428.

In a preferred embodiment of the invention, the compounds according to the invention are administered in combination with heparin or with a low molecular weight (LMW) heparin derivative.

In a preferred embodiment of the invention, the compounds according to the invention are administered in combination with a vitamin K antagonist, by way of example and with preference coumarin.

Hypotensive agents are preferably understood to mean compounds from the group of calcium antagonists, angiotensin AII antagonists, ACE inhibitors, endothelin antagonists, renin inhibitors, alpha-receptor blockers, beta-receptor blockers, mineralocorticoid receptor antagonists, and the diuretics.

In a preferred embodiment of the invention, the compounds according to the invention are administered in combination with a calcium antagonist, by way of example and with preference nifedipine, amlodipine, verapamil or diltiazem.

In a preferred embodiment of the invention, the compounds according to the invention are administered in combination with an alpha-1-receptor blocker, by way of example and with preference prazosin.

In a preferred embodiment of the invention, the compounds according to the invention are administered in combination with a beta-receptor blocker, by way of example and with preference propranolol, atenolol, timolol, pindolol, alprenolol, oxprenolol, penbutolol, bupranolol, metipranolol, nadolol, mepindolol, carazalol, sotalol, metoprolol, betaxolol, celiprolol, bisoprolol, carteolol, esmolol, labetalol, carvedilol, adaprolol, landiolol, nebivolol, epanolol or bucindolol.

In a preferred embodiment of the invention, the compounds according to the invention are administered in combination with an angiotensin AII antagonist, by way of example and with preference losartan, candesartan, valsartan, telmisartan or embusartan.

In a preferred embodiment of the invention, the compounds according to the invention are administered in combination with an ACE inhibitor, by way of example and with preference enalapril, captopril, lisinopril, ramipril, delapril, fosinopril, quinopril, perindopril or trandopril.

In a preferred embodiment of the invention, the compounds according to the invention are administered in combination with an endothelin antagonist, by way of example and with preference bosentan, darusentan, ambrisentan or sitaxsentan.

In a preferred embodiment of the invention, the compounds according to the invention are administered in combination with a renin inhibitor, by way of example and with preference aliskiren, SPP-600 or SPP-800.

In a preferred embodiment of the invention, the compounds according to the invention are administered in combination with a mineralocorticoid receptor antagonist, by way of example and with preference spironolactone or eplerenone.

In a preferred embodiment of the invention, the compounds according to the invention are administered in combination with a loop diuretic, for example furosemide, torasemide, bumetanide and piretanide, with potassium-sparing diuretics, for example amiloride and triamterene, with aldosterone antagonists, for example spironolactone, potassium canrenoate and eplerenone, and also thiazide diuretics, for example hydrochlorothiazide, chlorthalidone, xipamide and indapamide.

Lipid metabolism modifiers are preferably understood to mean compounds from the group of the CETP inhibitors, thyroid receptor agonists, cholesterol synthesis inhibitors such as HMG-CoA reductase inhibitors or squalene synthesis inhibitors, the ACAT inhibitors, MTP inhibitors, PPAR-alpha, PPAR-gamma and/or PPAR-delta agonists, cholesterol absorption inhibitors, polymeric bile acid adsorbents, bile acid reabsorption inhibitors, lipase inhibitors and the lipoprotein (a) antagonists.

In a preferred embodiment of the invention, the compounds according to the invention are administered in combination with a CETP inhibitor, by way of example and with preference dalcetrapib, BAY 60-5521, anacetrapib or CETP vaccine (CETi-1).

In a preferred embodiment of the invention, the compounds according to the invention are administered in combination with a thyroid receptor agonist, by way of example and with preference D-thyroxin, 3,5,3'-triiodothyronin (T3), CGS 23425 or axitirome (CGS 26214).

In a preferred embodiment of the invention, the compounds according to the invention are administered in combination with an HMG-CoA reductase inhibitor from the class of statins, by way of example and with preference lovastatin, simvastatin, pravastatin, fluvastatin, atorvastatin, rosuvastatin or pitavastatin.

In a preferred embodiment of the invention, the compounds according to the invention are administered in combination with a squalene synthesis inhibitor, by way of example and with preference BMS-188494 or TAK-475.

In a preferred embodiment of the invention, the compounds according to the invention are administered in combination with an ACAT inhibitor, by way of example and with preference avasimibe, melinamide, pactimibe, eflucimibe or SMP-797.

In a preferred embodiment of the invention, the compounds according to the invention are administered in combination with an MTP inhibitor, by way of example and with preference implitapide, BMS-201038, R-103757 or JTT-130.

In a preferred embodiment of the invention, the compounds according to the invention are administered in combination with a PPAR-gamma agonist, by way of example and with preference pioglitazone or rosiglitazone.

In a preferred embodiment of the invention, the compounds according to the invention are administered in combination with a PPAR-delta agonist, by way of example and with preference GW 501516 or BAY 68-5042.

In a preferred embodiment of the invention, the compounds according to the invention are administered in combination with a cholesterol absorption inhibitor, by way of example and with preference ezetimibe, tiqueside or pamaqueside.

In a preferred embodiment of the invention, the compounds according to the invention are administered in combination with a lipase inhibitor, a preferred example being orlistat.

In a preferred embodiment of the invention, the compounds according to the invention are administered in combination with a polymeric bile acid adsorbent, by way of example and with preference cholestyramine, colestipol, colesolvam, CholestaGel or colestimide.

In a preferred embodiment of the invention, the compounds according to the invention are administered in combination with a bile acid reabsorption inhibitor, by way of example and with preference ASBT (=IBAT) inhibitors, for example AZD-7806, S-8921, AK-105, BARI-1741, SC-435 or SC-635.

In a preferred embodiment of the invention, the compounds according to the invention are administered in combination with a lipoprotein(a) antagonist, by way of example and with preference gemcabene calcium (CI-1027) or nicotinic acid.

The present invention further provides medicaments which comprise at least one compound according to the invention, typically together with one or more inert, nontoxic, pharmaceutically suitable auxiliaries, and for the use thereof for the aforementioned purposes.

The compounds according to the invention may act systemically and/or locally. For this purpose, they can be administered in a suitable manner, for example by the oral, parenteral, pulmonal, nasal, sublingual, lingual, buccal, rectal, dermal, transdermal, conjunctival or otic route, or as an implant or stent.

The compounds according to the invention can be administered in administration forms suitable for these administration routes.

Administration forms which function according to the prior art, release the compounds according to the invention rapidly and/or in a modified manner and contain the compounds according to the invention in crystalline and/or amorphized and/or dissolved form are suitable for oral administration, such as e.g. tablets (non-coated or coated tablets, for example with enteric coatings or coatings that dissolve in a delayed manner or are insoluble and control the release of the compound according to the invention), tablets or films/oblates, films/lyophilisates or capsules which disintegrate rapidly in the oral cavity (for example hard or soft gelatine capsules), sugar-coated tablets, granules, pellets, powders, emulsions, suspensions, aerosols or solutions.

Parenteral administration can bypass an absorption step (e.g. intravenously, intraarterially, intracardially, intraspinally or intralumbally) or include an absorption (e.g. intramuscularly, subcutaneously, intracutaneously, percutaneously or intraperitoneally). Suitable administration forms for parenteral administration include injection and infusion formulations in the form of solutions, suspensions, emulsions, lyophilisates or sterile powders.

For the other administration routes, suitable examples are inhalable medicament forms (including powder inhalers, nebulizers), nasal drops, solutions or sprays, tablets, films/ oblates or capsules for lingual, sublingual or buccal administration, suppositories, ear or eye preparations, vaginal capsules, aqueous suspensions (lotions, shaking mixtures), lipophilic suspensions, ointments, creams, transdermal therapeutic systems (e.g. patches), milk, pastes, foams, sprinkling powders, implants or stents.

Preference is given to oral or parenteral administration, especially oral administration.

The compounds according to the invention can be converted to the administration forms mentioned. This can be done in a manner known per se, by mixing with inert, nontoxic, pharmaceutically suitable excipients. These excipients include carriers (for example microcrystalline cellulose, lactose, mannitol), solvents (e.g. liquid polyethylene glycols), emulsifiers and dispersing or wetting agents (for example sodium dodecylsulphate, polyoxysorbitan oleate), binders (for example polyvinylpyrrolidone), synthetic and natural polymers (for example albumin), stabilizers (e.g. antioxidants, for example ascorbic acid), dyes (e.g. inorganic pigments, for example iron oxides) and flavour and/or odour correctants.

In general, it has been found to be advantageous in the case of parenteral administration to administer amounts of about 0.001 to 1 mg/kg, preferably about 0.01 to 0.5 mg/kg, of body weight to achieve effective results. In the case of oral administration, the dose is about 0.001 to 2 mg/kg, preferably about 0.001 to 1 mg/kg, of body weight.

It may nevertheless be necessary where appropriate to deviate from the stated amounts, specifically as a function of the body weight, route of administration, individual response to the active compound, nature of the preparation and time or interval over which administration takes place.

For instance, in some cases, less than the aforementioned minimum amount may be sufficient, while in other cases the upper limit mentioned must be exceeded. In the case of administration of greater amounts, it may be advisable to divide them into several individual doses over the day.

The working examples which follow illustrate the invention. The invention is not limited to the examples.

The percentages in the tests and examples which follow are, unless indicated otherwise, percentages by weight; parts are parts by weight. Solvent ratios, dilution ratios and concentration figures for liquid/liquid solutions are each based on volume.

A. EXAMPLES

Abbreviations and Acronyms aq. aqueous solution
calc. calculated
br s broad singlet (in NMR)
DCI direct chemical ionization (in MS)
DMF dimethylformamide
DMSO dimethyl sulphoxide
eq. equivalent(s)
ESI electrospray ionization (in MS)
Et ethyl
h hour(s)
HPLC high-pressure, high-performance liquid chromatography
HRMS high-resolution mass spectrometry
conc. concentrated
LC-MS liquid chromatography-coupled mass spectrometry
Me methyl
min minute(s)
MS mass spectrometry
NMR nuclear magnetic resonance spectrometry PdCl2(dppf)CH2Cl2 1,1'-bis(diphenylphosphino)ferrocenepalladium(II) dichloride/dichloromethane complex
Ph phenyl
RT room temperature
R$_t$ retention time (in HPLC)
THF tetrahydrofuran
UV ultraviolet spectrometry
v/v ratio by volume (of a solution)
LC/MS and MS Methods:
Method 1 (LC-MS):
Instrument: Waters ACQUITY SQD UPLC System; column: Waters Acquity UPLC HSS T3 1.8μ 50×1 mm; mobile phase A: 1 l of water+0.25 ml of 99% strength formic acid, mobile phase B: 1 l of acetonitrile+0.25 ml of 99% strength formic acid; gradient: 0.0 min 90% A→1.2 min 5% A→2.0 min 5% A; oven: 50° C.; flow rate: 0.40 ml/min; UV detection: 208-400 nm.
Method 2 (LC-MS):
Instrument: Waters ACQUITY SQD UPLC System; column: Waters Acquity UPLC HSS T3 1.8μ 30×2 mm; mobile phase A: 1 l of water+0.25 ml of 99% strength formic acid, mobile phase B: 1 l of acetonitrile+0.25 ml of 99% strength formic acid; gradient: 0.0 min 90% A→1.2 min 5% A→2.0 min 5% A; oven: 50° C.; flow rate: 0.60 ml/min; UV detection: 208-400 nm.
Method 3 (LC-MS):
Instrument: Micromass Quattro Premier with Waters UPLC Acquity; column: Thermo Hypersil GOLD 1.9μ 50×1 mm; mobile phase A: 1 l of water+0.5 ml of 50% strength formic acid, mobile phase B: 1 l of acetonitrile+0.5 ml of 50% strength formic acid; gradient: 0.0 min 97% A→0.5 min 97% A→3.2 min 5% A→4.0 min 5% A; oven: 50° C.; flow rate: 0.3 ml/min; UV detection: 210 nm.
Method 4 (LC-MS):
MS instrument type: Waters ZQ; HPLC instrument type: Agilent 1100 Series; UV DAD; column: Thermo Hypersil GOLD 3μ 20 mm×4 mm; mobile phase A: 1 l of water+0.5 ml of 50% strength formic acid, mobile phase B: 1 l of acetonitrile+0.5 ml of 50% strength formic acid; gradient: 0.0 min 100% A→3.0 min 10% A→4.0 min 10% A oven: 55° C.; flow rate 2 ml/min; UV detection: 210 nm.
Method 5 (LC-MS):
Instrument: Micromass Quattro Premier with Waters UPLC Acquity; column: Thermo Hypersil GOLD 1.9μ 50×1 mm; mobile phase A: 1 l of water+0.5 ml of 50% strength formic acid, mobile phase B: 1 l of acetonitrile+0.5 ml of 50% strength formic acid; gradient: 0.0 min 90% A→0.1 min 90% A→1.5 min 10% A→2.2 min 10% A; oven: 50° C.; flow rate: 0.33 ml/min; UV detection: 210 nm.
Method 6 (MS):
Instrument: Thermo Fisher-Scientific DSQ; chemical ionization; reactant gas NH$_3$; source temperature: 200° C.; ionization energy 70 eV.
Method 7 (LC-MS):
MS instrument: Waters (Micromass) Quattro Micro; HPLC instrument: Agilent 1100 series; column: YMC-Triart C18 3μ 50×3 mm; mobile phase A: 1 l of water+0.01 mol of ammonium carbonate, mobile phase B: 1 l of acetonitrile; gradient: 0.0 min 100% A→2.75 min 5% A→4.5 min 5% A; oven: 40° C.; flow rate: 1.25 ml/min; UV detection: 210 nm.
Method 8:
Instrument: Thermo DFS, Trace GC Ultra; column: Restek RTX-35, 15 m×200 μm×0.33 μm; constant flow rate with helium: 1.20 ml/min; oven: 60° C.; inlet: 220° C.; gradient: 60° C., 30° C./min→300° C. (maintained for 3.33 min)

Method 9:
Instrument: Waters ACQUITY SQD UPLC System; column: Waters Acquity UPLC HSS T3 1.8μ 50×1 mm; mobile phase A: 1 l of water+0.25 ml of 99% strength formic acid, mobile phase B: 1 l of acetonitrile+0.25 ml of 99% strength formic acid; gradient: 0.0 min 95% A→6.0 min 5% A→7.5 min 5% A; oven: 50° C.; flow rate: 0.35 ml/min; UV detection: 210-400 nm.
Method 10:
Instrument: Micromass GCT, GC6890; column: Restek RTX-35, 15 m×200 μm×0.33 μm; constant helium flow rate: 0.88 ml/min; oven: 70° C.; inlet: 250° C.; gradient: 70° C., 30° C./min 310° C. (maintained for 3 min).
Starting Materials and Intermediates:

Example 1A

Methyl 3,3-dicyano-2,2-dimethylpropanoate

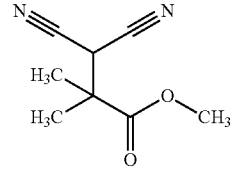

In THF (91 ml), 3 g (45.411 mmol) of malononitrile were added slowly to 1.816 g (45.411 mmol) of sodium hydride (60% in mineral oil). Subsequently, 5.876 ml (45.411 mmol) of methyl 2-bromo-2-methylpropanoate were added and the reaction mixture was stirred at room temperature overnight. Thereafter, another 5.876 ml (45.411 mmol) of methyl 2-bromo-2-methylpropanoate were added and the reaction mixture was heated to 50° C. overnight. Then yet another 1.762 ml (13.623 mmol) of methyl 2-bromo-2-methylpropanoate were added and the reaction mixture was heated to 50° C. for a further 4 h. Saturated aqueous sodium bicarbonate solution was then added, and the mixture was extracted three times with ethyl acetate. The combined organic phases were washed with saturated aqueous sodium chloride solution, dried over sodium sulphate, filtered and concentrated to dryness. This gave 8.9 g of crude product, which was purified by chromatography on silica gel (cyclohexane/ethyl acetate 4:1).

Yield: 6.47 g (85% of theory)

$^1$H NMR (400 MHz, DMSO-d$_6$): δ [ppm]=1.40 (s, 6H), 3.74 (s, 3H), 5.27 (s, 1H).

Example 2A 1-(2-Fluorobenzyl)-1H-pyrazolo[3,4-b]pyridine-3-carboximidamide hydrochloride

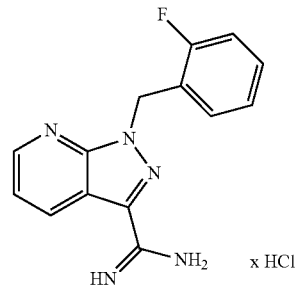 [SMILES: N=C(N)c1nn(Cc2ccccc2F)c2ncccc12]

The synthesis of this compound is described in WO 03/095451, example 6A.

Example 3A

Ethyl {2-[1-(2-fluorobenzyl)-1H-pyrazolo[3,4-b]pyridin-3-yl]-4-hydroxypyrimidin-5-yl}acetate

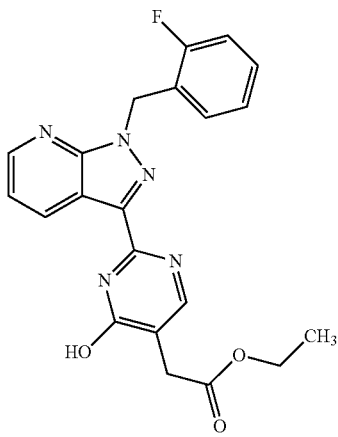

7.519 g (327 mmol) of sodium were added to ethanol (660 ml) and reacted completely under argon. 50.00 g (163.53 mmol) of Example 2A and, after 5 min, 40.45 g (188.01 mmol) of diethyl 2-formylbutanedioate (synthesis described in WO 2005/73234, page 43) were then added. The mixture was then heated at reflux for 12 h. After cooling, water and then 1N hydrochloric acid were added to the reaction mixture. The precipitate that formed was filtered off with suction and washed successively with water/ethanol (1:1, 200 ml), ethanol (100 ml) and finally with diethyl ether. After drying under high vacuum, 58.0 g of the title compound were obtained (83% of theory).

LC-MS (Method 1): $R_t$=1.00 min; MS (ESIpos): m/z=408 (M+H)$^+$ $^1$H NMR (400 MHz, DMSO-d$_6$): δ [ppm]=1.19 (t, 3H), 3.48 (s, 2H), 4.09 (q, 2H), 5.87 (s, 2H), 7.15 (t, 1H), 7.24 (t, 1H), 7.34-7.39 (m, 2H), 7.46 (dd, 1H), 8.10 (s br, 1H), 8.71 (dd, 1H), 8.74 (d, 1H), 12.83 (s br, 1H).

Example 4A

Ethyl {4-chloro-2-[1-(2-fluorobenzyl)-1H-pyrazolo[3,4-b]pyridin-3-yl]pyrimidin-5-yl}acetate

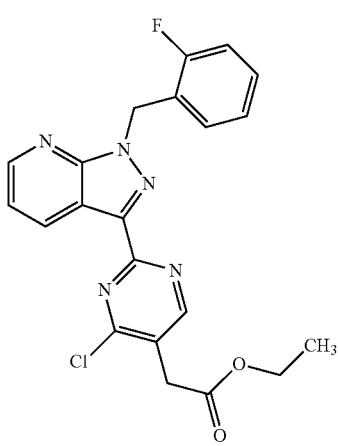 [SMILES: CCOC(=O)Cc1cnc(-c2nn(Cc3ccccc3F)c3ncccc23)nc1Cl]

55.00 g (135 mmol) of Example 3A were initially charged in sulpholane (220 ml), and 41.40 g (270 mmol) of phosphoryl chloride were added. The mixture was then heated at 120° C. for 1 h. After cooling, the mixture was added to warm water (1500 ml) and then neutralized with solid sodium bicarbonate. The precipitate that formed was filtered off with suction and washed with water. The product was purified further by chromatography on silica gel (mobile phase: cyclohexane/ethyl acetate 3:2). After drying under high vacuum, 43.0 g of the title compound were obtained (73% of theory).

LC-MS (Method 1): $R_t$=1.20 min; MS (ESIpos): m/z=426 (M+H)$^+$ $^1$H NMR (400 MHz, DMSO-d$_6$): δ [ppm]=1.21 (t, 3H), 3.96 (s, 2H), 4.15 (q, 2H), 5.90 (s, 2H), 7.16 (t, 1H), 7.22-7.27 (m, 2H), 7.36-7.39 (m, 1H), 7.49 (dd, 1H), 8.71 (dd, 1H), 8.84 (dd, 1H), 8.96 (s, 1H).

Example 5A

Ethyl {4-azido-2-[1-(2-fluorobenzyl)-1H-pyrazolo[3,4-b]pyridin-3-yl]pyrimidin-5-yl}acetate

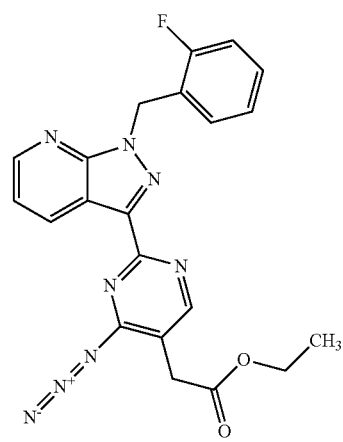 [SMILES: CCOC(=O)Cc1cnc(-c2nn(Cc3ccccc3F)c3ncccc23)nc1N=[N+]=[N-]]

10.00 g (23.482 mmol) of Example 4A were initially charged in DMF (200 ml), and 2.290 g (35.223 mmol) of sodium azide were added. The mixture was then heated at 60° C. for 1 h. After cooling, the reaction mixture was added to water and extracted three times with ethyl acetate. The organic phases were combined and washed once with saturated aqueous sodium chloride solution, then dried over sodium sulphate, filtered and concentrated. The residue was used for the next step without further purification.

LC-MS (Method 1): $R_t$=1.16 min; MS (ESIpos): m/z=433 (M+H)$^+$

Example 6A

Ethyl {4-amino-2-[1-(2-fluorobenzyl)-1H-pyrazolo[3,4-b]pyridin-3-yl]pyrimidin-5-yl}acetate

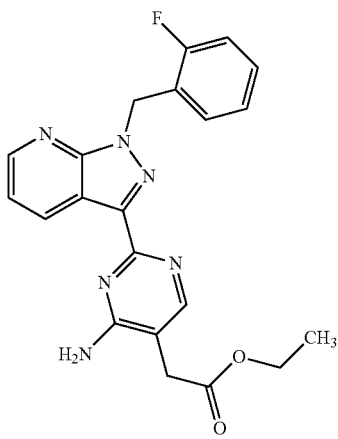 [SMILES: CCOC(=O)Cc1cnc(-c2nn(Cc3ccccc3F)c3ncccc23)nc1N]

10.15 g (23.482 mmol) of crude product from Example 5A in DMF (400 ml) were hydrogenated with palladium on carbon (10%) at standard hydrogen pressure overnight. The reaction mixture was then filtered through Celite and concentrated. The residue was used for the next step without further purification.

LC-MS (Method 1): $R_t$=0.83 min; MS (ESIpos): m/z=407 (M+H)$^+$

Example 7A

2-[1-(2-Fluorobenzyl)-1H-pyrazolo[3,4-b]pyridin-3-yl]-5,7-dihydro-6H-pyrrolo[2,3-d]pyrimidin-6-one

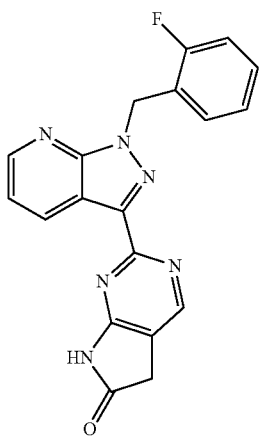 [SMILES: O=C1Cc2cnc(-c3nn(Cc4ccccc4F)c4ncccc34)nc2N1]

9.46 g (23.276 mmol) of Example 6A were initially charged in THF (400 ml), and 2.612 g (23.726 mmol) of potassium tert-butoxide were added. The mixture was stirred at RT for 1 h, water was then added, the mixture was adjusted to pH=5 with acetic acid and then stirred at RT for 10 min. The mixture was then extracted three times with ethyl acetate and the combined organic phases were washed with saturated aqueous sodium chloride solution. The organic phase was then dried over sodium sulphate, filtered and concentrated to dryness. The residue was suspended in methanol and filtered off with suction. The filter cake was washed repeatedly with methanol and then dried under high vacuum. This gave 6.61 g of the title compound as a solid (78% of theory).

LC-MS (Method 1): $R_t$=0.82 min; MS (ESIpos): m/z=361 (M+H)$^+$ $^1$H NMR (400 MHz, DMSO-d$_6$): δ [ppm]=3.68 (s, 2H), 5.85 (s, 2H), 7.14-7.18 (m, 1H), 7.21-7.27 (m, 2H), 7.34-7.38 (m, 1H), 7.42 (dd, 1H), 8.49 (s, 1H), 8.67 (dd, 1H), 8.88 (dd, 1H), 11.58 (s, 1H).

Example 8A

2-[1-(2-Fluorobenzyl)-1H-pyrazolo[3,4-b]pyridin-3-yl]-5H-pyrrolo[2,3-d]pyrimidine-5,6(7H)-dione

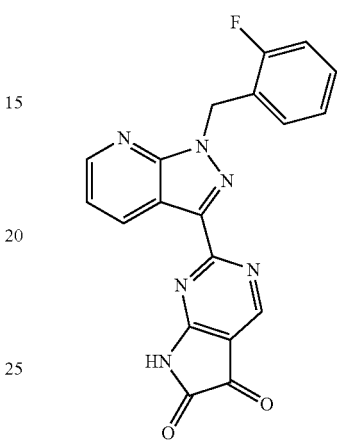

2.00 g (5.550 mmol) of Example 7A were initially charged in dioxane (200 ml), 3.079 g (27.751 mmol) of selenium dioxide were added and the mixture was then heated at reflux for 2 h. After cooling, the mixture was filtered and the filtrate was concentrated and purified by chromatography on silica gel (mobile phase:cyclohexane/ethyl acetate 1:1). This gave 890 mg of the title compound (42% of theory).

LC-MS (Method 1): $R_t$=0.93 min; MS (ESIpos): m/z=375 (M+H)$^+$ $^1$H NMR (400 MHz, DMSO-d$_6$): δ [ppm]=5.91 (s, 2H), 7.17 (ddd, 1H), 7.21-7.26 (m, 1H), 7.27-7.31 (ddd, 1H), 7.35-7.41 (m, 1H), 7.51 (dd, 1H), 8.72 (dd, 1H), 8.87 (s, 1H), 8.89 (dd, 1H), 12.21 (s, 1H).

Example 9A

2-[1-(2-Fluorobenzyl)-1H-pyrazolo[3,4-b]pyridin-3-yl]-5-hydroxy-5-(trifluoromethyl)-5,7-dihydro-6H-pyrrolo[2,3-d]pyrimidin-6-one

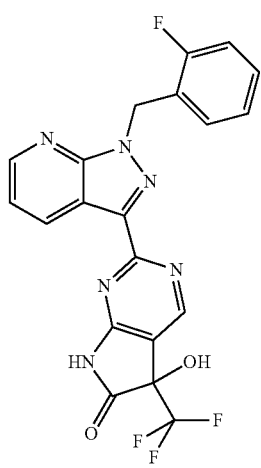 [SMILES: O=C1Nc2nc(-c3nn(Cc4ccccc4F)c4ncccc34)ncc2C1(O)C(F)(F)F]

405 mg (2.671 mmol) of caesium fluoride were dried under high vacuum for 1 h, and a solution of 1.00 g (2.671 mmol) of Example 8A in 20 ml of DMF was then added under argon. 3.945 ml (26.714 mmol) of (trifluoromethyl)trimethylsilane were then added dropwise, and then the mixture was stirred at RT overnight. The reaction mixture was then filtered through Celite, the filter cake was washed with DMF and the filtrate was concentrated. The residue obtained was dissolved in acetonitrile (30 ml), 2 ml of water were added and the mixture was stirred for 30 min. The mixture was then concentrated to dryness, and the residue was purified by preparative HPLC (acetonitrile:water (+0.05% formic acid) gradient). This gave 290 mg of the title compound (24% of theory).

LC-MS (Method 1): $R_t$=0.96 min; MS (ESIpos): m/z=445 (M+H)$^+$ $^1$H NMR (400 MHz, DMSO-d$_6$): δ [ppm]=5.88 (s, 2H), 7.16 (t, 1H), 7.22-7.29 (m, 2H), 7.35-7.41 (m, 1H), 7.47 (dd, 1H), 8.16 (s, 1H), 8.71 (dd, 1H), 8.76 (s, 1H), 8.87 (dd, 1H), 12.28 (s, 1H).

Example 10A

5-Chloro-2-[1-(2-fluorobenzyl)-1H-pyrazolo[3,4-b]pyridin-3-yl]-5-(trifluoromethyl)-5,7-dihydro-6H-pyrrolo[2,3-d]pyrimidin-6-one

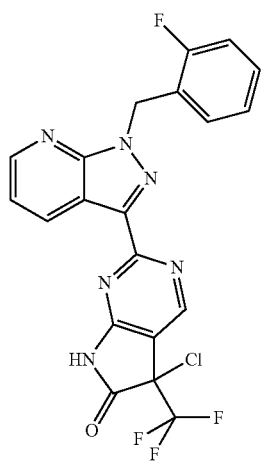 [SMILES: O=C1Nc2nc(-c3nn(Cc4ccccc4F)c4ncccc34)ncc2C1(Cl)C(F)(F)F]

232 mg (0.522 mmol) of Example 9A in dichloromethane (14 ml) were cooled to 0° C., and 436 µl (3.133 mmol) of triethylamine were then added. 190 µl (2.611 mmol) of thionyl chloride were then added dropwise, and the mixture was stirred at 0° C. for 15 min. The reaction mixture was subsequently diluted with dichloromethane and extracted three times with water. The phases were separated and the organic phase was dried with sodium sulphate, filtered and concentrated to dryness. The residue obtained was purified by preparative HPLC (acetonitrile:water (+0.05% formic acid) gradient). This gave 120 mg of the title compound (50% of theory).

LC-MS (Method 2): $R_t$=1.20 min; MS (ESIpos): m/z= 463 ($^{35}$Cl), 465 ($^{37}$Cl) (M+H)$^+$ $^1$H NMR (400 MHz, DMSO-d$_6$): δ [ppm]=5.89 (s, 2H), 7.17 (t, 1H), 7.22-7.30 (m, 2H), 7.36-7.40 (m, 1H), 7.50 (dd, 1H), 8.72 (dd, 1H), 8.86 (dd, 1H), 8.98 (s, 1H), 13.00 (s, 1H).

Example 11A 1-(2-Fluorobenzyl)-1H-pyrazolo[3,4-b]pyridine-3-carboximidohydrazide

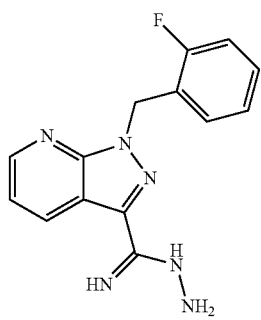 [SMILES: N=C(NN)c1nn(Cc2ccccc2F)c2ncccc12]

20.000 g (65.414 mmol) of the compound from Example 2A were dissolved in 320 ml of ethanol, and 26.477 g (261.656 mmol) of triethylamine and 4.093 g (65.414 mmol) of hydrazine hydrate (80% strength solution in water) were added at 0° C. The mixture was stirred at RT overnight and then concentrated on a rotary evaporator. This gave 26.84 g (100% of theory, purity 69%) of the title compound which was reacted further without further purification.

LC-MS (Method 5): $R_t$=0.64 min; MS (ESIpos): m/z=285 (M+H)$^+$

Example 12A 1,2-Diethyl 3-methyl 2-methyl-1-oxopropane-1,2,3-tricarboxylate

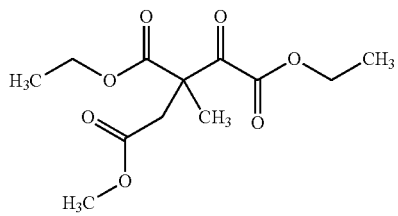 [SMILES: CCOC(=O)C(=O)C(C)(CC(=O)OC)C(=O)OCC]

624 mg (5.564 mmol) of potassium tert-butoxide were initially charged in toluene (40 ml), and 0.932 mg (4.945 mmol) of diethyl 2-methyl-3-oxobutanedioate were added. 3.073 ml (32.457 mmol) of methyl bromoacetate and 122 mg (0.465 mmol) of 18-crown-6 were then added, and the mixture was heated at reflux for 4 h. The reaction mixture was then cooled to 5° C. and added to diethyl ether and 7% strength hydrochloric acid. The phases were separated and the organic phase was extracted once more with 7% strength hydrochloric acid and twice with water. The organic phase was then dried over sodium sulphate, filtered and concentrated. The residue was dried under high vacuum overnight and then used without further purification. This gave 1.45 g of the title compound which were reacted further without further purification.

LC-MS (Method 2): $R_t$=0.96 min; MS (ESIpos): m/z=275 (M+H)$^+$

Example 13A

1-Ethyl 4-methyl 2-{3-[1-(2-fluorobenzyl)-1H-pyrazolo[3,4-b]pyridin-3-yl]-5-hydroxy-1,2,4-triazin-6-yl}-2-methylbutanedioate

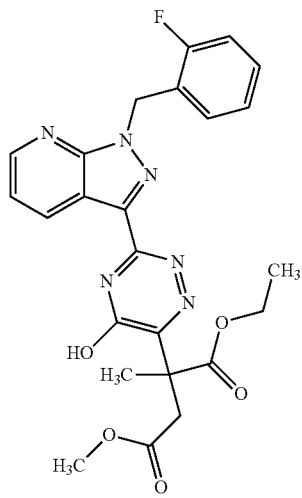 [SMILES: CCOC(=O)C(C)(CC(=O)OC)c1nnc(-c2nn(Cc3ccccc3F)c3ncccc23)nc1O]

1.45 g (about 4.950 mmol) of Example 12A were initially charged in ethanol (20 ml), a suspension of 1.37 g (about 3.300 mmol) of Example 11A in 20 ml of ethanol was added dropwise and the mixture was then heated at reflux overnight. After cooling, a precipitate was filtered off and washed with ethanol. The filtrate was concentrated and diethyl ether was added to the residue. Once more, a precipitate was filtered off and the filtrate was concentrated and then purified by preparative HPLC (methanol:water gradient). This gave 297 mg of the title compound (18% of theory).

LC-MS (Method 1): $R_t$=1.00 min; MS (ESIpos): m/z=495 (M+H)$^+$

Example 14A

5-Chloro-2-[1-(2-fluorobenzyl)-1H-pyrazolo[3,4-b]pyridin-3-yl]-5-(pentafluoroethyl)-5,7-dihydro-6H-pyrrolo[2,3-d]pyrimidin-6-one

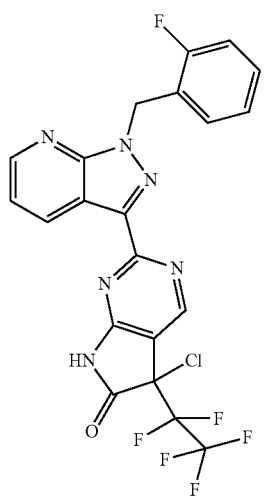 [SMILES: O=C1Nc2nc(-c3nn(Cc4ccccc4F)c4ncccc34)ncc2C1(Cl)C(F)(F)C(F)(F)F]

337 mg (0.682 mmol) of Example 3 were reacted analogously to Example 10A. This gave 236 mg of the title compound (67% of theory).

LC-MS (Method 2): $R_t$=1.27 min; MS (ESIpos): m/z= 513 ($^{35}$Cl), 515 ($^{37}$Cl) (M+H)$^+$ $^1$H NMR (400 MHz, DMSO-d$_6$): δ [ppm]=5.89 (s, 2H), 7.17 (t, 1H), 7.22-7.32 (m, 2H), 7.36-7.41 (m, 1H), 7.50 (dd, 1H), 8.72 (dd, 1H), 8.86 (dd, 1H), 8.97 (s, 1H), 13.00 (s, 1H).

Example 15A 2,6-Dichloro-5-fluoronicotinamide

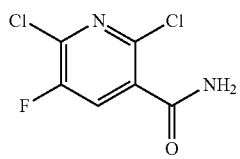 [SMILES: NC(=O)c1cc(F)c(Cl)nc1Cl]

A suspension of 25 g (130.90 mmol) of 2,6-dichloro-5-fluoro-3-cyanopyridine in conc. sulphuric acid (125 ml) was stirred at 60-65° C. for 1 h. After cooling to RT, the contents of the flask were poured onto ice-water and extracted three times with ethyl acetate (100 ml each time). The combined organic phases were washed with water (100 ml) and then with saturated aqueous sodium bicarbonate solution (100 ml), dried and concentrated on a rotary evaporator. The material obtained was dried under high vacuum.

Yield: 24.5 g (90% of theory)

$^1$H NMR (400 MHz, DMSO-d$_6$): δ=7.95 (br s, 1H), 8.11 (br s, 1H), 8.24 (d, 1H).

Example 16A

2-Chloro-5-fluoronicotinamide

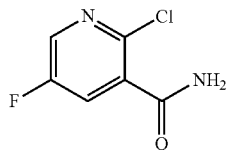

At RT, 44 g (210.58 mmol) of 2,6-dichloro-5-fluoronicotinamide were added to a suspension of 21.9 g (335.35 mmol) of zinc in methanol (207 ml). Acetic acid (18.5 ml) was then added, and the mixture was heated with stirring at reflux for 24 h. The contents of the flask were then decanted from the zinc, and ethyl acetate (414 ml) and saturated aqueous sodium bicarbonate solution (414 ml) were added, followed by intense extractive stirring. Subsequently the reaction mixture was filtered with suction through kieselguhr and the filter product was washed three times with ethyl acetate (517 ml each time). The organic phase was separated off and the aqueous phase was washed with ethyl acetate (258 ml). The combined organic phases were washed once with saturated aqueous sodium bicarbonate solution (414 ml), dried and concentrated under reduced pressure. Dichloromethane (388 ml) was added to the crystals thus obtained, and extraction was effected by stirring for 20 min. The mixture was once more filtered off with suction, washed with diethyl ether and sucked dry.

Yield: 20.2 g (53% of theory)

$^1$H NMR (400 MHz, DMSO-$d_6$): δ=7.87 (br s, 1H), 7.99 (dd, 1H), 8.10 (br s, 1H), 8.52 (d, 1H).

Example 17A

2-Chloro-5-fluoronicotinonitrile

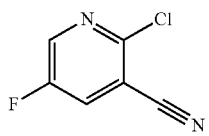

81.2 ml (582.25 mmol) of triethylamine were added to a suspension of 46.2 g (264.66 mmol) of 2-chloro-5-fluoronicotinamide in dichloromethane (783 ml), and the mixture was cooled to 0° C. Then, with stirring, 41.12 ml (291.13 mmol) of trifluoroacetic anhydride were added slowly dropwise, and the mixture was stirred at 0° C. for 1.5 h. The reaction solution was subsequently washed twice with saturated aqueous sodium bicarbonate solution (391 ml each time), dried and concentrated under reduced pressure.

Yield: 42.1 g (90% of theory)

$^1$H NMR (400 MHz, DMSO-$d_6$): δ=8.66 (dd, 1H), 8.82 (d, 1H).

Example 18A

5-Fluoro-1H-pyrazolo[3,4-b]pyridine-3-amine

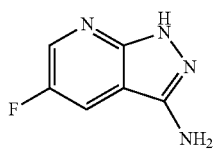

A suspension of 38.5 g (245.93 mmol) of 2-chloro-5-fluoronicotinonitrile was initially charged in 1,2-ethanediol (380 ml), and hydrazine hydrate (119.6 ml) was then added. With stirring, the mixture was heated at reflux for 4 h. The product precipitated on cooling. Water (380 ml) was added to the crystals, and the mixture was subjected to extractive stirring at RT for 10 min. The suspension was then filtered with suction over a frit, and the filter product was washed with water (200 ml) and with −10° C. cold THF (200 ml). Drying under high vacuum over phosphorus pentoxide.

Yield: 22.8 g (61% of theory)

$^1$H NMR (400 MHz, DMSO-$d_6$): δ=5.54 (s, 2H), 7.96 (dd, 1H), 8.38 (m, 1H), 12.07 (m, 1H).

Example 19A

5-Fluoro-3-iodo-1H-pyrazolo[3,4-b]pyridine

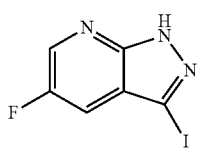 [SMILES: Fc1cnc2[nH]nc(I)c2c1]

10 g (65.75 mmol) of 5-fluoro-1H-pyrazolo[3,4-b]pyridine-3-amine were initially charged in THF (329 ml), and the mixture was cooled to 0° C. 16.65 ml (131.46 mmol) of boron trifluoride diethyl ether complex were then added slowly. The reaction mixture was cooled further to −10° C. A solution of 10.01 g (85.45 mmol) of isopentyl nitrite in THF (24.39 ml) was then added slowly, and the mixture was stirred for a further 30 min. The mixture was diluted with cold diethyl ether (329 ml) and the resulting solid was filtered off. The diazonium salt thus prepared was added a little at a time to a solution at 0° C. of 12.81 g (85.45 mmol) of sodium iodide in acetone (329 ml), and the mixture was stirred at RT for 30 min. The reaction mixture was poured into ice-water (1.8 l) and extracted twice with ethyl acetate (487 ml each time). The collected organic phases were washed with saturated aqueous sodium chloride solution (244 ml), dried, filtered and concentrated. This gave 12.1 g (86% purity, 60% of theory) of the title compound as a solid. The crude product was converted without further purification.

LC-MS (Method 4): $R_t$=1.68 min
MS (ESIpos): m/z=264 (M+H)+

Example 20A

5-Fluoro-1-(2-fluorobenzyl)-3-iodo-1H-pyrazolo[3,4-b]pyridine

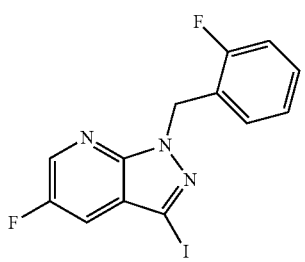 [SMILES: Fc1cnc2c(c1)c(I)nn2Cc1ccccc1F]

12.1 g (about 39.65 mmol) of the compound from Example 19A were initially charged in DMF (217 ml), and 8.25 g (43.62 mmol) of 2-fluorobenzyl bromide and 14.21 g (43.62 mmol) of caesium carbonate were then added. The mixture was stirred at RT for two hours. The reaction mixture was then poured onto water (1.17 l) and extracted twice with ethyl acetate (502 ml). The collected organic phases were washed with saturated aqueous sodium chloride solution (335 ml), dried, filtered and concentrated. The residue was chromatographed on silica gel (mobile phase: petroleum ether/ethyl acetate 97:3) and the product fractions were concentrated. This gave 9.0 g (61% of theory) of the title compound as a solid. The solid was taken up in ethyl acetate and washed with 10% strength aqueous sodium thiosulphate solution and then with saturated aqueous sodium chloride solution, dried and concentrated.

LC-MS (Method 4): $R_t$=2.57 min

MS (ESIpos): m/z=372 (M+H)$^+$ $^1$H NMR (400 MHz, DMSO-d$_6$): δ=5.73 (s, 2H), 7.13-7.26 (m, 3H), 7.33-7.41 (m, 1H), 7.94 (dd, 1H), 8.69-8.73 (m, 1H).

Example 21A

Ethyl 5-fluoro-1-(2-fluorobenzyl)-1H-pyrazolo[3,4-b]pyridine-3-carboxylate

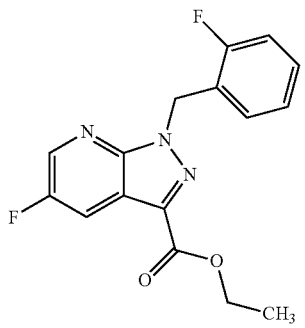 [SMILES: CCOC(=O)c1nn(Cc2ccccc2F)c2ncc(F)cc12]

13.487 g (51.228 mmol) of ethyl 5-amino-1-(2-fluorobenzyl)-1H-pyrazole-3-carboxylate (preparation described for example 20A in WO 00/06569) were initially charged in 300 ml of dioxane, and 6 g (51.228 mmol) of 3-(dimethylamino)-2-fluoroacrylaldehyde (preparation described in *Justus Liebigs Annalen der Chemie* 1970; 99-107) were added at RT. Subsequently, 4.736 ml (61.473 mmol) of trifluoroacetic acid were added and the mixture was heated at reflux while stirring for 3 days. After cooling, the mixture was concentrated under reduced pressure, and water and ethyl acetate were added to the residue. The phases were separated and the organic phase was washed twice with water. The combined aqueous phases were subsequently extracted twice with ethyl acetate. The combined organic phases were dried over sodium sulphate, filtered and concentrated under reduced pressure. The residue (22 g) was subsequently purified by chromatography on silica gel (mobile phase: dichloromethane). This gave 5.67 g (35% of theory) of the title compound.

LC-MS (Method 4): $R_t$=1.17 min

MS (ESIpos): m/z=318 (M+H)$^+$ $^1$H NMR (400 MHz, DMSO-d$_6$): δ=1.37 (t, 3H), 4.40 (q, 2H), 5.86 (s, 2H), 7.15-7.27 (m, 3H), 7.36-7.41 (m, 1H), 8.25 (d, 1H), 8.78 (s br., 1H).

Example 22A

5-Fluoro-1-(2-fluorobenzyl)-1H-pyrazolo[3,4-b]pyridine-3-carboxamide

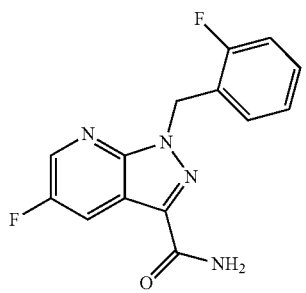 [SMILES: NC(=O)c1nn(Cc2ccccc2F)c2ncc(F)cc12]

1.00 g (3.152 mmol) of Example 21A was stirred in 10 ml of a 7N solution of ammonia in methanol at RT for three days. This was followed by concentration under reduced pressure. This gave 908 mg (99% of theory) of the title compound.

LC-MS (Method 4): $R_t$=0.85 min

MS (ESIpos): m/z=289 (M+H)$^+$ $^1$H NMR (400 MHz, DMSO-d$_6$): δ=5.87 (s, 2H), 7.12-7.26 (m, 3H), 7.34-7.40 (m, 1H), 7.60 (s br., 1H), 7.87 (s br., 1H), 8.28 (dd, 1H), 8.72 (dd, 1H).

Example 23A

5-Fluoro-1-(2-fluorobenzyl)-1H-pyrazolo[3,4-b]pyridine-3-carbonitrile

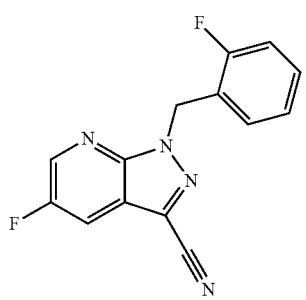 [SMILES: N#Cc1nn(Cc2ccccc2F)c2ncc(F)cc12]

Variant A:

A suspension of 16.03 g (43.19 mmol) of 5-fluoro-1-(2-fluorobenzyl)-3-iodo-1H-pyrazolo[3,4-b]pyridine (Example 20A) and 4.25 g (47.51 mmol) of copper cyanide was initially charged in DMSO (120 ml) and stirred at 150° C. for 2 h. After cooling, the contents of the flask were cooled to about 40° C. and poured onto a solution of conc. aqueous ammonia (90 ml) and water (500 ml), ethyl acetate (200 ml) was added and extraction was effected briefly by stirring. The aqueous phase was removed and extracted two more times with ethyl acetate (200 ml each time). The combined organic phases were washed twice with 10% aqueous sodium chloride solution (100 ml each time), dried and concentrated under reduced pressure. The crude product was converted without further purification.

Yield: 11.1 g (91% of theory)

Variant B:

900 mg (3.122 mmol) of the compound obtained in Example 22A were dissolved in THF (14 ml), and 0.646 ml (7.993 mmol) of pyridine was added. Thereafter, 1.129 ml (7.993 mmol) of trifluoroacetic anhydride were slowly added dropwise and then the mixture was stirred at RT overnight. Thereafter, the reaction mixture was poured onto water and extracted three times with ethyl acetate. The combined organic phases were extracted with saturated aqueous sodium hydrogencarbonate solution and 1N hydrochloric acid, and then washed with saturated aqueous sodium chloride solution. The organic phase was dried over sodium sulphate, filtered and concentrated. This gave 850 mg (99% of theory) of the title compound.

LC-MS (Method 4): $R_t$=1.06 min

MS (ESIpos): m/z=271 (M+H)$^+$ $^1$H NMR (400 MHz, DMSO-d$_6$): δ=5.87 (s, 2H), 7.17-7.42 (m, 4H), 8.52 (dd, 1H), 8.87 (dd, 1H).

Example 24A

5-Fluoro-1-(2-fluorobenzyl)-1H-pyrazolo[3,4-b]pyridine-3-carboximidamide acetate

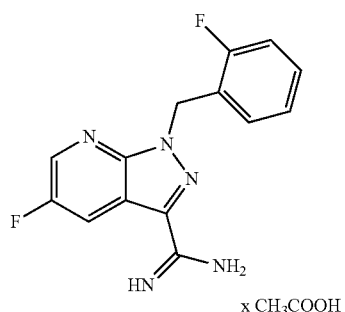

11.1 g (41.07 mmol) of 5-fluoro-1-(2-fluorobenzyl)-1H-pyrazolo[3,4-b]pyridine-3-carbonitrile (Example 23A) were added to 2.22 g (41.07 mmol) of sodium methoxide in methanol (270 ml), and the mixture was stirred at RT for 2 h. 2.64 g (49.29 mmol) of ammonium chloride and acetic acid (9.17 ml) were then added, and the mixture was heated at reflux overnight. It was then concentrated to dryness and the residue was taken up in water (100 ml) and ethyl acetate (100 ml) and adjusted to a pH of 10 using 2N aqueous sodium hydroxide solution. The mixture was stirred vigorously at RT for about 1 h. The resulting suspension was filtered with suction and washed through with ethyl acetate (100 ml), with water (100 ml) and once more with ethyl acetate (100 ml). The residue was dried under high vacuum over phosphorus pentoxide.

Yield: 9.6 g (78% of theory)

MS (ESIpos): m/z=288 (M+H)$^+$ $^1$H NMR (400 MHz, DMSO-d$_6$): δ=1.85 (s, 3H), 5.80 (s, 2H), 7.14-7.25 (m, 3H), 7.36 (m, 1H), 8.42 (dd, 1H), 8.72 (dd, 1H).

Example 25A

5-Fluoro-1-(2-fluorobenzyl)-1H-pyrazolo[3,4-b]pyridine-3-carboximidohydrazide

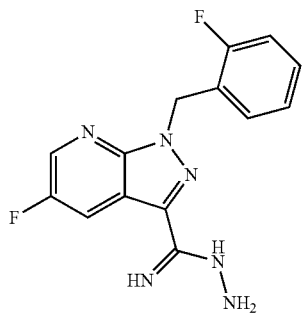 [SMILES: N=C(NN)c1nn(Cc2ccccc2F)c2ncc(F)cc12]

23.000 g (66.22 mmol) of Example 24A were dissolved in 322 ml of ethanol, and 26.804 g (264.88 mmol) of triethylamine and 6.027 g (66.22 mmol) of hydrazine hydrate (55% strength solution in water) were added at 0° C. The mixture was stirred at RT overnight and then added to 1.715 l of a 10% strength aqueous sodium chloride solution and extracted twice with ethyl acetate. The combined organic phases were washed with 10% strength aqueous sodium chloride solution, dried over sodium sulphate and concentrated on a rotary evaporator. The residue was purified on silica gel (mobile phase:dichloromethane/methanol 95:5). This gave 15.000 g (75% of theory) of the title compound.

LC-MS (Method 1): $R_t$=0.58 min; MS (ESIpos): m/z=303 (M+H)$^+$ $^1$H NMR (400 MHz, DMSO-d$_6$): δ [ppm]=5.38 (s, 2H), 5.54 (s, 2H), 5.72 (s, 2H), 7.10-7.15 (m, 2H), 7.20-7.25 (m, 1H), 7.32-7.38 (m, 1H), 8.21 (dd, 1H), 8.64 (dd, 1H).

Example 26A

Diethyl 2-(cyclopropylmethyl)-2-methyl-3-oxobutanedioate

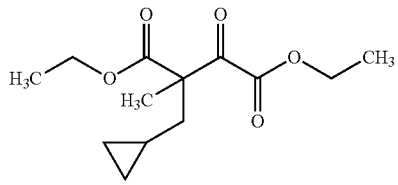 [SMILES: CCOC(=O)C(=O)C(C)(CC1CC1)C(=O)OCC]

Analogously to Example 12A, 9.444 ml (97.370 mmol) of (bromomethyl)cyclopropane were added to 2.796 ml (14.836 mmol) of diethyl 2-methyl-3-oxobutanedioate. This gave 3.62 g of the title compound which was reacted further without further purification.

MS (Method 6): MS m/z=257 (M+H)$^+$

Example 27A

Ethyl 3-cyclopropyl-2-{3-[5-fluoro-1-(2-fluorobenzyl)-1H-pyrazolo[3,4-b]pyridin-3-yl]-5-hydroxy-1,2,4-triazin-6-yl}-2-methylpropanoate

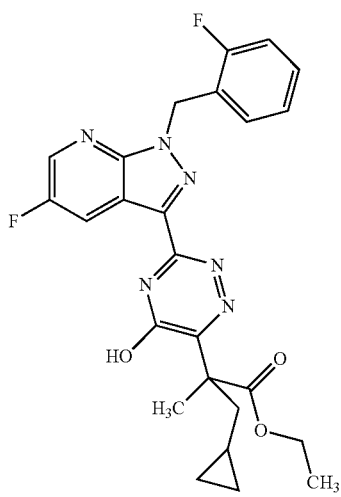 [SMILES: CCOC(=O)C(C)(CC1CC1)c1nnc(-c2nn(Cc3ccccc3F)c3ncc(F)cc23)nc1O]

1.272 g (about 4.962 mmol) of Example 26A were initially charged in 10 ml of ethanol and heated to reflux. A suspension of 1.00 g (3.308 mmol) of Example 25A in 40 ml of ethanol was then added dropwise. The mixture was heated overnight, a further 2.24 g of Example 26A were added and the mixture was heated at reflux for a further night. After cooling, a solid was filtered off with suction and washed with a little ethanol, and the filtrate was concentrated. The residue was purified by preparative HPLC (acetonitrile:water gradient). This gave 270 mg (16% of theory) of the title compound.

$^1$H NMR (400 MHz, DMSO-d$_6$): δ [ppm]=−0.15-−0.09 (m, 1H), −0.01-0.02 (m, 1H, superposed by TMS signal), 0.27-0.34 (m, 1H), 0.36-0.42 (m, 1H), 0.56-0.62 (m, 1H), 1.10 (t, 3H), 1.50 (s, 3H), 1.85 (dd, 1H), 1.95 (dd, 1H), 3.99-4.09 (m, 2H), 5.90 (s, 2H), 7.16 (dt, 1H), 7.22-7.32 (m, 2H), 7.36-7.41 (m, 1H), 8.42 (dd, 1H), 8.82 (dd, 1H), 14.55 (br s, 1H).

Example 28A

Diethyl 2-[(benzyloxy)methyl]-2-methyl-3-oxobutanedioate

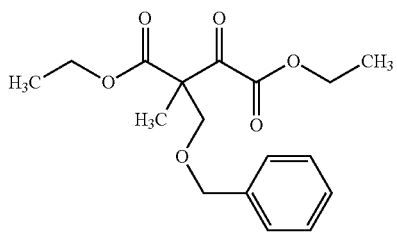 [SMILES: CCOC(=O)C(=O)C(C)(COCc1ccccc1)C(=O)OCC]

13.495 ml (97.370 mmol) of benzyl chloromethyl ether were added to 2.796 ml (14.836 mmol) of diethyl 2-methyl-3-oxobutanedioate analogously to the procedure of Example 12A. This gave, after filtration, 2.15 g of the title compound which were reacted in the next steps without further purification.

MS (Method 6): MS m/z=323 (M+H)$^+$

Example 29A

Ethyl 3-(benzyloxy)-2-{3-[5-fluoro-1-(2-fluorobenzyl)-1H-pyrazolo[3,4-b]pyridin-3-yl]-5-hydroxy-1,2,4-triazin-6-yl}-2-methylpropanoate

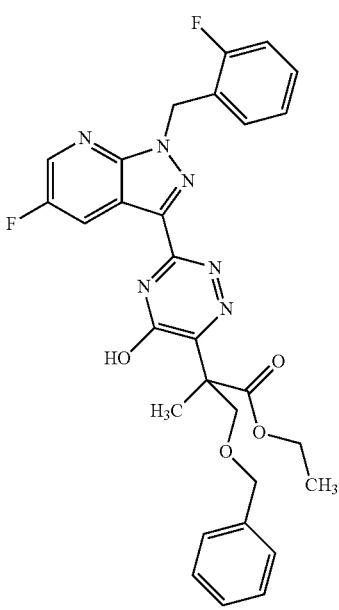 [SMILES: CCOC(=O)C(C)(COCc1ccccc1)c1nnc(-c2nn(Cc3ccccc3F)c3ncc(F)cc23)nc1O]

1.600 g (4.962 mmol) of the crude compound from Example 28A were reacted analogously to the procedure of Example 27A. The residue was purified by preparative HPLC (acetonitrile:water gradient). This gave 450 mg (24% of theory) of the title compound.

LC-MS (Method 1): R$_t$=1.23 min; MS (ESIpos): m/z=561 (M+H)$^+$

Example 30A

Diethyl 2-ethyl-2-methyl-3-oxobutanedioate

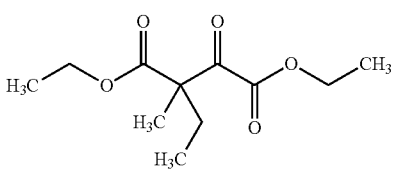 [SMILES: CCOC(=O)C(=O)C(C)(CC)C(=O)OCC]

7.788 ml (97.370 mmol) of iodoethane were added to 2.796 ml (14.836 mmol) of diethyl 2-methyl-3-oxobutanedioate analogously to the procedure of Example 12A. This gave 3.40 g of the title compound which was reacted in the next steps without further purification.

Example 31A

Ethyl 2-{3-[5-fluoro-1-(2-fluorobenzyl)-1H-pyrazolo[3,4-b]pyridin-3-yl]-5-hydroxy-1,2,4-triazin-6-yl}-2-methylbutanoate

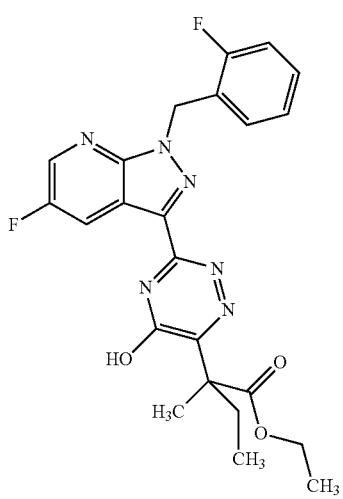 [SMILES: CCOC(=O)C(C)(CC)c1nnc(-c2nn(Cc3ccccc3F)c3ncc(F)cc23)nc1O]

1.143 g (4.962 mmol) of Example 30A were converted in analogy to Example 27A. The residue was purified by preparative HPLC (acetonitrile:water (+1% trifluoroacetic acid) gradient). This gave 334 mg (21% of theory) of the title compound.

LC-MS (Method 1): $R_t$=1.16 min; MS (ESIpos): m/z=469 (M+H)$^+$

Example 32A

5-Fluoro-3-iodo-1-(4-methoxybenzyl)-1H-pyrazolo[3,4-b]pyridine

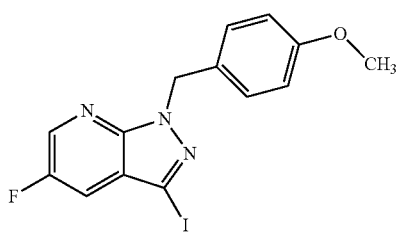 [SMILES: COc1ccc(Cn2nc(I)c3cc(F)cnc32)cc1]

10.00 g (38.021 mmol) of Example 19A were reacted analogously to the procedure of Example 20A with 4-methoxybenzyl chloride. Chromatography on silica gel (mobile phase: cyclohexane/ethyl acetate mixture) gave 8.94 g (61% of theory) of the title compound.

LC-MS (Method 2): $R_t$=1.25 min
MS (ESIpos): m/z=384 (M+H)$^+$

Example 33A

5-Fluoro-1-(4-methoxybenzyl)-1H-pyrazolo[3,4-b]pyridine-3-carbonitrile

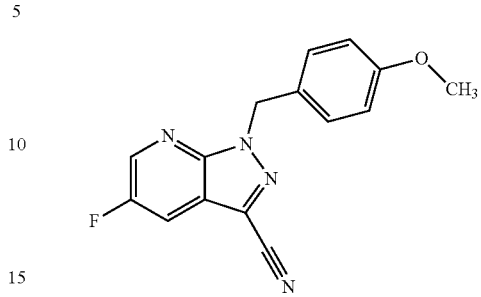

8.94 g (23.332 mmol) of Example 32A were reacted analogously to the procedure of Example 23A, variant A. The crude product obtained was reacted without further purification.
Yield: 6.52 g (99% of theory)
LC-MS (Method 1): $R_t$=1.11 min
MS (ESIpos): m/z=283 (M+H)$^+$

Example 34A

5-Fluoro-1-(4-methoxybenzyl)-1H-pyrazolo[3,4-b]pyridine-3-carboximidamide acetate

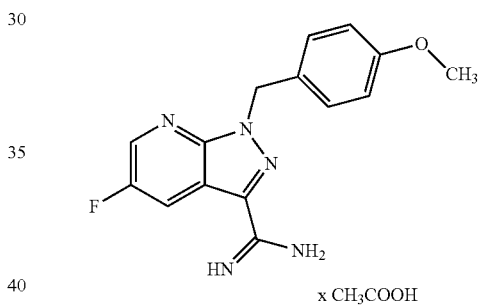

6.52 g (23.098 mmol) of Example 33A were reacted analogously to the procedure of Example 24A. Yield: 6.16 g (74% of theory)
LC-MS (Method 2): $R_t$=0.55 min
MS (ESIpos): m/z=300 (M+H)$^+$

Example 35A

5-Fluoro-1-(4-methoxybenzyl)-1H-pyrazolo[3,4-b]pyridine-3-carboximidohydrazide

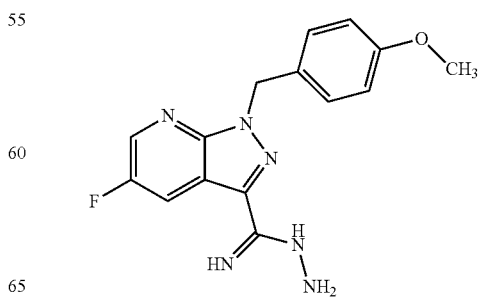

6.16 g (17.141 mmol) of Example 34 A were reacted analogously to the procedure of Example 25A. Purification on silica gel was dispensed with. This gave 4.90 g (90% of theory) of the title compound which was reacted without further purification.

LC-MS (Method 2): $R_t$=0.57 min; MS (ESIpos): m/z=315 (M+H)$^+$

Example 36A

Methyl 2-{3-[5-fluoro-1-(4-methoxybenzyl)-1H-pyrazolo[3,4-b]pyridin-3-yl]-5-hydroxy-1,2,4-triazin-6-yl}-2-methylpropanoate

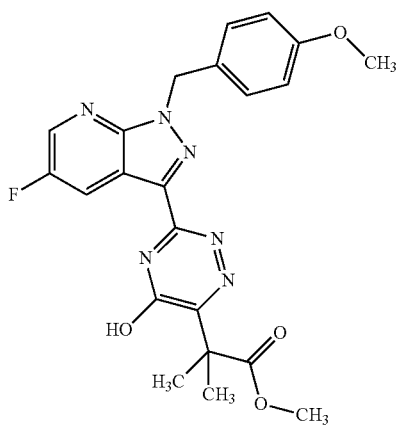 [SMILES: COC(=O)C(C)(C)c1nnc(-c2nn(Cc3ccc(OC)cc3)c3ncc(F)cc23)nc1O]

4.89 g (15.557 mmol) of the crude compound from Example 35A were reacted analogously to the procedure of Example 27A with 4.391 g (23.336 mmol) of dimethyl 2,2-dimethyl-3-oxobutanedioate (described in J. Am. Chem. Soc. 124(14), 3680-3691; 2002). After complete conversion, a solid was filtered off, washed with ethanol and then dried under high vacuum. This gave 6.04 g (85% of theory) of the title compound.

LC-MS (Method 2): $R_t$=1.05 min; MS (ESIpos): m/z=453 (M+H)$^+$

Example 37A

Methyl 1-[ethoxy(oxo)acetyl]cyclopentanecarboxylate

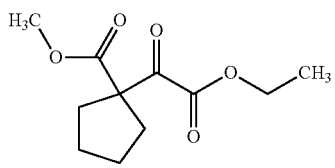 [SMILES: CCOC(=O)C(=O)C1(C(=O)OC)CCCC1]

At −78° C., 10.00 g (78.020 mmol) of methyl cyclopentanecarboxylate and 13.683 g (93.624 mmol) of ethyl oxalate were initially charged in 200 ml of tetrahydrofuran, 46.812 ml (93.624 mmol) of lithium diisopropylamide (2M in tetrahydrofuran/heptane/ethylbenzene) were added and the mixture was then stirred at −78° C. for 1 h. The cooling bath was then removed, and the mixture was stirred at room temperature for 1 h. The mixture was then cooled to 0° C., and 1M hydrochloric acid was added. The mixture was then extracted three times with ethyl acetate and the organic phases were combined. The organic phases were washed with saturated aqueous sodium chloride solution, dried over sodium sulphate, filtered and concentrated to dryness. The residue was purified by chromatography on silica gel (mobile phase: cyclohexane/ethyl acetate gradient). This gave 12.28 g (68% of theory) of the title compound.

MS (Method 6): MS: m/z=229 (M+H)$^+$

Example 38A

Methyl 1-{3-[5-fluoro-1-(2-fluorobenzyl)-1H-pyrazolo[3,4-b]pyridin-3-yl]-5-hydroxy-1,2,4-triazin-6-yl}cyclopentanecarboxylate

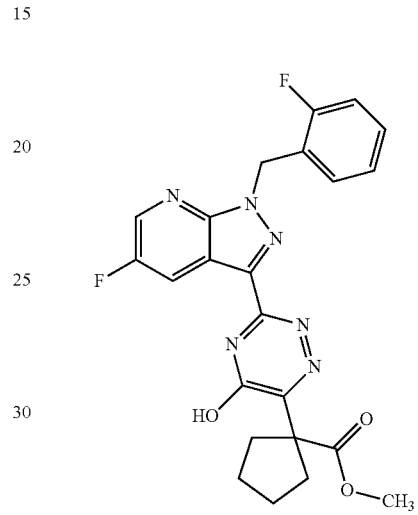

1.00 g (3.308 mmol) of the compound from Example 25A were reacted analogously to the procedure of Example 27A with 1.510 g (6.616 mmol) of Example 37A. This gave 0.458 g (29% of theory) of the title compound.

LC-MS (Method 1): $R_t$=1.13 min; MS (ESIpos): m/z=467 (M+H)$^+$

Example 39A

3-[5-Fluoro-1-(4-methoxybenzyl)-1H-pyrazolo[3,4-b]pyridin-3-yl]-7,7-dimethyl-5-{[2-(trimethylsilyl)ethoxy]methyl}-5,7-dihydro-6H-pyrrolo[2,3-e][1,2,4]triazin-6-one

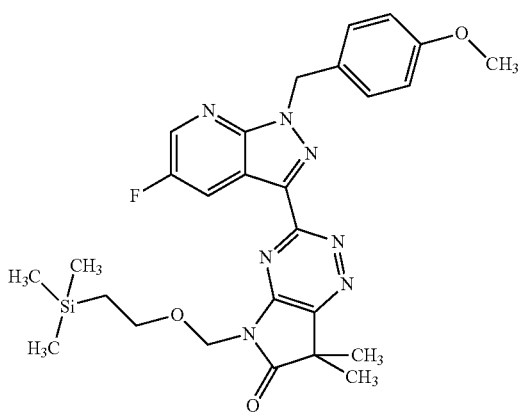

2.067 g (6.345 mmol) of caesium carbonate in DMF (30 ml) were added to 2.45 g (5.768 mmol) of the compound from Example 8. 1.221 ml (6.922 mmol) of 2-(trimethylsilyl)ethoxymethyl chloride were then added, and the mixture was stirred at room temperature for 1 h. The solids were then filtered off and washed with DMF, the filtrate was concentrated and the residue was dried under high vacuum. This gave 4.45 g of the title compound which were used without further purification for the next step.

LC-MS (Method 1): R$_t$=1.43 min; MS (EIpos): m/z=550 [M+H]$^+$.

Example 40A 3-(5-Fluoro-1H-pyrazolo[3,4-b]pyridin-3-yl)-7,7-dimethyl-5-{[2-(trimethylsilyl)ethoxy]methyl}-5,7-dihydro-6H-pyrrolo[2,3-e][1,2,4]triazin-6-one

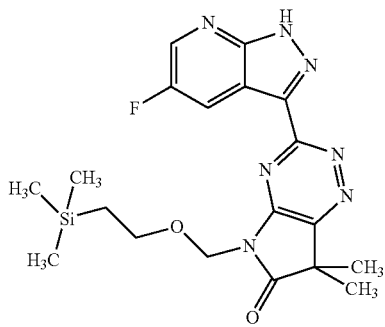

4.148 g (7.546 mmol) of the compound from Example 39A were taken up in acetonitrile (110 ml) and water (55 ml), 12.411 g (22.638 mmol) of ammonium cerium(IV) nitrate were added and the mixture was stirred at room temperature for 20 min. Plenty of water was then added, and a precipitate was filtered off. This solid was washed with water and subsequently with a little diethyl ether. This gave, after drying under high vacuum, 1.53 g (47% of theory) of the title compound.

LC-MS (Method 1): R$_t$=1.14 min; MS (EIpos): m/z=430 [M+H]$^+$.

Example 41A

3-[5-Fluoro-1-(2-fluoro-4-methylbenzyl)-1H-pyrazolo[3,4-b]pyridin-3-yl]-7,7-dimethyl-5-{[2-(trimethylsilyl)ethoxy]methyl}-5,7-dihydro-6H-pyrrolo[2,3-e][1,2,4]triazin-6-one

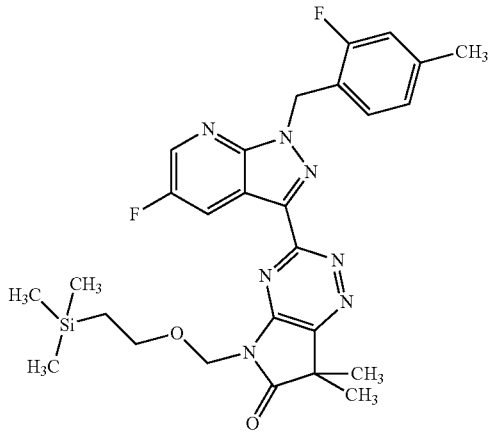

136 mg (0.419 mmol) of caesium carbonate and 78 mg (0.384 mmol) of 2-fluoro-4-methylbenzyl bromide were added to 0.150 g (0.349 mmol) of the compound from Example 40A in tetrahydrofuran (8 ml), and the mixture was stirred at room temperature overnight. After filtration, the mixture was purified by preparative HPLC (acetonitrile:water (+0.05% formic acid) gradient). This gave 112 mg of the title compound as a mixture of isomers (N1/N2-benzylated, ratio 2.3:1) (58% of theory).

LC-MS (Method 1): R$_t$=1.45 min (N2) and 1.50 min (N1); MS (EIpos): m/z=552 [M+H]$^+$.

Example 42A

3-[5-Fluoro-1-(2-fluoro-3-methoxybenzyl)-1H-pyrazolo[3,4-b]pyridin-3-yl]-7,7-dimethyl-5-{[2-(trimethylsilyl)ethoxy]methyl}-5,7-dihydro-6H-pyrrolo[2,3-e][1,2,4]triazin-6-one

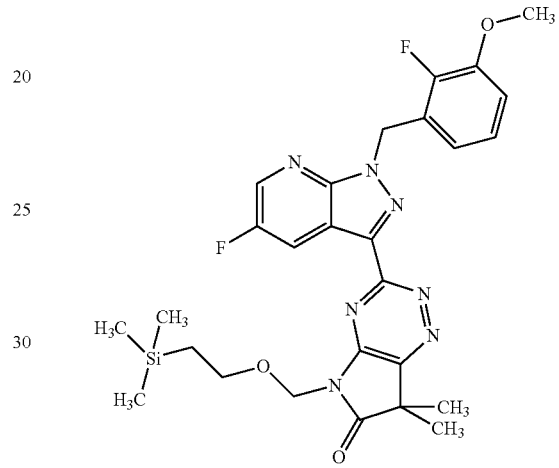

0.150 g (0.349 mmol) of the compound from Example 40A were reacted analogously to the procedure of Example 41A with 2-fluoro-3-methoxybenzyl bromide. After filtration, the mixture was purified by preparative HPLC (acetonitrile:water (+0.05% formic acid) gradient). This gave 92 mg of the title compound (46% of theory).

LC-MS (Method 1): R$_t$=1.43 min; MS (EIpos): m/z=568 [M+H]$^+$.

Example 43A

3-[5-Fluoro-1-(2-fluoro-3-methylbenzyl)-1H-pyrazolo[3,4-b]pyridin-3-yl]-7,7-dimethyl-5-{[2-(trimethylsilyl)ethoxy]methyl}-5,7-dihydro-6H-pyrrolo[2,3-e][1,2,4]triazin-6-one

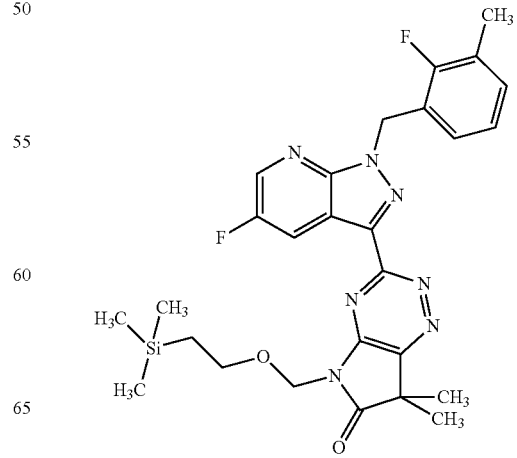

0.150 g (0.349 mmol) of the compound from Example 40A were reacted analogously to the procedure of Example 41A with 1-(bromomethyl)-2-fluoro-3-methylbenzene. After filtration, the mixture was purified by preparative HPLC (acetonitrile:water (+0.05% formic acid) gradient). This gave 83 mg of the title compound (44% of theory).

LC-MS (Method 1): $R_t$=1.50 min; MS (EIpos): m/z=551 [M+H]$^+$.

Example 44A

Diethyl 2-(2-ethoxyethyl)-2-methyl-3-oxobutanedioate

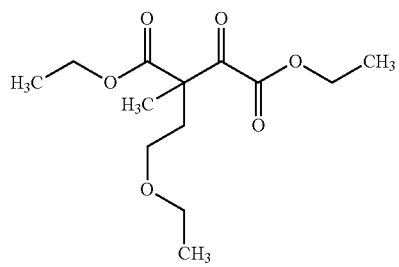 [SMILES: CCOCCC(C)(C(=O)OCC)C(=O)C(=O)OCC]

Analogously to the procedure of Example 12A, 10.980 ml (97.370 mmol) of 2-bromoethyl ethyl ether were added to 2.796 ml (14.836 mmol) of diethyl 2-methyl-3-oxobutanedioate. This gave 3.38 g of the title compound which was reacted in the next step without further purification.

Example 45A

Ethyl 4-ethoxy-2-{3-[5-fluoro-1-(2-fluorobenzyl)-1H-pyrazolo[3,4-b]pyridin-3-yl]-5-hydroxy-1,2,4-triazin-6-yl}-2-methylbutanoate

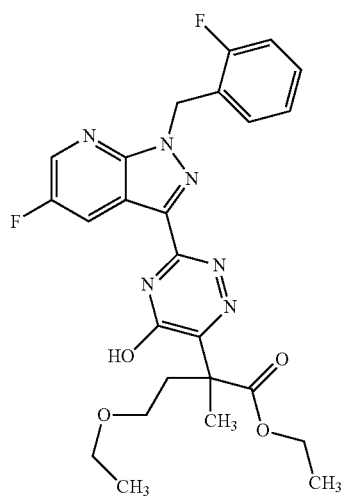 [SMILES: CCOCCC(C)(C(=O)OCC)c1nnc(-c2nn(Cc3ccccc3F)c3ncc(F)cc23)nc1O]

0.50 g (1.654 mmol) of the compound from Example 44A were reacted analogously to the procedure of Example 27A with 907 mg (3.308 mmol) of Example 25A. This gave 42 mg (5% of theory) of the title compound.

LC-MS (Method 1): $R_t$=1.10 min; MS (ESIpos): m/z=513 (M+H)$^+$

Example 46A

4-Amino-2-[1-(2-fluorobenzyl)-1H-pyrazolo[3,4-b]pyridin-3-yl]-5,5-dimethyl-5,7-dihydro-6H-pyrrolo[2,3-d]pyrimidin-6-one

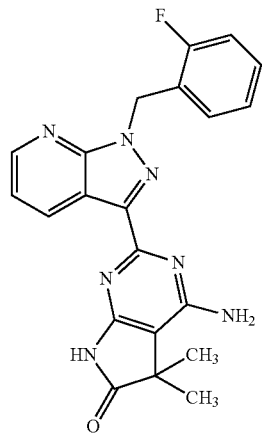 [SMILES: CC1(C)C(=O)Nc2nc(-c3nn(Cc4ccccc4F)c4ncccc34)nc(N)c21]

5.887 g (19.256 mmol) of Example 2A were initially charged in tert-butanol (50 ml), and 2.593 g (23.107 mmol) of potassium tert-butoxide were added. Subsequently, 3.2 g (19.256 mmol) of Example 1A in tert-butanol (25 ml) were added dropwise and the mixture was heated to reflux overnight. The next day, another 0.64 g (3.851 mmol) of Example 1A was added and the mixture was heated to reflux for a further day. After cooling, a precipitate was filtered off, which was washed with diethyl ether. Subsequently, the precipitate was slurried in water, filtered off once more and washed with diethyl ether. After drying under high vacuum, 6.65 g of the title compound were obtained (85% of theory).

LC-MS (Method 1): $R_t$=0.90 min; MS (ESIpos): m/z=404 (M+H)$^+$ $^1$H NMR (400 MHz, DMSO-d$_6$): δ [ppm]=1.35 (s, 6H), 5.82 (s, 2H), 6.82 (br s, 2H), 7.14-7.25 (m, 3H), 7.33-7.40 (m, 2H), 8.63 (dd, 1H), 9.03 (dd, 1H), 10.98 (s br, 1H).

Example 47A

2-[1-(2-Fluorobenzyl)-1H-pyrazolo[3,4-b]pyridin-3-yl]-4-iodo-5,5-dimethyl-5,7-dihydro-6H-pyrrolo[2,3-d]pyrimidin-6-one

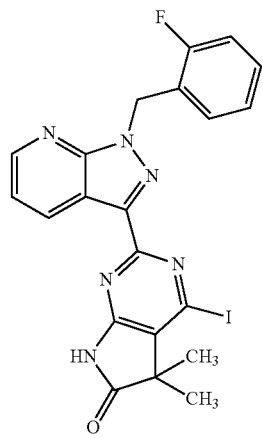 [SMILES: CC1(C)C(=O)Nc2nc(-c3nn(Cc4ccccc4F)c4ncccc34)nc(I)c21]

5.00 g (12.394 mmol) of Example 46A were initially charged in isopentyl nitrite (35.87 ml) and diiodomethane (1.16 mol, 93.71 ml), and the mixture was heated at 85° C. for 12 h. After cooling, solids were filtered off, the mixture was concentrated and the residue was then purified by chromatography on silica gel (mobile phase: initially cyclohexane/dichloromethane gradient, then dichloromethane/methanol gradient). This gave 5.50 g of the title compound (67% of theory).

LC-MS (Method 1): $R_t$=1.19 min; MS (ESIpos): m/z=515 (M+H)$^+$ $^1$H NMR (400 MHz, DMSO-d$_6$): δ [ppm]=1.42 (s, 6H), 5.88 (s, 2H), 7.13-7.26 (m, 3H), 7.34-7.38 (m, 1H), 7.48 (dd, 1H), 8.69 (dd, 1H), 8.79 (dd, 1H), 11.78 (s br, 1H).

Example 48A

5-Fluoro-6-methyl-1H-pyrazolo[3,4-b]pyridine-3-amine

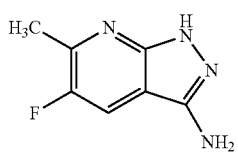

58 g (340.027 mmol) of 2-chloro-5-fluoro-6-methylnicotinonitrile (preparation described in WO2007/41052, Example U-2, page 80) were initially charged in 1,2-ethanediol (580 ml), and hydrazine hydrate (24.813 ml) and 56.091 ml (340.027 mmol) of diisopropylethylamine were then added. With stirring, the mixture was heated at 80° C. for 16 h and then at 120° C. for 66 h. After cooling, water (2.5 l) and ethyl acetate (2.5 l) were added, and the mixture was filtered off with suction. The solid obtained was dried. This gave 28.4 g (47% of theory) of the target compound.

LC-MS (Method 7): $R_t$=1.77 min; MS (ESIpos): m/z=167 (M+H)

Example 49A

5-Fluoro-3-iodo-6-methyl-1H-pyrazolo[3,4-b]pyridine

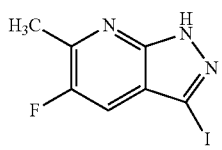

28 g (168.513 mmol) of Example 48A were reacted analogously to the procedure of Example 19A. Chromatography on silica gel (cyclohexane:ethyl acetate 9:1) gave 14.9 g (31% of theory) of the title compound.

LC-MS (Method 1): $R_t$=0.84 min; MS (ESIpos): m/z=278 (M+H)

Example 50A

5-Fluoro-1-(2-fluorobenzyl)-3-iodo-6-methyl-1H-pyrazolo[3,4-b]pyridine

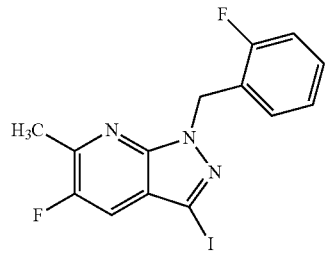 [SMILES: Cc1nc2c(cc1F)c(I)nn2Cc1ccccc1F]

13 g (46.925 mmol) of Example 49A were reacted analogously to the procedure of Example 20A. Chromatography on silica gel (cyclohexane:ethyl acetate gradient) gave 8.4 g (43% of theory) of the title compound.

LC-MS (Method 1): $R_t$=1.32 min; MS (ESIpos): m/z=386 (M+H)

Example 51A

5-Fluoro-1-(2-fluorobenzyl)-6-methyl-1H-pyrazolo[3,4-b]pyridine-3-carbonitrile

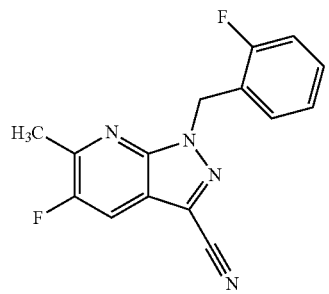 [SMILES: Cc1nc2c(cc1F)c(C#N)nn2Cc1ccccc1F]

9.3 g (24.146 mmol) of Example 50A were reacted analogously to the procedure of Example 23A, variant A. Chromatography on silica gel (cyclohexane:ethyl acetate gradient) gave 5.7 g (80% of theory, about 95% pure) of the title compound.

LC-MS (Method 1): $R_t$=1.20 min; MS (ESIpos): m/z=285 (M+H)$^+$

Example 52A

5-Fluoro-1-(2-fluorobenzyl)-6-methyl-1H-pyrazolo[3,4-b]pyridine-3-carboximidamide acetate

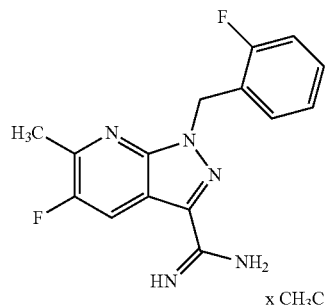

5.7 g (18.908 mmol, about 95% pure) of Example 51A were reacted analogously to the procedure of Example 24A. This gave 6.6 g (96% of theory) of the title compound.

LC-MS (Method 1): $R_t$=0.66 min; MS (ESIpos): m/z=302 (M+H)$^+$

Example 53A

5-Fluoro-1-(2-fluorobenzyl)-6-methyl-1H-pyrazolo[3,4-b]pyridine-3-carboximidohydrazide

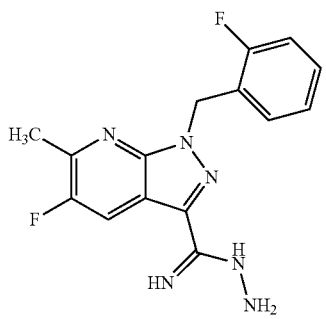 [SMILES: Cc1nc2c(cc1F)c(C(=N)NN)nn2Cc1ccccc1F]

500 mg (1.384 mmol) of Example 52A were reacted analogously to the procedure of Example 25A. This gave 365 mg (83% of theory) of the title compound.

LC-MS (Method 1): $R_t$=0.68 min; MS (ESIpos): m/z=317 (M+H)$^+$

Example 54A

Methyl 2-{3-[5-fluoro-1-(2-fluorobenzyl)-6-methyl-1H-pyrazolo[3,4-b]pyridin-3-yl]-5-hydroxy-1,2,4-triazin-6-yl}-2-methylpropanoate

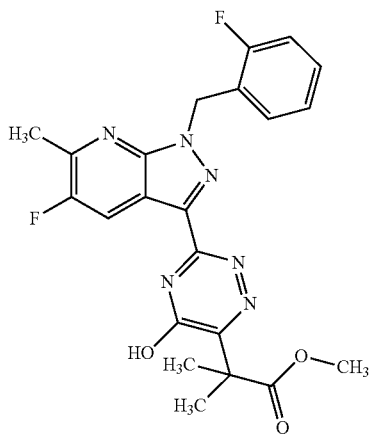

365 mg (1.154 mmol) of Example 53A were reacted analogously to the procedure of Example 13A with 325 mg (1.731 mmol) of dimethyl 2,2-dimethyl-3-oxobutanedioate. This gave 589 mg (92% of theory, purity 82%) of the title compound.

LC-MS (Method 1): $R_t$=1.08 min; MS (ESIpos): m/z=455 (M+H)$^+$

Example 55A

4-Amino-2-[5-fluoro-1-(2-fluorobenzyl)-6-methyl-1H-pyrazolo[3,4-b]pyridin-3-yl]-5,5-dimethyl-5,7-dihydro-6H-pyrrolo[2,3-d]pyrimidin-6-one

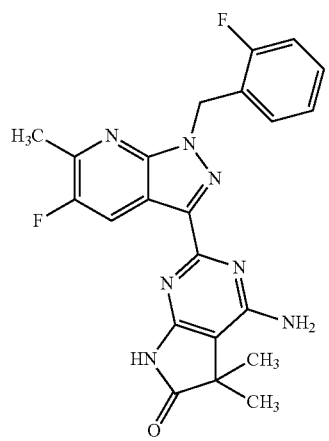 [SMILES: Cc1nc2c(cc1F)c(-c1nc(N)c3c(n1)NC(=O)C3(C)C)nn2Cc1ccccc1F]

1 g (2.767 mmol) of Example 52A were reacted analogously to the procedure of Example 46A. This gave 971 mg (80% of theory) of the title compound.

LC-MS (Method 1): $R_t$=1.05 min; MS (ESIpos): m/z=436 (M+H)$^+$

Example 56A

2-[5-Fluoro-1-(2-fluorobenzyl)-6-methyl-1H-pyrazolo[3,4-b]pyridin-3-yl]-4-iodo-5,5-dimethyl-5,7-dihydro-6H-pyrrolo[2,3-d]pyrimidin-6-one

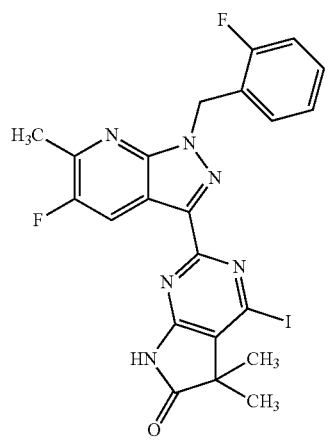 [SMILES: Cc1nc2c(cc1F)c(-c1nc(I)c3c(n1)NC(=O)C3(C)C)nn2Cc1ccccc1F]

960 mg (2.205 mmol) of Example 55A were reacted analogously to the procedure of Example 47A. This gave 749 mg (62% of theory, 84% pure) of the title compound.

LC-MS (Method 1): $R_t$=1.35 min; MS (ESIpos): m/z=547 (M+H)$^+$

Example 57A (rac) Ethyl 2-{3-[1-(2-fluorobenzyl)-1H-pyrazolo[3,4-b]pyridin-3-yl]-5-hydroxy-1,2,4-triazin-6-yl}-2-methylhex-5-enoate

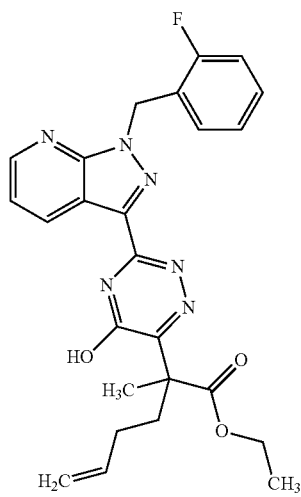 [SMILES: C=CCCC(C)(C(=O)OCC)c1nnc(-c2nn(Cc3ccccc3F)c3ncccc23)nc1O]

6.34 g (about 24.74 mmol) of the compound from Example 59A were initially introduced into 80 ml of ethanol. The mixture was heated to reflux and 3.91 g (12.37 mmol, purity 90%) of the compound from Example 11A were added a little at a time. Stirring of the mixture at reflux was continued overnight. After cooling, the precipitated solid was filtered off. The filtrate was concentrated under reduced pressure. The residue (9.2 g) was dissolved in about 40 ml of acetonitrile/methanol and purified by prep. HPLC (Daiso C18 10 μm Bio 300×100 mm: neutral, gradient: water/acetonitrile (60-90%).

Drying under high vacuum gave 704 mg (12% of theory) of the title compound.

LC-MS (Method 1): $R_t$=1.18 min; MS (ESIpos): m/z=477 (M+H)$^+$ $^1$H NMR (400 MHz, DMSO-d$_6$): δ [ppm]=1.10 (t, 3H) 1.43 (s, 3H) 1.78-2.04 (m, 1H) 2.06-2.23 (m, 1H), 4.05 (m, 2H) 4.87-5.10 (m, 2H), 5.67-5.85 (m, 1H), 5.91 (s, 2H), 7.06-7.29 (m, 3H), 7.32-7.44 (m, 1H) 7.47-7.57 (m, 1H) 8.67-8.82 (m, 2H) 14.53 (br. s, 1H).

Example 58A (rac) Ethyl 2-{5-chloro-3-[1-(2-fluorobenzyl)-1H-pyrazolo[3,4-b]pyridin-3-yl]-1,2,4-triazin-6-yl}-2-methylhex-5-enoate

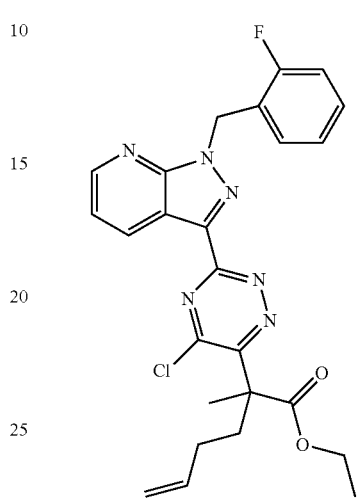

At room temperature, 10 ml of phosphoryl chloride were added to 700 mg (1.47 mmol) of the compound from Example 57A, and the mixture was stirred at room temperature overnight. The reaction solution was processed further without any work-up.

LC-MS (Method 1): $R_t$=1.40 min; MS (ESIpos): m/z=495 (M+H)$^+$

Example 59A

Diethyl 2-(but-3-en-1-yl)-2-methyl-3-oxobutanedioate

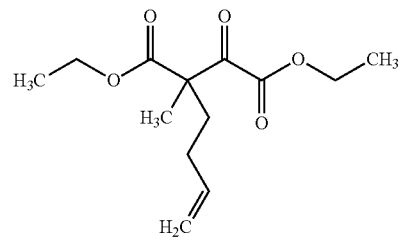 [SMILES: C=CCCC(C)(C(=O)OCC)C(=O)C(=O)OCC]

Under argon, 6.24 g (55.64 mmol) of potassium tert-butoxide were initially charged in 400 ml of toluene. At room temperature, 10 g of diethyl oxalpropionate were slowly added dropwise. 32.95 ml (324.57 mmol) of 4-bromo-1-butene and 1.23 g (4.65 mmol) of 18-crown-6 were then added. The mixture was heated under reflux for 4 h. This was followed by cooling to 5° C. The reaction mixture was added to a cooled mixture of diethyl ether and 7% strength aqueous hydrochloric acid. The phases were separated. The organic phase was washed once with ice-cold 7% strength aqueous hydrochloric acid and twice with water. After drying over sodium sulphate, the mixture was concentrated and the residue was dried under high vacuum overnight. This gave 13.42 g of the title compound as a crude product, which was used for the subsequent reactions.

$^1$H NMR (400 MHz, CDCl$_3$): d [ppm]=1.19-1.31 (t, 3H), 1.32-1.41 (t, 3H), 1.84 (s, 3H), 2.42-2.47 (m, 2H), 3.93 (t, 2H), 4.10-4.24 (q, 2H), 4.26-4.41 (q, 2H), 5.09-5.16 (m, 2H), 5.76-5.84 (m, 1H).

Example 60A

2-[1-(2-Fluorobenzyl)-1H-pyrazolo[3,4-b]pyridin-3-yl]-5,5-dimethyl-6-oxo-6,7-dihydro-5H-pyrrolo[2,3-d]pyrimidine-4-carbonitrile

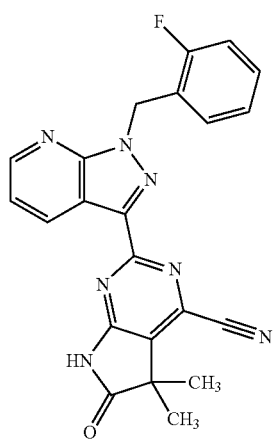 [SMILES: CC1(C)C(=O)Nc2nc(-c3nn(Cc4ccccc4F)c4ncccc34)nc(C#N)c21]

Under argon, 5 g (8.26 mmol) of the compound from Example 47A (85% pure) and 814 mg (9.09 mmol) of copper(I) cyanide were initially charged in 87 ml of DMSO. The suspension was stirred at 150° C. for 3 h. The mixture was cooled and a mixture of saturated aqueous ammonium chloride solution and 33% strength aqueous ammonia solution (3:1) and ethyl acetate was cautiously added, and the mixture was stirred at RT for 30 min. The mixture was then filtered with suction through Celite, and the filter cake was washed with ethyl acetate. After phase separation, the organic phase was washed three times with ammonium chloride/ammonia solution (3:1) and once with saturated aqueous sodium chloride solution. The organic phase was dried over sodium sulphate and concentrated under reduced pressure. The residue was dissolved in dichloromethane and chromatographed on silica gel using dichloromethane/acetone (99:1). The product fractions were concentrated and dried under high vacuum. This gave 1.44 g (33% of theory, purity 77%) of the title compound.

LC-MS (Method 1): R$_t$=1.10 min; MS (ESIpos): m/z=414 (M+H)$^+$

Example 61A (rac)N-Cyclopropyl-4-iodo-5-methyl-6-oxo-2-[1-(3,3,3-trifluoropropyl)-1H-pyrazolo[3,4-b]pyridin-3-yl]-6,7-dihydro-5H-pyrrolo[2,3-d]pyrimidine-5-carboxamide

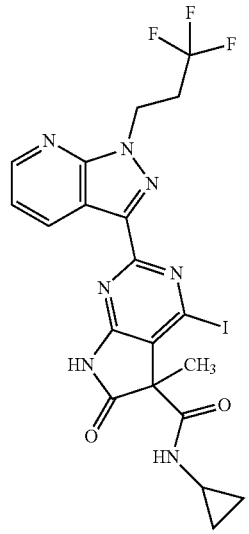 [SMILES: CC1(C(=O)NC2CC2)C(=O)Nc2nc(-c3nn(CCC(F)(F)F)c4ncccc34)nc(I)c21]

Under an argon atmosphere, 305 mg (0.66 mmol) of 4-amino-N-cyclopropyl-5-methyl-6-oxo-2-[1-(3,3,3-trifluoropropyl)-1H-pyrazolo[3,4-b]pyridin-3-yl]-6,7-dihydro-5H-pyrrolo[2,3-d]pyrimidine-5-carboxamide (described in WO 2011/149921, Expl. 181B) and 0.27 ml (1.99 mmol) of isopentyl nitrite were initially charged in 12 ml of dioxane, and 0.16 ml (1.99 mmol) of diiodomethane was added. After 8 h of stirring at 85° C., the mixture was cooled, concentrated under reduced pressure and purified by preparative HPLC (gradient 0.05% formic acid in water/20-95% acetonitrile). This gave 111.8 mg of the title compound (18% of theory, purity 60%).

LC-MS (Method 9): R$_t$=2.90 min; MS (ESIpos): m/z=572 (M+H)$^+$

Example 62A

3-[1-(2-Fluorobenzyl)-1H-pyrazolo[3,4-b]pyridin-3-yl]-1,2,4-triazin-5(4H)-one

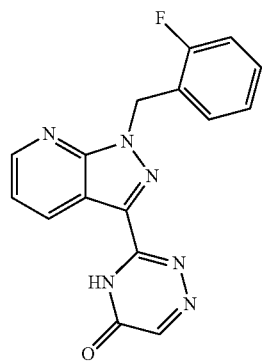 [SMILES: O=c1cnnc(-c2nn(Cc3ccccc3F)c3ncccc23)[nH]1]

6.17 ml (31.13 mmol) of ethyl glyoxylate (50% in toluene) were initially charged in 50 ml of ethanol. 5.90 g (20.75 mmol) of Example 11A, suspended in 200 ml of ethanol, were added dropwise and the mixture was heated at reflux overnight. After cooling, the precipitated solid was filtered off, washed with ethanol and dried under high vacuum overnight. This gave 2.95 g (44% of theory) of the title compound.

The filtrate was concentrated under reduced pressure. Ethanol was added to the residue and the insoluble solid was filtered off and washed with ethanol. Drying under high vacuum gave 0.61 g (9% of theory) of the title compound.

The filtrate was concentrated under reduced pressure and the residue was dried under high vacuum. This gave 3.14 g (43% of theory, 43% pure) of the title compound.

LC-MS (Method 1): $R_t$=0.80 min; MS (ESIpos): m/z=323 $(M+H)^+$ $^1$H NMR (400 MHz, DMSO-$d_6$): δ [ppm]=5.91 (s, 2H) 7.10-7.19 (m, 1H) 7.22-7.30 (m, 2H) 7.33-7.43 (m, 1H) 7.51 (dd, 1H) 8.69-8.79 (m, 2H) 14.46 (br.s, 1H).

Example 63A 3-(5,6-Dichloro-1,2,4-triazin-3-yl)-1-(2-fluorobenzyl)-1H-pyrazolo[3,4-b]pyridine

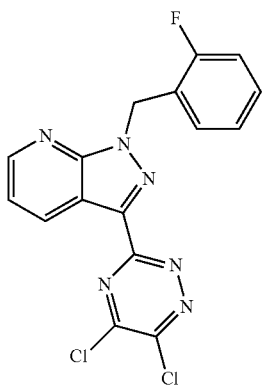

Under argon, 3.56 g (11.04 mmol) of the compound from Example 62A were initially charged in 28 ml of thionyl chloride. The mixture was heated at reflux for 8 h. Another 12 ml of thionyl chloride were then added, and the mixture was heated at reflux overnight. The mixture was subsequently cooled and concentrated under reduced pressure. Twice, toluene was added to the residue and each time the mixture was then concentrated under reduced pressure. Drying of the solid under high vacuum gave 4.19 g (82% of theory) of the title compound as a crude product which was reacted without further purification.

LC-MS (Method 1): $R_t$=1.23 min; MS (ESIpos): m/z=375 $(M+H)^+$

Example 64A

6-Chloro-3-[1-(2-fluorobenzyl)-1H-pyrazolo[3,4-b]pyridin-3-yl]-1,2,4-triazine-5-amine

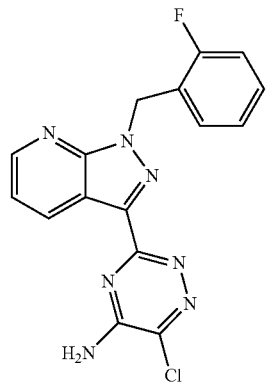 [SMILES: Fc1ccccc1Cn1nc(-c2nnc(Cl)c(Cl)n2)c2cccnc21]

Under argon, 100 mg (0.27 mmol) of Example 63A were initially charged in 3 ml of THF. At 0° C., 56 μl (0.32 mmol) of N,N-diisopropylethylamine were added, and 0.16 ml (0.32 mmol) of ammonia (2M in ethanol) was added dropwise. The mixture was then stirred at RT overnight. The mixture was then partitioned between dichloromethane and 1N aqueous hydrochloric acid, the aqueous phase was extracted with dichloromethane and the combined organic phases were dried over sodium sulphate and concentrated under reduced pressure. DMF, acetonitrile and water were added to the residue and the precipitated solid was filtered off with suction and discarded. The filtrate was purified by preparative HPLC (water with 0.05% formic acid/acetonitrile, gradient 20-95% acetonitrile). The product fractions were concentrated under reduced pressure. Drying under high vacuum gave 12.5 mg (13% of theory) of the title compound.

LC-MS (Method 2): $R_t$=0.92 min; MS (ESIpos): m/z=356 $(M+H)^+$ $^1$H NMR (400 MHz, DMSO-$d_6$): δ [ppm]=5.86 (s, 2H) 7.10-7.19 (m, 1H) 7.19-7.30 (m, 2H) 7.32-7.41 (m, 1H) 7.44 (dd, 1H) 7.89 (br. s., 1H) 8.60-8.76 (m, 2H) 8.85 (dd, 1H).

Example 65A (rac) Diethyl 2-allyl-2-methyl-3-oxobutanedioate

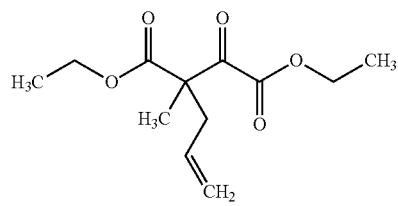 [SMILES: C=CCC(C)(C(=O)OCC)C(=O)C(=O)OCC]

Under argon, 49.94 g (0.445 mol) of potassium tert-butoxide were initially charged in 3.20 l of toluene. At room temperature, 225 ml (2.60 mmol) of allyl bromide were added dropwise. 9.83 g (37.19 mmol) of 18-crown-6 were then added, and the mixture was boiled at reflux for 4 h. The reaction mixture was then cooled to 5° C. and 500 ml of 7% strength aqueous hydrochloric acid were added. The phases were separated and the organic phase was washed with 300 ml of ice-cold 7% strength aqueous hydrochloric acid and twice with in each case 200 ml of water. The mixture was dried over sodium sulphate and then concentrated. This gave 102 g of the title compound as a crude product, which was reacted further without further purification.

GC-MS (Method 8): $R_t$=4.23 min; MS (EI): m/z=242 (M+)$^+$ $^1$H NMR (400 MHz, DMSO-d$_6$): δ [ppm]=1.10-1.17 (t, 3H), 1.21-1.29 (t, 3H), 1.34 (s, 3H), 2.30 (s, 1H), 2.44-2.68 (m, 5H), 3.33 (s, 3H), 4.04-4.17 (m, 2H), 4.27 (q, 2H), 5.01-5.17 (m, 2H), 5.54-5.66 (m, 1H).

Example 66A (rac) Ethyl 2-{3-[1-(2-fluorobenzyl)-1H-pyrazolo[3,4-b]pyridin-3-yl]-5-hydroxy-1,2,4-triazin-6-yl}-2-methylpent-4-enoate

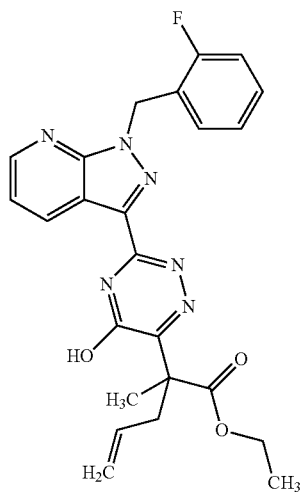 [SMILES: C=CCC(C)(C(=O)OCC)c1nnc(-c2nn(Cc3ccccc3F)c3ncccc23)nc1O]

84.37 g (348.23 mmmol) of Example 65A were initially charged in 1.10 l of ethanol. Under reflux, 55 g (0.174 mol, purity 90%) of Example 11A were added a little at a time, and heating under reflux was continued overnight. The reaction was then combined with a test batch starting with 11.1 g (35.1 mmol) of Example 65A. The mixture was then cooled to 5° C. and the precipitated solid was filtered off and washed with tert-butyl methyl ether. The solid was discarded. The filtrate was concentrated under reduced pressure, 500 ml of tert-butyl methyl ether were added to the residue and the mixture was stirred at room temperature for 1 h. Once more, a solid was filtered off, washed with diethyl ether and discarded. The filtrate was concentrated under reduced pressure, and diethyl ether was added. The residue was then filtered off, washed with diethyl ether and dried. This gave 40.40 g (42% of theory) of the title compound.

LC-MS (Method 1): $R_t$=1.13 min; MS (ESIpos): m/z=463 (M+H)$^+$ $^1$H NMR (400 MHz, DMSO-d$_6$): δ [ppm]=1.10 (t, 3H), 1.38 (s, 2H), 2.57-2.90 (m, 2H), 3.94-4.10 (m, 2H), 4.97-5.10 (m, 2H), 5.58-5.74 (m, 1H), 5.94 (s, 2H), 7.11-7.20 (m, 1H), 7.20-7.31 (m, 2H), 7.33-7.44 (m, 1H), 7.46-7.56 (m, 1H), 8.68-8.78 (m, 2H).

Example 68A

3-Iodo-1-(3,3,4,4,4-pentafluorobutyl)-1H-pyrazolo[3,4-b]pyridine

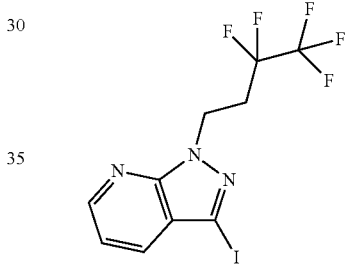

Under an argon atmosphere, 10 g (40.81 mmol) of 3-iodo-1H-pyrazolo[3,4-b]pyridine (WO 2006/130673, Ex. 4b) and 14.63 g (44.89 mmol) of caesium carbonate were initially charged in 170 ml of N,N-dimethylformamide, and 12.3 g (44.89 mmol) of 1,1,1,2,2-pentafluoro-4-iodobutane, dissolved in 30 ml of N,N-dimethylformamide, were added. The mixture was stirred at room temperature for 2 days. Another 14.63 g (44.89 mmol) of caesium carbonate and 12.3 g (44.89 mmol) of 1,1,1,2,2-pentafluoro-4-iodobutane were then added. The mixture was stirred at room temperature over the weekend, and another 3.49 g (12.72 mmol) of 1,1,1,2,2-pentafluoro-4-iodobutane and 4.14 g (12.72 mmol) of caesium carbonate were added. After a further night at room temperature, 5 g (18.25 mmol) of 1,1,1,2,2-pentafluoro-4-iodobutane and 5.95 g (18.25 mmol) of caesium carbonate were added. After 6 days of stirring at room temperature, the mixture was heated at 70° C. for 2 days. The mixture was then cooled and filtered and the residue was washed with N,N-dimethylformamide. The filtrate was concentrated and purified by preparative HPLC (gradient 0.1% formic acid in water/60-90% methanol. This gave 5.48 g (34% of theory) of the title compound.

LC-MS (Method 1): $R_t$=1.23 min; MS (ESIpos): m/z=392 (M+H)$^+$ $^1$H NMR (400 MHz, DMSO-$d_6$): δ [ppm]=2.85-3.02 (m, 2H), 4.81 (t, 2H), 7.33 (dd, 1H), 7.98 (dd, 1H), 8.65 (dd, 1H).

Example 69A

2-[1-(2-Fluorobenzyl)-1H-pyrazolo[3,4-b]pyridin-3-yl]-4-iodo-5,5-dimethyl-7-{[2-(trimethylsilyl)ethoxy]methyl}-5,7-dihydro-6H-pyrrolo[2,3-d]pyrimidin-6-one

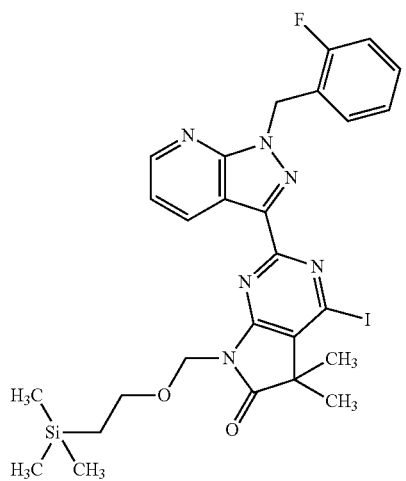 [SMILES: CC1(C)C(=O)N(COCC[Si](C)(C)C)c2nc(-c3nn(Cc4ccccc4F)c4ncccc34)nc(I)c21]

Under argon, 4.9 g (9.53 mmol) of Example 47A and 3.75 g (11.43 mmol) of caesium carbonate were initially charged in 15 ml of N,N-dimethylformamide With ice cooling, 2 ml (11.4 mmol) of 2-(trimethylsilyl)ethoxymethyl chloride were then added dropwise, and the mixture was stirred at room temperature overnight. After addition of 375 mg (1.14 mmol) of caesium carbonate and 0.2 ml (1.14 mmol) of 2-(trimethylsilyl)ethoxymethyl chloride, the mixture was stirred at room temperature for a further night. The mixture was then diluted with ethyl acetate and the inorganic solid was filtered off. The filtrate was concentrated under reduced pressure and dried under high vacuum (6.9 g). This residue was purified by flash chromatography on silica gel (mobile phase: cyclohexane/ethyl acetate 3:1). After drying under high vacuum, 4.3 g of the title compound were obtained (70% of theory).

LC-MS (Method 1): $R_t$=1.54 min; MS (ESIpos): m/z=645 (M+H)$^+$ $^1$H NMR (400 MHz, DMSO-$d_6$): δ [ppm]=−0.13 (s, 9H), 0.88 (t, 2H), 1.49 (s, 6H), 3.65 (t, 2H), 5.23 (s, 2H), 5.91 (s, 2H), 7.05-7.16 (m, 2H), 7.19-7.28 (m, 1H), 7.31-7.41 (m, 1H), 7.48 (dd, 1H), 8.69 (dd, 1H), 8.88 (dd, 1H).

Example 70A

Ethyl 3-(2-[1-(2-fluorobenzyl)-1H-pyrazolo[3,4-b]pyridin-3-yl]-5,5-dimethyl-6-oxo-7-{[2-(trimethylsilyl)ethoxy]methyl}-6,7-dihydro-5H-pyrrolo[2,3-d]pyrimidin-4-yl)acrylate

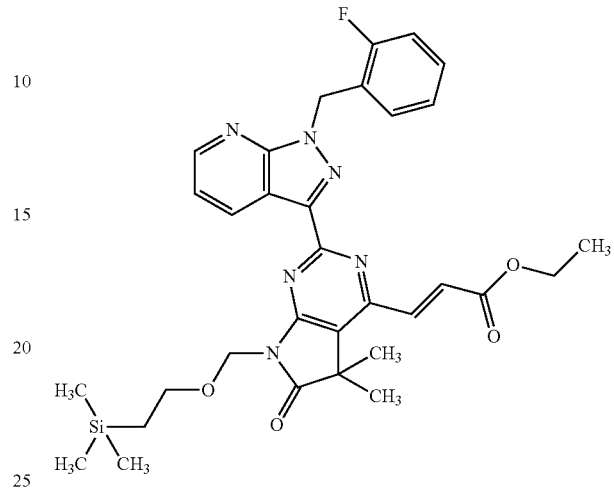

Under argon, 100 mg (0.16 mmol) of Example 69A were initially charged in 3.3 ml of a mixture of DMF, water and triethylamine (25:4:4), 170 μl (1.55 mmol) of ethyl acrylate, 25 mg (0.03 mmol) of palladium(II) acetate and 115 mg (0.31 mmol) of tetra-n-butylammonium iodide were added and the mixture was stirred at 60° C. for 9 h. A further 170 μl (1.55 mmol) of ethyl acrylate, 25 mg (0.03 mmol) of palladium(II) acetate and 115 mg (0.31 mmol) of tetra-n-butylammonium iodide were added, and the mixture was stirred at 90° C. for 9 h. The addition of these chemicals was repeated two more times, with stirring at 90° C. for 2.5 h after the first addition and for 3 h after the second addition. The mixture was finally diluted with acetonitrile and purified by prep. HPLC (gradients of water with 0.1% formic acid/acetonitrile 10-95%).

Yield: 37 mg (39% of theory)

LC-MS (Method 1): $R_t$=1.51 min; MS (ESIpos): m/z=617 (M+H)$^+$

Example 71A

Ethyl 3-{2-[1-(2-fluorobenzyl)-1H-pyrazolo[3,4-b]pyridin-3-yl]-7-(hydroxymethyl)-5,5-dimethyl-6-oxo-6,7-dihydro-5H-pyrrolo[2,3-d]pyrimidin-4-yl}acrylate

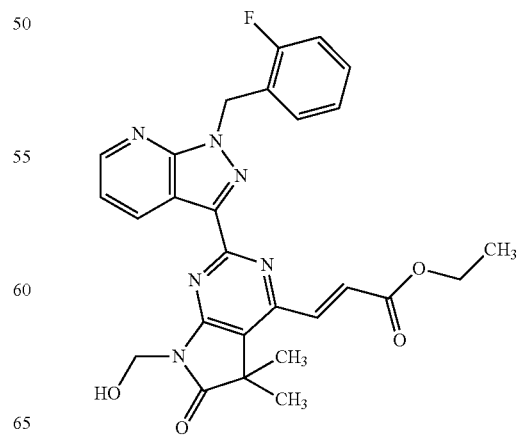

37 mg (0.06 mmol) of Example 70A were dissolved in 0.5 ml of dichloromethane, 100 µl (1.30 mmol) of trifluoroacetic acid were added and the mixture was stirred at room temperature for 2 h. The mixture was then concentrated under reduced pressure and dried under high vacuum. The crude product was reacted further without purification.

LC-MS (Method 1): $R_t$=1.19 min; MS (ESIpos): m/z=517 (M+H)$^+$ $^1$H NMR (400 MHz, DMSO-d$_6$): δ [ppm]=1.31 (t, 3H), 1.50 (s, 6H), 4.28 (q, 2H), 5.22 (s, 2H), 5.94 (s, 2H), 7.06-7.28 (m, 4H), 7.32-7.39 (m, 1H), 7.51 (dd, 1H), 7.68 (d, 1H), 8.70 (d, 1H), 8.94 (d, 1H).

Example 72A

Iodo(4,4,4-trifluorobutyl)zinc

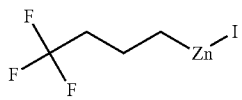

1.65 g (25.2 mmol) of zinc powder were initially charged in 5.5 ml of tetrahydrofuran. 0.15 ml (1.78 mmol) of 1,2-dibromoethane was added with stirring. Four times, the mixture was heated to reflux and cooled back to room temperature. 0.062 ml (0.49 mmol) of trimethylsilyl chloride was then added, and the mixture was stirred for 10 min. A solution of 2 g (8.40 mmol) of 4,4,4-trifluoro-1-iodobutane in 5.5 ml of tetrahydrofuran was added dropwise, with the mixture being maintained at RT by cooling with ice-water. The mixture was finally stirred at RT for 15 min, and the solution was then removed via a syringe with HPLC filter. A content of 0.76 M was assumed.

Example 73A

Iodo(3,3,3-trifluoropropyl)zinc

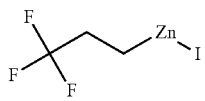

1.75 g (26.8 mmol) of zinc powder were initially charged in 5.5 ml of tetrahydrofuran. 0.16 ml (1.89 mmol) of 1,2-dibromoethane was added with stirring. Four times, the mixture was heated to reflux and cooled back to room temperature. 0.066 ml (0.52 mmol) of trimethylsilyl chloride was then added, and the mixture was stirred for 10 min. A solution of 2 g (8.93 mmol) of 1,1,1-trifluoro-3-iodopropane in 5.5 ml of tetrahydrofuran was added dropwise, with the mixture being maintained at RT by cooling with ice-water. The mixture was finally stirred at RT for 15 min, and the solution was then removed via a syringe with HPLC filter. A content of 0.81 M was assumed.

Example 74A

Diethyl (dicyanomethyl)(methyl)malonate

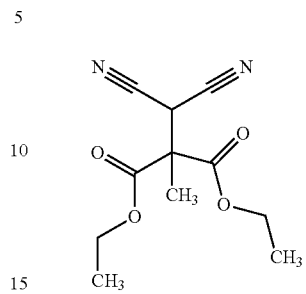

Under argon, 19.16 g (75.69 mmol) of diethyl 2-bromo-2-methylmalonate were initially charged in 120 ml of tetrahydrofuran. After addition of 5 g (75.69 mmol) of malononitrile and 8.49 g (75.69 mmol) of potassium tert-butoxide, the mixture was stirred at a bath temperature of 85° C. overnight. The mixture was cooled and ethyl acetate and saturated aqueous ammonium chloride solution were added. The phases were separated and the aqueous phase was extracted twice with ethyl acetate. The combined organic phases were washed with saturated sodium chloride solution, dried over sodium sulphate and concentrated on a rotary evaporator. The residue was purified by flash chromatography on silica gel (mobile phase: cyclohexane/ethyl acetate 9:1). After drying under high vacuum, 5.94 g of the title compound were obtained (33% of theory).

GC-MS (Method 8): $R_t$=4.29 min; MS (EI): m/z=210 (M−28)$^+$ $^1$H NMR (400 MHz, CDCl$_3$): δ [ppm]=1.27-1.37 (m, 6H), 1.80 (s, 3H), 4.18-4.44 (m, 4H), 4.53 (s, 1H).

Example 75A (rac) Ethyl 4-amino-2-[1-(2-fluorobenzyl)-1H-pyrazolo[3,4-b]pyridin-3-yl]-5-methyl-6-oxo-6,7-dihydro-5H-pyrrolo[2,3-d]pyrimidine-5-carboxylate

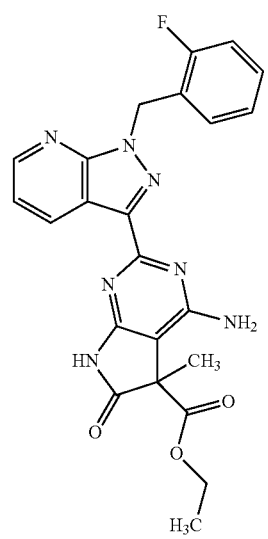 [SMILES: CCOC(=O)C1(C)C(=O)Nc2nc(-c3nn(Cc4ccccc4F)c4ncccc34)nc(N)c21]

Under an atmosphere of argon, 4.69 g (15.32 mmol) of Example 2A were initially charged in 120 ml of tert-butanol, and 3.07 g (30.66 mmol) of potassium bicarbonate and 4.2 g (17.63 mmol) of Example 74A were added at room temperature. The mixture was stirred at a bath temperature of 85° C. for 5 h. After cooling, water was added and the reaction mixture was stirred at room temperature for 30 min. The precipitated solid was filtered off and washed with water and diethyl ether. Drying under high vacuum gave 6.2 g (88% of theory) of the title compound.

LC-MS (Method 1): $R_t$=0.95 min; MS (ESIpos): m/z=462 (M+H)$^+$ $^1$H NMR (400 MHz, DMSO-d$_6$): δ [ppm]=1.12 (t, 3H), 1.62 (s, 3H), 4.01-4.21 (m, 2H), 5.83 (s, 2H), 6.76 (br. s, 2H), 7.07-7.29 (m, 3H), 7.31-7.45 (m, 2H), 8.64 (dd, 1H), 9.03 (dd, 1H), 11.34 (s, 1H).

Example 76A (rac) 2-[1-(2-Fluorobenzyl)-1H-pyrazolo[3,4-b]pyridin-3-yl]-5-methyl-6-oxo-6,7-dihydro-5H-pyrrolo[2,3-d]pyrimidine-5-carbohydrazide

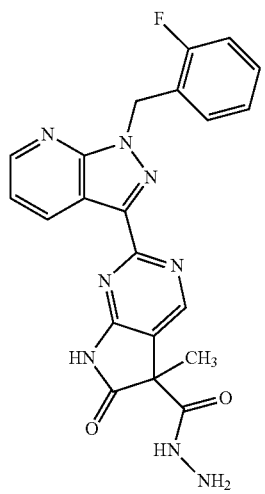 [SMILES: CC1(C(=O)NN)C(=O)Nc2nc(-c3nn(Cc4ccccc4F)c4ncccc34)ncc21]

Under an atmosphere of argon, 600 mg (0.77 mmol, purity 57%) of Example 33 were initially charged and 2.50 ml (64.12 mmol) of 80% pure hydrazine hydrate were added. The mixture was stirred at 80° C. for 30 min, cooled, concentrated on a rotary evaporator and dried under high vacuum. This gave 566 mg of the title compound as a crude product.

LC-MS (Method 1): $R_t$=0.80 min; MS (ESIpos): m/z=433 (M+H)$^+$

Example 77A (rac) 2-[1-(2-Fluorobenzyl)-1H-pyrazolo[3,4-b]pyridin-3-yl]-N'-formyl-5-methyl-6-oxo-6,7-dihydro-5H-pyrrolo[2,3-d]pyrimidine-5-carbohydrazide

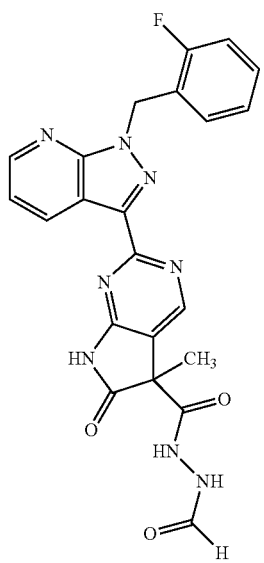 [SMILES: CC1(C(=O)NNC=O)C(=O)Nc2nc(-c3nn(Cc4ccccc4F)c4ncccc34)ncc21]

1 ml (26.88 mmol) of formic acid was added to 55 mg (0.13 mmol) of Example 76A in 1 ml of acetonitrile. The mixture was stirred at a bath temperature of 80° C. for 1.5 h, cooled and concentrated. Ethyl acetate was added to the residue and the mixture was washed in each case once with saturated aqueous sodium bicarbonate solution and saturated aqueous sodium chloride solution and then dried over sodium sulphate and concentrated. This gave 29.7 mg (50% of theory) of the title compound.

LC-MS (Method 1): $R_t$=0.84 min; MS (ESIpos): m/z=461 (M+H)$^+$

Example 78A 1-(3,3,4,4,4-Pentafluorobutyl)-1H-pyrazolo[3,4-b]pyridine-3-carboximidamide acetate (1:1)

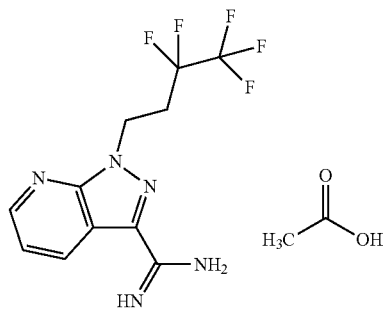

Under an atmosphere of argon, 668 mg (12.37 mmol) of sodium methoxide were initially charged in 40 ml of methanol, and 3.59 g (12.37 mmol) of Example 1-(3,3,4,4,4-pentafluorobutyl)-1H-pyrazolo[3,4-b]pyridine-3-carbonitrile (WO 2011/149921, Expl. 158 D), dissolved in 20 ml of methanol, were added. After 2 h of stirring at room temperature, 794 mg (14.85 mmol) of ammonium chloride and 2.76 ml (48.25 mmol) of acetic acid were added. The mixture was heated at reflux overnight, cooled and concentrated under reduced pressure, and ethyl acetate and 1 M aqueous sodium hydroxide solution were added. After 1 h of stirring at room temperature, the solid was filtered off, washed with ethyl acetate and water and dried under high vacuum overnight. 507 mg (11% of theory) of the title compound were obtained.

The phases of the filtrate were separated. The aqueous phase was extracted twice with ethyl acetate. The combined organic phases were washed once with water and once with saturated sodium chloride solution, dried over sodium sulphate, concentrated under reduced pressure and dried under high vacuum overnight. 2.76 g (43% of theory) of the title compound were obtained.

LC-MS (Method 1): $R_t$=0.58 min; MS (ESIpos): m/z=308 (M+H)$^+$ $^1$H NMR (400 MHz, DMSO-d$_6$): δ [ppm]=1.84 (s, 3H), 3.02 (tt, 2H), 4.85 (t, 2H), 7.40 (dd, 1H), 8.59-8.70 (m, 2H).

Example 79A (rac)Ethyl 4-amino-5-methyl-6-oxo-2-[1-(3,3,4,4,4-pentafluorobutyl)-1H-pyrazolo[3,4-b]pyridin-3-yl]-6,7-dihydro-5H-pyrrolo[2,3-d]pyrimidine-5-carboxylate

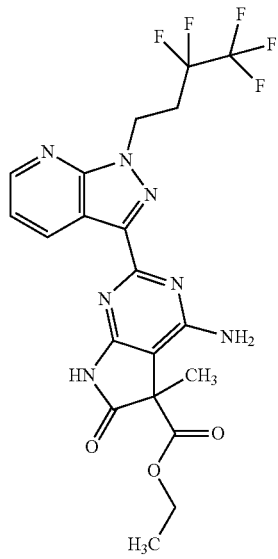 [SMILES: CCOC(=O)C1(C)C(=O)Nc2nc(-c3nn(CCC(F)(F)C(F)(F)F)c4ncccc34)nc(N)c21]

Under an atmosphere of argon, 500 mg (1.36 mmol) of Example 78A were initially charged in 10 ml of t-butanol, and 272.6 mg (2.72 mmol) of potassium bicarbonate and 373 mg (1.57 mmol) of Example 74A were added. After 5 h of stirring at 85° C., the mixture was cooled and water was added. After 30 min of stirring at room temperature, the precipitated solid was filtered off and washed with water and a little ether. Drying under high vacuum gave 458 mg (63% of theory) of the title compound.

The filtrate was extracted with ethyl acetate, the phases were separated and the aqueous phase was extracted twice with ethyl acetate. The combined organic phases were washed once with water and once with saturated sodium chloride solution, dried over sodium sulphate, concentrated under reduced pressure and dried under high vacuum. This gave 218 mg (23% of theory, purity 71%) of the title compound.

LC-MS (Method 1): $R_t$=1.00 min; MS (ESIpos): m/z=500 (M+H)$^+$

Example 80A (rac)Ethyl 2-{3-[5-fluoro-1-(2-fluorobenzyl)-1H-pyrazolo[3,4-b]pyridin-3-yl]-5-hydroxy-1,2,4-triazin-6-yl}-2-methylpent-4-enoate

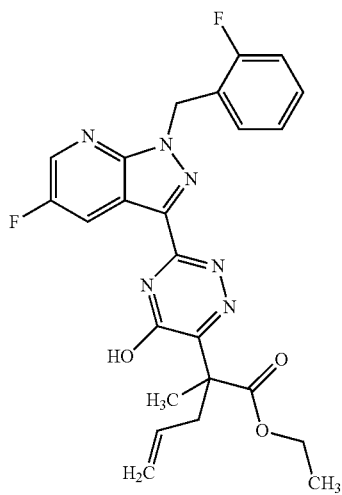 [SMILES: C=CCC(C)(C(=O)OCC)c1nnc(-c2nn(Cc3ccccc3F)c3ncc(F)cc23)nc1O]

4.12 g (13.62 mmol) of Example 25A were converted in analogy to Example 66A. This gave 2.03 g (22% of theory, purity 70%) of the title compound.

LC-MS (Method 1): $R_t$=1.19 min; MS (ESIpos): m/z=481 (M+H)$^+$

Example 81A

2-[5-Fluoro-1-(2-fluorobenzyl)-1H-pyrazolo[3,4-b]pyridin-3-yl]-5,5-dimethyl-6-oxo-6,7-dihydro-5H-pyrrolo[2,3-c]pyrimidine-4-carbonitrile

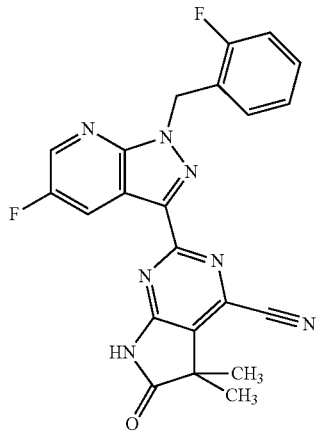 [SMILES: CC1(C)C(=O)Nc2nc(-c3nn(Cc4ccccc4F)c4ncc(F)cc34)nc(C#N)c21]

Under argon, 0.19 g (2.09 mmol) of copper(I) cyanide was added to 1.53 g (1.90 mmol) of 2-[5-fluoro-1-(2-fluorobenzyl)-1H-pyrazolo[3,4-b]pyridin-3-yl]-4-iodo-5,5-dimethyl-5,7-dihydro-6H-pyrrolo[2,3-c]pyrimidin-6-one (described in WO2012/004258, see also Example 56A) in 20 ml of DMSO, and the mixture was stirred at 150° C. for 3 h. After cooling, saturated aqueous ammonium chloride solution/33% strength aqueous ammonia solution (3:1) and ethyl acetate were added carefully, the mixture was stirred at room temperature for 30 min and filtered off with suction through Celite, and the filter cake was washed with ethyl acetate. The phases were separated and the organic phase was washed three times with saturated aqueous ammonium chloride solution/33% strength ammonia solution (3:1) and once with saturated sodium chloride solution, dried over sodium sulphate, concentrated under reduced pressure and dried under high vacuum overnight. This gave 1.22 g (89% of theory, purity 59%) of the title compound.

LC-MS (Method 1): $R_t$=1.17 min; MS (ESIpos): m/z=432 (M+H)$^+$

Example 82A (rac) Ethyl 4-bromo-2-[1-(2-fluorobenzyl)-1H-pyrazolo[3,4-b]pyridin-3-yl]-5-methyl-6-oxo-6,7-dihydro-5H-pyrrolo[2,3-d]pyrimidine-5-carboxylate

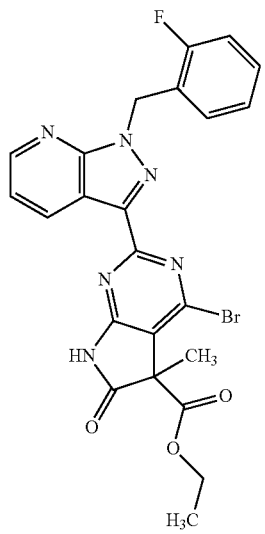

Under an atmosphere of argon, 3 g (6.50 mmol) of Example 75A were initially charged in 100 ml of dichloroethane. 1.31 ml (9.75 mmol) of isopentyl nitrite and 1.74 g (7.80 mmol) of copper(II) bromide were added and the mixture was stirred at a bath temperature of 65° C. overnight. After cooling, water and dichloromethane were added. The phases were separated and the aqueous phase was extracted twice with dichloromethane. The combined organic phases were dried over sodium sulphate, concentrated and purified by flash chromatography on silica gel (mobile phase: dichloromethane/methanol 100:1). Drying under high vacuum gave 2.32 g of the title compound (68% of theory).

LC-MS (Method 1): $R_t$=1.20 min; MS (ESIpos): m/z=525 (M+H)$^+$

Example 83A

Ethyl 5-amino-1-(2-fluorobenzyl)-4-formyl-1H-pyrazole-3-carboxylate

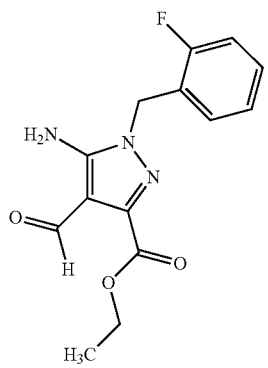 [SMILES: CCOC(=O)c1nn(Cc2ccccc2F)c(N)c1C=O]

Ethyl 5-amino-1-(2-fluorobenzyl)-4-formyl-1H-pyrazole-3-carboxylate was prepared analogously to compounds known from the literature from 2-fluorobenzyl bromide and sodium 1,4-diethoxy-1,4-dioxobut-2-en-2-olate (cf. Kelley et al. J. Med. Chem. 1995, 38, 3884-3888, Toche et al. J. Het. Chem. 2010, 47, 287-291 and patent: U.S. Pat. No. 4,833, 246, column 24.

a) Preparation of (2-fluorobenzyl)hydrazine

With stirring, 190 g (1.0 mol) of 2-fluorobenzyl bromide were added to a mixture of 250 g (5.0 mol) of hydrazine hydrate and 137 g (1.0 mol) of potassium carbonate in 2 l of ethanol. The mixture was stirred at room temperature for 2 d and then concentrated under reduced pressure. The residue was extracted with diethyl ether. The organic phase was dried over sodium sulphate and concentrated. The crude product was purified by chromatography on silica gel. This gave 109 g (76% of theory) of the target compound.

b) Preparation of ethyl 1-(2-fluorobenzyl)-5-oxo-4, 5-dihydro-1H-pyrazole-3-carboxylate A solution of 160 g (0.76 mol) of sodium 1,4-diethoxy-1,4-dioxobut-2-en-2-olate and 109 g (0.76 mol) of (2-fluorobenzyl)hydrazine in 1 l of glacial acetic acid was heated at 100° C. for 20 h. After cooling, the mixture was concentrated under reduced pressure. Water and dichloromethane were added to the residue, and the precipitate was filtered off and dried. 80 g (40% of theory) of the target compound were obtained.

c) Preparation of ethyl 5-chloro-1-(2-fluorobenzyl)-4-formyl-1H-pyrazole-3-carboxylate 79 g (1.08 mol) of dimethylformamide (DMF) were added dropwise to a cooled (10° C.) mixture of 70 g (0.27 mol) of ethyl 1-(2-fluorobenzyl)-5-oxo-4,5-dihydro-1H-pyrazole-3-carboxylate and 200 ml of phosphorus oxychloride, and the reaction mixture was stirred at 10° C. for 2 h and then at 100° C. for 5 h. The phosphorus oxychloride was distilled off under reduced pressure and the residue was added to water. The precipitate formed was filtered off and dried. 78 g (94% of theory) of the target compound were obtained.

d) Preparation of ethyl 5-azido-1-(2-fluorobenzyl)-4-formyl-1H-pyrazole-3-carboxylate 9 g (0.14 mol) of sodium azide were added to a cooled (0° C.) mixture of 31 g (0.1 mol) of ethyl-5-chloro-1-(2-fluorobenzyl)-4-formyl-1H-pyrazole-3-carboxylate and 200 ml of dimethylformamide (DMF). The reaction mixture was stirred at room temperature for 4 d, added to water and extracted with ethyl acetate. The organic phase was separated off, dried over sodium sulphate and concentrated under reduced pressure, giving 34 g (100% of theory) of the target compound.

e) Preparation of ethyl 5-amino-1-(2-fluorobenzyl)-4-formyl-1H-pyrazole-3-carboxylate A mixture of 33 g (0.11 mol) of ethyl 5-azido-1-(2-fluorobenzyl)-4-formyl-1H-pyrazolo-3-carboxylate and 51 g (0.3 mol) of sodium dithionite in 400 ml of ethanol was heated under reflux for 5 h. After cooling, the reaction mixture was added to 2 l of water. The precipitate formed was filtered off and dried under reduced pressure. 20 g (65% of theory) of the target compound were obtained.

$^1$H NMR (300 MHz, CDCl$_3$): δ [ppm]=1.39 (t, 3H), 4.43 (q, 2H), 544 (s, 2H), 6.96-7.12 (m, 3H), 7.18-7.27 (m, 1H), 10.38 (s, 1H).

Example 84A

Ethyl 1-(2-fluorobenzyl)-6-(trifluoromethyl)-1H-pyrazolo[3,4-b]pyridine-3-carboxylate

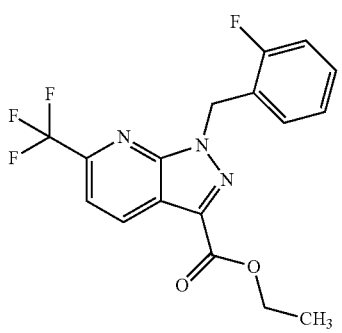 [SMILES: CCOC(=O)c1nn(Cc2ccccc2F)c2nc(C(F)(F)F)ccc12]

5.00 g (17.17 mmol) of ethyl 5-amino-1-(2-fluorobenzyl)-4-formyl-1H-pyrazole-3-carboxylate were dissolved in 80 ml of ethanol, 2.31 g (20.60 mmol) of 1,1,1-trifluoroacetone and 1.19 g (10.30 mmol) of L-proline were added and the mixture was divided into 4 microwave vessels and stirred in a microwave at 180° C. for 5 h. After cooling, the batches were combined and concentrated under reduced pressure. The residue was purified by preparative HPLC (acetonitrile:water (+0.05% formic acid) gradient). This gave 2.20 g of the title compound (34% of theory).

LC-MS (Method 1): R$_t$=1.28 min; MS (EIpos): m/z=368 [M+H]$^+$ $^1$H NMR (400 MHz, DMSO-d$_6$): δ [ppm]=1.39 (t, 3H), 4.43 (q, 2H), 5.89 (s, 2H), 7.17-7.26 (m, 2H), 7.32-7.43 (m, 2H), 7.94 (d, 1H), 8.78 (d, 1H).

Example 85A 1-(2-Fluorobenzyl)-6-(trifluoromethyl)-1H-pyrazolo[3,4-b]pyridine-3-carboxamide

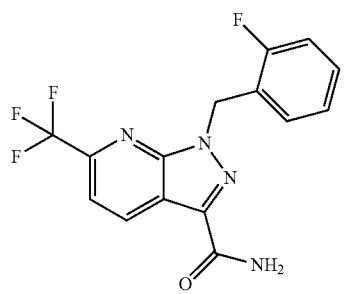 [SMILES: NC(=O)c1nn(Cc2ccccc2F)c2nc(C(F)(F)F)ccc12]

2.19 g (5.84 mmol) of ethyl 1-(2-fluorobenzyl)-6-(trifluoromethyl)-1H-pyrazolo[3,4-b]pyridine-3-carboxylate and 5.26 g (116.86 mmol) of formamide were suspended in absolute ethanol, and 1.22 ml of a 30% strength solution of sodium methoxide in methanol were added at room temperature. The mixture was stirred at 120° C. for 30 min. The solution, which had become clear, was allowed to stand at room temperature overnight, and the resulting precipitate was filtered off with suction. The filter cake was washed with water three times and dried under high vacuum. This gave 1.19 g of the target compound (60% of theory).

LC-MS (Method 1): R$_t$=1.06 min; MS (EIpos): m/z=339 [M+H]$^+$.

$^1$H NMR (400 MHz, DMSO-d$_6$): δ [ppm]=5.85 (s, 2H), 7.17 (dt, 1H), 7.21-7.28 (m, 2H), 7.35-7.41 (m, 1H), 7.86 (d, 1H), 7.96 (s, 2H), 8.85 (d, 1H).

Example 86A 1-(2-Fluorobenzyl)-6-(trifluoromethyl)-1H-pyrazolo[3,4-b]pyridine-3-carbonitrile

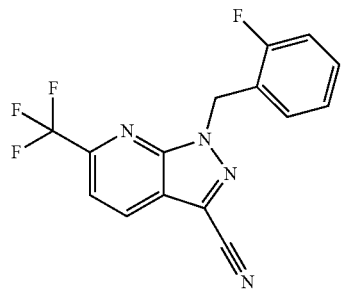 [SMILES: N#Cc1nn(Cc2ccccc2F)c2nc(C(F)(F)F)ccc12]

1.18 g (3.45 mmol) of 1-(2-fluorobenzyl)-6-(trifluoromethyl)-1H-pyrazolo[3,4-b]pyridine-3-carboxamide (Ex. 85A) were dissolved in 10 ml of phosphoryl chloride, and the solution was stirred at 120° C. for 30 min. After cooling, the phosphoryl chloride was distilled off and the residue was dried under high vacuum. The residue was purified by preparative HPLC (acetonitrile:water (+0.05% formic acid) gradient). This gave 671 mg of the title compound (57% of theory).

LC-MS (Method 1): R$_t$=1.23 min; MS (DCI): m/z=339 [M+H]$^+$ $^1$H NMR (400 MHz, DMSO-d$_6$): δ [ppm]=5.91 (s, 2H), 7.19-7.27 (m, 2H), 7.39-7.45 (m, 2H), 8.01 (d, 1H), 8.85 (d, 1H).

Example 87A 1-(2-Fluorobenzyl)-6-(trifluoromethyl)-1H-pyrazolo[3,4-b]pyridine-3-carboximidamide

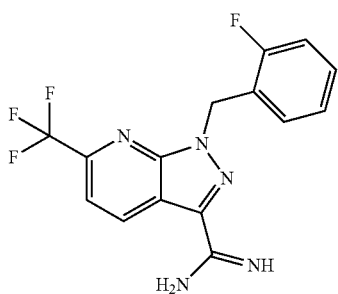 [SMILES: N=C(N)c1nn(Cc2ccccc2F)c2nc(C(F)(F)F)ccc12]

Under an atmosphere of argon, 660 mg (1.94 mmol) of 1-(2-fluorobenzyl)-6-(trifluoromethyl)-1H-pyrazolo[3,4-b]pyridine-3-carbonitrile (Ex. 86A) were dissolved in 6.2 ml of absolute methanol, 527 mg (1.94 mmol) of a 25% strength solution of sodium methoxide in methanol was added and the mixture was stirred at room temperature for 1 h. 107 mg (2.33 mmol) of ammonium chloride and 453 mg (7.56 mmol) of glacial acetic acid were added and the reaction mixture was heated under reflux for 2 h. After cooling, 20 ml of methanol were added and the mixture was adjusted to pH 10 with 1 N aqueous sodium hydroxide solution and stirred for 1 h. The methanol was distilled off on a rotary evaporator and the aqueous residue was extracted with ethyl acetate. The organic phase was dried over sodium sulphate, concentrated under reduced pressure and dried under high vacuum. This gave 530 mg of the title compound (73% of theory).

LC-MS (Method 1): R$_t$=0.78 min; MS (Elpos): m/z=338 [M+H]$^+$ $^1$H NMR (400 MHz, DMSO-d$_6$): δ [ppm]=5.82 (s, 2H), 7.03 (br. s, 3H), 7.16 (t, 1H), 7.21-7.27 (m, 2H), 7.35-7.41 (m, 1H), 7.83 (d, 1H), 8.97 (d, 1H).

Example 88A 1-(2-Fluorobenzyl)-6-(trifluoromethyl)-1H-pyrazolo[3,4-b]pyridine-3-carboximidohydrazide

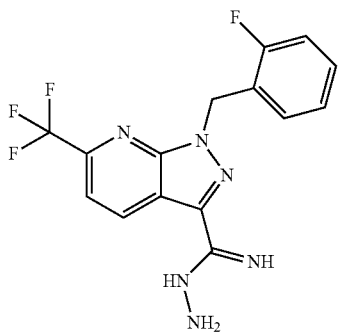 [SMILES: N=C(NN)c1nn(Cc2ccccc2F)c2nc(C(F)(F)F)ccc12]

530 mg (1.57 mmol) of 1-(2-fluorobenzyl)-6-(trifluoromethyl)-1H-pyrazolo[3,4-b]pyridine-3-carboximidamide (Ex. 87A) were dissolved in ethanol, and 98 mg of a 80% strength hydrazine hydrate solution were added at 0° C. The mixture was allowed to warm to room temperature and stirred for 16 h. The reaction mixture was then concentrated on a rotary evaporator and the residue was taken up in ethyl acetate and washed three times with a saturated sodium chloride solution. The organic phase was dried over sodium sulphate, concentrated on a rotary evaporator and dried under high vacuum. 495 mg of the title compound were obtained (69% purity; 62% of theory).

LC-MS (Method 1): R$_t$=0.76 min; MS (Elpos): m/z=353 [M+H]$^+$

Example 89A

Methyl 2-{3-[1-(2-fluorobenzyl)-6-(trifluoromethyl)-1H-pyrazolo[3,4-b]pyridin-3-yl]-5-hydroxy-1,2,4-triazin-6-yl}-2-methylpropanoate

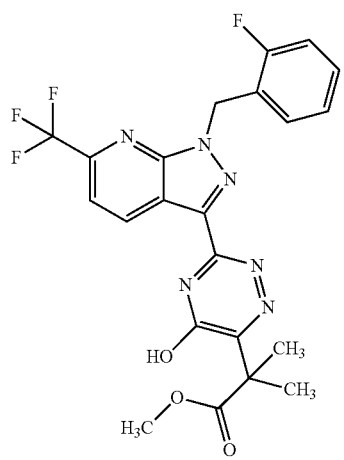 [SMILES: COC(=O)C(C)(C)c1nnc(-c2nn(Cc3ccccc3F)c3nc(C(F)(F)F)ccc23)nc1O]

490 mg (0.96 mmol, purity 69%) of 1-(2-fluorobenzyl)-6-(trifluoromethyl)-1H-pyrazolo[3,4-b]pyridine-3-carboximidohydrazide (Ex. 88A) were dissolved in 16 ml of ethanol, 325 mg (1.73 mmol) of dimethyl 2,2-dimethyl-3-oxobutanedioate (see Daley *J. Am. Chem. Soc.* 2002, 124, 3680-3691) were added and the mixture was stirred under reflux overnight. After cooling, the reaction mixture was concentrated on a rotary evaporator, the residue was stirred with diethyl ether and the precipitate was filtered off. The precipitate was purified by preparative HPLC (acetonitrile:water (+0.05% formic acid) gradient). This gave 265 mg of the title compound (50% of theory).

LC-MS (Method 1): R$_t$=1.18 min; MS (Elpos): m/z=491 [M+H]$^+$.

$^1$H NMR (400 MHz, DMSO-d$_6$): δ [ppm]=1.45 (s, 6H), 3.31 (s, 3H), 5.94 (s, 2H), 7.16-7.27 (m, 2H), 7.34-7.43 (m, 2H), 7.99 (d, 1H), 9.02 (d, 1H), 14.64 (s br, 1H).

Example 90A

Ethyl 3-(2-[1-(2-fluorobenzyl)-1H-pyrazolo[3,4-b]pyridin-3-yl]-5,5-dimethyl-6-oxo-7-{[2-(trimethylsilyl)ethoxy]methyl}-6,7-dihydro-5H-pyrrolo[2,3-d]pyrimidin-4-yl)prop-2-ynoate

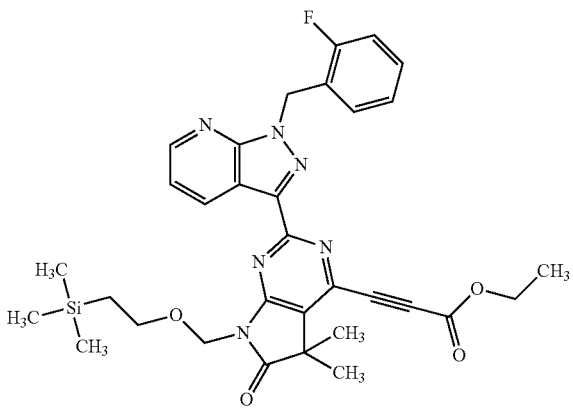 [SMILES: CCOC(=O)C#Cc1nc(-c2nn(Cc3ccccc3F)c3ncccc23)nc2c1C(C)(C)C(=O)N2COCC[Si](C)(C)C]

Under argon, 500 mg (0.78 mmol) of Example 69A, 14.8 mg (0.08 mmol) of copper(I) iodide, 127 mg (1.51 mmol) of sodium bicarbonate, 0.31 ml (304.4 mg, 3.1 mmol) of ethyl propiolate and 54.6 mg (0.08 mmol) of dichlorobistriphenylphosphinepalladium(II) in 7 ml of DMF were stirred at 60° C. overnight. Aqueous ammonium chloride solution was added and the mixture was extracted with ethyl acetate. The organic phases were dried and concentrated under reduced pressure and the residue was purified by column chromatography on silica gel using cyclohexane/ethyl acetate.

Yield: 141.4 mg (28% of theory)

LC-MS (Method 1): $R_t$=1.55 min; MS (ESIpos): m/z=615 (M+H)$^+$ $^1$H NMR (400 MHz, DMSO-d$_6$): δ [ppm]=−0.13 (s, 9H), 0.82-0.93 (m, 2H), 1.26-1.34 (m, 3H), 1.51 (s, 6H), 3.61-3.71 (m, 2H), 4.26-4.40 (m, 2H), 5.24 (s, 2H), 5.85-5.93 (m, 2H), 7.09-7.17 (m, 2H), 7.18-7.28 (m, 1H), 7.31-7.40 (m, 1H), 7.47 (dd, 1H), 8.69 (dd, 1H), 8.89 (dd, 1H).

Example 91A

Ethyl 3-(2-[1-(2-fluorobenzyl)-1H-pyrazolo[3,4-b]pyridin-3-yl]-5,5-dimethyl-6-oxo-7-{[2-(trimethylsilyl)ethoxy]methyl}-6,7-dihydro-5H-pyrrolo[2,3-d]pyrimidin-4-yl)propanoate

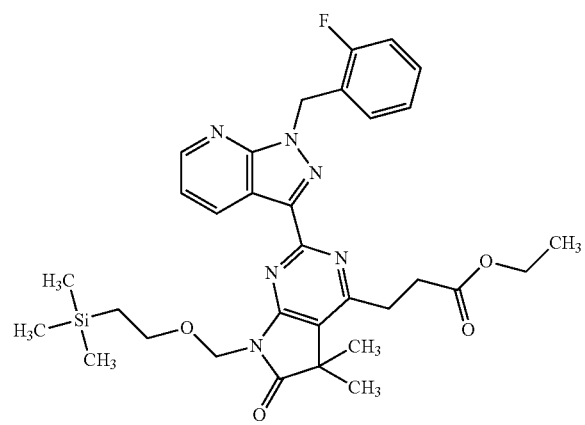 [SMILES: CCOC(=O)CCc1nc(-c2nn(Cc3ccccc3F)c3ncccc23)nc2c1C(C)(C)C(=O)N2COCC[Si](C)(C)C]

140 mg (0.23 mmol) of Example 90A were dissolved in 15 ml of ethyl acetate, 50 mg of 10% palladium on carbon were added and the mixture was hydrogenated at standard pressure for 3 h. Another 50 mg of 10% palladium on carbon were added and the mixture was hydrogenated overnight. The mixture was filtered through kieselguhr, the filter cake was washed with ethyl acetate and the filtrate was concentrated. The residue was purified by flash chromatography on silica gel (gradient DCM/MeOH (0.5-1%).

Yield: 118.6 mg (82% of theory)

LC-MS (Method 1): $R_t$=1.46 min; MS (ESIpos): m/z=619 (M+H)$^+$ $^1$H NMR (400 MHz, DMSO-d$_6$): δ [ppm]=−0.14 (s, 9H), 0.82-0.91 (m, 2H), 0.98-1.11 (m, 5H), 1.46 (s, 6H), 2.90-3.00 (m, 2H), 3.08-3.18 (m, 2H), 3.42-3.58 (m, 5H), 3.53 (t, 2H), 4.01 (q, 2H), 5.19 (s, 2H), 5.89 (s, 2H), 6.99-7.13 (m, 2H), 7.16-7.27 (m, 1H), 7.29-7.38 (m, 1H), 7.44 (dd, 1H), 8.62-8.68 (m, 1H), 8.89 (dd, 1H).

Example 92A

2-[1-(2-Fluorobenzyl)-1H-pyrazolo[3,4-b]pyridin-3-yl]-4-(3-hydroxy-3-methylbutyl)-5,5-dimethyl-7-{[2-(trimethylsilyl)ethoxy]methyl}-5,7-dihydro-6H-pyrrolo[2,3-d]pyrimidin-6-one

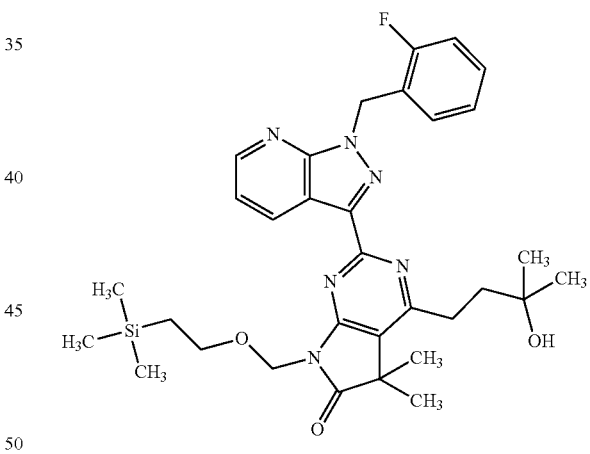

Under argon and at 0° C., 0.28 ml of a 1 M solution of methylmagnesium bromide in THF was added dropwise with stirring to 50 mg (0.08 mmol) of Example 91A in THF, external cooling was then removed and stirring was continued at RT for 2 h. A further 0.16 ml of the 1 M solution of methylmagnesium bromide in THF was then added and the mixture was stirred at RT overnight. Aqueous ammonium chloride solution was added and the mixture was extracted repeatedly with dichloromethane. The combined organic phases were washed with saturated aqueous sodium chloride solution, dried over sodium sulphate and concentrated. The crude product (42.8 mg (88% of theory) was reacted further without purification.

LC-MS (Method 1): $R_t$=1.43 min; MS (ESIpos): m/z=605 (M+H)$^+$

Example 93A

2-[1-(2-Fluorobenzyl)-1H-pyrazolo[3,4-b]pyridin-3-yl]-4-hydroxy-5,5-dimethyl-5,7-dihydro-6H-pyrrolo[2,3-d]pyrimidin-6-one

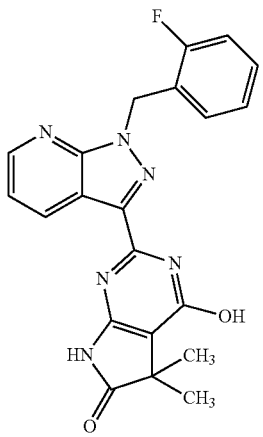 [SMILES: CC1(C)C(=O)Nc2nc(-c3nn(Cc4ccccc4F)c4ncccc34)nc(O)c21]

6.0 g (14.87 mmol) of 4-amino-2-[1-(2-fluorobenzyl)-1H-pyrazolo[3,4-b]pyridin-3-yl]-5,5-dimethyl-5,7-dihydro-6H-pyrrolo[2,3-d]pyrimidin-6-one (WO2012/004258, Example 13A) were dissolved in 60 ml of trifluoroacetic acid and cooled in an ice bath. With stirring, 6.7 ml of water and then, in small portions over a period of 1 h, 1.54 g (22.3 mmol) of sodium nitrite were added. The reaction mixture was then poured into 250 ml of water and the resulting precipitate was filtered off. The solid was added to 50 ml of water, the mixture was adjusted to pH 6 with conc. aqueous sodium bicarbonate solution, the solid was triturated, once more filtered off with suction, washed with water and dried. Yield: 5.75 g (94% of theory)

LC-MS (Method 1): $R_t$=0.92 min; MS (ESIpos): m/z=405 [M+H]$^+$ $^1$H NMR (400 MHz, DMSO-d$_6$): δ [ppm]=1.33 (s, 6H), 5.86 (s, 2H), 7.16 (t, 1H), 7.23 (t, 1H), 7.28-7.41 (m, 2H), 7.49 (dd, 1H), 8.61-8.85 (m, 2H), 11.11 (s, 1H), 12.12 (br. s, 0.2H), 12.44 (br. s, 0.8H).

Example 94A

4-Chloro-2-[1-(2-fluorobenzyl)-1H-pyrazolo[3,4-b]pyridin-3-yl]-7-(4-methoxybenzyl)-5,5-dimethyl-5,7-dihydro-6H-pyrrolo[2,3-d]pyrimidin-6-one

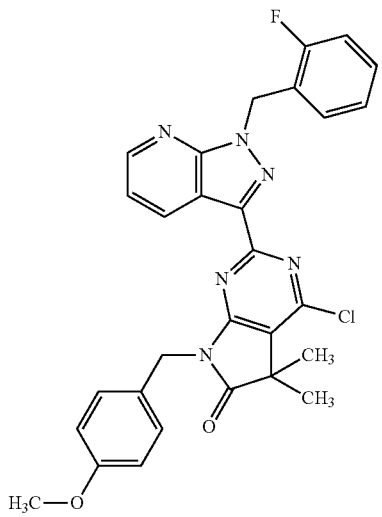 [SMILES: COc1ccc(CN2C(=O)C(C)(C)c3c(Cl)nc(-c4nn(Cc5ccccc5F)c5ncccc45)nc32)cc1]

1.0 g (2.37 mmol) of Example 60 were dissolved in 20 ml of anhydrous DMF and stirred with 847.6 mg (2.60 mmol) of caesium carbonate and 0.32 ml (2.37 mmol) of 4-methoxybenzyl chloride at RT for 2 h. 0.1 ml (0.71 mmol) of 4-methoxybenzyl chloride was added and the mixture was stirred overnight. Water was added, the reaction mixture was partially concentrated under reduced pressure and the residue was partitioned between ethyl acetate and water. The water phase was extracted repeatedly with ethyl acetate, and the combined organic phases were dried over sodium sulphate and concentrated. The residue was purified first by flash chromatography on silica gel (gradient DCM/EE 0-20%) and then by preparative HPLC (gradient: 0.1% formic acid in water/5-95% acetonitrile).

Yield: 936 mg (73% of theory)

LC-MS (Method 1): $R_t$=1.41 min; MS (ESIpos): m/z=543 (M+H)$^+$ $^1$H NMR (400 MHz, DMSO-d$_6$): [ppm]=1.49 (s, 6H), 3.70 (s, 3H), 4.97 (s, 2H), 5.90 (s, 2H), 6.89 (d, 2H), 7.10-7.28 (m, 3H), 7.30-7.40 (m, 3H), 7.45 (dd, 1H), 8.66-8.75 (m, 2H).

Example 95A

Ethyl cyano{2-[1-(2-fluorobenzyl)-1H-pyrazolo[3,4-b]pyridin-3-yl]-7-(4-methoxybenzyl)-5,5-dimethyl-6-oxo-6,7-dihydro-5H-pyrrolo[2,3-d]pyrimidin-4-yl}acetate

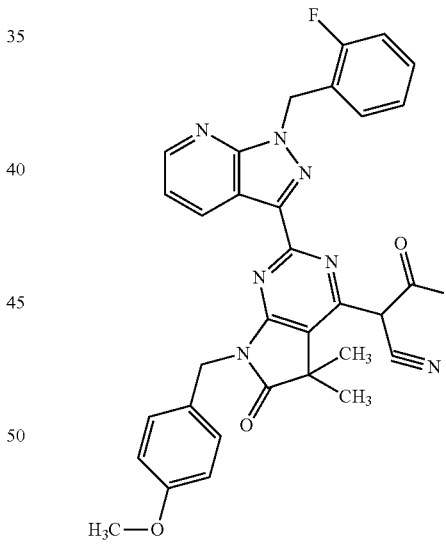

330 mg (0.61 mmol) of Example 94A in 4.4 ml of DMF and 0.19 ml of ethyl cyanoacetate (1.82 mmol) and 136.4 mg (1.22 mmol) of potassium tert-butoxide were stirred at RT for 5 min and at 60° C. overnight. Water was added, the mixture was extracted repeatedly with ethyl acetate and the combined organic phases were concentrated under reduced pressure. The residue was purified by preparative HPLC (gradient: 0.1% formic acid in water/5-95% acetonitrile).

Yield: 303 mg (81% of theory)

LC-MS (Method 1): $R_t$=1.41 min; MS (ESIpos): m/z=543 (M+H)$^+$

WORKING EXAMPLES

Example 1

5-Amino-2-[1-(2-fluorobenzyl)-1H-pyrazolo[3,4-b]pyridin-3-yl]-5-(trifluoromethyl)-5,7-dihydro-6H-pyrrolo[2,3-d]pyrimidin-6-one

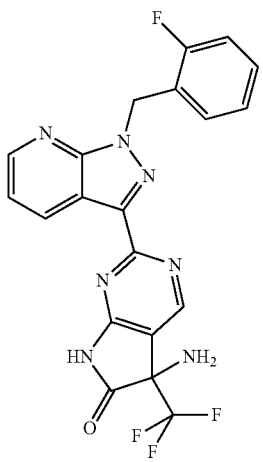

4 ml of a 2N solution of ammonia in ethanol were added to 119 mg (0.257 mmol) of Example 10A, and the mixture was then treated at 100° C. in a microwave for 30 min. This was followed by concentration to dryness. The residue obtained was purified by preparative HPLC (acetonitrile:water (+0.05% formic acid) gradient). This gave 16 mg of the title compound (14% of theory).

LC-MS (Method 2): $R_t$=1.00 min; MS (ESIpos): m/z=444 (M+H)$^+$ $^1$H NMR (400 MHz, DMSO-d$_6$): δ [ppm]=5.88 (s, 2H), 7.16 (t, 1H), 7.21-7.28 (m, 2H), 7.35-7.40 (m, 1H), 7.47 (dd, 1H), 8.69-8.71 (m, 2H), 8.87 (dd, 1H), 8.98 (s, 1H), 12.16 (s, 1H).

Example 2

Ethyl 3-[1-(2-fluorobenzyl)-1H-pyrazolo[3,4-b]pyridin-3-yl]-8-methyl-6-oxo-5,6,7,8-tetrahydropyrido[2,3-e][1,2,4]triazine-8-carboxylate

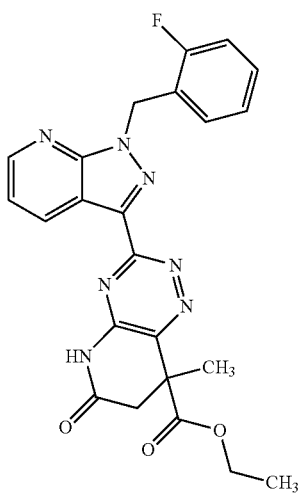 [SMILES: CCOC(=O)C1(C)CC(=O)Nc2nc(-c3nn(Cc4ccccc4F)c4ncccc34)nnc21]

Phosphoryl chloride (1.861 ml) was added to 148 mg (0.299 mmol) of Example 13A, and the mixture was stirred at room temperature overnight. Without any further treatment, this mixture was dissolved in 20 ml of acetonitrile and, with ice cooling, stirred into 13 ml of concentrated ammonia solution. The reaction mixture was stirred at RT overnight and concentrated on a rotary evaporator. Water and ethyl acetate were added to the residue and the phases were separated. The aqueous phase was extracted twice with ethyl acetate. The combined organic phases were washed with saturated aqueous sodium chloride solution and then dried over sodium sulphate, filtered and concentrated on a rotary evaporator. The residue obtained was purified by preparative HPLC (acetonitrile:water (+0.05% formic acid) gradient). This gave 85 mg of the title compound (61% of theory).

LC-MS (Method 2): $R_t$=1.00 min; MS (ESIpos): m/z=462 (M+H)$^+$ $^1$H NMR (400 MHz, DMSO-d$_6$): δ [ppm]=1.10 (t, 3H), 1.74 (s, 3H), 3.07 (q, 2H), 4.09 (q, 2H), 5.90 (s, 2H), 7.15 (t, 1H), 7.21-7.26 (m, 2H), 7.34-7.40 (m, 1H), 7.48 (dd, 1H), 8.72 (dd, 1H), 8.95 (dd, 1H), 11.80 (s, 1H).

Example 3

2-[1-(2-Fluorobenzyl)-1H-pyrazolo[3,4-b]pyridin-3-yl]-5-hydroxy-5-(pentafluoroethyl)-5,7-dihydro-6H-pyrrolo[2,3-d]pyrimidin-6-one

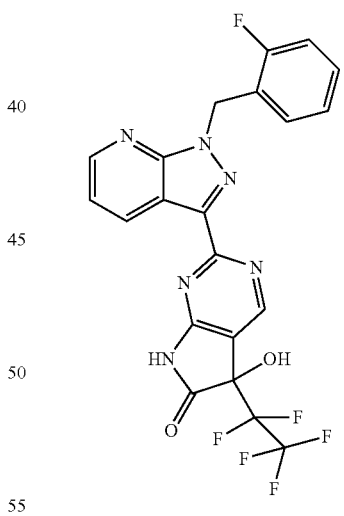

290 mg (0.775 mmol) of Example 8A were reacted analogously to the procedure of Example 9A with (pentafluoroethyl)trimethylsilane. This gave 218 mg of the title compound (57% of theory).

LC-MS (Method 2): $R_t$=1.08 min; MS (ESIpos): m/z=495 (M+H)$^+$ $^1$H NMR (400 MHz, DMSO-d$_6$): δ [ppm]=5.88 (s, 2H), 7.17 (t, 1H), 7.22-7.30 (m, 2H), 7.35-7.41 (m, 1H), 7.48 (dd, 1H), 8.19 (s, 1H), 8.71 (dd, 1H), 8.73 (s, 1H), 8.87 (dd, 1H), 12.29 (s, 1H).

Example 4

5-Amino-2-[1-(2-fluorobenzyl)-1H-pyrazolo[3,4-b]pyridin-3-yl]-5-(pentafluoroethyl)-5,7-dihydro-6H-pyrrolo[2,3-d]pyrimidin-6-one

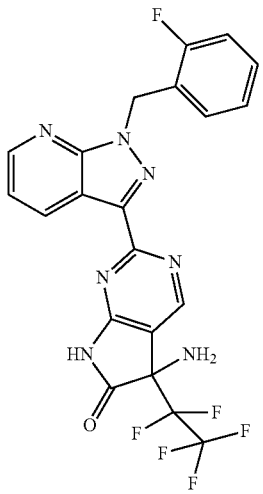 [SMILES: NC1(C(F)(F)C(F)(F)F)C(=O)Nc2nc(-c3nn(Cc4ccccc4F)c4ncccc34)ncc21]

233 mg (0.454 mmol) of Example 14A were reacted analogously to the procedure of Example 1. This gave 22 mg of the title compound (9% of theory).

LC-MS (Method 2): $R_t$=1.08 min; MS (ESIpos): m/z=494 (M+H)$^+$ $^1$H NMR (400 MHz, DMSO-$d_6$): δ [ppm]=5.88 (s, 2H), 7.16 (t, 1H), 7.22-7.28 (m, 2H), 7.34-7.40 (m, 1H), 7.48 (dd, 1H), 8.66 (s, 1H), 8.71 (dd, 1H), 8.87 (dd, 1H), 12.22 (s, 1H).

Example 5

7-(Cyclopropylmethyl)-3-[5-fluoro-1-(2-fluorobenzyl)-1H-pyrazolo[3,4-b]pyridin-3-yl]-7-methyl-5,7-dihydro-6H-pyrrolo[2,3-e][1,2,4]triazin-6-one (racemate)

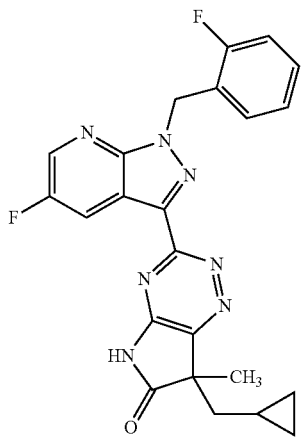 [SMILES: CC1(CC2CC2)C(=O)Nc2nc(-c3nn(Cc4ccccc4F)c4ncc(F)cc34)nnc21]

3 ml of phosphoryl chloride were added to 270 mg (0.546 mmol) of the compound from Example 27A, and the mixture was stirred at RT overnight. The reaction mixture was then dissolved in 36 ml of acetonitrile and, with ice-cooling, stirred into a mixture of 36 ml of concentrated aqueous ammonia solution (33% strength). The mixture was stirred at room temperature overnight. The mixture was then concentrated to dryness. The residue was taken up in ethyl acetate and water and the phases were separated. The aqueous phase was extracted twice with ethyl acetate. The combined organic phases were washed with saturated aqueous sodium chloride solution, dried over sodium sulphate, filtered and concentrated. Acetonitrile was added to the residue. A precipitate formed, which was filtered off and washed with a little acetonitrile. After drying under high vacuum, this gave 158 mg (64% of theory) of the title compound.

LC-MS (Method 1): $R_t$=1.16 min; MS (EIpos): m/z=448 [M+H]$^+$.

$^1$H NMR (400 MHz, DMSO-$d_6$): δ [ppm]=-0.19--0.13 (m, 1H), 0.02-0.06 (m, 1H), 0.15-0.23 (m, 1H), 0.27-0.32 (m, 1H), 0.42-0.48 (m, 1H), 1.46 (s, 3H), 1.84 (dd, 1H), 1.90 (dd, 1H), 5.88 (s, 2H), 7.16-7.32 (m, 3H), 7.35-7.41 (m, 1H), 8.57 (dd, 1H), 8.80 (dd, 1H), 12.32 (s br, 1H).

Separation into Enantiomers:

137 mg of the racemate obtained were separated into the enantiomers by preparative SFC (mobile phase: (CO$_2$:ethanol 71/29, pressure 150 bar, flow rate 114 g/min, temperature mobile phase 38° C., wavelength: 210 nm) on a chiral phase (Daicel Chiralpak AD-H (SFC), 5 µM 250×20 mm)

Example 5-1

Enantiomer 1

Yield: 66 mg
ee>99% (analytical SFC: (mobile phase: (CO$_2$:ethanol 70/30) on a chiral phase (Chiralpak AD-H, 5 µM 250*4.6 mm)
$R_t$=3.050 min

Example 5-2

Enantiomer 2

Yield: 57 mg
ee>99% (analytical SFC: (mobile phase: (CO$_2$:ethanol 70/30) on a chiral phase (Chiralpak AD-H, 5 µM 250*4.6 mm)
$R_t$=5.775 min

Example 6

7-[(Benzyloxy)methyl]-3-[5-fluoro-1-(2-fluorobenzyl)-1H-pyrazolo[3,4-b]pyridin-3-yl]-7-methyl-5,7-dihydro-6H-pyrrolo[2,3-e][1,2,4]triazin-6-one (racemate)

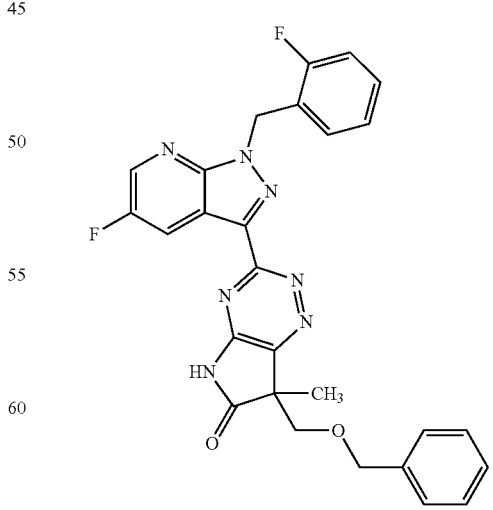

450 mg (0.803 mmol) of the compound from Example 29A were reacted analogously to the procedure of Example 5. This gave 204 mg (49% of theory) of the title compound.

LC-MS (Method 2): $R_t$=1.22 min; MS (EIpos): m/z=514 [M+H]$^+$.

$^1$H NMR (400 MHz, DMSO-d$_6$): δ [ppm]=1.39 (s, 3H), 3.86 (d, 1H), 3.92 (d, 1H), 4.37 (d, 1H), 4.41 (d, 1H), 5.89 (s, 2H), 7.07-7.09 (m, 2H), 7.17 (t, 1H), 7.21-7.31 (m, 5H), 7.35-7.41 (m, 1H), 8.56 (dd, 1H), 8.80 (dd, 1H), 12.33 (s br, 1H).

Example 7

7-Ethyl-3-[5-fluoro-1-(2-fluorobenzyl)-1H-pyrazolo[3,4-b]pyridin-3-yl]-7-methyl-5,7-dihydro-6H-pyrrolo[2,3-e][1,2,4]triazin-6-one (racemate)

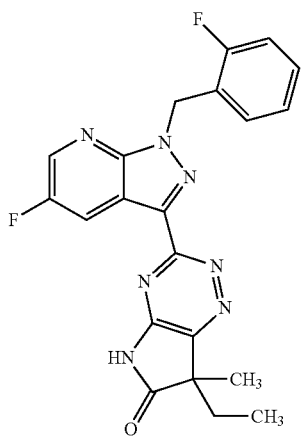 [SMILES: CCC1(C)C(=O)Nc2nc(-c3nn(Cc4ccccc4F)c4ncc(F)cc34)nnc21]

323 mg (0.689 mmol) of the compound from Example 31A were reacted analogously to the procedure of Example 5. After drying under high vacuum, this gave 188 mg (63% of theory) of the title compound.

LC-MS (Method 2): $R_t$=1.11 min; MS (EIpos): m/z=422 [M+H]$^+$.

$^1$H NMR (400 MHz, DMSO-d$_6$): δ [ppm]=0.78 (t, 3H), 1.45 (s, 3H), 1.86-1.99 (m, 2H), 5.88 (s, 2H), 7.15-7.31 (m, 3H), 7.35-7.41 (m, 1H), 8.57 (dd, 1H), 8.79 (dd, 1H), 12.27 (s br, 1H).

Separation into Enantiomers:

185 mg of the racemate obtained were separated into the enantiomers by preparative SFC (mobile phase: (CO$_2$:ethanol 70/30, pressure 150 bar, flow rate 114 g/min, temperature mobile phase 38° C., wavelength: 254 nm) on a chiral phase (Daicel Chiralpak AD-H (SFC), 5 μM 250*20 mm)

Example 7-1

Enantiomer 1

Yield: 72 mg
ee>99% (analytical SFC: (mobile phase: (CO$_2$:methanol 70/30) on a chiral phase (Chiralpak AD-H, 5 μM 250*4.6 mm)
$R_t$=5.205 min;

Example 7-2

Enantiomer 2

Yield: 74 mg
ee 91% (analytical SFC: (mobile phase: (CO$_2$:methanol 70/30) on a chiral phase (Chiralpak AD-H, 5 μM 250×4.6 mm)
$R_t$=7.504 min Example 8

3-[5-Fluoro-1-(4-methoxybenzyl)-1H-pyrazolo[3,4-b]pyridin-3-yl]-7,7-dimethyl-5,7-dihydro-6H-pyrrolo[2,3-e][1,2,4]triazin-6-one

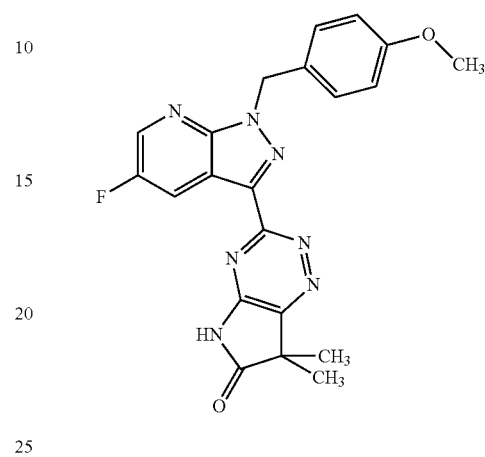

6.04 g (13.350 mmol) of the compound from Example 36A were reacted analogously to the procedure of Example 5. After drying under high vacuum, this gave 1.27 g (22% of theory) of the title compound.

LC-MS (Method 1): $R_t$=1.02 min; MS (EIpos): m/z=420 [M+H]$^+$.

$^1$H NMR (400 MHz, DMSO-d$_6$): δ [ppm]=1.45 (s, 6H), 3.70 (s, 3H), 5.75 (s, 2H), 6.88 (d, 2H), 7.29 (d, 2H), 8.53 (dd, 1H), 8.78 (dd, 1H), 12.18 (s br, 1H).

Example 9

3'-[5-Fluoro-1-(2-fluorobenzyl)-1H-pyrazolo[3,4-b]pyridin-3-yl]spiro[cyclopentane-1,7'-pyrrolo[2,3-e][1,2,4]triazin]-6'(5'H)-one

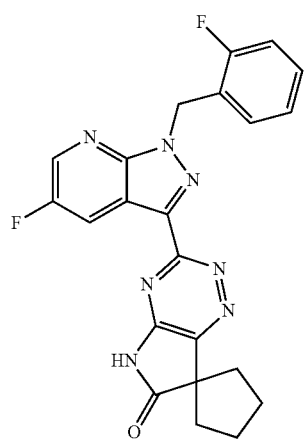 [SMILES: O=C1Nc2nc(-c3nn(Cc4ccccc4F)c4ncc(F)cc34)nnc2C12CCCC2]

0.456 g (0.978 mmol) of the compound from Example 38A were reacted analogously to the procedure of Example 5. After drying under high vacuum, this gave 0.274 g (64% of theory) of the title compound.

LC-MS (Method 1): $R_t$=1.10 min; MS (EIpos): m/z=434 [M+H]$^+$.

$^1$H NMR (400 MHz, DMSO-d$_6$): δ [ppm]=1.85-2.20 (m, 8H), 5.88 (s, 2H), 7.15-7.30 (m, 3H), 7.35-7.41 (m, 1H), 8.56 (dd, 1H), 8.78 (dd, 1H), 12.14 (s, 1H).

Example 10

3-[5-Fluoro-1-(2-fluoro-4-methylbenzyl)-1H-pyrazolo[3,4-b]pyridin-3-yl]-7,7-dimethyl-5,7-dihydro-6H-pyrrolo[2,3-e][1,2,4]triazin-6-one

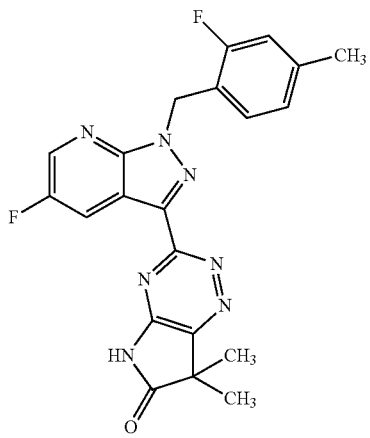 [SMILES: Cc1ccc(Cn2nc(-c3nnc4c(n3)NC(=O)C4(C)C)c3cc(F)cnc32)c(F)c1]

0.111 mg (0.201 mmol) of the compound from Example 41A were stirred in dichloromethane (4 ml) and trifluoroacetic acid (1 ml) at room temperature for 3 h. The mixture was then concentrated to dryness. The residue was stirred in ethanol/2N hydrochloric acid (4:1, 10 ml) at 45° C. for 3 h. This was followed by concentration to dryness. The residue obtained was purified by preparative HPLC (methanol:water (+1% trifluoroacetic acid) gradient). This gave 29 mg of the title compound (34% of theory).

LC-MS (Method 1): R$_t$=1.10 min; MS (EIpos): m/z=422 [M+H]$^+$.

$^1$H NMR (400 MHz, DMSO-d$_6$): δ [ppm]=1.45 (s, 6H), 2.28 (s, 3H), 5.82 (s, 2H), 6.97 (d, 1H), 7.04 (d, 1H), 7.18 (t, 1H), 8.54 (dd, 1H), 8.76 (dd, 1H), 12.18 (s br, 1H).

Example 11

3-[5-Fluoro-1-(2-fluoro-3-methoxybenzyl)-1H-pyrazolo[3,4-b]pyridin-3-yl]-7,7-dimethyl-5,7-dihydro-6H-pyrrolo[2,3-e][1,2,4]triazin-6-one

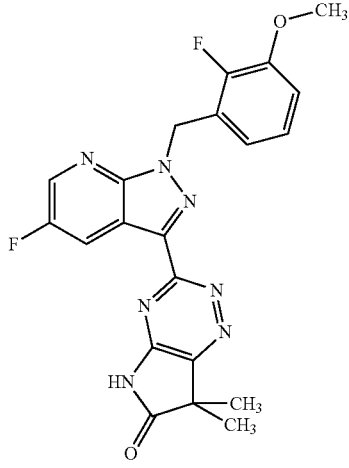 [SMILES: COc1cccc(Cn2nc(-c3nnc4c(n3)NC(=O)C4(C)C)c3cc(F)cnc32)c1F]

88 mg (0.156 mmol) of the compound from Example 42A were reacted analogously to the procedure of Example 10. Purification by preparative HPLC (methanol:water gradient) gave 29 mg of the title compound (42% of theory).

LC-MS (Method 1): R$_t$=1.03 min; MS (EIpos): m/z=438 [M+H]$^+$.

$^1$H NMR (400 MHz, DMSO-d$_6$): δ [ppm]=1.45 (s, 6H), 3.82 (s, 3H), 5.87 (s, 2H), 6.75-6.78 (m, 1H), 7.05-7.14 (m, 2H), 8.55 (dd, 1H), 8.78 (dd, 1H), 12.18 (s br, 1H).

Example 12

3-[5-Fluoro-1-(2-fluoro-3-methylbenzyl)-1H-pyrazolo[3,4-b]pyridin-3-yl]-7,7-dimethyl-5,7-dihydro-6H-pyrrolo[2,3-e][1,2,4]triazin-6-one

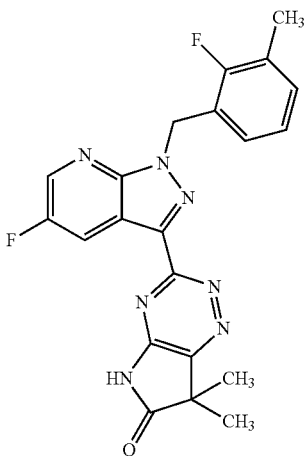 [SMILES: Cc1cccc(Cn2nc(-c3nnc4c(n3)NC(=O)C4(C)C)c3cc(F)cnc32)c1F]

81 mg (0.148 mmol) of the compound from Example 43A were reacted analogously to Example 10. Purification by preparative HPLC (acetonitrile:water (+1% trifluoroacetic acid) gradient) gave 17 mg of the title compound (27% of theory).

LC-MS (Method 1): R$_t$=1.05 min; MS (EIpos): m/z=422 [M+H]$^+$.

$^1$H NMR (400 MHz, DMSO-d$_6$): δ [ppm]=1.45 (s, 6H), 2.22 (d, 3H), 5.86 (s, 2H), 7.02-7.10 (m, 2H), 7.22-7.26 (m, 1H), 8.55 (dd, 1H), 8.78 (dd, 1H), 12.17 (s br, 1H).

Example 13

7-(2-Ethoxyethyl)-3-[5-fluoro-1-(2-fluorobenzyl)-1H-pyrazolo[3,4-b]pyridin-3-yl]-7-methyl-5,7-dihydro-6H-pyrrolo[2,3-e][1,2,4]triazin-6-one

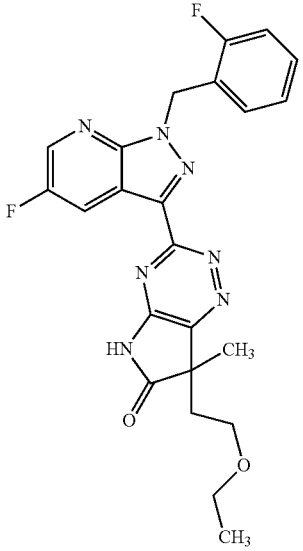 [SMILES: CCOCCC1(C)C(=O)Nc2nc(-c3nn(Cc4ccccc4F)c4ncc(F)cc34)nnc21]

40 mg (0.078 mmol) of the compound from Example 45A were reacted analogously to the procedure of Example 5. After purification by preparative HPLC (acetonitrile:water (+0.05% formic acid) gradient), this gave 16 mg (44% of theory) of the title compound.

LC-MS (Method 1): $R_t$=1.08 min; MS (EIpos): m/z=466 [M+H]$^+$.

$^1$H NMR (400 MHz, DMSO-d$_6$): δ [ppm]=0.74 (t, 3H), 1.45 (s, 3H), 2.18-2.28 (m, 2H), 2.99-3.13 (m, 2H), 3.21-3.27 (m, 1H), 3.29-3.35 (m, 1H superimposed by water signal), 5.87 (dd, 2H), 7.15-7.31 (m, 3H), 7.35-7.41 (m, 1H), 8.55 (dd, 1H), 8.78 (dd, 1H), 12.16 (s, 1H).

Example 14

4-(6-Ethoxypyridin-3-yl)-2-[1-(2-fluorobenzyl)-1H-pyrazolo[3,4-b]pyridin-3-yl]-5,5-dimethyl-5,7-dihydro-6H-pyrrolo[2,3-d]pyrimidin-6-one

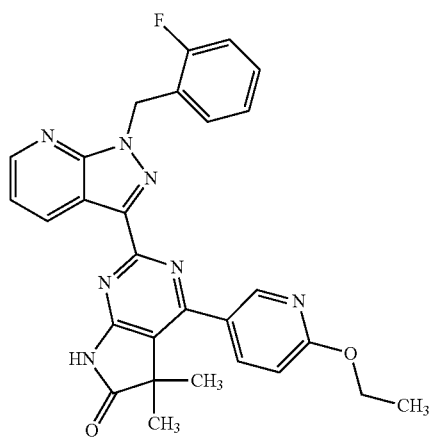 [SMILES: CCOc1ccc(-c2nc(-c3nn(Cc4ccccc4F)c4ncccc34)nc3c2C(C)(C)C(=O)N3)cn1]

Under an atmosphere of argon, 150 mg (0.18 mmol) of 2-[1-(2-fluorobenzyl)-1H-pyrazolo[3,4-b]pyridin-3-yl]-4-iodo-5,5-dimethyl-5,7-dihydro-6H-pyrrolo[2,3-d]pyrimidin-6-one (Example 47A) were suspended in 4 ml of absolute dioxane, 91 mg (0.54 mmol) of 6-ethoxypyridin-3-yl) boronic acid, 10 mg (0.04 mmol) of tricyclohexylphosphine and 0.72 ml (0.72 mmol) of 1 N aqueous potassium carbonate solution were added and the mixture was stirred in a stream of argon for 10 min. 20 mg (0.03 mmol) of 1,1'-bis(diphenylphosphino)ferrocenepalladium(II) chloride and 31 mg (0.03 mmol) of tetrakis(triphenylphosphine)palladium(0) were added and the mixture was stirred at 140° C. in a microwave for 30 min. After cooling, the reaction mixture was filtered through an Extrelut cartridge, the cartridge was rinsed with dichloromethane/methanol (v/v=2:1) and the filtrate was concentrated on a rotary evaporator. The residue was purified by preparative HPLC (mobile phase: acetonitrile/water, gradient 20:80→100:0). 29 mg of the target compound were obtained (30% of theory).

LC-MS (Method 1) $R_t$=1.22 min; MS (ESIpos): m/z=510 (M+H)$^+$ $^1$H NMR (400 MHz, DMSO-d$_6$): δ [ppm]=1.25 (s, 6H), 1.38 (t, 3H), 4.42 (q, 2H), 5.87 (s, 2H), 7.01 (d, 1H), 7.12-7.25 (m, 3H), 7.33-7.39 (m, 1H), 7.42 (dd, 1H), 7.98 (dd, 1H), 8.44 (d, 1H), 8.66 (dd, 1H), 8.79 (dd, 1H), 11.79 (s, 1H).

Example 15

2-[1-(2-Fluorobenzyl)-1H-pyrazolo[3,4-b]pyridin-3-yl]-5,5-dimethyl-4-(1H-pyrazol-5-yl)-5,7-dihydro-6H-pyrrolo[2,3-d]pyrimidin-6-one

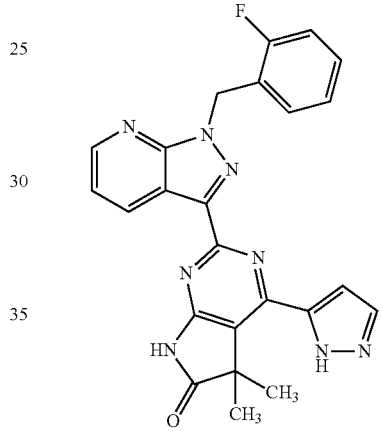

Under an atmosphere of argon, 150 mg (0.18 mmol) of 2-[1-(2-fluorobenzyl)-1H-pyrazolo[3,4-b]pyridin-3-yl]-4-iodo-5,5-dimethyl-5,7-dihydro-6H-pyrrolo[2,3-d]pyrimidin-6-one (Example 47A) were suspended in 4 ml of absolute dioxane, 105 mg (0.54 mmol) of 5-(4,4,5,5-tetramethyl-1,3,2-dioxaborolan-2-yl)-1H-pyrazole and 0.72 ml (0.72 mmol) of 1 N aqueous potassium carbonate solution were added and the mixture was stirred in a stream of argon for 10 min. 42 mg (0.04 mmol) of tetrakis(triphenylphosphine)palladium(0) were added and the mixture was stirred at 140° C. in a microwave for 30 min. After cooling, the reaction mixture was filtered through an Extrelut cartridge, the cartridge was rinsed with dichloromethane/methanol (v/v=2:1) and the filtrate was concentrated on a rotary evaporator. The residue was purified by preparative HPLC (mobile phase: acetonitrile/water, gradient 20:80→100:0). 66 mg of the target compound were obtained (80% of theory).

LC-MS (Method 1) $R_t$=0.99 min; MS (ESIpos): m/z=455 (M+H)$^+$ $^1$H NMR (400 MHz, DMSO-d$_6$): δ [ppm]=1.61 (s, 6H), 5.88 (s, 2H), 7.13-7.26 (m, 4H), 7.34-7.39 (m, 1H), 7.50 (dd, 1H), 7.98 (s, 1H), 8.69 (dd, 1H), 8.98 (dd, 1H), 11.63 (s, 1H), 13.48 (s, 1H).

Example 16

4-(Cyclopropylethynyl)-2-[1-(2-fluorobenzyl)-1H-pyrazolo[3,4-b]pyridin-3-yl]-5,5-dimethyl-5,7-dihydro-6H-pyrrolo[2,3-d]pyrimidin-6-one

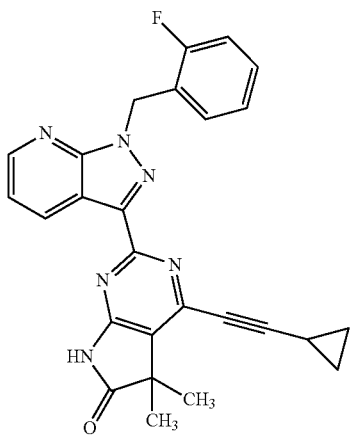 [SMILES: CC1(C)C(=O)Nc2nc(-c3nn(Cc4ccccc4F)c4ncccc34)nc(C#CC3CC3)c21]

Under an atmosphere of argon, 1.000 g (1.23 mmol) of 2-[1-(2-fluorobenzyl)-1H-pyrazolo[3,4-b]pyridin-3-yl]-4-iodo-5,5-dimethyl-5,7-dihydro-6H-pyrrolo[2,3-d]pyrimidin-6-one (Example 47A) and 243 mg (3.68 mmol) of ethynylcyclopropane were initially charged in 20 ml of absolute THF. 372 mg (3.68 mmol) of diisopropylamine, 70 mg (0.37 mmol) of copper(I) iodide and 172 mg (0.25 mmol) of dichlorobis(triphenylphosphine)palladium(II) were added, and the mixture was heated at reflux for 48 h. The reaction mixture was concentrated and the residue was taken up in DMSO. The mixture was filtered and the filtrate was purified by preparative HPLC (mobile phase: acetonitrile/water, gradient 20:80→100:0). This gave 198 mg of the target compound (purity 89%; 32% of theory).

LC-MS (Method 1) $R_t$=1.18 min; MS (ESIpos): m/z=453 (M+H)$^+$ $^1$H NMR (400 MHz, DMSO-d$_6$): δ [ppm]=0.89-0.93 (m, 2H), 1.03-1.08 (m, 2H), 1.41 (s, 6H), 1.73-1.80 (m, 1H), 5.86 (s, 2H), 7.13-7.26 (m, 3H), 7.34-7.39 (m, 1H), 7.46 (dd, 1H), 8.68 (dd, 1H), 8.84 (dd, 1H), 11.68 (s, 1H).

Example 17

4-(2-Cyclopropylethyl)-2-[1-(2-fluorobenzyl)-1H-pyrazolo[3,4-b]pyridin-3-yl]-5,5-dimethyl-5,7-dihydro-6H-pyrrolo[2,3-d]pyrimidin-6-one

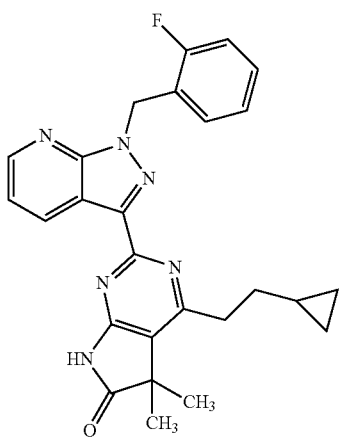 [SMILES: CC1(C)C(=O)Nc2nc(-c3nn(Cc4ccccc4F)c4ncccc34)nc(CCC3CC3)c21]

140 mg (0.28 mmol) of 4-(cyclopropylethynyl)-2-[1-(2-fluorobenzyl)-1H-pyrazolo[3,4-b]pyridin-3-yl]-5,5-dimethyl-5,7-dihydro-6H-pyrrolo[2,3-d]pyrimidin-6-one (Ex. 16) were dissolved in 14 ml of absolute THF. The solution was hydrogenated in a flow hydrogenation reactor (H-Cube from Thales Nano, Budapest, model HC-2-SS) fitted with a 10% palladium on carbon cartridge at a hydrogen pressure of 10 bar. The reaction mixture was concentrated and the residue was purified by preparative HPLC (mobile phase: acetonitrile/water, gradient 20:80→100:0). 54 mg of the target compound were obtained (43% of theory).

LC-MS (Method 1) $R_t$=1.28 min; MS (ESIpos): m/z=457 (M+H)$^+$ $^1$H NMR (400 MHz, DMSO-d$_6$): δ [ppm]=0.08-0.12 (m, 2H), 0.40-0.43 (m, 2H), 0.78-0.86 (m, 1H), 1.42 (s, 6H), 1.77 (q, 2H), 2.89 (t, 2H), 5.86 (s, 2H), 7.12-7.25 (m, 3H), 7.34-7.38 (m, 1H), 7.45 (dd, 1H), 8.66 (dd, 1H), 8.89 (dd, 1H), 11.54 (s, 1H).

Example 18

4-[(Z)-2-Cyclopropylvinyl]-2-[1-(2-fluorobenzyl)-1H-pyrazolo[3,4-b]pyridin-3-yl]-5,5-dimethyl-5,7-dihydro-6H-pyrrolo[2,3-d]pyrimidin-6-one

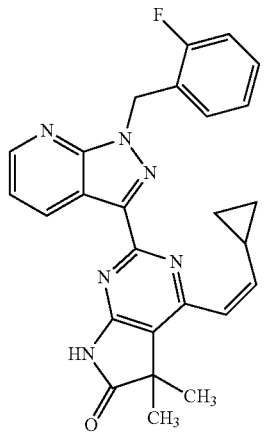 [SMILES: CC1(C)C(=O)Nc2nc(-c3nn(Cc4ccccc4F)c4ncccc34)nc(/C=C\C3CC3)c21]

140 mg (0.28 mmol) of 4-(cyclopropylethynyl)-2-[1-(2-fluorobenzyl)-1H-pyrazolo[3,4-b]pyridin-3-yl]-5,5-dimethyl-5,7-dihydro-6H-pyrrolo[2,3-d]pyrimidin-6-one (Ex. 16) were dissolved in 14 ml of absolute THF. The solution was hydrogenated in an H-Cube from Thales Nano, Budapest, model HC-2-SS, fitted with a 10% palladium on carbon cartridge at a hydrogen pressure of 10 bar. The reaction mixture was concentrated and the residue was purified by preparative HPLC (mobile phase: acetonitrile/water, gradient 20:80→100:0). 23 mg of the target compound were obtained (18% of theory).

LC-MS (Method 1) $R_t$=1.21 min; MS (ESIpos): m/z=455 (M+H)$^+$ $^1$H NMR (400 MHz, DMSO-d$_6$): δ [ppm]=0.63-0.66 (m, 2H), 0.92-0.96 (m, 2H), 1.40 (s, 6H), 3.24-3.28 (m, 1H), 5.51 (t, 1H), 5.83 (s, 2H), 6.44 (d, 1H), 7.13-7.30 (m, 3H), 7.34-7.39 (m, 1H), 7.44 (dd, 1H), 8.66 (dd, 1H), 8.89 (dd, 1H), 11.55 (s, 1H).

Example 19

3-[1-(2-Fluorobenzyl)-6-(trifluoromethyl)-1H-pyrazolo[3,4-b]pyridin-3-yl]-7,7-dimethyl-5,7-dihydro-6H-pyrrolo[2,3-e][1,2,4]triazin-6-one

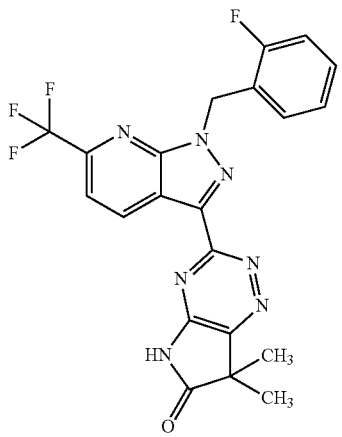 [SMILES: CC1(C)C(=O)Nc2nc(-c3nn(Cc4ccccc4F)c4nc(C(F)(F)F)ccc34)nnc21]

8 ml of phosphoryl chloride were added to 255 mg (0.46 mmol) of methyl 2-{3-[1-(2-fluorobenzyl)-6-(trifluoromethyl)-1H-pyrazolo[3,4-b]pyridin-3-yl]-5-hydroxy-1,2,4-triazin-6-yl}-2-methylpropanoate (Ex. 89A), and the mixture was stirred at RT for 1.5 h. With ice cooling, the reaction mixture was stirred into 50 ml of a concentrated aqueous ammonia solution (35% strength). The mixture was stirred at room temperature overnight. The precipitate was filtered off, washed with water and recrystallized from ethanol. This gave 98 mg (47% of theory) of the title compound.

LC-MS (Method 1): $R_t$=1.18 min; MS (EIpos): m/z=458 [M+H]$^+$.

$^1$H NMR (400 MHz, DMSO-d$_6$): δ [ppm]=1.46 (s, 6H), 5.92 (s, 2H), 7.17-7.26 (m, 2H), 7.34-7.42 (m, 2H), 7.97 (d, 1H), 9.14 (d, 1H), 12.23 (br. s, 1H).

Example 20

2-[5-Fluoro-1-(2-fluorobenzyl)-6-methyl-1H-pyrazolo[3,4-b]pyridin-3-yl]-5,5-dimethyl-5,7-dihydro-6H-pyrrolo[2,3-d]pyrimidin-6-one

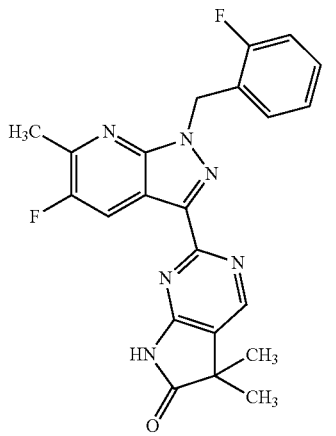 [SMILES: Cc1nc2c(cc1F)c(-c1ncc3c(n1)NC(=O)C3(C)C)nn2Cc1ccccc1F]

100 mg (0.183 mmol) of Example 56A in DMF (10 ml) were hydrogenated with palladium on carbon (10%) at standard pressure. After complete conversion, the mixture was filtered through Celite, the filter residue was washed with DMF, the filtrate was concentrated and the residue was purified by preparative HPLC (acetonitrile:water (+0.05% formic acid) gradient). This gave 61 mg of the target compound (80% of theory).

LC-MS (Method 1) $R_t$=1.16 min; MS (ESIpos): m/z=421 (M+H)$^+$ $^1$H NMR (400 MHz, DMSO-d$_6$): δ [ppm]=1.37 (s, 6H), 2.63 (d, 3H), 5.80 (s, 2H), 7.13-7.26 (m, 3H), 7.34-7.40 (m, 1H), 8.47 (d, 1H), 8.61 (s, 1H), 11.54 (s br, 1H).

Example 21

3-[5-Fluoro-1-(2-fluorobenzyl)-6-methyl-1H-pyrazolo[3,4-b]pyridin-3-yl]-7,7-dimethyl-5,7-dihydro-6H-pyrrolo[2,3-e][1,2,4]triazin-6-one

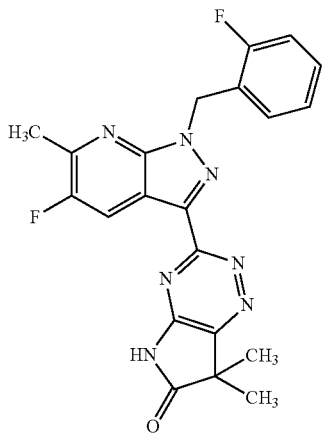 [SMILES: Cc1nc2c(cc1F)c(-c1nnc3c(n1)NC(=O)C3(C)C)nn2Cc1ccccc1F]

522 mg (1.150 mmol) of Example 54A were reacted analogously to the procedure of Example 5. After purification by preparative HPLC (acetonitrile:water (+0.05% formic acid) gradient), this gave 90 mg of the target compound (18% of theory).

LC-MS (Method 1) $R_t$=1.10 min; MS (ESIpos): m/z=422 (M+H)$^+$ $^1$H NMR (400 MHz, DMSO-d$_6$): δ [ppm]=1.45 (s, 6H), 2.65 (d, 3H), 5.83 (s, 2H), 7.14-7.26 (m, 3H), 7.35-7.40 (m, 1H), 8.43 (d, 1H), 12.15 (s br, 1H).

Example 22

2-[1-(2-Fluorobenzyl)-1H-pyrazolo[3,4-b]pyridin-3-yl]-4,5,5-trimethyl-5,7-dihydro-6H-pyrrolo[2,3-d]pyrimidin-6-one

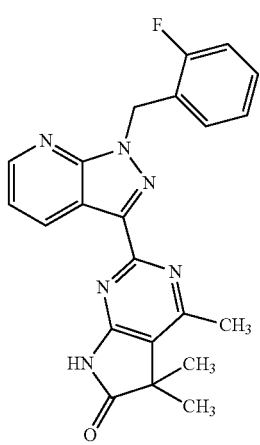 [SMILES: Cc1nc(-c2nn(Cc3ccccc3F)c3ncccc23)nc2c1C(C)(C)C(=O)N2]

Under argon, 500 mg (0.49 mmol) of Example 47A were initially charged in dioxane. 19.8 mg (0.02 mmol) of PdCl$_2$(dppf)CH$_2$Cl$_2$ were then added, and 0.97 ml (1.94 mmol) of a 2M solution of dimethylzinc in toluene was added dropwise over a period of 15 min. After 20 min of stirring under argon, the reaction mixture was heated in a microwave at 120° C. for 4 h. Water was then added carefully at 10° C. and the mixture was concentrated under reduced pressure. The residue was purified by preparative HPLC (gradient of 0.1% formic acid in water/acetonitrile, 10-95%). This gave 270.8 mg of the target compound (69% of theory).

LC-MS (Method 1) R$_t$=1.04 min; MS (ESIpos): m/z=403 (M+H)$^+$ $^1$H NMR (400 MHz, DMSO-d$_6$): δ [ppm]=1.40 (s, 6H), 5.84 (s, 2H), 7.09-7.28 (m, 3H), 7.31-7.40 (m, 1H), 7.44 (dd, 1H), 8.67 (dd, 1H), 8.93 (dd, 1H), 11.51 (br. s, 1H) (CH$_3$ group under DMSO peak).

Example 23

(rac) (7S)-7-(But-3-en-1-yl)-3-[1-(2-fluorobenzyl)-1H-pyrazolo[3,4-b]pyridin-3-yl]-7-methyl-5,7-dihydro-6H-pyrrolo[2,3-e][1,2,4]triazin-6-one

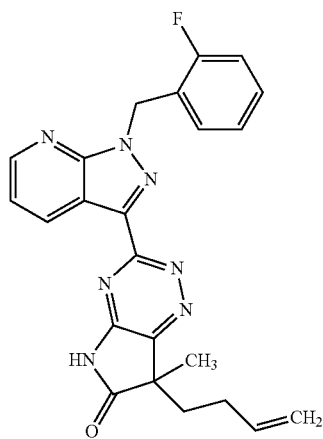 [SMILES: C=CCCC1(C)C(=O)Nc2nc(-c3nn(Cc4ccccc4F)c4ncccc34)nnc21]

The crude product of the compound from Example 58A was carefully diluted with 50 ml of acetonitrile and slowly added dropwise to a 33% strength aqueous ammonia solution cooled to 0° C. (80 ml) (temperature increase to 12° C.). The 2-phase mixture was stirred at room temperature overnight. The phases were separated and the aqueous phase was extracted twice with ethyl acetate. The combined organic phases were washed with saturated aqueous sodium chloride solution, dried over sodium sulphate and concentrated. The residue was purified by preparative HPLC gradient: water+0.05% formic acid/acetonitrile 20-95%. This gave 415.9 mg of the target compound (66% of theory).

LC-MS (Method 1) R$_t$=1.11 min; MS (ESIpos): m/z=430 (M+H)$^+$ $^1$H NMR (400 MHz, DMSO-d$_6$): δ [ppm]=1.47 (s, 3H), 1.85-2.10 (m, 4H), 4.79-4.97 (m, 2H), 5.59-5.74 (m, 1H), 5.89 (s, 2H), 7.10-7.29 (m, 3H), 7.32-7.42 (m, 1H), 7.49 (dd, 1H), 8.64-8.75 (m, 1H), 8.87 (dd, 1H), 12.28 (s, 1H).

Example 24

N-({2-[1-(2-Fluorobenzyl)-1H-pyrazolo[3,4-b]pyridin-3-yl]-5,5-dimethyl-6-oxo-6,7-dihydro-5H-pyrrolo[2,3-d]pyrimidin-4-yl}methyl)methanesulphonamide

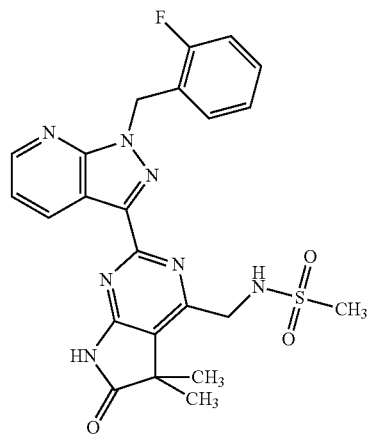 [SMILES: CC1(C)C(=O)Nc2nc(-c3nn(Cc4ccccc4F)c4ncccc34)nc(CNS(C)(=O)=O)c21]

Under argon, 55 mg (0.091 mmol, 79% pure) of Example 45 were initially charged in 0.564 ml of dichloromethane and 0.564 ml of DMF. 35 μl (0.20 mmol) of N,N-diisopropylethylamine and 8 μl (0.1 mmol) of methanesulphonyl chloride were then added. The mixture was stirred at room temperature for 1 h. The mixture was then freed from the solvent under reduced pressure. The residue was purified by flash chromatography on silica gel (gradient: CH/EA, 0-100%). This gave 9.9 mg (22% of theory) of the target compound.

LC-MS (Method 1) R$_t$=0.90 min; MS (ESIpos): m/z=496 (M+H)$^+$ $^1$H NMR (400 MHz, DMSO-d$_6$): δ [ppm]=1.43 (s, 6H), 3.00 (s, 3H), 4.36 (d, 2H), 5.86 (s, 2H), 7.11-7.28 (m, 3H), 7.32-7.39 (m, 1H), 7.43 (dd, 1H), 7.79 (t, 1H), 8.68 (dd, 1H), 9.11 (dd, 1H), 11.69 (s, 1H).

Example 25

(rac) Ethyl 3-[1-(2-fluorobenzyl)-1H-pyrazolo[3,4-b]pyridin-3-yl]-6-oxo-6,7-dihydro-5H-pyrrolo[2,3-e][1,2,4]triazine-7-carboxylate

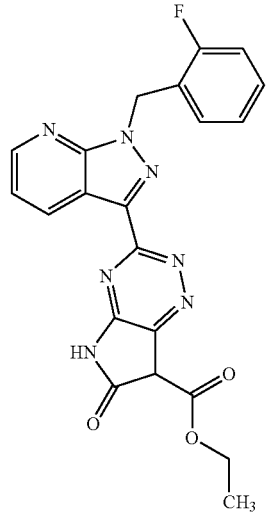 [SMILES: CCOC(=O)C1C(=O)Nc2nc(-c3nn(Cc4ccccc4F)c4ncccc34)nnc21]

Under argon, 343 mg (8.58 mmol) of 60% sodium hydride were initially charged in 10 ml of 1-methyl-2-pyrrolidone. 0.651 ml (4.29 mmol) of ethyl malonate was then added slowly. After 5 min of stirring, 290 mg (0.82 mmol) of Example 64A were added. The mixture was stirred at room temperature for 15 min and then heated to 120° C. overnight. The mixture was partitioned between ethyl acetate and saturated aqueous ammonium chloride solution, the phases were separated and the aqueous phase was extracted twice with ethyl acetate. The combined organic phases were washed with saturated aqueous sodium chloride solution, dried over sodium sulphate and concentrated under reduced pressure. The residue was purified by preparative HPLC (gradient: water+0.05% formic acid/acetonitrile 10-95%). This gave 46.5 mg (13% of theory) of the target compound.

LC-MS (Method 1) $R_t$=0.90 min; MS (ESIpos): m/z=434 $(M+H)^+$ $^1$H NMR (400 MHz, DMSO-$d_6$): δ [ppm]=1.29 (t, 3H), 4.19-4.33 (m, 2H), 5.85 (s, 2H), 7.11-7.31 (m, 3H), 7.32-7.41 (m, 1H), 7.47 (dd, 1H), 8.65-8.77 (m, 2H), 11.91 (br.s, 1H), 14.27 (br. s, 1H).

Example 26

(rac) {3-[1-(2-Fluorobenzyl)-1H-pyrazolo[3,4-b]pyridin-3-yl]-7-methyl-6-oxo-6,7-dihydro-5H-pyrrolo[2,3-e][1,2,4]triazin-7-yl}acetic acid

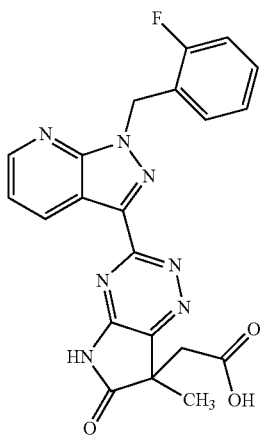 [SMILES: CC1(CC(=O)O)C(=O)Nc2nc(-c3nn(Cc4ccccc4F)c4ncccc34)nnc21]

50 mg (0.12 mmol) of Example 28 were initially charged in 2 ml of acetonitrile. 3 ml of dioxane were then added. At room temperature, 0.70 mg (0.003 mmol) of ruthenium trichloride hydrate and 180 mg (0.842 mmol) of sodium periodate dissolved in 1 ml of water were added. The mixture was then stirred at room temperature overnight. The mixture was then partitioned between ethyl acetate and water and the phases were separated. The aqueous phase was extracted twice with ethyl acetate. The combined organic phases were washed with saturated aqueous sodium chloride solution, dried over sodium sulphate and concentrated under reduced pressure. The residue was purified by preparative HPLC (acetonitrile:water (+0.05% formic acid) gradient). This gave 13.1 mg (25% of theory) of the target compound.

LC-MS (Method 1) $R_t$=0.87 min; MS (ESIpos): m/z=434 $(M+H)^+$ $^1$H NMR (400 MHz, DMSO-$d_6$): δ [ppm]=1.42 (s, 3H), 3.05-3.25 (m, 2H), 5.83-5.95 (m, 2H), 7.11-7.30 (m, 3H), 7.32-7.43 (m, 1H), 7.48 (dd, 1H), 8.68-8.76 (m, 1H), 8.86 (dd, 1H), 12.27 (br. s, 1H) 12.70 (br. s., 1H).

Example 27

Ethyl 3-{2-[1-(2-fluorobenzyl)-1H-pyrazolo[3,4-b]pyridin-3-yl]-5,5-dimethyl-6-oxo-6,7-dihydro-5H-pyrrolo[2,3-d]pyrimidin-4-yl}acrylate

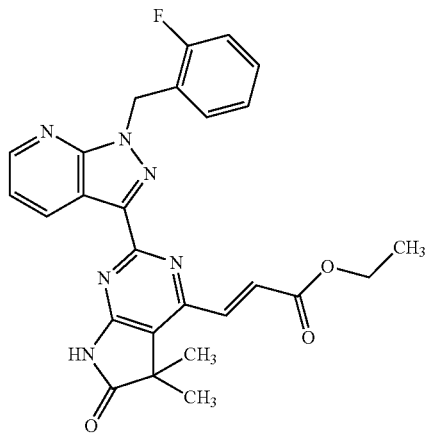 [SMILES: CCOC(=O)/C=C/c1nc(-c2nn(Cc3ccccc3F)c3ncccc23)nc2c1C(C)(C)C(=O)N2]

The crude product from Example 71A (0.06 mmol) was dissolved in 1 ml of dioxane. 1 ml of 2 N aqueous hydrochloric acid was then added, and the mixture was stirred at room temperature for 3 h. The mixture was taken up in acetonitrile and purified by prep. HPLC [gradient of water with 0.1% formic acid/acetonitrile 10-95%)]. The product fractions (mixture of Ex. 71A and Ex. 27) were dissolved in 2 ml of acetonitrile and 1 ml of ethanol, 1 ml of 1 N aqueous hydrochloric acid was added and, after 5 h at RT, the mixture was once more purified by preparative HPLC [gradient of water with 0.1% formic acid/acetonitrile (10-95%)]. This gave 9 mg (18% of theory, purity 70%) of the target compound.

LC-MS (Method 1) $R_t$=1.18 min; MS (ESIpos): m/z=487 $(M+H)^+$ $^1$H NMR (400 MHz, DMSO-$d_6$): δ [ppm]=1.31 (t, 3H), 1.46 (s, 6H), 4.29 (q, 2H), 5.89 (s, 2H), 7.06-7.31 (m, 3H), 7.31-7.43 (m, 1H), 7.45-7.57 (m, 1H), 8.63-8.76 (m, 1H), 8.84-8.92 (m, 1H), 11.89 (br. s, 1H).

Example 28

(rac) 7-Allyl-3-[1-(2-fluorobenzyl)-1H-pyrazolo[3,4-b]pyridin-3-yl]-7-methyl-5,7-dihydro-6H-pyrrolo[2,3-e][1,2,4]triazin-6-one

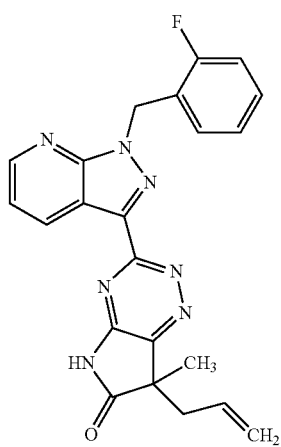 [SMILES: C=CCC1(C)C(=O)Nc2nc(-c3nn(Cc4ccccc4F)c4ncccc34)nnc21]

10 g (21.62 mmol) of Example 66A in 180 ml (1.95 mmol) of phosphoryl chloride were stirred at room temperature overnight. The intermediate, (rac) ethyl 2-{5-chloro-3-[1-(2-fluorobenzyl)-1H-pyrazolo[3,4-b]pyridin-3-yl]-1,2,4-triazin-6-yl}-2-methylpent-4-enoate, was detected in the LC-MS:

LC-MS (Method 1): R$_t$=1.37 min; MS (ESIpos): m/z=481 (M+H)$^+$

The reaction solution was diluted with 944 ml of anhydrous acetonitrile and slowly added dropwise to a 33% strength aqueous ammonia solution (1.18 l) cooled to 0° C. (temperature increase to 12° C.). The mixture was stirred at room temperature overnight. In each case 1 l of water and ethyl acetate were added, and the reaction solution was stirred well. The phases were separated and the aqueous phase was re-extracted with 500 ml of ethyl acetate. The combined organic phases were washed with 500 ml saturated aqueous sodium chloride solution. After drying over sodium sulphate, the mixture was concentrated under reduced pressure. This gave 4.70 g (33% of theory, purity 64%) of the title compound.

LC-MS (Method 1): R$_t$=1.06 min; MS (ESIpos): m/z=416 (M+H)$^+$

A sample was purified by prep. HPLC (water with 0.05% formic acid/acetonitrile, gradient 20-95% acetonitrile).

$^1$H NMR (400 MHz, DMSO-d$_6$): δ [ppm]=1.43 (s, 3H), 2.57-2.70 (m, 2H), 4.94-5.14 (m, 2H), 5.48-5.73 (m, 1H), 5.89 (s, 2H), 7.10-7.30 (m, 3H), 7.31-7.43 (m, 1H), 7.49 (dd, 1H), 8.72 (dd, 1H), 8.87 (dd, 1H), 12.27 (s, 1H).

Example 29

2-[1-(2-Fluorobenzyl)-1H-pyrazolo[3,4-b]pyridin-3-yl]-4-isobutyl-5,5-dimethyl-5,7-dihydro-6H-pyrrolo[2,3-d]pyrimidin-6-one

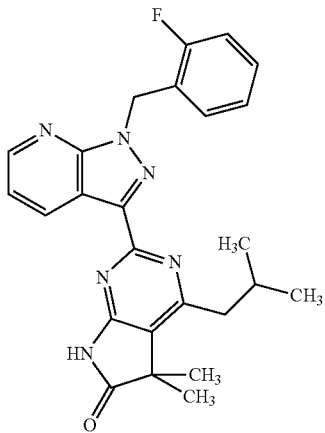 [SMILES: CC(C)Cc1nc(-c2nn(Cc3ccccc3F)c3ncccc23)nc2c1C(C)(C)C(=O)N2]

Under argon, 200 mg (0.39 mmol) of Example 47A were initially charged in 8 ml of dioxane. 31.8 mg (0.04 mmol) of PdCl$_2$(dppf) CH$_2$Cl$_2$ were then added, and 3.11 ml (1.56 mmol) of a 0.5 M solution of isobutylzinc bromide in tetrahydrofuran were added dropwise. The mixture was then heated in a microwave at 120° C. for 3 h. Water was added carefully, and the mixture was extracted with dichloromethane. The organic phase was dried over sodium sulphate and concentrated under reduced pressure and the residue was purified by preparative HPLC (gradient of 0.1% formic acid in water/acetonitrile, 60-85%). This gave 51.7 mg (30% of theory) of the target compound.

LC-MS (Method 1) R$_t$=1.30 min; MS (ESIpos): m/z=445 (M+H)$^+$ $^1$H NMR (400 MHz, DMSO-d$_6$): δ [ppm]=1.01 (d, 6H), 1.40 (s, 6H), 2.68 (d, 2H), 5.86 (s, 2H), 7.10-7.28 (m, 3H), 7.32-7.41 (m, 1H), 7.46 (dd, 1H), 8.67 (d, 1H), 8.88 (d, 1H), 11.59 (s, 1H), (C-H signal superposed by DMSO peak).

Example 30

2-[1-(2-Fluorobenzyl)-1H-pyrazolo[3,4-b]pyridin-3-yl]-5,5-dimethyl-4-(4,4,4-trifluorobutyl)-5,7-dihydro-6H-pyrrolo[2,3-d]pyrimidin-6-one

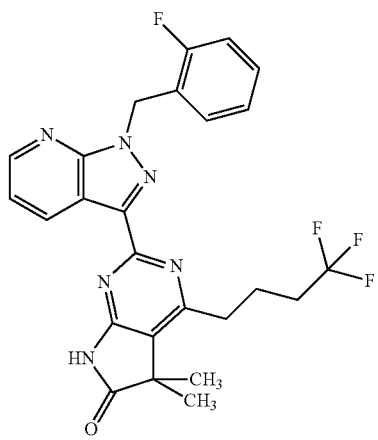 [SMILES: CC1(C)C(=O)Nc2nc(-c3nn(Cc4ccccc4F)c4ncccc34)nc(CCCC(F)(F)F)c21]

Under argon, 200 mg (0.39 mmol) of Example 47A were initially charged in 8 ml of dioxane. 31.8 mg (0.04 mmol) of PdCl$_2$(dppf) CH$_2$Cl$_2$ were then added, and 2.05 ml (1.57 mmol) of the solution from Example 72A were added dropwise. The mixture was then heated in a microwave at 120° C. for 3 h. Once more, the same amounts of PdCl$_2$(dppf) CH$_2$Cl$_2$ and the solution from Example 72A were added and the mixture was heated in a microwave for a further 3 h. Water was added carefully, and the mixture was extracted with dichloromethane. The organic phase was dried over sodium sulphate and concentrated under reduced pressure, and the residue was purified by prep. HPLC (gradient of 0.1% formic acid in water/acetonitrile, 60-85%). This gave 50 mg (30% of theory) of the target compound.

LC-MS (Method 1) R$_t$=1.22 min; MS (ESIpos): m/z=499 (M+H)$^+$ $^1$H NMR (400 MHz, DMSO-d$_6$): δ [ppm]=1.41 (s, 6H), 2.02-2.14 (m, 2H), 2.92 (t, 2H), 5.86 (s, 2H), 7.11-7.27 (m, 3H), 7.32-7.40 (m, 1H), 7.44 (dd, 1H), 8.67 (dd, 1H), 8.88 (dd, 1H), 11.61 (br. s, 1H), (CH2 group under DMSO peak).

Example 31

2-[1-(2-Fluorobenzyl)-1H-pyrazolo[3,4-b]pyridin-3-yl]-5,5-dimethyl-4-(3,3,3-trifluoropropyl)-5,7-dihydro-6H-pyrrolo[2,3-d]pyrimidin-6-one

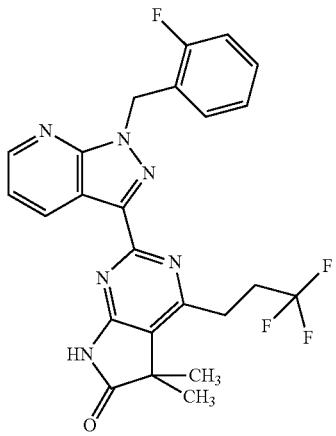 [SMILES: CC1(C)C(=O)Nc2nc(-c3nn(Cc4ccccc4F)c4ncccc34)nc(CCC(F)(F)F)c21]

Under argon, 200 mg (0.39 mmol) of Example 47A were initially charged in 8 ml of dioxane. 25.4 mg (0.03 mmol) of PdCl$_2$(dppf) CH$_2$Cl$_2$ were then added, and 1.92 ml (1.56 mmol) of the solution from Example 73A were added dropwise. The mixture was then heated in a microwave at 120° C. for 3 h. Water was added carefully, and the mixture was extracted with dichloromethane. The organic phase was dried over sodium sulphate and concentrated under reduced pressure, and the residue was purified by prep. HPLC (gradient of 0.1% formic acid in water/acetonitrile, 60-85%). This gave 54 mg (28% of theory) of the target compound.

LC-MS (Method 1) R$_t$=1.19 min; MS (ESIpos): m/z=485 (M+H)$^+$ $^1$H NMR (400 MHz, DMSO-d$_6$): δ [ppm]=1.41 (s, 6H), 2.85-3.00 (m, 2H), 3.01-3.10 (m, 2H), 5.87 (s, 2H), 7.10-7.27 (m, 3H), 7.31-7.40 (m, 1H), 7.47 (dd, 1H), 8.68 (dd, 1H), 8.88 (dd, 1H), 11.69 (br. s, 1H).

Example 32

2-[1-(2-Fluorobenzyl)-1H-pyrazolo[3,4-b]pyridin-3-yl]-5,5-dimethyl-4-propyl-5,7-dihydro-6H-pyrrolo[2,3-d]pyrimidin-6-one

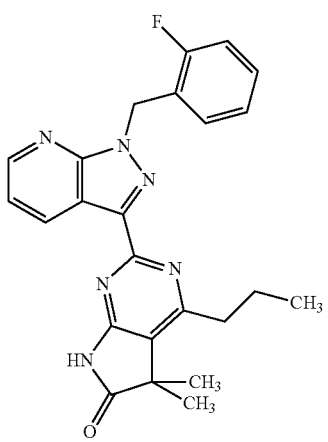 [SMILES: CCCc1nc(-c2nn(Cc3ccccc3F)c3ncccc23)nc2c1C(C)(C)C(=O)N2]

Under argon, 200 mg (0.39 mmol) of Example 47A were initially charged in 5 ml of dioxane. 7.9 mg (0.01 mmol) of PdCl$_2$(dppf) CH$_2$Cl$_2$ were then added, and 3.11 ml (1.56 mmol) of a 0.5 M solution of propylzinc bromide in tetrahydrofuran were added dropwise. The mixture was then heated in a microwave at 120° C. for 3 h and at 140° C. for 2 h. A further 20 mg (0.03 mmol) of PdCl$_2$(dppf) CH$_2$Cl$_2$ and 1.6 ml (0.80 mmol) of 0.5 M propylzinc bromide solution were added, and the mixture was heated in a microwave at 120° C. for 3 h. Water was added carefully, and the mixture was extracted with dichloromethane. The organic phase was dried over sodium sulphate and concentrated under reduced pressure. The residue (254 mg) was purified by silica gel chromatography (mobile phase DCM/acetonitrile, 3:1) and then by prep. HPLC (gradient of 0.1% formic acid in water/acetonitrile, 60-85%). This gave 46 mg (27% of theory) of the target compound.

LC-MS (Method 1) R$_t$=1.21 min; MS (ESIpos): m/z=431 (M+H)$^+$ $^1$H NMR (400 MHz, DMSO-d$_6$): δ [ppm]=1.02 (t, 3H), 1.40 (s, 6H), 1.88 (sxt, 2H), 2.78 (t, 2H), 5.86 (s, 2H), 7.11-7.28 (m, 3H), 7.32-7.40 (m, 1H), 7.46 (dd, 1H), 8.67 (dd, 1H), 8.90 (dd, 1H), 11.58 (s, 1H).

Example 33

(rac) Ethyl 2-[1-(2-fluorobenzyl)-1H-pyrazolo[3,4-b]pyridin-3-yl]-5-methyl-6-oxo-6,7-dihydro-5H-pyrrolo[2,3-d]pyrimidine-5-carboxylate

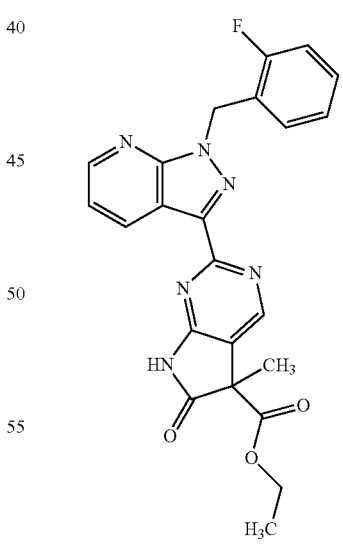

Under an atmosphere of argon, 874.4 mg (1.53 mmol) of Example 43 were dissolved in 15 ml of N,N-dimethylformamide, and 200 mg of 10% palladium on activated carbon were added. The mixture was hydrogenated at standard pressure. After addition of a further 100 mg of 10% palladium on activated carbon, the mixture was once more hydrogenated at standard pressure overnight. Another 50 mg of 10% palladium on activated carbon were added, and the mixture was hydrogenated at standard pressure for another night. The mixture was filtered through Celite and concentrated. Drying under high vacuum gave 1.19 g of crude target compound which was processed further as such. A sample was purified by prep. HPLC (gradient of 0.05% formic acid in water/acetonitrile, 30-95%).

LC-MS (Method 1) $R_t$=1.06 min; MS (ESIpos): m/z=447 (M+H)$^+$ $^1$H NMR (400 MHz, DMSO-d$_6$): δ [ppm]=1.10 (t, 3H) 1.65 (s, 3H) 4.06-4.19 (m, 2H) 5.87 (s, 2H) 7.12-7.19 (m, 1H) 7.19-7.29 (m, 2H) 7.32-7.41 (m, 1H) 7.45 (dd, 1H) 8.64 (s, 1H) 8.69 (dd, 1H) 8.87 (dd, 1H) 11.92 (br.s, 1H).

Example 34

(rac) 2-[1-(2-Fluorobenzyl)-1H-pyrazolo[3,4-b]pyridin-3-yl]-5-methyl-5-(1,3,4-thiadiazol-2-yl)-5,7-dihydro-6H-pyrrolo[2,3-d]pyrimidin-6-one

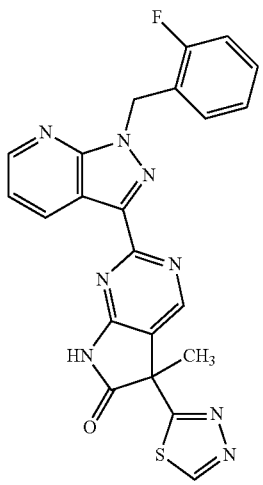 [SMILES: CC1(c2nncs2)C(=O)Nc2nc(-c3nn(Cc4ccccc4F)c4ncccc34)ncc21]

167.5 mg (0.36 mmol) of Example 77A were initially charged in 5 ml of toluene and, with 154.5 mg (0.38 mmol) of 4-methoxyphenyldithiophosphonic anhydride, stirred at a bath temperature of 100° C. for 3 h and allowed to stand at room temperature overnight. After addition of 2 ml of tetrahydrofuran, the mixture was stirred at 100° C. for a further 3 h. 73.6 mg (0.18 mmol) of 4-methoxyphenyldithiophosphonic anhydride were added, and the mixture was stirred at 100° C. overnight. The mixture was then purified by prep. HPLC (gradient of 0.05% formic acid in water/20-95% acetonitrile). This gave 84.5 mg (51% of theory) of the target compound.

LC-MS (Method 1) $R_t$=0.96 min; MS (ESIpos): m/z=459 (M+H)$^+$ $^1$H NMR (400 MHz, DMSO-d$_6$): δ [ppm]=1.95 (s, 3H), 5.88 (s, 2H), 7.11-7.19 (m, 1H), 7.20-7.28 (m, 2H), 7.31-7.41 (m, 1H), 7.46 (dd, 1H), 8.69 (dd, 1H), 8.84 (s, 1H), 8.90 (dd, 1H), 9.65 (s, 1H), 12.18 (br. s, 1H).

Example 35

2-[1-(2-Fluorobenzyl)-1H-pyrazolo[3,4-b]pyridin-3-yl]-5,5-dimethyl-4-(2-methyl-1,3-thiazol-5-yl)-5,7-dihydro-6H-pyrrolo[2,3-d]pyrimidin-6-one

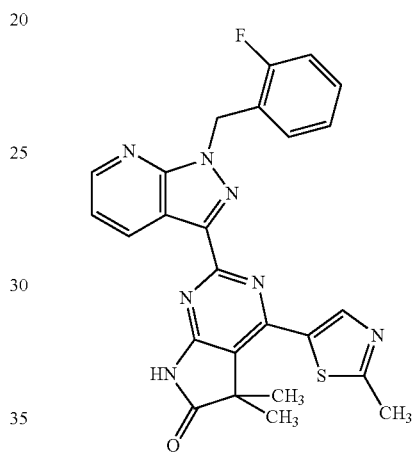

Under an atmosphere of argon, 200 mg (0.24 mmol, purity 62%) of Example 47A were suspended in 5 ml of dioxane, and 162.83 mg (0.72 mmol) of 2-methyl-5-(4,4,5,5-tetramethyl-1,3,2-dioxaborolan-2-yl)-1,3-thiazole and 0.96 ml (0.96 mmol) of 1 N aqueous potassium carbonate solution were added. After 10 min, 55 mg (0.05 mmol) of tetrakis(triphenylphosphine)palladium(0) were added and the mixture was stirred at 140° C. in a microwave for 1 h. Another 162.83 mg (0.72 mmol) of 2-methyl-5-(4,4,5,5-tetramethyl-1,3,2-dioxaborolan-2-yl)-1,3-thiazole were added, followed by 20.28 mg (0.07 mmol) of tricyclohexylphosphine and 26.46 mg (0.04 mmol) of 1,1'-bis(diphenylphosphino)ferrocenepalladium(II) chloride. After 1 h at 140° C. in the microwave, the mixture was filtered and separated twice by prep. HPLC (acetonitrile:water (+0.1% formic acid) gradient). This gave 11 mg (9% of theory) of the target compound.

LC-MS (Method 1) $R_t$=1.09 min; MS (ESIpos): m/z=486 (M+H)$^+$

1H NMR (400 MHz, DMSO-d$_6$): δ [ppm]=1.51 (s, 6H), 2.78 (s, 3H), 5.88 (s, 2H), 7.07-7.18 (m, 1H), 7.18-7.28 (m, 2H), 7.31-7.41 (m, 1H), 7.51 (dd, 1H), 8.31 (s, 1H), 8.70 (dd, 1H), 8.93 (m, 1H), 11.87 (br s, 1H).

Example 36

4-(2,4-Dimethyl-1,3-thiazol-5-yl)-2-[1-(2-fluorobenzyl)-1H-pyrazolo[3,4-b]pyridin-3-yl]-5,5-dimethyl-5,7-dihydro-6H-pyrrolo[2,3-d]pyrimidin-6-one

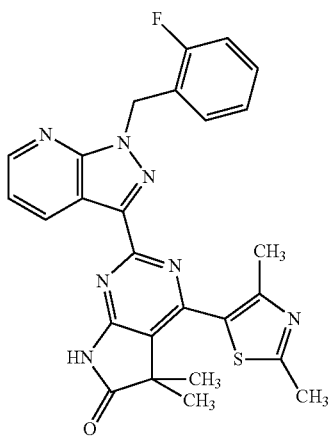 [SMILES: Cc1nc(C)c(-c2nc(-c3nn(Cc4ccccc4F)c4ncccc34)nc3c2C(C)(C)C(=O)N3)s1]

200 mg (0.24 mmol, purity 62%) of Example 47A were reacted analogously to Example 35 with 173 mg (0.72 mmol) of 2,4-dimethyl-5-(4,4,5,5-tetramethyl-1,3,2-dioxaborolan-2-yl)-1,3-thiazole. This gave 40 mg of the title compound (27% of theory).

LC-MS (Method 1) $R_t$=1.08 min; MS (ESIpos): m/z=500 (M+H)$^+$ $^1$H NMR (400 MHz, DMSO-d$_6$): δ [ppm]=1.26 (s, 6H), 2.27 (s, 3H), 2.72 (s, 3H), 5.87 (s, 2H), 7.12-7.25 (m, 3H), 7.33-7.39 (m, 1H), 7.43 (dd, 1H), 8.66 (dd, 1H), 8.74 (dd, 1H), 11.83 (s, 1H).

Example 37

2-[1-(2-Fluorobenzyl)-1H-pyrazolo[3,4-b]pyridin-3-yl]-4-(2-isopropyl-4-methyl-1,3-thiazol-5-yl)-5,5-dimethyl-5,7-dihydro-6H-pyrrolo[2,3-d]pyrimidin-6-one

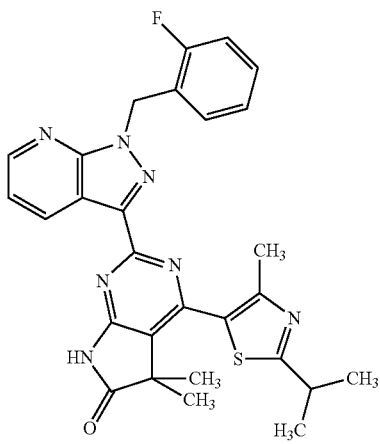 [SMILES: Cc1nc(C(C)C)sc1-c1nc(-c2nn(Cc3ccccc3F)c3ncccc23)nc2c1C(C)(C)C(=O)N2]

200 mg (0.24 mmol, purity 62%) of Example 47A were reacted analogously to Example 35 with 193 mg (0.72 mmol) of 2-isopropyl-4-methyl-5-(4,4,5,5-tetramethyl-1,3,2-dioxaborolan-2-yl)-1,3-thiazole. This gave 60 mg of the title compound (44% of theory).

LC-MS (Method 1) $R_t$=1.24 min; MS (ESIpos): m/z=528 (M+H)$^+$ $^1$H NMR (400 MHz, DMSO-d$_6$): δ [ppm]=1.25 (s, 6H), 1.39 (d, 6H), 2.29 (s, 3H), 3.33 (sept, 1H), 5.87 (s, 2H), 7.12-7.25 (m, 3H), 7.33-7.39 (m, 2H), 8.67 (dd, 1H) 8.75 (dd, 1H) 11.84 (br s, 1H).

Example 38

4-(1,3-Dimethyl-1H-pyrazol-5-yl)-2-[1-(2-fluorobenzyl)-1H-pyrazolo[3,4-b]pyridin-3-yl]-5,5-dimethyl-5,7-dihydro-6H-pyrrolo[2,3-d]pyrimidin-6-one

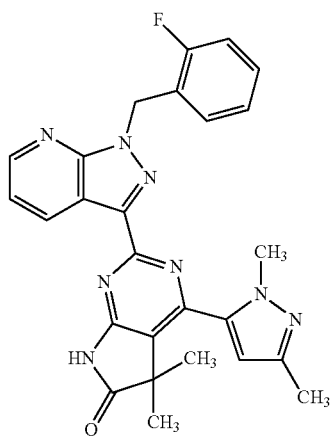 [SMILES: Cc1cc(-c2nc(-c3nn(Cc4ccccc4F)c4ncccc34)nc3c2C(C)(C)C(=O)N3)n(C)n1]

200 mg (0.24 mmol, purity 62%) of Example 47A were reacted analogously to Example 35 with 101 mg (0.72 mmol) of (1,3-dimethyl-1H-pyrazol-5-yl)boronic acid. This gave 41 mg of the title compound (33% of theory).

LC-MS (Method 1) $R_t$=1.05 min; MS (ESIpos): m/z=483 (M+H)$^+$ $^1$H NMR (400 MHz, DMSO-d$_6$): δ [ppm]=1.24 (s, 6H), 2.26 (s, 3H), 3.71 (s, 3H), 5.87 (s, 2H), 6.40 (s, 1H), 7.15 (dt, 3H), 7.34-7.39 (m, 1H), 7.44 (dd, 1H), 8.67 (dd, 1H), 8.75 (dd, 1H), 11.84 (s, 1H).

Example 39

2-[1-(2-Fluorobenzyl)-1H-pyrazolo[3,4-b]pyridin-3-yl]-4-(1-isopropyl-1H-pyrazol-3-yl)-5,5-dimethyl-5,7-dihydro-6H-pyrrolo[2,3-d]pyrimidin-6-one

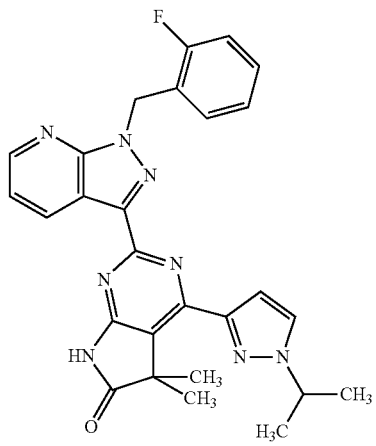 [SMILES: CC(C)n1ccc(-c2nc(-c3nn(Cc4ccccc4F)c4ncccc34)nc3c2C(C)(C)C(=O)N3)n1]

200 mg (0.24 mmol, purity 62%) of Example 47A were reacted analogously to Example 35 with 171 mg (0.72 mmol) of 1-isopropyl-3-(4,4,5,5-tetramethyl-1,3,2-dioxaborolan-2-yl)-1H-pyrazole. This gave 58 mg of the title compound (45% of theory).

LC-MS (Method 1) $R_t$=1.12 min; MS (ESIpos): m/z=497 (M+H)$^+$ $^1$H NMR (400 MHz, DMSO-d$_6$): δ [ppm]=1.47 (s, 6H), 1.51 (d, 6H), 4.77 (sept, 1H), 5.87 (s, 2H), 7.13-7.26 (m, 3H), 7.34-7.39 (m, 1H), 7.48 (dd, 1H), 8.17 (s, 1H), 8.42 (s, 1H), 8.69 (dd, 1H), 8.94 (dd, 1H), 11.66 (s, 1H).

Example 40

2-[1-(2-Fluorobenzyl)-1H-pyrazolo[3,4-b]pyridin-3-yl]-5,5-dimethyl-4-(1-methyl-1H-pyrazol-5-yl)-5,7-dihydro-6H-pyrrolo[2,3-d]pyrimidin-6-one

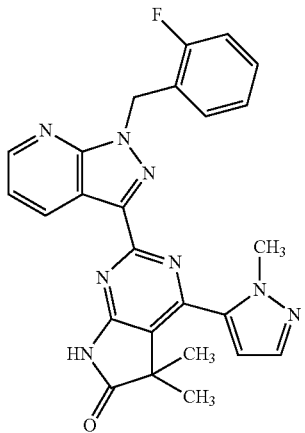 [SMILES: Cn1nccc1-c1nc(-c2nn(Cc3ccccc3F)c3ncccc23)nc2c1C(C)(C)C(=O)N2]

200 mg (0.24 mmol, purity 62%) of Example 47A were reacted analogously to Example 35 with 150 mg (0.72 mmol) of 1-methyl-5-(4,4,5,5-tetramethyl-1,3,2-dioxaborolan-2-yl)-1H-pyrazole. This gave 45 mg of the title compound (38% of theory).

LC-MS (Method 1) $R_t$=1.01 min; MS (ESIpos): m/z=469 (M+H)$^+$ $^1$H NMR (400 MHz, DMSO-d$_6$): δ [ppm]=1.23 (s, 6H), 3.80 (s, 3H), 5.88 (s, 2H), 6.63 (d, 1H), 7.13-7.25 (m, 3H), 7.34-7.39 (m, 1H), 7.44 (dd, 1H), 7.61 (d, 1H), 8.65-8.67 (dd, 1H), 8.75 (dd, 1H), 11.87 (s, 1H).

Example 41

2-[1-(2-Fluorobenzyl)-1H-pyrazolo[3,4-b]pyridin-3-yl]-5,5-dimethyl-4-[1-methyl-3-(trifluoromethyl)-1H-pyrazol-5-yl]-5,7-dihydro-6H-pyrrolo[2,3-d]pyrimidin-6-one

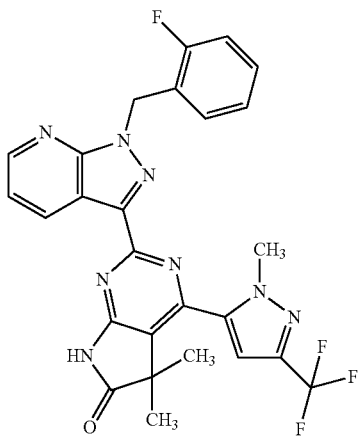 [SMILES: Cn1nc(C(F)(F)F)cc1-c1nc(-c2nn(Cc3ccccc3F)c3ncccc23)nc2c1C(C)(C)C(=O)N2]

Under an atmosphere of argon, 200 mg (0.24 mmol, purity 62%) of Example 47A were suspended in 5 ml of dioxane, and 140 mg (0.72 mmol) of [1-methyl-3-(trifluoromethyl)-1H-pyrazol-5-yl]boronic acid and 0.96 ml (0.96 mmol) of 1 N aqueous potassium carbonate solution were added. After 10 min, 55 mg (0.05 mmol) of tetrakis(triphenylphosphine)palladium(0) were added. After 1 h at 140° C. in the microwave, the mixture was filtered and separated by prep. HPLC (acetonitrile:water (+0.1% formic acid) gradient). This gave 70 mg (54% of theory) of the target compound.

LC-MS (Method 1) $R_t$=1.23 min; MS (ESIpos): m/z=537 (M+H)$^+$ $^1$H NMR (400 MHz, DMSO-d$_6$): δ [ppm]=1.22 (s, 6H), 3.31 (s, 3H), 5.88 (s, 2H), 7.13-7.17 (m, 2H), 7.20-7.25 (m, 2H), 7.34-7.39 (m, 1H), 7.44 (dd, 1H,) 8.68 (dd, 1H), 8.76 (dd, 1H), 11.96 (s, 1H).

Example 42

5-{2-[1-(2-Fluorobenzyl)-1H-pyrazolo[3,4-b]pyridin-3-yl]-5,5-dimethyl-6-oxo-6,7-dihydro-5H-pyrrolo[2,3-d]pyrimidin-4-yl}-1-methyl-1H-pyrrole-2-carbonitrile

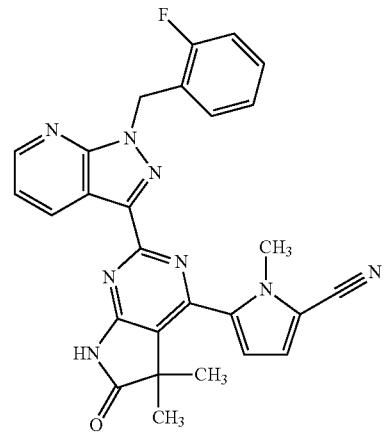 [SMILES: Cn1c(C#N)ccc1-c1nc(-c2nn(Cc3ccccc3F)c3ncccc23)nc2c1C(C)(C)C(=O)N2]

200 mg (0.24 mmol, purity 62%) of Example 47A were reacted analogously to Example 41 with 108 mg (0.72 mmol) of (5-cyano-1-methyl-1H-pyrrol-2-yl)boronic acid. This gave 77 mg of the title compound (62% of theory).

LC-MS (Method 1) $R_t$=1.14 min; MS (ESIpos): m/z=493 (M+H)$^+$ $^1$H NMR (400 MHz, DMSO-d$_6$): δ [ppm]=1.24 (s, 6H), 3.70 (s, 3H), 5.87 (s, 2H), 6.58 (d, 1H), 7.13-7.17 (m, 2H), 7.20-7.25 (m, 2H), 7.33-7.39 (m, 1H), 7.44 (dd, 1H), 8.67 (dd, 1H), 8.77 (dd, 1H), 11.86 (s, 1H).

Example 43

(rac) Ethyl 2-[1-(2-fluorobenzyl)-1H-pyrazolo[3,4-b]pyridin-3-yl]-4-iodo-5-methyl-6-oxo-6,7-dihydro-5H-pyrrolo[2,3-d]pyrimidine-5-carboxylate

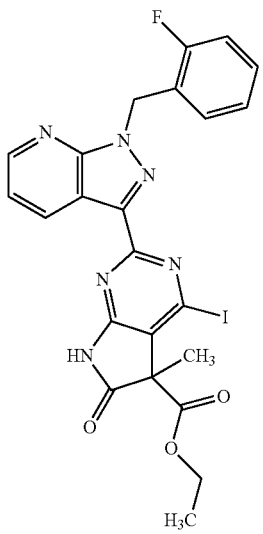 [SMILES: CCOC(=O)C1(C)C(=O)Nc2nc(-c3nn(Cc4ccccc4F)c4ncccc34)nc(I)c21]

Under an atmosphere of argon, 1 g (2.17 mmol) of Example 75A was initially charged in 6.3 ml isopentyl nitrite and 9.44 ml of diiodomethane and the mixture was stirred at a bath temperature of 85° C. overnight. After cooling, the mixture was concentrated and the residue was purified twice by flash chromatography on silica gel (mobile phase: dichloromethane/methanol, then cyclohexane/ethyl acetate). After drying under high vacuum, 887.5 mg of the title compound were obtained (72% of theory).

LC-MS (Method 1): $R_t$=1.22 min; MS (ESIpos): m/z=573 (M+H)$^+$ $^1$H NMR (400 Hz, DMSO-d$_6$): δ [ppm]=1.14 (t, 3H), 1.67 (s, 3H), 4.05-4.27 (m, 2H), 5.89-(s, 2H), 7.10-7.30 (m, 3H), 7.32-7.43 (m, 1H), 7.50 (dd, 1H), 8.71 (dd, 1H), 8.75-8.85 (m, 1H), 12.25 (s, 1H).

Example 44

4-(Aminomethyl)-2-[5-fluoro-1-(2-fluorobenzyl)-1H-pyrazolo[3,4-b]pyridin-3-yl]-5,5-dimethyl-5,7-dihydro-6H-pyrrolo[2,3-d]pyrimidin-6-one formate

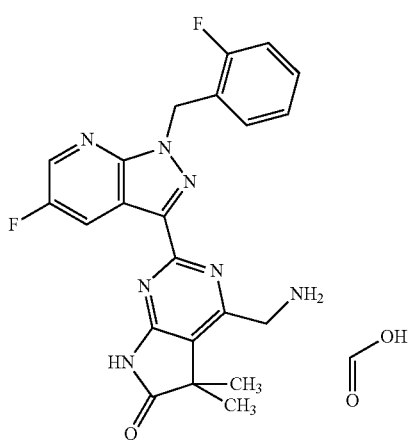 [SMILES: CC1(C)C(=O)Nc2nc(-c3nn(Cc4ccccc4F)c4ncc(F)cc34)nc(CN)c21 ; O=CO]

Under argon, 23.7 mg of 10% palladium on activated carbon were initially charged in 1 ml of acetic acid, and 1.22 g (1.68 mmol) of crude substance from Example 81A dissolved in 10 ml of acetic acid and 6 ml of DMF were added. The mixture was hydrogenated at room temperature under standard pressure overnight, and 10 ml of DMF and 300 mg of 10% palladium on activated carbon were then added. After 4 days of hydrogenation at room temperature under standard pressure, another 300 mg of 10% palladium on activated carbon and 10 ml of DMF were added. After one night of hydrogenation at room temperature and 3 bar, 10 ml of acetic acid and 300 mg of 10% palladium on activated carbon were added. After one night of hydrogenation at 3 bar, another 300 mg of 10% palladium on activated carbon were added. After a further night of hydrogenation at 3 bar, the mixture was filtered off through Celite, the filter cake was washed with DMF and the mother liquor was concentrated under reduced pressure and dried under high vacuum overnight. Part of the residue was purified by preparative HPLC (gradient 0.05% formic acid in water/10-95% acetonitrile). This gave 23.7 mg (3% of theory) of the title compound.

$^1$H NMR (400 MHz; DMSO-d$_6$): δ [ppm]=1.32-1.48 (m, 6H), 3.96 (s, 2H), 5.86 (s, 2H), 7.10-7.29 (m, 3H), 7.32-7.42 (m, 1H), 8.25 (br. s., 1H), 8.70-8.85 (m, 2H).

Example 45

4-(Aminomethyl)-2-[5-fluoro-1-(2-fluorobenzyl)-1H-pyrazolo[3,4-b]pyridin-3-yl]-5,5-dimethyl-5,7-dihydro-6H-pyrrolo[2,3-d]pyrimidin-6-one acetate

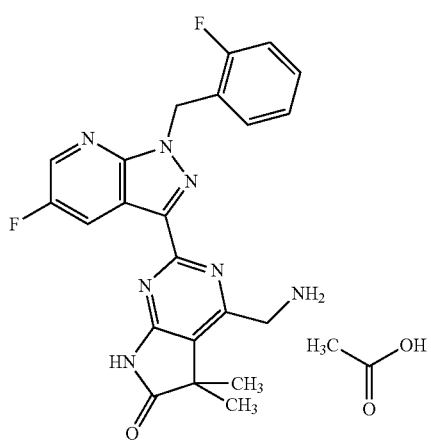

The remaining residue from the preparation of Example 44 was purified by flash chromatography on silica gel (mobile phase: dichloromethane/methanol (3-10%). This gave 327 mg (39% of theory) of the title compound as the acetate.

LC-MS (Method 1): $R_t$=0.73 min; MS (ESIpos): m/z=436 (M+H)$^+$ $^1$H NMR (400 MHz, DMSO-d$_6$): δ [ppm]=1.35-1.45 (m, 6H), 1.91 (s, 3H), 3.93 (s, 2H), 5.86 (s, 2H), 7.12-7.19 (m, 1H), 7.19-7.29 (m, 2H), 7.32-7.42 (m, 1H), 8.71-8.81 (m, 2H).

Example 46

2-[1-(2-Fluorobenzyl)-1H-pyrazolo[3,4-b]pyridin-3-yl]-4-(3-methoxypropyl)-5,5-dimethyl-5,7-dihydro-6H-pyrrolo[2,3-d]pyrimidin-6-one

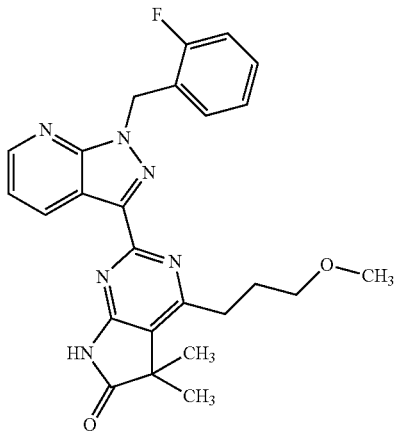 [SMILES: COCCCc1nc(-c2nn(Cc3ccccc3F)c3ncccc23)nc2c1C(C)(C)C(=O)N2]

375 mg (0.57 mmol, purity 69%) of Example 63 were dissolved in tetrahydrofuran and the mixture was diluted with 50 ml of ethanol and hydrogenated with 120 mg (0.11 mmol) of 10% palladium on activated carbon at standard pressure overnight. The mixture was filtered through Celite, concentrated under reduced pressure and separated by preparative HPLC (gradient: 0.1% formic acid in water/acetonitrile). Drying under high vacuum gave 130 mg (50% of theory) of the title compound.

LC-MS (Method 1): $R_t$=1.11 min; MS (ESIpos): m/z=461 (M+H)$^+$ $^1$H NMR (400 MHz, DMSO-d$_6$): δ [ppm]=1.40 (s, 6H), 2.05-2.12 (m, 2H), 2.82-2.86 (m, 2H), 3.25 (s, 3H), 3.45 (t, 2H), 5.86 (s, 2H), 7.12-7.25 (m, 3H), 7.33-7.40 (m, 1H), 7.45 (dd, 1H), 8.67 (dd, 1H), 8.89 (dd, 1H), 11.57 (s, 1H).

Example 47

(rac) Ethyl 5-methyl-6-oxo-2-[1-(3,3,4,4,4-pentafluorobutyl)-1H-pyrazolo[3,4-b]pyridin-3-yl]-6,7-dihydro-5H-pyrrolo[2,3-d]pyrimidine-5-carboxylate

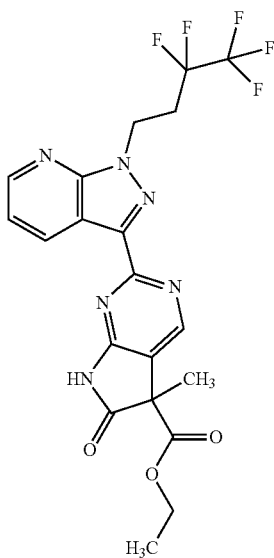 [SMILES: CCOC(=O)C1(C)C(=O)Nc2nc(-c3nn(CCC(F)(F)C(F)(F)F)c4ncccc34)ncc21]

Under an atmosphere of argon, 76.5 mg of 10% palladium on activated carbon were initially charged in 1 ml of N,N-dimethylformamide, 190 mg (0.30 mmol) of (rac) ethyl 4-bromo-5-methyl-6-oxo-2-[1-(3,3,4,4,4-pentafluorobutyl)-1H-pyrazolo[3,4-b]pyridin-3-yl]-6,7-dihydro-5H-pyrrolo[2,3-d]pyrimidine-5-carboxylate (WO 2011/14992, Ex. 187A), dissolved in 18 ml of N,N-dimethylformamide, were added and the mixture was hydrogenated at room temperature under standard pressure overnight. Another 85 mg of 10% palladium on activated carbon were then added, and the mixture was hydrogenated at room temperature under standard pressure for 4 days. The mixture was filtered off through Celite, and the filter cake was washed with N,N-dimethylformamide. The filtrate was concentrated under reduced pressure and purified by preparative HPLC (gradient 0.1% formic acid in water/60-90% methanol). This gave 36 mg (19% of theory, purity 77%) of the title compound.

LC-MS (Method 1): $R_t$=1.08 min; MS (ESIpos): m/z=485 (M+H)$^+$ $^1$H NMR (400 Hz, DMSO-d$_6$): δ [ppm]=1.11 (t, 3H), 1.66 (s, 3H), 2.95-3.08 (m, 2H), 4.09-4.17 (m, 2H), 4.91-4.97 (m, 2H), 7.45 (dd, 1H), 8.66 (s, 1H), 8.69 (dd, 1H), 8.86 (dd, 1H), 12.01 (br s, 1H).

Example 48

(rac) N-Cyclopropyl-5-methyl-6-oxo-2-[1-(3,3,4,4,4-pentafluorobutyl)-1H-pyrazolo[3,4-b]pyridin-3-yl]-6,7-dihydro-5H-pyrrolo[2,3-d]pyrimidine-5-carboxamide

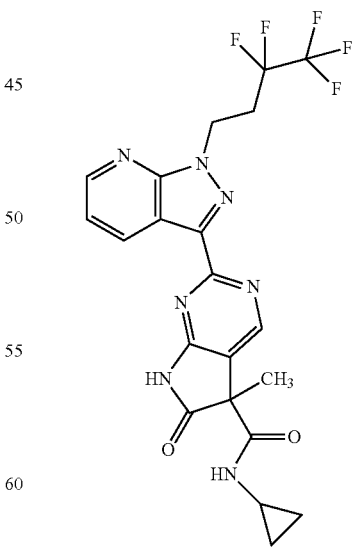

Under an atmosphere of argon, 34 mg (0.05 mmol, purity 77%) of Example 47 in 0.5 ml of methanol with 30.86 mg (0.54 mmol) of cyclopropylamine were stirred in a microwave at 80° C. for one day and purified by preparative HPLC (gradient 0.1% formic acid in water/60-90% methanol). 13.5 mg (50% of theory) of the title compound were obtained.

LC-MS (Method 1): R$_t$=0.99 min; MS (ESIpos): m/z=496 (M+H)$^+$ $^1$H NMR (400 Hz, DMSO-d$_6$): δ [ppm]=0.39-0.48 (m, 2H), 0.60 (d, 2H), 1.61 (s, 3H), 2.60-2.69 (m, 1H), 2.95-3.08 (m, 2H), 4.93 (t, 2H), 7.44 (dd, 1H), 7.76 (d, 1H), 8.58 (s, 1H), 8.68 (d, 1H), 8.88 (d, 1H), 11.79 (s, 1H).

Example 49

(rac) N-Cyclopropyl-5-methyl-6-oxo-2-[1-(3,3,3-trifluoropropyl)-1H-pyrazolo[3,4-b]pyridin-3-yl]-6,7-dihydro-5H-pyrrolo[2,3-d]pyrimidine-5-carboxamide

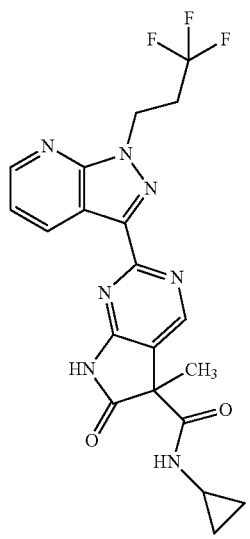 [SMILES: CC1(C(=O)NC2CC2)C(=O)Nc2nc(-c3nn(CCC(F)(F)F)c4ncccc34)ncc21]

Under an atmosphere of argon, 30 mg of 10% palladium on activated carbon were initially charged in 2 ml of N,N-dimethylformamide, and 111 mg (0.12 mmol, purity 60%) of Example 61A, dissolved in 8 ml of N,N-dimethylformamide, were added. The mixture was hydrogenated at room temperature overnight and then filtered through Celite, and the filter residue was washed with N,N-dimethylformamide. The filtrate was concentrated under reduced pressure and the residue was purified by preparative HPLC (gradient 0.05% formic acid in water/20-95% acetonitrile). 32 mg (60% of theory) of the title compound were obtained.

LC-MS (Method 1): R$_t$=0.89 min; MS (ESIpos): m/z=446 (M+H)$^+$ $^1$H NMR (400 MHz, DMSO-d$_6$): δ [ppm]=0.38-0.49 (m, 2H), 0.60 (d, 2H), 1.61 (s, 3H), 2.60-2.69 (m, 1H), 2.98-3.12 (m, 2H), 4.79-4.93 (m, 2H), 7.38-7.50 (m, 1H), 7.76 (d, 1H), 8.58 (s, 1H), 8.63-8.71 (m, 1H), 8.88 (dd, 1H), 11.80 (br. s., 1H).

Example 50 tert-Butyl 3-{2-[1-(2-fluorobenzyl)-1H-pyrazolo[3,4-b]pyridin-3-yl]-5,5-dimethyl-6-oxo-6,7-dihydro-5H-pyrrolo[2,3-d]pyrimidin-4-yl}prop-2-ynoate

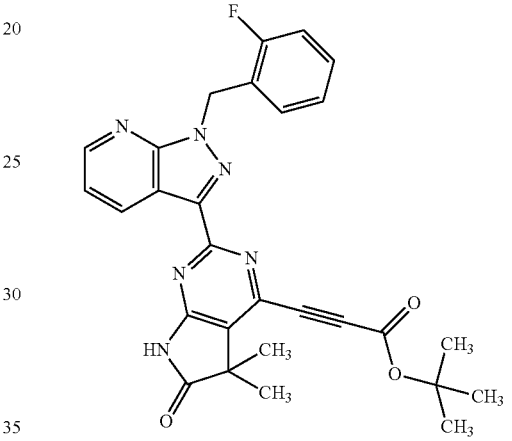

Under argon, 100 mg (0.19 mmol) of Example 47A together with 98 mg (0.78 mmol) of tert-butyl propiolate, 3.7 mg (0.02 mmol) of copper(I) iodide, 32.7 mg (0.39 mmol) of sodium bicarbonate and 6.8 mg (0.01 mmol) of dichlorobistriphenylphosphinepalladium(II) in 1 ml of DMF were stirred at 60° C. overnight. 98 mg (0.78 mmol) of tert-butyl propiolate, 3.7 mg (0.02 mmol) of copper(I) iodide, 32.7 mg (0.39 mmol) of sodium bicarbonate and 6.8 mg (0.01 mmol) of dichlorobistriphenylphosphinepalladium(II) were then added, and the mixture was stirred at 60° C. for a further 10 h. Water was added and the mixture was extracted with ethyl acetate. The organic phases were dried over sodium sulphate and concentrated. The residue was purified by preparative HPLC (gradient: 0.1% formic acid in water/5-95% acetonitrile).

Yield: 16 mg (16% of theory)

LC-MS (Method 9): Rt=4.18 min; MS (ESIpos): m/z=513 (M+H)$^+$ $^1$H NMR (400 MHz, DMSO-d$_6$): d [ppm]=1.45 (s, 6H), 1.54 (s, 9H), 5.88 (s, 2H), 7.11-7.28 (m, 3H), 7.31-7.41 (m, 1H), 7.49 (dd, 1H), 8.70 (dd, 1H), 8.78-8.86 (m, 1H), 11.95 (s, 1H).

Example 51

(rac) 7-Allyl-3-[5-fluoro-1-(2-fluorobenzyl)-1H-pyrazolo[3,4-b]pyridin-3-yl]-7-methyl-5,7-dihydro-6H-pyrrolo[2,3-e][1,2,4]triazin-6-one

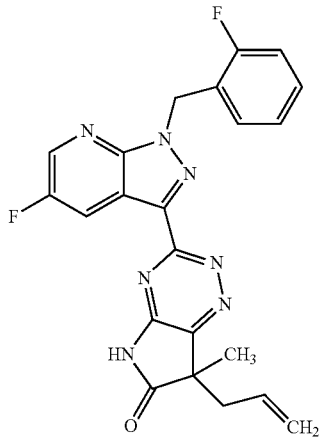 [SMILES: C=CCC1(C)C(=O)Nc2nc(-c3nn(Cc4ccccc4F)c4ncc(F)cc34)nnc21]

2.03 g (2.96 mmol) of Example 88A were reacted analogously to Example 28. The intermediate, (rac) ethyl 2-{5-chloro-3-[5-fluoro-1-(2-fluorobenzyl)-1H-pyrazolo[3,4-b]pyridin-3-yl]-1,2,4-triazin-6-yl}-2-methylpent-4-enoate, was detected in the LC-MS:

LC-MS (Method 1): $R_t$=1.44 min; MS (ESIpos): m/z=499 (M+H)$^+$

The intermediate was reacted further analogously to Example 28. The crude product was purified by means of preparative HPLC (gradient: 1% ammonia in water/acetonitrile, 5-95%). This gave 0.78 g (89% of theory) of the title compound.

LC-MS (Method 1): $R_t$=1.12 min; MS (ESIpos): m/z=434 (M+H)$^+$ $^1$H NMR (400 MHz, DMSO-d$_6$): δ [ppm]=1.46 (s, 3H), 2.58-2.70 (m, 2H), 4.95-5.11 (m, 2H), 5.54-5.70 (m, 1H), 5.88 (s, 1H), 7.11-7.33 (m, 3H), 7.34-7.44 (m, 1H), 8.57 (dd, 1H) 8.79 (s, 1H), 12.28 (s, 1H).

Example 52

(rac){3-[5-Fluoro-1-(2-fluorobenzyl)-1H-pyrazolo[3,4-b]pyridin-3-yl]-7-methyl-6-oxo-6,7-dihydro-5H-pyrrolo[2,3-e][1,2,4]triazin-7-yl}acetic acid

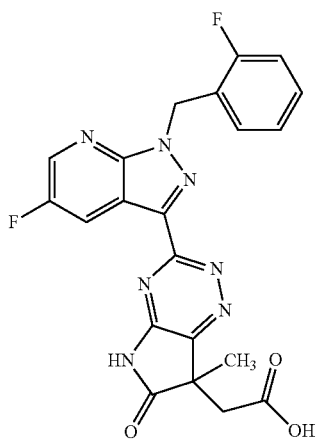 [SMILES: CC1(CC(=O)O)C(=O)Nc2nc(-c3nn(Cc4ccccc4F)c4ncc(F)cc34)nnc21]

725 mg (1.67 mmol) of Example 51 were initially charged in 28 ml of acetonitrile, and 42 ml of dioxane, 9.76 mg (0.043 mmol) of ruthenium trichloride hydrate and 2.50 g of sodium periodate, dissolved in 14 ml of water, were added. The mixture was stirred at room temperature overnight and partitioned between ethyl acetate and water, the phases were separated and the aqueous phase was extracted twice with ethyl acetate. The combined organic phases were washed once with saturated sodium chloride solution, dried over sodium sulphate, concentrated under reduced pressure and purified by means of preparative HPLC (gradient 0.05% formic acid in water/10-95% acetonitrile). 172.6 mg (20% of theory) of the title compound were obtained.

LC-MS (Method 1): $R_t$=0.95 min; MS (ESIpos): m/z=452 (M+H)$^+$ $^1$H NMR (400 MHz; DMSO-d$_6$): δ [ppm]=1.42 (s, 3H), 3.03-3.24 (m, 2H), 5.89 (s, 2H), 7.12-7.32 (m, 3H), 7.33-7.43 (m, 1H), 8.56 (dd, 1H), 8.79 (s, 1H), 12.28 (br. s., 1H), 12.70 (br. s., 1H).

Example 53

Ethyl 3-{2-[1-(2-fluorobenzyl)-1H-pyrazolo[3,4-b]pyridin-3-yl]-5,5-dimethyl-6-oxo-6,7-dihydro-5H-pyrrolo[2,3-d]pyrimidin-4-yl}prop-2-ynoate

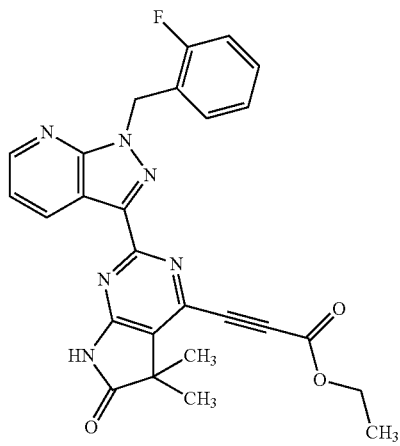 [SMILES: CCOC(=O)C#Cc1nc(-c2nn(Cc3ccccc3F)c3ncccc23)nc2c1C(C)(C)C(=O)N2]

Analogously to the preparation of Example 50, 100 mg (0.16 mmol, purity 84%) of Example 47A were reacted with 96 mg (0.98 mmol) of ethyl propiolate (in two portions). The crude product was purified by preparative HPLC (gradient: 0.1% formic acid in water/5-95% acetonitrile) and flash chromatography on silica gel (gradient: CH/EA 25-33%).

Yield: 13.1 mg (17% of theory)

LC-MS (Method 9): Rt=3.72 min; MS (ESIpos): m/z=485 (M+H)$^+$

¹H NMR (400 MHz, DMSO-d₆): [ppm]=1.31 (t, 3H), 1.46 (s, 6H), 4.34 (q, 2H), 5.88 (s, 2H), 7.10-7.18 (m, 1H), 7.18-7.28 (m, 2H), 7.31-7.41 (m, 1H), 7.49 (dd, 1H), 8.70 (dd, 1H), 8.84 (dd, 1H), 11.96 (s, 1H).

Example 54

2-[5-Fluoro-1-(2-fluorobenzyl)-1H-pyrazolo[3,4-b]pyridin-3-yl]-5,5-dimethyl-4-[(2-oxopyrrolidin-1-yl)methyl]-5,7-dihydro-6H-pyrrolo[2,3-d]pyrimidin-6-one

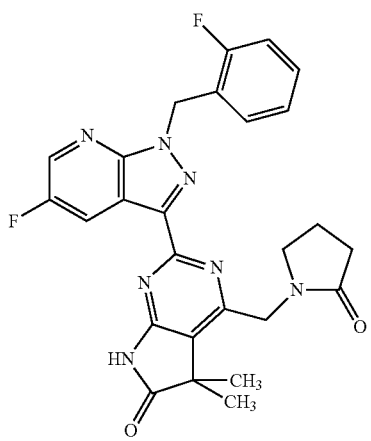 [SMILES: CC1(C)C(=O)Nc2nc(-c3nn(Cc4ccccc4F)c4ncc(F)cc34)nc(CN3CCCC3=O)c21]

Under an atmosphere of argon, 80 mg (0.16 mmol) of Example 45 were initially charged in 1 ml of dichloromethane and 1 ml of DMF, and 62 µl (0.36 mmol) of N,N-diisopropylethylamine and 20 µl (0.18 mmol) of 4-chlorobutanoyl chloride were added. After 8 h of stirring at room temperature, the mixture was concentrated under reduced pressure and 1 ml of DMF and 7.8 mg (0.19 mmol) of 60% sodium hydride were added. After 8 h of stirring at room temperature, the mixture was heated at 50° C. for 8 h. After another addition of 7.8 mg (0.19 mmol) of 60% sodium hydride, the mixture was stirred at 90° C. for 3 h. The mixture was cooled, 1 M aqueous hydrochloric acid was added and the mixture was stirred at room temperature for 10 min and concentrated under reduced pressure. The residue was purified by preparative HPLC (gradient 0.05% formic acid in water/20-95% acetonitrile). This gave 11.3 mg (14% of theory) of the title compound.

LC-MS (Method 1): R$_t$=1.01 min; MS (ESIpos): m/z=504 (M+H)⁺

¹H NMR (400 MHz, DMSO-d₆): δ [ppm]=1.47 (s, 6H) 1.97 (quin, 2H), 2.36 (t, 2H), 3.37-3.45 (m, 2H, superposed by water signal), 4.61 (s, 2H), 5.85 (s, 2H), 7.11-7.32 (m, 3H), 7.32-7.41 (m, 1H), 8.53 (m, 1H), 8.75 (s, 1H), 11.71 (br.s, 1H).

Example 55

N-({2-[5-Fluoro-1-(2-fluorobenzyl)-1H-pyrazolo[3,4-b]pyridin-3-yl]-5,5-dimethyl-6-oxo-6,7-dihydro-5H-pyrrolo[2,3-d]pyrimidin-4-yl}methyl)cyclopropanesulphonamide

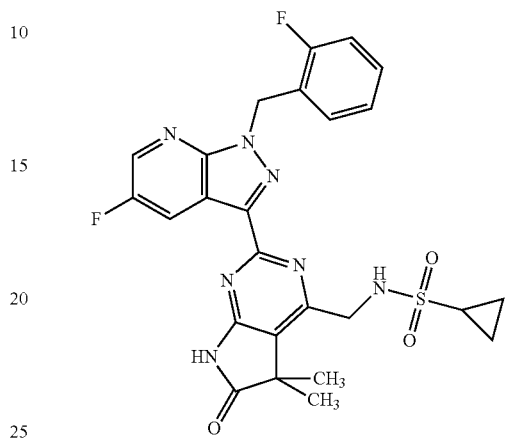

Under an atmosphere of argon, 62 µl (0.36 mmol) of N,N-diisopropylethylamine and 18 µl (0.180 mmol) of cyclopropanesulphonyl chloride were added to 80 mg (0.16 mmol) of Example 45 in 1 ml of dichloromethane and 1 ml of DMF, and the mixture was stirred at room temperature overnight. The mixture was concentrated under reduced pressure and the residue was purified by preparative HPLC (gradient 0.05% formic acid in water/20-95% acetonitrile). 52.5 mg (60% of theory) of the title compound were obtained.

LC-MS (Method 1): R$_t$=1.04 min; MS (ESIpos): m/z=540 (M+H)⁺

¹H NMR (400 MHz; DMSO-d₆): δ [ppm]=0.73-0.84 (m, 2H), 0.84-0.94 (m, 2H), 1.43 (s, 6H), 2.59-2.69 (m, 1H), 4.38 (d, 2H), 5.85 (s, 2H), 7.11-7.30 (m, 3H), 7.32-7.43 (m, 1H), 7.99 (t, 1H), 8.74 (dd, 1H), 8.97 (dd, 1H), 11.69 (s, 1H).

Example 56

N-({2-[5-Fluoro-1-(2-fluorobenzyl)-1H-pyrazolo[3,4-b]pyridin-3-yl]-5,5-dimethyl-6-oxo-6,7-dihydro-5H-pyrrolo[2,3-d]pyrimidin-4-yl}methyl)cyclopropanecarboxamide

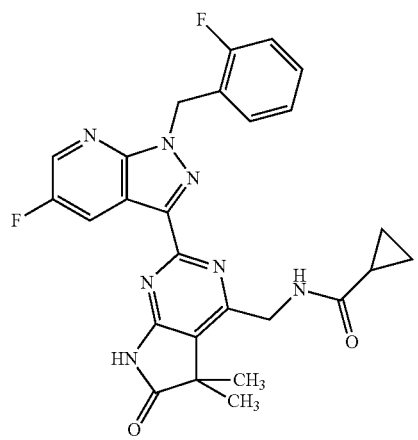 [SMILES: CC1(C)C(=O)Nc2nc(-c3nn(Cc4ccccc4F)c4ncc(F)cc34)nc(CNC(=O)C3CC3)c21]

80 mg (016 mmol) of Example 44 were reacted analogously to Example 55 with 16 μl (0.18 mmol) of cyclopropanecarbonyl chloride. 61.8 mg (76% of theory) of the title compound were obtained.

LC-MS (Method 1): $R_t$=1.04 min; MS (ESIpos): m/z=540 (M+H)$^+$ $^1$H NMR (400 MHz; DMSO-d$_6$): δ [ppm]=0.62-0.81 (m, 4H), 1.42 (s, 6H), 1.71-1.82 (m, 1H), 4.49 (d, 2H), 5.85 (s, 2H), 7.10-7.29 (m, 3H), 7.32-7.42 (m, 1H), 8.68-8.79 (m, 2H), 8.86 (t, 1H), 11.65 (s, 1H).

Example 57

2-[5-Fluoro-1-(2-fluorobenzyl)-1H-pyrazolo[3,4-b]pyridin-3-yl]-5,5-dimethyl-4-{[(2,2,2-trifluoroethyl)amino]methyl}-5,7-dihydro-6H-pyrrolo[2,3-d]pyrimidin-6-one

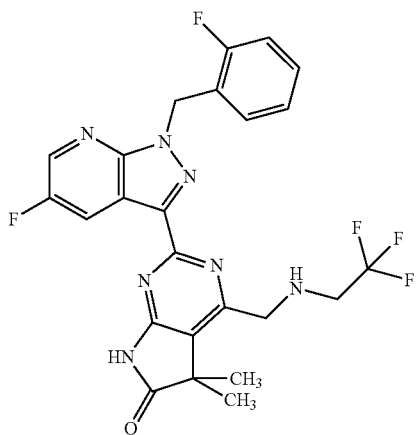 [SMILES: CC1(C)C(=O)Nc2nc(-c3nn(Cc4ccccc4F)c4ncc(F)cc34)nc(CNCC(F)(F)F)c21]

Under an atmosphere of argon, 50 mg (0.04 mmol) of Example 45 were initially charged in 2 ml of DMF, and 17 μl (0.10 mmol) of N,N-diisopropylethylamine and 9 μl (0.06 mmol) of 2,2,2-trifluoroethyl trichloromethanesulphonate were added. After stirring at room temperature overnight, the mixture was left at room temperature over the weekend and then purified by preparative HPLC (gradient 0.05% formic acid in water/20-95% acetonitrile). 15 mg (67% of theory) of the title compound were obtained.

LC-MS (Method 1): $R_t$=1.15 min; MS (ESIpos): m/z=518 (M+H)$^+$ $^1$H NMR (400 MHz; DMSO-d$_6$): δ [ppm]=1.40 (s, 6H), 3.11-3.25 (m, 1H), 3.38-3.53 (m, 2H), 4.00 (d, 2H), 5.86 (s, 2H), 7.10-7.30 (m, 3H), 7.31-7.43 (m, 1H), 8.69-8.82 (m, 2H), 11.65 (s, 1H).

Example 58

2-[5-Fluoro-1-(2-fluorobenzyl)-1H-pyrazolo[3,4-b]pyridin-3-yl]-5,5-dimethyl-4-(3,3,3-trifluoropropyl)-5,7-dihydro-6H-pyrrolo[2,3-d]pyrimidin-6-one

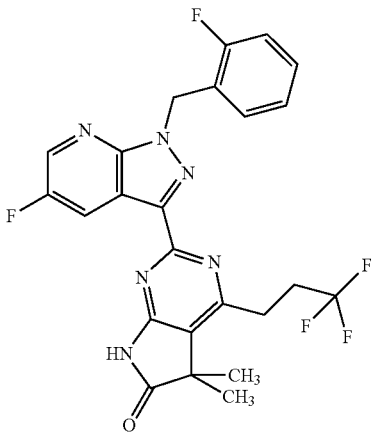 [SMILES: CC1(C)C(=O)Nc2nc(-c3nn(Cc4ccccc4F)c4ncc(F)cc34)nc(CCC(F)(F)F)c21]

Under argon, 2.84 ml (2.30 mmol) of the 0.81 molar solution of Example 73A were added dropwise to 153.3 mg (0.29 mmol) of 2-[5-fluoro-1-(2-fluorobenzyl)-1H-pyrazolo[3,4-b]pyridin-3-yl]-4-iodo-5,5-dimethyl-5,7-dihydro-6H-pyrrolo[2,3-d]pyrimidin-6-one (described in WO2012/004258, Ex. 56A) and PdCl$_2$(dppf) CH$_2$Cl$_2$ in 6 ml of dioxane. After 3 h of stirring in a microwave at 120° C., another 18.8 mg (0.02 mmol) of PdCl$_2$(dppf) CH$_2$Cl$_2$ and 2.84 ml (2.30 mmol) of the 0.81 molar solution of Example 73A were added. After a further 3 h of stirring at 120° C. in a microwave, water was added and the mixture was extracted with ethyl acetate. The organic phases were concentrated under reduced pressure and purified by preparative HPLC (gradient 0.1% formic acid in water/5-95% acetonitrile). 32.8 mg (22% of theory) of the title compound were obtained.

LC-MS (Method 1): $R_t$=1.26 min; MS (ESIpos): m/z=503 (M+H)$^+$ $^1$H NMR (400 MHz; DMSO-d$_6$): δ [ppm]=1.41 (s, 6H), 2.83-2.98 (m, 2H), 3.01-3.12 (m, 2H), 5.87 (s, 2H), 7.10-7.29 (m, 3H), 7.32-7.42 (m, 1H), 8.61 (dd, 1H), 8.75 (s, 1H), 11.68 (s, 1H).

Example 59

2-[1-(2-Fluorobenzyl)-1H-pyrazolo[3,4-b]pyridin-3-yl]-4-(3-hydroxy-3-methylbutyl)-5,5-dimethyl-5,7-dihydro-6H-pyrrolo[2,3-d]pyrimidin-6-one

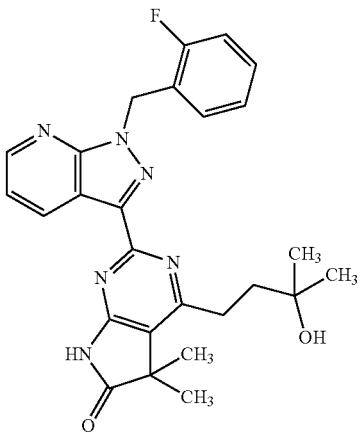 [SMILES: CC(C)(O)CCc1nc(-c2nn(Cc3ccccc3F)c3ncccc23)nc2c1C(C)(C)C(=O)N2]

39.9 mg (0.07 mmol) of Example 92A were dissolved in 0.97 ml of dichloromethane, 0.39 ml of TFA were added and the mixture was stirred at room temperature for 4 h. The solvents were removed under reduced pressure and the residue was dried under high vacuum. The intermediate, 2-[1-(2-fluorobenzyl)-1H-pyrazolo[3,4-b]pyridin-3-yl]-7-(hydroxymethyl)-4-(3-hydroxy-3-methylbutyl)-5,5-dimethyl-5,7-dihydro-6H-pyrrolo[2,3-d]pyrimidin-6-one, was detected in the LC-MS:

LC-MS (Method 1): $R_t$=1.03 min; MS (ESIpos): m/z=505 (M+H)$^+$.

The residue was dissolved in 2 ml of dioxane and stirred with 2 ml of 0.5 M aqueous hydrochloric acid at room temperature for 1 d and under reflux for 5 h. The mixture was diluted with acetonitrile and purified by preparative HPLC (gradient: 0.1% formic acid in water/5-95% acetonitrile).

Yield: 3.1 mg (9% of theory)+6.8% mixed fraction (15% of theory, purity: 80.5%)

LC-MS (Method 9): $R_t$=2.97 min; MS (ESIpos): m/z=475 (M+H)$^+$ $^1$H-NMR (500 MHz, DMSO-d$_6$): δ [ppm]=1.22 (s, 6H), 1.42 (s, 6H), 1.79-1.90 (m, 2H), 2.77-2.87 (m, 2H), 4.44 (s, 1H), 5.86 (s, 2H), 7.09-7.27 (m, 3H), 7.31-7.39 (m, 1H), 7.45 (dd, 1H), 8.67 (d, 1H), 8.90 (d, 1H), 11.55 (s, 1H).

Example 60

4-Chloro-2-[1-(2-fluorobenzyl)-1H-pyrazolo[3,4-b]pyridin-3-yl]-5,5-dimethyl-5,7-dihydro-6H-pyrrolo[2,3-d]pyrimidin-6-one

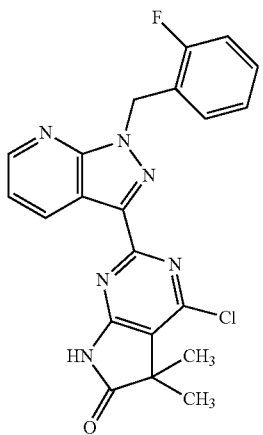 [SMILES: CC1(C)C(=O)Nc2nc(-c3nn(Cc4ccccc4F)c4ncccc34)nc(Cl)c21]

6.4 g (15.83 mmol) of Example 93A (2-[1-(2-fluorobenzyl)-1H-pyrazolo[3,4-b]pyridin-3-yl]-4-hydroxy-5,5-dimethyl-5,7-dihydro-6H-pyrrolo[2,3-d]pyrimidin-6-one) in 50 ml of phosphorus oxychloride were stirred at a bath temperature of 105° C. for 4 h. The phosphorus oxychloride was then removed under reduced pressure and the residue was, under external cooling with ice-water, triturated with solid ice. The residue was allowed to stand at RT until the ice had melted and the precipitate formed was filtered off, washed with water and dried under high vacuum.

Yield: 5.57 g (71% of theory)

LC-MS (Method 1): Rt=1.17 min; MS (ESIpos): m/z=423 (M+H)$^+$ $^1$H-NMR (400 MHz, DMSO-d$_6$): δ [ppm]=1.44 (s, 6H), 5.88 (s, 2H), 7.12-7.28 (m, 3H), 7.33-7.41 (m, 1H), 7.49 (dd, 1H), 8.70 (dd, 1H), 8.82 (dd, 1H), 11.97 (br. s, 1H).

Example 61

2-{2-[1-(2-Fluorobenzyl)-1H-pyrazolo[3,4-b]pyridin-3-yl]-5,5-dimethyl-6-oxo-6,7-dihydro-5H-pyrrolo[2,3-d]pyrimidin-4-yl}acetamide

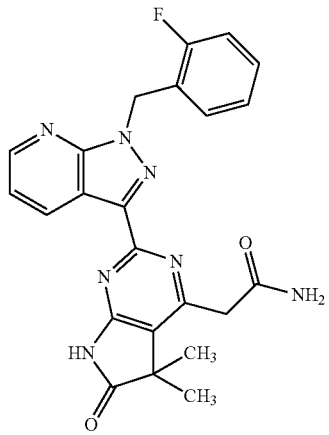 [SMILES: CC1(C)C(=O)Nc2nc(-c3nn(Cc4ccccc4F)c4ncccc34)nc(CC(N)=O)c21]

40 mg (0.065 mmol) of Example 95A were dissolved in 2.6 ml of trifluoroacetic acid, 35 µl (0.207 mmol) of trifluoromethanesulphonic anhydride were added and the mixture was stirred in a microwave at 120° C. for 15 min. 70 µl (0.414 mmol) of trifluoromethanesulphonic anhydride were added, and the mixture was heated in a microwave at 120° C. for another 15 min. The mixture was concentrated under reduced pressure and the residue was purified by preparative HPLC (gradient: 0.1% formic acid in water/5-95% acetonitrile).

Yield: 13.2 mg (46% of theory)

LC-MS (Method 1): Rt=0.82 min; MS (ESIpos): m/z=446 (M+H)$^+$ $^1$H-NMR (400 MHz, DMSO-d$_6$): d [ppm]=1.42 (s, 6H), 3.70 (s, 2H), 5.86 (s, 2H), 7.09-7.27 (m, 4H), 7.31-7.47 (m, 2H), 7.64 (br. s., 1H), 8.61-8.71 (m, 1H), 8.97 (dd, 1H), 11.63 (s, 1H).

Example 62

3-{2-[1-(2-Fluorobenzyl)-1H-pyrazolo[3,4-b]pyridin-3-yl]-5,5-dimethyl-6-oxo-6,7-dihydro-5H-pyrrolo[2,3-d]pyrimidin-4-yl}prop-2-ynoic acid

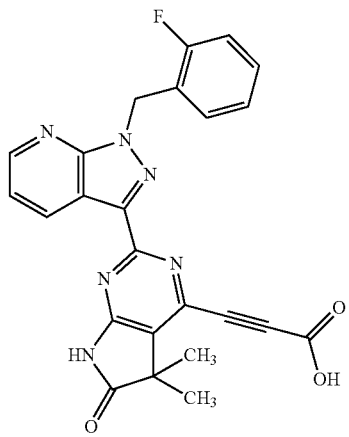 [SMILES: CC1(C)C(=O)Nc2nc(-c3nn(Cc4ccccc4F)c4ncccc34)nc(C#CC(=O)O)c21]

12.9 mg (0.025 mmol) of Example 62 were stirred in 1.3 ml of dichloromethane and 0.3 ml of TFA at RT for 3 d. The mixture was concentrated under reduced pressure and the residue was purified by preparative HPLC (gradient: 0.1% formic acid in water/5-95% acetonitrile).

Yield: 1.3 mg (11% of theory)

LC-MS (Method 1): Rt=0.83 min; MS (ESIpos): m/z=457 (M+H)+

$^1$H NMR (400 MHz, DMSO-d$_6$): [ppm]=1.47 (s, 6H), 5.87 (s, 2H), 7.12-7.18 (m, 1H), 7.19-7.27 (m, 2H), 7.31-7.41 (m, 1H), 7.47 (dd, 1H), 8.68 (dd, 1H), 8.85 (dd, 1H), 11.81 (s, 1H).

Example 63

2-[1-(2-Fluorobenzyl)-1H-pyrazolo[3,4-b]pyridin-3-yl]-4-(3-methoxyprop-1-yn-1-yl)-5,5-dimethyl-5,7-dihydro-6H-pyrrolo[2,3-d]pyrimidin-6-one

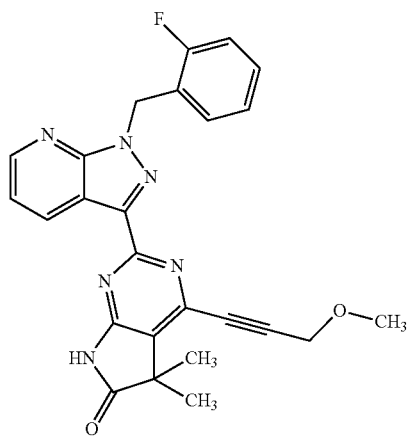 [SMILES: COCC#Cc1nc(-c2nn(Cc3ccccc3F)c3ncccc23)nc2c1C(C)(C)C(=O)N2]

Under argon, 1 g (1.23 mmol, purity 63%) of Example 47A and 0.29 ml (3.68 mmol) of 3-methoxyprop-1-yne were initially charged in 19 ml of THF, and 0.52 ml (3.68 mmol) of diisopropylamine, 69.99 mg (0.37 mmol) of copper(I) iodide and 171.96 mg (0.25 mmol) of dichlorobis(triphenylphosphine)palladium(II) were added. After 2 days of stirring under reflux, the mixture was concentrated under reduced pressure, dissolved in dimethyl sulphoxide, filtered and separated by preparative HPLC (acetonitrile:water with 0.1% formic acid gradient). This gave 380 mg (47% of theory, purity 69%) of the title compound.

LC-MS (Method 1): R$_t$=1.10 min; MS (ESIpos): m/z=457 (M+H)+

Example 64

Ethyl 3-{2-[1-(2-fluorobenzyl)-1H-pyrazolo[3,4-b]pyridin-3-yl]-5,5-dimethyl-6-oxo-6,7-dihydro-5H-pyrrolo[2,3-d]pyrimidin-4-yl}propanoate

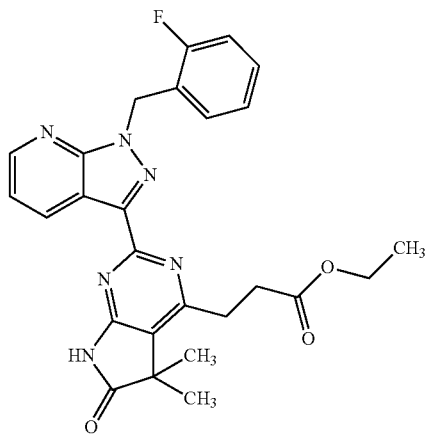 [SMILES: CCOC(=O)CCc1nc(-c2nn(Cc3ccccc3F)c3ncccc23)nc2c1C(C)(C)C(=O)N2]

Under argon, 143 mg (0.30 mmol) of Example 53 were dissolved in 8 ml of ethyl acetate and hydrogenated with 25 mg of 10% palladium on carbon under standard pressure overnight. The catalyst was filtered off through silica gel and washed with ethyl acetate, and the filtrate was concentrated under reduced pressure. The residue was purified by preparative HPLC (gradient: 0.1% formic acid in water/5-95% acetonitrile).

Yield: 39 mg (27% of theory)

LC-MS (Method 1): R$_t$=1.12 min; MS (ESIpos): m/z=489 (M+H)+

$^1$H NMR (400 MHz; DMSO-d$_6$): δ [ppm]=1.07 (t, 3H), 1.42 (s, 6H), 2.93-3.01 (m, 2H), 3.07-3.15 (m, 2H), 4.01 (q, 2H), 5.86 (s, 2H), 7.10-7.27 (m, 3H), 7.32-7.40 (m, 1H), 7.45 (dd, 1H), 8.67 (dd, 1H), 8.86 (dd, 1H), 11.60 (s, 1H).

Example 65

2-[1-(2-Fluorobenzyl)-1H-pyrazolo[3,4-b]pyridin-3-yl]-4-(3-hydroxypropyl)-5,5-dimethyl-5,7-dihydro-6H-pyrrolo[2,3-d]pyrimidin-6-one

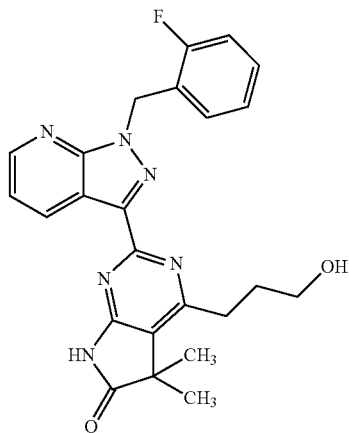 [SMILES: CC1(C)C(=O)Nc2nc(-c3nn(Cc4ccccc4F)c4ncccc34)nc(CCCO)c21]

At 0° C. and with stirring, 0.27 ml (0.27 mmol) of a 1 M solution of lithium triethylborohydride in THF were added dropwise to a solution of 33 mg (0.07 mmol) of Example 64 in 0.7 ml of anhydrous THF. After 10 min, cooling was removed and the mixture was stirred at room temperature overnight. Methanol and 5 M formic acid were added and the solvents were removed under reduced pressure. The residue was purified by preparative HPLC (gradient: 0.1% formic acid in water/5-95% acetonitrile).

Yield: 14.5 mg (48% of theory)

LC-MS (Method 1): $R_t$=0.92 min; MS (ESIpos): m/z=447 $(M+H)^+$ $^1$H NMR (400 MHz, DMSO-$d_6$): δ [ppm]=1.41 (s, 6H), 1.92-2.05 (m, 2H), 2.84 (t, 2H), 3.56 (t, 2H), 4.63 (br. s., 1H), 5.86 (s, 2H), 7.09-7.28 (m, 3H), 7.31-7.41 (m, 1H), 7.45 (dd, 1H), 8.67 (dd, 1H), 8.91 (dd, 1H), 11.57 (s, 1H).

B. ASSESSMENT OF PHARMACOLOGICAL EFFICACY

The pharmacological effect of the compounds according to the invention can be shown in the following assays:

B-1. Vasorelaxant Effect In Vitro

Rabbits are stunned by a blow to the neck and exsanguinated. The aorta is removed, freed from adhering tissue and divided into rings of a width of 1.5 mm. The rings are placed individually under an initial tension in 5 ml organ baths with Krebs-Henseleit solution which is at 37° C., is gassed with carbogen and has the following composition (in each case mM): sodium chloride: 119; potassium chloride: 4.8; calcium chloride dihydrate: 1; magnesium sulphate heptahydrate: 1.4; potassium dihydrogenphosphate: 1.2; sodium bicarbonate: 25; glucose: 10. The contractile force is determined with Statham UC2 cells, amplified and digitalized using A/D transducers (DAS-1802 HC, Keithley Instruments Munich), and recorded in parallel on linear recorders.

To produce a contraction, phenylephrine is added to the bath cumulatively in increasing concentration. After several control cycles, the substance to be investigated is added in each further run in increasing dosage in each case, and the height of the contraction achieved is compared with the height of the contraction reached in the last preceding run. This is used to calculate the concentration needed to reduce the magnitude of the control value by 50% ($IC_{50}$ value). The standard administration volume is 5 μl; the DMSO content in the bath solution corresponds to 0.1%.

Representative $IC_{50}$ values for the compounds according to the invention are shown in the table below (Table 1):

TABLE 1

| Example No. | $IC_{50}$ [nM] |
| --- | --- |
| 1 | 37 |
| 3 | 266 |
| 4 | 215 |
| 5 | 137 |
| 5-1 | 321 |
| 5-2 | 661 |
| 6 | 246 |
| 7 | 41 |
| 7-1 | 59 |
| 7-2 | 185 |
| 9 | 198 |
| 10 | 276 |
| 11 | 237 |
| 12 | 677 |
| 13 | 1590 |
| 14 | 420 |
| 15 | 738 |

TABLE 1-continued

| Example No. | $IC_{50}$ [nM] |
| --- | --- |
| 16 | 617 |
| 17 | 2380 |
| 18 | 836 |
| 20 | 345 |
| 28 | 209 |
| 29 | 779 |
| 30 | 415 |
| 31 | 309 |
| 32 | 244 |
| 34 | 218 |
| 35 | 496 |
| 36 | 218 |
| 37 | 1430 |
| 38 | 91 |
| 39 | 225 |
| 40 | 227 |
| 41 | 4210 |
| 42 | 728 |
| 43 | 968 |
| 44 | 501 |
| 46 | 71 |
| 51 | 413 |
| 57 | 422 |
| 58 | 9800 |

B-2. Effect on a Recombinant Guanylate Cyclase Reporter Cell Line

The cellular activity of the compounds according to the invention is determined using a recombinant guanylate cyclase reporter cell line, as described in F. Wunder et al., Anal. Biochem. 339, 104-112 (2005).

Representative values (MEC=minimum effective concentration) for the compounds according to the invention are shown in the table below (Table 2):

TABLE 2

| Example No. | MEC [nM] |
| --- | --- |
| 1 | 30 |
| 2 | 300 |
| 3 | 30 |
| 4 | 100 |
| 5 | 100 |
| 5-1 | 100 |
| 5-2 | 300 |
| 6 | 100 |
| 7 | 30 |
| 7-1 | 100 |
| 7-2 | 100 |
| 8 | 3000 |
| 9 | 30 |
| 10 | 300 |
| 11 | 300 |
| 12 | 100 |
| 13 | 100 |
| 14 | 300 |
| 15 | 10 |
| 16 | 30 |
| 17 | 100 |
| 18 | 100 |
| 19 | 1000 |
| 20 | 100 |
| 21 | 30 |
| 22 | 100 |
| 23 | 30 |
| 24 | 30 |
| 25 | 100 |
| 26 | 300 |
| 27 | 300 |
| 28 | 30 |
| 29 | 100 |
| 30 | 100 |
| 31 | 100 |
| 32 | 100 |

TABLE 2-continued

| Example No. | MEC [nM] |
|---|---|
| 33 | 10 |
| 34 | 30 |
| 35 | 30 |
| 36 | 100 |
| 37 | 1000 |
| 38 | 30 |
| 39 | 30 |
| 40 | 30 |
| 41 | 300 |
| 42 | 10 |
| 43 | 100 |
| 44 | 30 |
| 46 | 100 |
| 49 | 300 |
| 50 | 300 |
| 51 | 30 |
| 52 | 1000 |
| 53 | 100 |
| 54 | 100 |
| 55 | 30 |
| 56 | 30 |
| 57 | 30 |
| 58 | 300 |
| 59 | 300 |
| 60 | 300 |
| 61 | 30 |
| 62 | 30 |

B-3. Radiotelemetric Measurement of Blood Pressure on Conscious Spontaneously Hypertensive Rats A commercially available telemetry system from DATA SCIENCES INTERNATIONAL DSI, USA, is employed for the blood pressure measurement on conscious rats described below.

The system consists of 3 main components:
implantable transmitters (Physiotel® telemetry transmitter)
receivers (Physiotel® receiver) which are linked via a multiplexer (DSI Data Exchange Matrix) to a
data acquisition computer.

The telemetry system makes it possible to continuously record blood pressure, heart rate and body motion of conscious animals in their usual habitat.

Animal Material

The investigations are carried out on adult female spontaneously hypertensive rats (SHR Okamoto) with a body weight of >200 g. SHR/NCrl from the Okamoto Kyoto School of Medicine, 1963 were a cross of male Wistar Kyoto rats with highly elevated blood pressure and female rats having a slightly elevated blood pressure and at F13 handed over to the U.S. National Institutes of Health.

After transmitter implantation, the experimental animals are housed singly in type 3 Makrolon cages. They have free access to standard feed and water.

The day/night rhythm in the experimental laboratory is changed by the room lighting at 6:00 am and at 7:00 pm.

Transmitter Implantation

The telemetry transmitters TA11 PA-C40 used are surgically implanted under aseptic conditions in the experimental animals at least 14 days before the first experimental use. The animals instrumented in this way can be employed repeatedly after the wound has healed and the implant has settled.

For the implantation, the fasted animals are anaesthetized with pentobarbital (Nembutal, Sanofi: 50 mg/kg i.p.) and shaved and disinfected over a large area of their abdomens. After the abdominal cavity has been opened along the linea alba, the liquid-filled measuring catheter of the system is inserted into the descending aorta in the cranial direction above the bifurcation and fixed with tissue glue (Vet-BonD™, 3M). The transmitter housing is fixed intraperitoneally to the abdominal wall muscle, and layered closure of the wound is performed.

An antibiotic (Tardomyocel COMP, Bayer, 1 ml/kg s.c.) is administered postoperatively for prophylaxis of infection.

Substances and Solutions

Unless stated otherwise, the substances to be studied are administered orally by gavage to a group of animals in each case (n=6). In accordance with an administration volume of 5 ml/kg of body weight, the test substances are dissolved in suitable solvent mixtures or suspended in 0.5% tylose.

A solvent-treated group of animals is employed as control.

Test Procedure

The telemetry measuring unit present is configured for 24 animals. Each experiment is recorded under an experiment number (Vyear month day).

Each of the instrumented rats living in the system is assigned a separate receiving antenna (1010 Receiver, DSI).

The implanted transmitters can be activated externally by means of an incorporated magnetic switch and are switched to transmission in the run-up to the experiment. The signals emitted can be detected online by a data acquisition system (Dataquest™ A.R.T. for WINDOWS, DSI) and processed accordingly. The data are stored in each case in a file created for this purpose and bearing the experiment number.

In the standard procedure, the following are measured for 10-second periods in each case:
systolic blood pressure (SBP)
diastolic blood pressure (DBP)
mean arterial pressure (MAP)
heart rate (HR)
activity (ACT).

The acquisition of measurements is repeated under computer control at 5-minute intervals. The source data obtained as absolute value are corrected in the diagram with the currently measured barometric pressure (Ambient Pressure Reference Monitor; APR-1) and stored as individual data. Further technical details are given in the extensive documentation from the manufacturing company (DSI).

Unless indicated otherwise, the test substances are administered at 9.00 am on the day of the experiment. Following the administration, the parameters described above are measured over 24 hours.

Evaluation

After the end of the experiment, the acquired individual data are sorted using the analysis software (DATAQUEST™ A.R.T.™ ANALYSIS). The blank value is assumed to be the time 2 hours before administration, and so the selected data set encompasses the period from 7.00 am on the day of the experiment to 9.00 am the following day.

The data are smoothed over a presettable time by determination of the average (15-minute average) and transferred as a text file to a storage medium. The measured values presorted and compressed in this way are transferred into Excel templates and tabulated. For each day of the experiment, the data obtained are stored in a dedicated file bearing the number of the experiment. Results and test protocols are filed in paper form sorted by numbers.

LITERATURE

Klaus Witte, Kai Hu, Johanna Swiatek, Claudia Müssig, Georg Ertl and Björn Lemmer: Experimental heart failure in rats: effects on cardiovascular circadian rhythms and on myocardial β-adrenergic signaling. Cardiovasc Res 47 (2): 203-405, 2000; Kozo Okamoto: Spontaneous hypertension in rats. Int Rev Exp Pathol 7: 227-270, 1969; Maarten van den Buuse: Circadian Rhythms of Blood Pressure, Heart Rate, and Locomotor Activity in Spontaneously Hypertensive Rats as Measured With Radio-Telemetry. Physiology & Behavior 55(4): 783-787, 1994

B-4. Determination of Pharmacokinetic Parameters Following Intravenous and Oral Administration The pharmacokinetic parameters of the inventive compounds are determined in male CD-1 mice, male Wistar rats and female beagles. Intravenous administration in the case of mice and rats is effected by means of a species-specific plasma/DMSO formulation, and in the case of dogs by means of a water/PEG400/ethanol formulation. In all species, oral administration of the dissolved substance is performed via gavage, based on a water/PEG400/ethanol formulation. The removal of blood from rats is simplified by inserting a silicone catheter into the right Vena jugularis externa prior to substance administration. The operation is effected at least one day prior to the experiment with isofluran anaesthesia and administration of an analgesic (atropine/rimadyl (3/1) 0.1 ml s.c.). The blood is taken (generally more than 10 time points) within a time window including terminal time points of at least 24 to a maximum of 72 hours after substance administration. The blood is removed into heparinized tubes. The blood plasma is then obtained by centrifugation; if required, it can be stored at −20° C. until further processing.

An internal standard (which may also be a chemically unrelated substance) is added to the samples of the inventive compounds, calibration samples and qualifiers, and there follows protein precipitation by means of acetonitrile in excess. Addition of a buffer solution matched to the LC conditions, and subsequent vortexing, is followed by centrifugation at 1000 g. The supernatant is analysed by means of LC-MS/MS using C18 reversed-phase columns and variable mobile phase mixtures. The substances are quantified via the peak heights or areas from extracted ion chromatograms of specific selected ion monitoring experiments.

The plasma concentration/time plots determined are used to calculate the pharmacokinetic parameters such as AUC, $C_{max}$, biz (terminal half life), MRT (mean residence time) and CL (clearance), using a validated pharmacokinetic calculation program.

Since the substance quantification is performed in plasma, it is necessary to determine the blood/plasma distribution of the substance in order to be able to adjust the pharmacokinetic parameters correspondingly. For this purpose, a defined amount of substance is incubated in heparinized whole blood of the species in question in a rocking roller mixer for 20 min. After centrifugation at 1000 g, the plasma concentration is measured (by means of LC-MS/MS; see above) and determined by calculating the ratio of the $c_{blood}/c_{plasma}$ value.

B-5. Metabolic Study

To determine the metabolic profile of the compounds according to the invention, they are incubated with recombinant human cytochrome P450 (CYP) enzymes, liver microsomes or primary fresh hepatocytes from various animal species (e.g. rats, dogs), and also of human origin, in order to obtain and to compare information about a very substantially complete hepatic phase I and phase II metabolism, and about the enzymes involved in the metabolism.

The compounds according to the invention were incubated with a concentration of about 0.1-10 µM. To this end, stock solutions of the compounds according to the invention having a concentration of 0.01-1 mM in acetonitrile were prepared, and then pipetted with 1:100 dilution into the incubation mixture. Liver microsomes and recombinant enzymes were incubated at 37° C. in 50 mM potassium phosphate buffer pH 7.4 with and without NADPH-generating system consisting of 1 mM NADP+, 10 mM glucose-6-phosphate and 1 unit glucose-6-phosphate dehydrogenase. Primary hepatocytes were incubated in suspension in Williams E medium, likewise at 37° C. After an incubation time of 0-4 h, the incubation mixtures were quenched with acetonitrile (final concentration about 30%) and the protein was centrifuged off at about 15 000×g. The samples thus stopped were either analysed directly or stored at −20° C. until analysis.

The analysis is effected by means of high-performance liquid chromatography with ultraviolet and mass spectrometry detection (HPLC-UV-MS/MS). To this end, the supernatants of the incubation samples are chromatographed with suitable C18 reversed-phase columns and variable mobile phase mixtures of acetonitrile and 10 mM aqueous ammonium formate solution or 0.05% formic acid. The UV chromatograms in conjunction with mass spectrometry data serve for identification, structural elucidation and quantitative estimation of the metabolites, and for quantitative metabolic assessment of the compound according to the invention in the incubation mixtures.

B-6. Inhibition of Human Phosphodiesterase 5 (PDE 5)

PDE 5 preparations are obtained from human platelets by disruption (Microfluidizer®, 800 bar, 3 passes), followed by centrifugation (75 000 g, 60 min, 4° C.) and ion exchange chromatography of the supernatant on a Mono Q 10/10 column (linear sodium chloride gradient, elution with a 0.2-0.3M solution of sodium chloride in buffer (20 mM Hepes pH 7.2, 2 mM magnesium chloride). Fractions having PDE 5 activity are combined (PDE 5 preparation) and stored at −80° C.

To determine their in vitro action on human PDE 5, the test substances are dissolved in 100% DMSO and serially diluted. Typically, dilution series (1:3) from 200 µM to 0.091 µM are prepared (resulting final concentrations in the test: 4 µM to 0.0018 µM). In each case 2 µl of the diluted substance solutions are placed into the wells of microtitre plates (Isoplate-96/200W; Perkin Elmer). Subsequently, 50 µl of a dilution of the above-described PDE 5 preparation are added. The dilution of the PDE 5 preparation is chosen such that during the later incubation less than 70% of the substrate are converted (typical dilution: 1:100; dilution buffer: 50 mM Tris/hydrochloric acid pH 7.5, 8.3 mM magnesium chloride, 1.7 mM EDTA, 0.2% BSA). The substrate, [8-$^3$H] cyclic guanosine-3',5'-monophosphate (1 µCi/µl; Perkin Elmer) is diluted 1:2000 with assay buffer (50 mM tris/hydrochloric acid pH 7.5, 8.3 mM magnesium chloride, 1.7 mM EDTA) to a concentration of 0.0005 µCi/µl. By addition of 50 µl (0.025 µCi) of the diluted substrate, the enzyme reaction is finally started. The test mixtures are incubated at room temperature for 60 min and the reaction is stopped by adding 25 µl of a suspension of 18 mg/ml yttrium scintillation proximity beads in water (phosphodiesterase beads for SPA assays, RPNQ 0150, Perkin Elmer). The microtitre plates are sealed with a film and left to stand at room temperature for 60 min. Subsequently, the plates are analysed for 30 s per well in a Microbeta scintillation counter (Perkin Elmer). $IC_{50}$ values are determined using the graphic plot of the substance concentration against percentage PDE 5 inhibition.

Representative $IC_{50}$ values for the inventive compounds are reproduced in the table below (Table 3):

TABLE 3

| Example No. | IC$_{50}$ [nM] |
| --- | --- |
| 1 | 1200 |
| 2 | 490 |
| 3 | 2400 |
| 4 | 1300 |
| 5 | 260 |
| 5-1 | 350 |
| 5-2 | 250 |
| 6 | 1100 |
| 7 | 340 |
| 7-1 | 200 |
| 7-2 | 350 |
| 8 | 150 |
| 9 | 2000 |
| 10 | 15 |
| 11 | 250 |
| 12 | 580 |
| 13 | 660 |
| 14 | 2000 |
| 15 | 40 |
| 16 | 410 |
| 17 | 260 |
| 18 | 150 |
| 19 | 38 |
| 20 | 920 |
| 21 | 22 |
| 22 | 130 |
| 23 | 140 |
| 24 | 48 |
| 25 | 1500 |
| 26 | 3400 |
| 27 | 215 |
| 28 | 310 |
| 29 | 420 |
| 30 | 130 |
| 31 | 260 |
| 32 | 110 |
| 33 | 870 |
| 34 | 1200 |
| 35 | 120 |
| 36 | 1100 |
| 37 | 500 |
| 38 | 690 |
| 39 | 240 |
| 40 | 250 |
| 41 | 1600 |
| 42 | 1300 |
| 43 | 1750 |
| 44 | 870 |
| 46 | 120 |
| 49 | 4000 |
| 51 | 140 |
| 52 | 3900 |
| 53 | 41 |
| 54 | 145 |
| 55 | 190 |
| 56 | 570 |
| 57 | 320 |
| 58 | 660 |
| 61 | 15 |

B-7. Determination of Organ-Protective Effects in a Long-Term Experiment on Rats The organ-protective effects of the sGC stimulators were shown in a therapeutically relevant "low nitric oxide (NO)/high renin" hypertension model in rats. The study was conducted following a recently published article (Sharkovska Y, Kalk P, Lawrenz B, Godes M, Hoffmann L S, Wellkisch K, Geschka S, Relle K, Hocher B, Stasch J P. NO-independent stimulation of soluble guanylate cyclase reduces target organ damage in low- and high-renin models of hypertension. J. Hypertension. 2010; 28: 1666-1675). This involved treating renin-transgenic rats (TGR(mRen2) 27) to which the NO synthase inhibitor L-NAME had been administered via drinking water simultaneously with an sGC stimulator or vehicle over several weeks. Haemodynamic and renal parameters were determined during the treatment period. At the end of the long-term study, organ protection (kidney, lung, heart, aorta) was shown by histopathological studies, biomarkers, expression analyses and cardiovascular plasma parameters.

C. WORKING EXAMPLES OF PHARMACEUTICAL COMPOSITIONS

The compounds according to the invention can be converted to pharmaceutical formulations as follows:

Tablet:

Composition:

100 mg of the compound according to the invention, 50 mg of lactose (monohydrate), 50 mg of corn starch (native), 10 mg of polyvinylpyrrolidone (PVP 25) (BASF, Ludwigshafen, Germany) and 2 mg of magnesium stearate.

Tablet weight 212 mg, diameter 8 mm, radius of curvature 12 mm.

Production:

The mixture of compound according to the invention, lactose and starch is granulated with a 5% solution (w/w) of the PVP in water. The granules are dried and mixed with the magnesium stearate for 5 minutes. This mixture is pressed with a conventional tableting press (for tablet dimensions see above). The guide value used for the pressing is a pressing force of 15 kN.

Suspension which can be Administered Orally:

Composition:

1000 mg of the compound according to the invention, 1000 mg of ethanol (96%), 400 mg of Rhodigel® (xanthan gum from FMC, Pennsylvania, USA) and 99 g of water.

A single dose of 100 mg of the compound according to the invention corresponds to 10 ml of oral suspension.

Production:

The Rhodigel is suspended in ethanol and the compound according to the invention is added to the suspension. The water is added while stirring. The mixture is stirred for about 6 h until swelling of the Rhodigel is complete.

Solution which can be Administered Orally:

Composition:

500 mg of the compound according to the invention, 2.5 g of polysorbate and 97 g of polyethylene glycol 400. A single dose of 100 mg of the compound according to the invention corresponds to 20 g of oral solution.

Production:

The compound according to the invention is suspended in the mixture of polyethylene glycol and polysorbate while stirring. The stirring operation is continued until dissolution of the compound according to the invention is complete.

i.v. Solution:

The compound according to the invention is dissolved in a concentration below the saturation solubility in a physiologically acceptable solvent (e.g. isotonic saline, glucose solution 5% and/or PEG 400 solution 30%). The solution is subjected to sterile filtration and dispensed into sterile and pyrogen-free injection vessels.

The invention claimed is:

1. A compound of the formula (I)

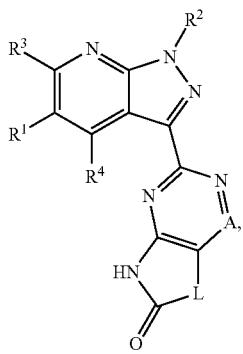

(I)

in which

A represents nitrogen,

L represents a $\#^1\text{-}CR^{6A}R^{6B}\text{—}(CR^{7A}R^{7B})_m\text{-}\#^2$ group, where $\#^1$ is the point of attachment to the carbonyl group, $\#^2$ is the point of attachment to the triazine ring, m is a number 0, $R^{6A}$ represents methyl, $R^{6B}$ represents methyl, $R^1$ represents hydrogen or fluorine, $R^2$ is a group of the formula

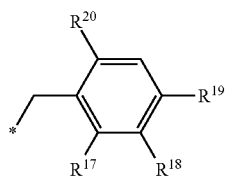

where

* is the point of attachment to the pyrazolopyridine, and $R^{17}$, $R^{18}$, $R^{19}$ and $R^{20}$ independently of one another represent hydrogen, fluorine, methyl or methoxy, with the proviso that 1-3 of the radicals $R^{17}$, $R^{18}$, $R^{19}$ and $R^{20}$ is different from hydrogen as long as 1-3 of the radicals $R^{17}$, $R^{18}$, $R^{19}$ and $R^{20}$ is hydrogen, and with the proviso that in each case only one of the radicals $R^{17}$, $R^{18}$, $R^{19}$ or $R^{20}$ represents methyl or methoxy, $R^3$ represents methyl or trifluoromethyl, and $R^4$ represents hydrogen, or an N-oxide, salt or salt of an N-oxide thereof.

2. A process for preparing the compound of claim 1, comprising reacting a compound of the formula (II)

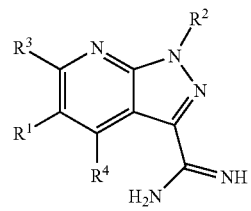

(II)

in which $R^1$, $R^2$, $R^3$ and $R^4$ each have the meanings given in claim 1 in an inert solvent in the presence of a suitable base with hydrazine hydrate to give a compound of the formula (X)

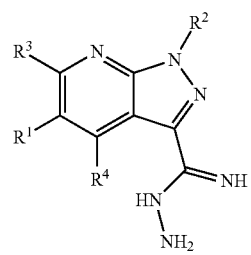

(X)

in which $R^1$, $R^2$, $R^3$ and $R^4$ each have the meanings given above, reacting the compound of formula (X) an inert solvent with a compound of the formula (XI)

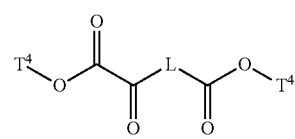

(XI)

in which L has the meaning given in claim 1 and $T^4$ represents $(C_1\text{-}C_4)$-alkyl, to give a compound of the formula (XII)

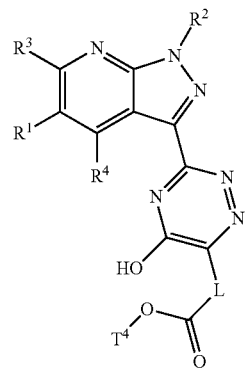

(XII)

in which L, $R^1$, $R^2$, $R^3$, $R^4$ and $T^4$ each have the meanings given above, converting the compound of formula (XII) with phosphoryl chloride into a compound of the formula (XIII)

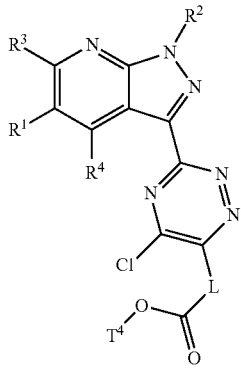

(XIII)

in which L, R$^1$, R$^2$, R$^3$, R$^4$ and T$^4$ each have the meanings given above, reacting the compound of formula (XIII) directly with ammonia to give a compound of the formula (XIV)

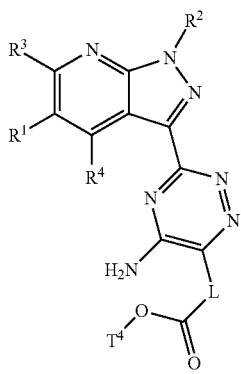

(XIV)

in which L, R$^1$, R$^2$, R$^3$, R$^4$ and T$^4$ each have the meanings given above, and cyclizing the compound of formula (XIV) in an inert solvent, optionally in the presence of a suitable base, to give a compound of the formula (I-C)

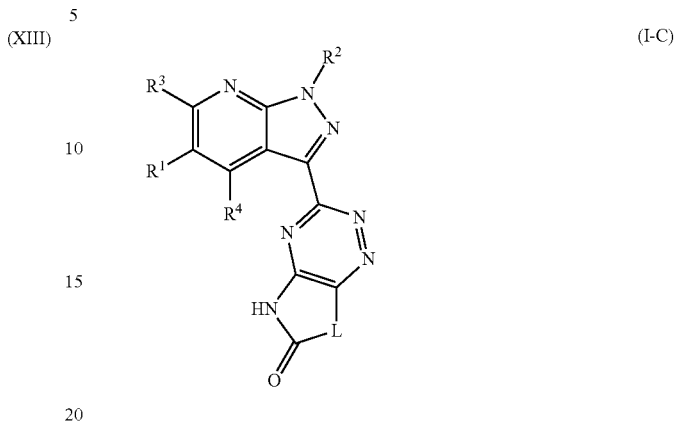

(I-C)

in which L, R$^1$, R$^2$, R$^3$ and R$^4$ each have the meanings given above and optionally converting the resulting compounds of the formula (I-C) with a (i) solvent and/or (ii) acid or base into a salt thereof.

3. A pharmaceutical composition comprising the compound of claim 1 and an inert, non-toxic, pharmaceutically suitable excipient.

4. A pharmaceutical composition comprising the compound of the claim 1, and an active compound selected from the group consisting, of an organic nitrate, an NO donor, a cGMP-PDE inhibitor, an antithrombotic agent, a hypotensive agent and a lipid metabolism modifier.

5. A method for the treatment of heart failure, angina pectoris, hypertension, pulmonary hypertension, ischaemias, vascular disorders, renal insufficiency, thromboembolic disorders and arteriosclerosis comprising administering an effective amount of the compound of claim 1 to a human or animal in need thereof.

6. A method for the treatment of heart failure, angina pectoris, hypertension, pulmonary hypertension, ischaemias, vascular disorders, renal insufficiency, thromboembolic disorders and arteriosclerosis comprising administering an effective amount of the pharmaceutical composition of claim 4 to a human or animal in need thereof.

* * * * *